US012612411B1

(12) United States Patent
Janin et al.

(10) Patent No.: US 12,612,411 B1
(45) Date of Patent: Apr. 28, 2026

(54) IMIDAZOPYRAZINE DERIVATIVES, PROCESS FOR PREPARATION THEREOF, AND THEIR USES AS LUCIFERINS

(71) Applicants: INSTITUT PASTEUR, Paris (FR); CENTRE NATIONAL DE LA RECHERCHE SCIENTIFIQUE, Paris (FR)

(72) Inventors: Yves-Louis Janin, Paris (FR); Eloi Paul Coutant, Montrouge (FR); Vincent Hervin, Le Perreux-sur-Marne (FR); Glwadys Gagnot, Paris (FR); Yves Jacob, Maintenon (FR); Sophie Goyard, Paris (FR); Thierry Rose, Paris (FR)

(73) Assignees: INSTITUT PASTEUR, Paris (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 0 days.

(21) Appl. No.: 19/246,196

(22) Filed: Jun. 23, 2025

Related U.S. Application Data

(60) Continuation of application No. 18/424,207, filed on Jan. 26, 2024, which is a division of application No. 16/607,058, filed as application No. PCT/EP2018/061050 on Apr. 30, 2018, now Pat. No. 11,938,199.

(30) Foreign Application Priority Data

Apr. 28, 2017 (EP) .................................... 17168838

(51) Int. Cl.

| | |
|---|---|
| ***C07D 487/04*** | (2006.01) |
| ***A61K 49/00*** | (2006.01) |
| ***G01N 21/76*** | (2006.01) |
| ***G01N 33/573*** | (2006.01) |

(52) U.S. Cl.

CPC ........ *C07D 487/04* (2013.01); *A61K 49/0013* (2013.01); *G01N 21/763* (2013.01); *G01N 33/573* (2013.01)

(58) Field of Classification Search

CPC .............. C07D 487/04; A61K 49/0013; G01N 21/763; G01N 33/573

See application file for complete search history.

(56) References Cited

U.S. PATENT DOCUMENTS

| | | | | |
|---|---|---|---|---|
| 7,537,912 | B2 | 5/2009 | Wood | |
| 9,765,381 | B2 | 9/2017 | Inouye | |
| 9,777,311 | B2 | 10/2017 | Encell | |
| 9,790,537 | B2 | 10/2017 | Zhou | |
| 11,768,203 | B2 | 9/2023 | Chaudhary | |
| 11,938,199 | B2 | 3/2024 | Janin | |
| 2012/0107849 | A1 | 5/2012 | Klaubert | |
| 2012/0174242 | A1 | 7/2012 | Binkowski | |
| 2014/0194325 | A1* | 7/2014 | Hitko | G01N 33/542 435/8 |
| 2014/0302539 | A1 | 10/2014 | Inouye | |
| 2015/0212078 | A1 | 7/2015 | Zhou | |
| 2020/0386748 | A1 | 12/2020 | Kirkland | |
| 2021/0262941 | A1 | 8/2021 | Kincaid | |

FOREIGN PATENT DOCUMENTS

EP 2970412 B1 8/2022

OTHER PUBLICATIONS

Levi, Jelena, et al. "Bisdeoxycoelenterazine derivatives for improvement of bioluminescence resonance energy transfer assays." Journal of the American Chemical Society 129.39 (2007): 11900-11901.

International Search Report issued in PCT/EP2018/061050 on Aug. 20, 2018, 5 pages.

Written Opinion issued in PCT/EP2018/061050 on Aug. 20, 2018, 8 pages.

Brown, Nathan. "Bioisosterism in medicinal chemistry." Bioisosteres in medicinal chemistry (2012): 1-13, 242 pages.

* cited by examiner

*Primary Examiner* — Shafiqul Haq

(74) *Attorney, Agent, or Firm* — Greenberg Traurig, LLP

(57) ABSTRACT

The present invention is in the field of bioluminescence in biology and/or medicine. In particular, the invention provides imidazopyrazine derivatives, processes for preparation thereof, and their uses as luciferins.

6 Claims, 5 Drawing Sheets

IMIDAZOPYRAZINE DERIVATIVES, PROCESS FOR PREPARATION THEREOF, AND THEIR USES AS LUCIFERINS

CROSS-REFERENCE TO RELATED APPLICATIONS

This application is a continuation of U.S. application Ser. No. 18/424,207, filed Jan. 26, 2024, which is a divisional of U.S. application Ser. No. 16/607,058 filed on Oct. 21, 2019, which is a U.S. Natl. Stage of International Application PCT/EP2018/061050 filed Apr. 30, 2018, which claims the benefit of European application 17168838.5 filed Apr. 28, 2017.

FIELD OF INVENTION

The present invention is in the field of bioluminescence in biology and/or medicine. In particular, the invention provides imidazopyrazine derivatives, processes for preparation thereof, and their uses as luciferins.

BACKGROUND

In the recent past, bioluminescent reporting systems, made out of an expressed luciferase/photoprotein and a luciferin, have become important tools in many research domains such as biological and biochemical studies, whole cell or animal imaging, diagnostics as well as in many types of screenings for potential biological activities of small molecules. Few types of luciferases have been used as bioluminescent reporters for such assays. The relatively big firefly luciferases (i.e. 65 kDa) which requires a luciferin, oxygen as well as ATP were initially adapted and, later on, smaller (i.e. 19-35 kDa) luciferases from marine origin were often found more appropriate since they are ATP-independent and smaller. Many kind of calcium-binding photoproteins and luciferases found in a very diverse set of marine creatures are actually using luciferins featuring an imidazo [1,2-a]pyrazin-3(7H)-one ring system. Coelenterazine (1) is the natural substrate of the Cnidaria *Aequorea, Mitrocoma, Obelia*, and *Periphylla* photoproteins, or the hydroid *Clytia* photoprotein. Moreover, it is also the natural substrate of the luciferases of the sea pansy *Renilla*, the shrimp *Oplophorus*, and the planktonic copepods *Gaussia* and *Metridia*. Finally, the *Vargula* luciferin/vargulin (2) is the substrate of the luciferases of the ostracods *Conchoecia* and *Vargula* or the fish *Porichthys*.

(1)

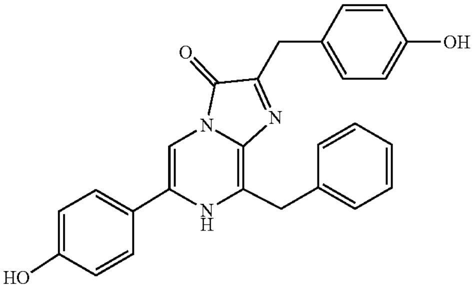

coelenterazine

-continued (2)

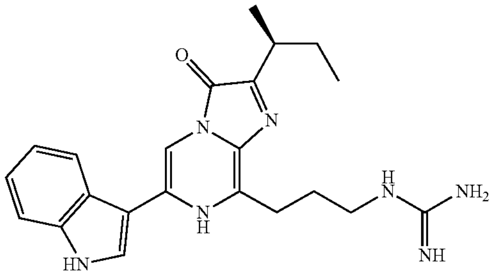

Vargula luciferin

Extensive researches have focused on the improvement of such bioluminescent systems. The use of luciferin analogues such as compounds 4-9 in combination with various forms of *Renilla* luciferases led to purple-shifted signals and/or more intense one.

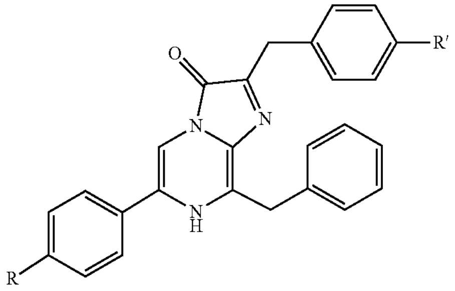

4: R = H, R′ = H
5: R = OH, R′ = H
6: R = OMe, R′ = OMe

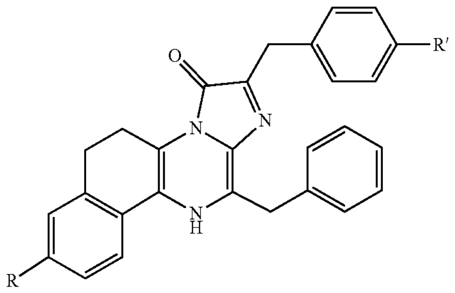

7: R = OMe, R′ = OMe
8: R = OMe, R′ = F
9: R = OH, R′ = OH

Another achievement came from the use of artificial luciferases made out of modified catalytic fragments of *Oplophorus* luciferase in combination with a variety of non-natural substrates. Strongly improved signals were thus obtained with furimazine (12).

12

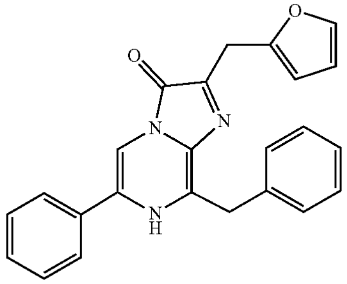

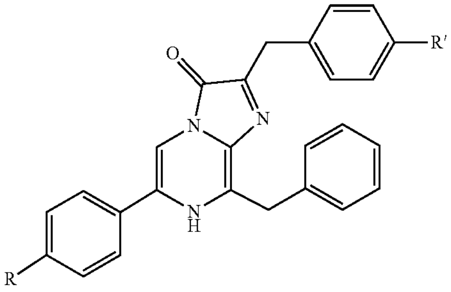

4 (bis-CTZ): R = H, R′ = H
13 (6h-f-CTZ): R = H, R′ = F
14 (h-CTZ): R = OH, R′ = H
15 (f-CTZ): R = OH, R′ = F

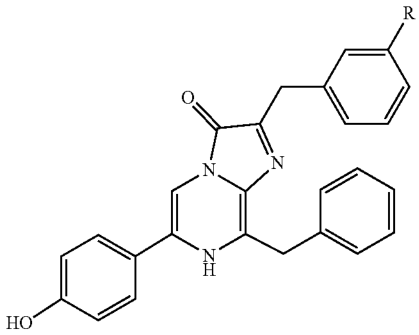

16 (3me-CTZ): R = Me
17 (3meo-CTZ): R = OMe
18 (3iso-CTZ): R = OH

With many of these artificial luciferin/luciferase systems, improvements were seen in the intensity of the bioluminescence signal as well as in its duration in comparison with the use of the corresponding wild type luciferases and their natural substrate coelenterazine (1).

However, there is a need of bioluminescent systems providing stronger signal (with higher signal to noise ratio) for longer time. Indeed, the use of such systems as reporters in high-throughput screenings requires a strong bioluminescence signal for at least 30 minutes to allow for delays inherent to robotic-based procedures. Moreover, the stronger the signal of a given assay, the more the miniaturization of this assay is possible, which is desirable when considering the cost involved in undertaking large high-throughput screenings campaigns. In whole-cell imaging, a high initial bioluminescent intensity as well as a high "bioluminescent signal" over "chemiluminescent noise" ratio is also desirable in many instances. For instance, such signal strength can enable the design of very diverse biological tools based on the use of a small luciferase (so far 19 kDa for the smallest), a luciferin, and a common microscope instead of the many tools based on the monitoring of a fluorescence signal, which requires the use of a fluorophore, such as the larger green fluorescent protein (27 kDa), and a microscope featuring a device to illuminate this fluorophore at a given wavelength in order to detect a signal at the emitting wavelength of the fluorophore.

Furthermore, the recommended storage conditions of these luciferins (in solution or as a dry powder) require the use of very low temperature (−80° C.) as solutions of such compounds have been reported to be very unstable overnight at room temperature (US 20140302539).

SUMMARY OF INVENTION

Accordingly, it is an object of the present invention to provide alternative to conventional luciferins, leading to substantially better bioluminescence signals in terms of intensity, signal-to-noise ratio, and/or duration.

Another aim of the present invention is to provide stable precursors of luciferins, storable in convenient conditions prior to their use.

Another aim of the present invention is to provide an easy, versatile and reliable method of deprotection of these stable precursors of luciferins. In particular, such an easy method of deprotection would not require to be conducted under inert gas.

Another aim of the present invention is to provide a versatile and reliable process of preparation of said luciferins and luciferin precursors, which give access to the unexplored chemical space surrounding these compounds, and/or enable kilo-scale preparation and purification.

Inventors have for the first time demonstrated that compounds of formula (I) can be easily deprotected by contacting them with a strong acid.

In addition, Inventors have for the first time demonstrated that a selection of imidazopyrazine derivatives yield excellent bioluminent signals.

In particular, Inventors have found that compounds of formula (III) are providing markedly improved bioluminescent signals, in terms of intensity, signal-to-noise ratio, and/or duration, in comparison with previously reported substrates such as furimazine (12).

Thus, in one aspect, the present invention relates to the use of a compound of following formula (I) in presence of a solution comprising a strong acid to detect, and/or measure the enzymatic activity of, a luminogenic protein, in vitro, in cellulo or ex vivo;

(I)

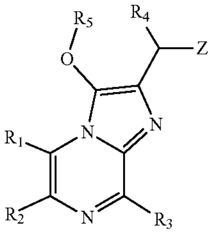

wherein:

$R_1$ represents H or a group selected from $C_3$-$C_6$ alkyl, $C_3$-$C_7$ cycloalkyl, $C_6$-$C_{10}$ aryl, aralkyl and $C_5$-$C_{10}$-membered heteroaryl groups, said $C_1$-$C_6$ alkyl, $C_3$-$C_7$ cycloalkyl, $C_6$-$C_{10}$ aryl, aralkyl and $C_5$-$C_{10}$-membered heteroaryl groups being optionally substituted by at least one $Y_1$ group;

$R_2$ represents a group selected from $C_6$-$C_{10}$ aryl and $C_5$-$C_{10}$-membered heteroaryl groups, said $C_6$-$C_{10}$ aryl and $C_5$-$C_{10}$-membered heteroaryl groups being optionally substituted by at least one $Y_2$ group;

or $R_1$ and $R_2$ together form with the two carbon atom to which they are respectively attached a $C_5$-$C_7$ cycloalkene group, a $C_4$-$C_7$ heterocycloalkene group, or a $C_1$-$C_{10}$ arene, said $C_5$-$C_7$ cycloalkene group and $C_4$-$C_7$ heterocycloalkene groups being fused with a $C_6$-$C_{10}$ arene, said $C_5$-$C_7$ cycloalkene group, $C_4$-$C_7$ heterocycloalkene group, $C_6$-$C_{10}$ arene, $C_5$-$C_7$ cycloalkene group and $C_4$-$C_7$ heterocycloalkene groups being optionally substituted by at least one $Y_{12}$ group;

$R_3$ represents H, a $C_1$-$C_6$ alkyl, an aralkyl group, a hetaralkyl group or a heterocycloalkyl-$CH_2$— group, said $C_1$-$C_6$ alkyl, aralkyl group, hetaralkyl group and heterocycloalkyl-$CH_2$— group being optionally substituted by at least one $Y_3$ group;

$R_4$ represents H or a group selected from $C_1$-$C_6$ alkyl and $C_3$-$C_7$ cycloalkyl groups, said $C_1$-$C_6$ alkyl and $C_3$-$C_7$ cycloalkyl groups being optionally substituted by at least one $Y_4$ group;

$R_5$ represents a —C(═O) $R_a$ group or a —C(O)O$R_a$ group, said C(═O)$R_a$ group and —C(═O)O$R_a$ group being optionally substituted by at least one $Y_3$ group;

$R_a$ represents H, a $C_1$-$C_6$ alkyl group, a $C_5$-$C_7$ cycloalkyl group, a $C_6$-$C_{10}$ aryl, or an aralkyl group, said $C_1$-$C_6$ alkyl group, $C_3$-$C_7$ cycloalkyl group, $C_6$-$C_{10}$ aryl, and aralkyl group being optionally substituted by at least one $Y_a$ group;

Z represents a $C_6$-$C_{10}$ aryl, a $C_5$-$C_{10}$-membered heteroaryl groups, a $C_1$-$C_6$ alkyl, a $C_1$-$C_7$ cycloalkyl, a $C_4$-$C_7$ heterocycloalkyl, Z being in particular selected from phenyl, furanyl, thiophenyl, pyridinyl, imidazolyl, oxazolyl, oxadiaxolyl, cyclopentyl, cyclohexyl, tetrahydrofuranyl and dioxolanyl, said $C_6$-$C_{10}$ aryl, $C_5$-$C_{10}$-membered heteroaryl groups, $C_1$-$C_6$ alkyl, $C_3$-$C_7$ cycloalkyl and $C_4$-$C_7$ heterocycloalkyl being optionally substituted by at least one $Y_Z$ group;

said $Y_1$, $Y_2$, $Y_{12}$, $Y_3$, $Y_4$, $Y_5$, $Y_a$ and $Y_Z$ groups being each independently selected from:

a $C_1$-$C_6$ alkyl;
a $C_3$-$C_7$ cycloalkyl;
a $C_6$-$C_{10}$ aryl;
a $C_5$-$C_{10}$-membered heteroaryl group;
an halogen, in particular —F;
a —$CF_3$ group;
a —CN group;
a —O$R_i$ group;
a —$OSO_3H$ group;
a —N$R_i$$R_{ii}$ group;
a guanidinyl group;
a —C(═O)O$R_a$ group, $R_a$ being as defined above;

$R_i$ and $R_{ii}$ each independently represent H, a $C_1$-$C_6$ alkyl group, a $C_3$-$C_{10}$ cycloalkyl group, an aralkyl group or an ad hoc protective group; or together form with the nitrogen atom to which they are attached a $C_4$-$C_7$ heterocycloalkyl group.

The presence of the strong acid enables the obtaining of the corresponding deprotected compound (after removal of the $R_5$ moiety), which is a luciferin, i.e. in the framework of the present invention an imidazopyrazinone capable of emitting photons under basic conditions and/or in the presence of a luminogenic protein, in particular an adequate enzyme called luciferase.

Said luciferin, that may be in presence of the strong acid, can be used diluted in a buffered media, e.g. comprising 2-(N-morpholino)ethanesulfonic acid (MES), tris(hydroxymethyl)aminomethane (TRIS), 4-(2-hydroxyethyl)-1-piperazineethanesulfonic acid (HEPES), and/or phosphate-buffered saline (PBS), preferably leading to a pH between 6 and 9, more preferably leading to a pH between 7 and 8, to detect, and/or measure the enzymatic activity of, a luminogenic protein, in vitro, in cellulo or ex vivo.

In a particular embodiment, the strong acid is hydrochloric acid.

In a particular embodiment, the solution comprising a strong acid is an ethanoic hydrochloric acid solution.

In a particular embodiment, the volume fraction of hydrochloric acid (37% in water) in said solution is 0.1 to 10%, in particular about 1%.

Once the deprotection performed, the corresponding deprotected compound in presence of the solution comprising the strong acid may be directly used in buffered media known by the skilled person in the art, with no need of a neutralization prior to said use in buffered media.

Hence, the compound of following formula (I) is in particular contacted with a strong acid prior to be used in a buffered media to detect, and/or measure the enzymatic activity of, a luminogenic protein, in vitro, in cellulo or ex vivo.

In other terms, the compound of following formula (I) can be used in presence of a solution comprising a strong acid (enabling deprotection of said compound of following formula (I)) to detect, and/or measure the enzymatic activity of, a luminogenic protein, in vitro, in cellulo or ex vivo, in particular after dilution of the deprotected compound in a buffered media (e.g. MES, TRIS, HEPES, PBS) preferably leading to a pH between 6 and 9, more preferably leading to a pH between 7 and 8.

In a particular embodiment, $R_1$ represents H.

In a particular embodiment, $R_4$ represents H.

In a particular embodiment, $R_5$ represents (C═O)Me.

In a particular embodiment, $R_3$ represents an aralkyl group or a hetaralkyl group, optionally substituted as defined above.

In a more particular embodiment, $R_3$ represents a benzyl, optionally substituted as defined above, in particular by at least one halogen, more particularly F.

In an even more particular embodiment, $R_3$ represents a benzyl, substituted by at least one halogen, more particularly F. In this case, $R_3$ may represent a benzyl, substituted by one halogen, more particularly F, or a benzyl, substituted by two halogen that are identical or different, more particularly F and/or Cl, the substitution being for example in 2,3; 2,5; 2,6 or 3,5.

For example, $R_3$ is selected from the group consisting of:

(3a)

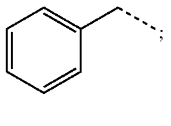

(3b)

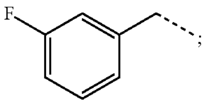

(3c)

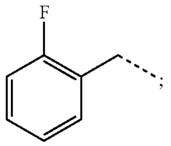

-continued (3d)
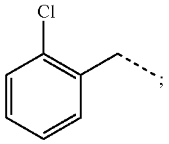

(3e)
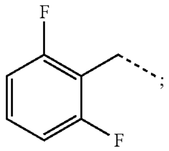

(3f)
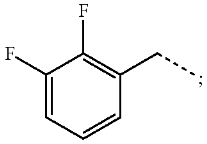

(3g)
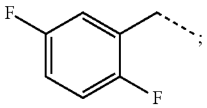

(3h)
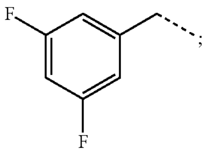

(3i)
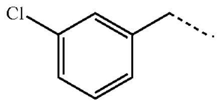

In a particular embodiment, $R_2$ represents a phenyl, optionally substituted as defined in above, $R_2$ representing in particular a phenyl optionally substituted by at least one group $Y_2$ selected from:

a $C_1$-$C_6$ alkyl, in particular a methyl;

an halogen, in particular F;

a —$OR_i$ group;

$R_i$ representing H, a $C_1$-$C_6$ alkyl group, a $C_3$-$C_{10}$ cycloalkyl group, an aralkyl group or an ad hoc protective group, $R_i$ representing in particular H, Me or Bn, $R_i$ representing more particularly H;

$R_2$ being more particularly selected from the group consisting of:

(2a)
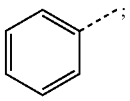

(2b)
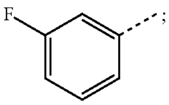

-continued (2c)
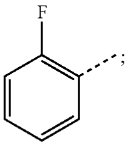

(2d)
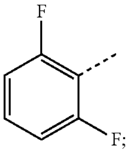

(2e)
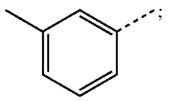

(2f)
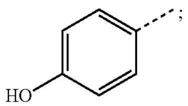

(2h)
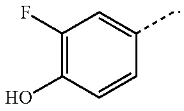

In a particular embodiment, Z is selected from phenyl, furanyl, thiophenyl, and is optionally substituted as defined in above.

Z representing in particular a phenyl, furanyl, or thiophenyl, optionally substituted by at least one $Y_Z$ group selected from:

a $C_1$-$C_6$ alkyl;

a $C_3$-$C_7$ cycloalkyl;

an halogen, in particular F or Cl;

a —$CF_3$ group;

a —$OR_i$ group, in particular a —OMe group;

Z being more particularly selected from the group consisting of:

(Za)
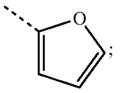

(Zb)
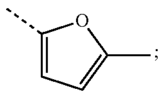

(Zc)
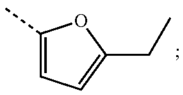

(Zd)
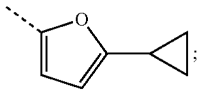

-continued (Ze)

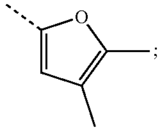

(Zf)

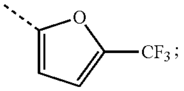

(Zg)

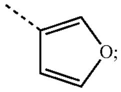

(Zh)

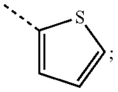

(Zi)

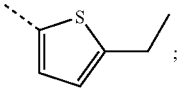

(Zj)

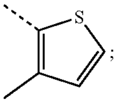

(Zk)

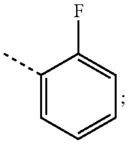

(Zl)

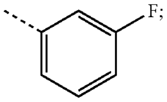

(Zm)

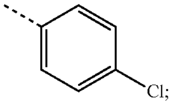

(Zn)

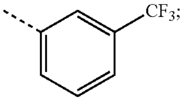

(Zo)

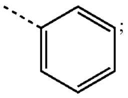

(Zp)

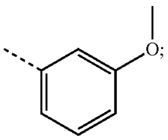

(Zq)

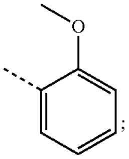

-continued (Zr)

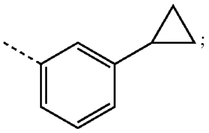

(Zs)

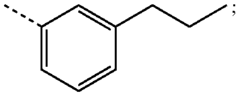

(Zt)

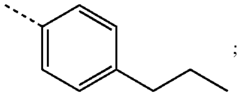

(Zu)

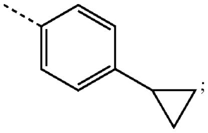

(Zv)

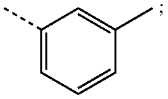

(Zw)

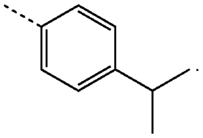

It is to be noted that the present invention includes the combination of all the embodiments listed hereabove for $R_1$, $R_2$, $R_3$, $R_4$ and/or Z.

In particular, $R_3$ represents a benzyl, optionally substituted by at least one halogen, more particularly F, and Z represents a furanyl, or thiophenyl, optionally substituted by at least one $Y_Z$ as defined above.

In a particular embodiment, the present invention relates to the use as defined above, of a compound of following formula (Ia):

(Ia)

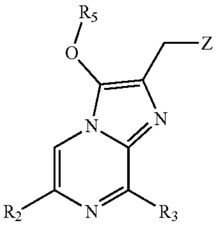

wherein:

$R_2$ is selected from the group consisting of:

(2a)

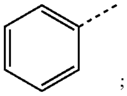

-continued
(2b)
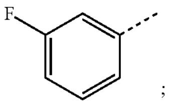
(2c)
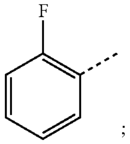
(2d)
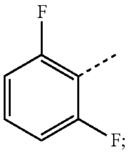
(2e)
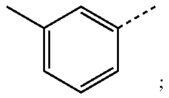
$R_3$ represents an aralkyl group, in particular a benzyl, optionally substituted as defined above, in particular by at least one halogen, more particularly F, or a hetaralkyl group;
$R_5$ is as defined above;
Z is selected from the group consisting of:
(Za)
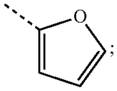
(Zb)
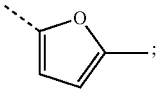
(Zc)
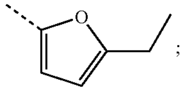
(Zd)
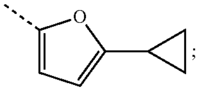
(Ze)
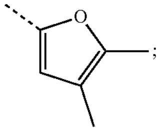
(Zf)
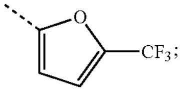
(Zg)
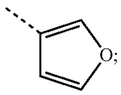
-continued
(Zh)
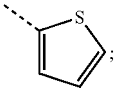
(Zi)
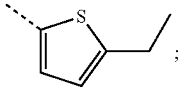
(Zj)
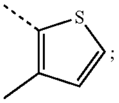
(Zk)
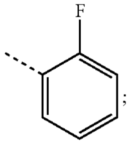
(Zl)
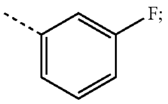
(Zm)
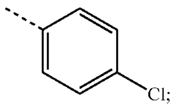
(Zn)
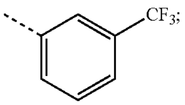
(Zo)
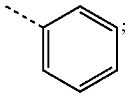
(Zp)
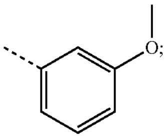
(Zq)
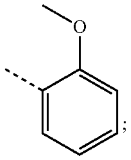
(Zr)
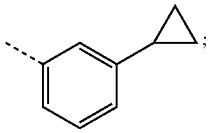
(Zs)
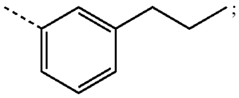

-continued (Zt)

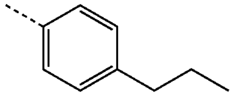

;

(Zu)

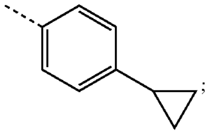

;

(Zv)

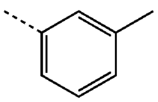

;

(Zw)

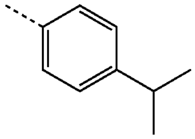

.

In a particular embodiment, the luminogenic protein is a luciferase derived from *Oplophorus* luciferase, more particularly the nanoKAZ luciferase.

In a particular embodiment, the present invention relates to the use as defined above, of a compound of following formula (IV) as defined below.

The present invention also relates to a compound of formula (I) as defined above for use, after contacting with a solution comprising a strong acid, in a method in vivo of detecting, and/or measuring the enzymatic activity of, a luminogenic protein.

The present invention also relates to the use of a compound of formula (I) as defined above for the implementation of a kit comprising said compound of formula (I) and a solution comprising a strong acid.

The present invention also relates to a kit comprising:

i) A compound of formula (I) as defined above; and ii) A solution comprising a strong acid.

In a particular embodiment, the compound of formula (I) and the solution comprising a strong acid are in separated containers.

In a particular embodiment, the kit as defined above further comprises a compound selected from the group consisting of a luminogenic protein, a polynucleotide encoding the luminogenic protein, a recombinant vector comprising the polynucleotide, and a transformant comprising the polynucleotide.

In a more particular embodiment of the invention, the luminogenic protein is chosen from the luciferases and photoproteins found in marine organisms such as Cnidaria *Aequorea, Mitrocoma, Obelia*, and *Periphylla*, hydroid *Clytia*; sea pansy *Renilla*, shrimp *Oplophorus*, planktonic copepods *Gaussia* and *Metridia*; ostracods *Conchoecia* and *Vargula*; the fish *Porichthys*; these luciferases and photoproteins being in particular collected from natural sources or produced by genetic engineering.

any mutant in which amino acid sequence is mutated from the natural sequence of the luciferases and photoproteins as defined above by gene recombination technology;

a domain that catalyzes luminescence of the native luciferases and photoproteins as defined above or its mutated proteins, in particular the 19 kDa protein of *Oplophorus* luciferase (GenBank accession BAB 13776, 196 amino acids) or its mutated proteins.

These luminogenic proteins and their mutated proteins can be produced by the methods well known from the skilled person in the art.

Alternatively, some of them may be commercially available from JNC Corporation (Cosmo Bio), Wako Pure Chemicals Industries, Promega Corporation, Prolume, etc.

In particular, the luminogenic protein corresponds to an optimized (in terms of sequence, production, stability as well as bioluminescence properties) luciferase catalytic domain (nanoKAZ, 19 kDa) from the *Oplophorus*-derived luciferase. This optimization can be performed by well-known techniques of the one skilled in the art.

In an even more particular embodiment, the luminogenic protein is an *Oplophorus* luciferase, in particular the nanoKAZ luciferase (NCBI GenBank reference: AB823628.1);

In particular, the present invention relates to a kit comprising:

i) A compound of formula (I) as defined above;

ii) A solution comprising a strong acid; and iii) A buffered media.

The present invention also relates to the kit as defined above, as an in vitro or ex vivo diagnostic tool.

The present invention also relates to a kit as defined above for use as an in vivo diagnostic tool.

The present invention also relates to a method for producing luminescence, which comprises contacting a compound of formula (I) with a solution comprising a strong acid to obtain a deprotected compound;

contacting said deprotected compound with a luminogenic protein, in particular an *Oplophorus* luciferase, more particularly the nanoKAZ luciferase.

The present invention also relates to a method for producing luminescence, which comprises contacting a compound of formula (I) with a solution comprising a strong acid to obtain a concentrated solution comprising a deprotected compound;

diluting said concentrated solution comprising a deprotected compound in a buffered media to obtain a diluted solution comprising said deprotected compound;

contacting said diluted solution comprising said deprotected compound with a luminogenic protein, in particular an *Oplophorus* luciferase, more particularly the nanoKAZ luciferase.

Said concentrated solution comprises the deprotected compound and in particular further comprises said strong acid.

The present invention also relates to a method of detecting luminescence in a sample comprising contacting a compound of formula (I) with a solution comprising a strong acid to obtain a deprotected compound;

contacting a sample with said deprotected compound;

optionally contacting the sample with a luminogenic protein, in particular an *Oplophorus* luciferase, more particularly the nanoKAZ luciferase, if not present in the sample; and detecting luminescence.

The present invention also relates to a method of detecting luminescence in a sample comprising contacting a compound of formula (I) with a solution comprising a strong acid to obtain a concentrated solution comprising a deprotected compound;

diluting said concentrated solution comprising a deprotected compound in a buffered media to obtain a diluted solution comprising said deprotected compound;

contacting a sample with said diluted solution comprising said deprotected compound;

optionally contacting the sample with a luminogenic protein, in particular an *Oplophorus* luciferase, more particularly the nanoKAZ luciferase, if not present in the sample; and detecting luminescence.

In a particular embodiment, the sample contains live cells.

In another particular embodiment, the sample contains a luminogenic protein, in particular an *Oplophorus* luciferase, more particularly the nanoKAZ luciferase.

The present invention also relates to a method for detecting luminescence in a transgenic animal expressing a luminogenic protein, comprising:

contacting a compound of formula (I) with a solution comprising a strong acid to obtain a deprotected compound;

administrating said deprotected compound to said animal; and detecting luminescence.

The present invention also relates to a method for detecting luminescence in a transgenic animal expressing a luminogenic protein or a animal hosting a transgenic organism expressing a luminogenic protein, comprising:

contacting a compound of formula (I) with a solution comprising a strong acid to obtain a concentrated solution comprising a deprotected compound;

diluting said concentrated solution comprising a deprotected compound in a buffered media to obtain a diluted solution comprising said deprotected compound;

administrating said diluted solution comprising said deprotected compound to said animal; and detecting luminescence. The present invention also relates to a method for assaying the activity of a sequence associated with promoter regulation, which comprises contacting a compound of formula (I) with a solution comprising a strong acid to obtain a deprotected compound;

using a polynucleotide encoding a luminogenic protein as a reporter gene and, as a luminescence substrate, a deprotected compound as defined above.

The present invention also relates to a method for assaying the activity of a sequence associated with promoter regulation, which comprises contacting a compound of formula (I) with a solution comprising a strong acid to obtain a concentrated solution comprising a deprotected compound;

diluting said concentrated solution comprising a deprotected compound in a buffered media to obtain a diluted solution comprising said deprotected compound;

using a polynucleotide encoding a luminogenic protein as a reporter gene and, as a luminescence substrate, a deprotected compound within the diluted solution as defined above. In the foregoing, the compound of formula (I) is in particular of formula (IV) or of formula (II) as defined below.

In the methods defined above, the compound of formula (I) is in particular, prior to use, within a kit as defined above. Hence, the methods as defined above reciting a compound of formula (I), a strong acid and optionally a buffered media can be understood as methods wherein the different parts of the above-mentioned kits are used.

The present invention also relates to a compound of following formula (II):

(II)

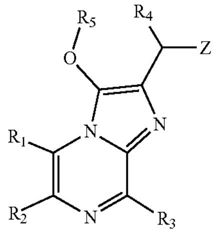

$R_1$ represents H or a group selected from $C_1$-$C_6$ alkyl, $C_3$-$C_7$ cycloalkyl, $C_6$-$C_{10}$ aryl, aralkyl and, $C_5$-$C_{10}$-membered heteroaryl groups, said $C_1$-$C_6$ alkyl, $C_3$-$C_7$ cycloalkyl, $C_6$-$C_{10}$ aryl, aralkyl and $C_5$-$C_{10}$-membered heteroaryl groups being optionally substituted by at least one $Y_1$ group;

$R_2$ represents a group selected from $C_6$-$C_{10}$ aryl and $C_5$-$C_{10}$-membered heteroaryl groups, said $C_6$-$C_{10}$ aryl and $C_5$-$C_{10}$-membered heteroaryl groups being optionally substituted by at least one $Y_2$ group;

or $R_1$ and $R_2$ together form with the two carbon atom to which they are respectively attached a $C_5$-$C_7$ cycloalkene group, a $C_4$-$C_7$ heterocycloalkene group, or a $C_5$-$C_{10}$ arene, said $C_5$-$C_7$ cycloalkene group and $C_4$-$C_7$ heterocycloalkene groups being fused with a $C_6$-$C_{10}$ arene, said $C_5$-$C_7$ cycloalkene group, $C_4$-$C_7$ heterocycloalkene group, $C_6$-$C_{10}$ arene, $C_5$-$C_7$ cycloalkene group and $C_4$-$C_7$ heterocycloalkene groups being optionally substituted by at least one $Y_{12}$ group;

$R_3$ represents H, a $C_1$-$C_6$ alkyl, an aralkyl group, a hetaralkyl group or a heterocycloalkyl-$CH_2$— group, said $C_1$-$C_6$ alkyl, aralkyl group, hetaralkyl group and heterocycloalkyl-$CH_2$— group being optionally substituted by at least one $Y_3$ group;

$R_4$ represents H or a group selected from $C_1$-$C_6$ alkyl and $C_3$-$C_7$ cycloalkyl groups, said $C_1$-$C_6$ alkyl and $C_3$-$C_7$ cycloalkyl groups being optionally substituted by at least one $Y_4$ group;

$R_5$ represents a —C(═O)$R_a$ group or a —C(═O)O$R_a$ group, said C(═O)$R_a$ group and —C(═O)O$R_a$ group being optionally substituted by at least one $Y_5$ group;

$R_a$ represents H, a $C_1$-$C_6$ alkyl group, a $C_3$-$C_7$ cycloalkyl group, a $C_5$-$C_{10}$ aryl, or an aralkyl group, said $C_1$-$C_6$ alkyl group, $C_3$-$C_7$ cycloalkyl group, $C_6$-$C_{10}$ aryl, and aralkyl group being optionally substituted by at least one $Y_a$ group;

Z represents a $C_6$-$C_{10}$ aryl, a $C_5$-$C_{10}$-membered heteroaryl groups, a $C_1$-$C_6$ alkyl, a $C_3$-$C_7$ cycloalkyl, a $C_4$-$C_7$ heterocycloalkyl, Z being in particular selected from phenyl, furanyl, thiophenyl, pyridinyl, imidazolyl, oxazolyl, oxadiazolyl, cyclopentyl, cyclohexyl, tetrahydrofuranyl and dioxolanyl, said $C_6$-$C_{10}$ aryl, $C_5$-$C_{10}$-membered heteroaryl groups, $C_1$-$C_6$ alkyl, $C_3$-$C_7$ cycloalkyl and $C_4$-$C_7$ heterocycloalkyl being optionally substituted by at least one $Y_Z$ group;

said $Y_1$, $Y_2$, $Y_{12}$, $Y_3$, $Y_4$, $Y_5$, $Y_a$ and $Y_Z$ groups being each independently selected from:

a $C_1$-$C_6$ alkyl;

a $C_3$-$C_7$ cycloalkyl;

a $C_6$-$C_{10}$ aryl;

a $C_5$-$C_{10}$-membered heteroaryl group;

an halogen, in particular —F;

a —$CF_3$ group;

a —CN group;

a —O$R_i$ group;

a —$OSO_3H$ group;
a —$NR_iR_{ii}$ group;
a guanidinyl group;
a —C(═O)$OR_a$ group, $R_a$ being as defined above;

$R_i$ and $R_{ii}$ each independently represent H, a $C_1$-$C_6$ alkyl group, a $C_3$-$C_{10}$ cycloalkyl group, an aralkyl group of an ad hoc protective group; or together form with the nitrogen atom to which they are attached a $C_4$-$C_7$ heterocycloalkyl group;

with the proviso that when $R_1$ and $R_4$ represent H, then:

$R_2$ is different from unsubstituted phenyl, and 4-hydroxy-phenyl optionally protected by an ad hoc protective group, or $R_3$ is different from unsubstituted benzyl, or Z is different from unsubstituted phenyl, 4-hydroxyphenyl, optionally protected by an ad hoc protective group, and from unsubstituted furan.

In a particular embodiment, the present invention relates to compounds with the general formula II and the following names:

8-benzyl-2-(furan-2-ylmethyl)-6-phenylimidazo[1,2-a]pyrazin-3-yl acetate
2,8-dibenzyl-6-phenylimidazo[1,2-a]pyrazin-3-yl acetate
8-benzyl-2-((5-methylfuran-2-yl)methyl)-6-phenylimidazo[1,2-a]pyrazin-3-yl acetate
8-benzyl-2-(furan-3-ylmethyl)-6-phenylimidazo[1,2-a]pyrazin-3-yl acetate
2-((1,3-dioxolan-2-yl)methyl)-8-benzyl-6-phenylimidazo[1,2-a]pyrazin-3-yl acetate
8-benzyl-2-(4-(benzyloxy)benzyl)-6-(4-(benzyloxy)phenyl)imidazo[1,2-a]pyrazin-3-yl acetate
2-benzyl-6-phenylimidazo[1,2-a]pyrazin-3-yl acetate
2-benzyl-8-methyl-6-phenylimidazo[1,2-a]pyrazin-3-yl acetate
8-benzyl-2-(furan-2-ylmethyl)-6-(2-methoxyphenyl)imidazo[1,2-a]pyrazin-3-yl acetate
8-benzyl-2-(furan-3-ylmethyl)-6-(2-methoxyphenyl)imidazo[1,2-a]pyrazin-3-yl acetate
2,8-dibenzyl-6-(2-methoxyphenyl)imidazo[1,2-a]pyrazin-3-yl acetate
8-benzyl-2-((5-ethylfuran-2-yl)methyl)-6-phenylimidazo[1,2-a]pyrazin-3-yl acetate
8-benzyl-6-phenyl-2-(thiophen-2-ylmethyl)imidazo[1,2-a]pyrazin-3-yl acetate
8-benzyl-2-(3-methylbenzyl)-6-phenylimidazo[1,2-a]pyrazin-3-yl acetate
8-benzyl-2-(4-fluorobenzyl)-6-phenylimidazo[1,2-a]pyrazin-3-yl acetate
8-benzyl-2-((4,5-dimethylfuran-2-yl)methyl)-6-phenylimidazo[1,2-a]pyrazin-3-yl acetate
8-benzyl-6-phenyl-2-(pyridin-2-ylmethyl)imidazo[1,2-a]pyrazin-3-yl acetate
8-benzyl-2-(3-methoxybenzyl)-6-phenylimidazo[1,2-a]pyrazin-3-yl acetate
8-benzyl-6-phenyl-2-((tetrahydrofuran-2-yl)methyl)imidazo[1,2-a]pyrazin-3-yl acetate
2,8-dibenzyl-6-(2-fluorophenyl)imidazo[1,2-a]pyrazin-3-yl acetate
8-benzyl-6-(2-fluorophenyl)-2-(furan-2-ylmethyl)imidazo[1,2-a]pyrazin-3-yl acetate
2-benzyl-6-phenyl-8-((tetrahydrofuran-2-yl)methyl)imidazo[1,2-a]pyrazin-3-yl acetate
2-(furan-2-ylmethyl)-6-phenyl-8-((tetrahydrofuran-2-yl)methyl)imidazo[1,2-a]pyrazin-3-yl acetate
4-(3-acetoxy-2-(4-acetoxybenzyl)-8-benzylimidazo[1,2-a]pyrazin-6-yl)phenyl acetate
2,12-dibenzyl-5H-chromeno[4,3-e]imidazo[1,2-a]pyrazin-3-yl acetate
8-benzyl-6-(2,6-difluorophenyl)-2-(furan-2-ylmethyl)imidazo[1,2-a]pyrazin-3-yl acetate
8-benzyl-6-phenyl-2-((5-(trifluoromethyl)furan-2-yl)methyl)imidazo[1,2-a]pyrazin-3-yl acetate
2,8-dibenzyl-6-(2,6-difluorophenyl)imidazo[1,2-a]pyrazin-3-yl acetate
8-benzyl-6-phenyl-2-(2-(trifluoromethyl)benzyl)imidazo[1,2-a]pyrazin-3-yl acetate
8-benzyl-6-phenyl-2-(3-(trifluoromethyl)benzyl)imidazo[1,2-a]pyrazin-3-yl acetate
8-benzyl-6-phenyl-2-(4-(trifluoromethyl)benzyl)imidazo[1,2-a]pyrazin-3-yl acetate
8-benzyl-6-(2-fluorophenyl)-2-((5-methylfuran-2-yl)methyl)imidazo[1,2-a]pyrazin-3-yl acetate
8-benzyl-6-(4-fluorophenyl)-2-((5-methylfuran-2-yl)methyl)imidazo[1,2-a]pyrazin-3-yl acetate
8-benzyl-2-((5-cyclopropylfuran-2-yl)methyl)-6-phenylimidazo[1,2-a]pyrazin-3-yl acetate
8-benzyl-6-(4-methoxyphenyl)-2-((5-methylfuran-2-yl)methyl)imidazo[1,2-a]pyrazin-3-yl acetate
8-benzyl-2-(4-isopropylbenzyl)-6-phenylimidazo[1,2-a]pyrazin-3-yl acetate
8-benzyl-6-phenyl-2-(3-propylbenzyl)imidazo[1,2-a]pyrazin-3-yl acetate
8-benzyl-2-(3-fluorobenzyl)-6-phenylimidazo[1,2-a]pyrazin-3-yl acetate
8-benzyl-2-(4-methoxybenzyl)-6-phenylimidazo[1,2-a]pyrazin-3-yl acetate
2-benzyl-6-phenyl-8-(pyridin-3-ylmethyl)imidazo[1,2-a]pyrazin-3-yl acetate
8-benzyl-6-phenyl-2-(4-propylbenzyl)imidazo[1,2-a]pyrazin-3-yl acetate
8-benzyl-2-((5-methylfuran-2-yl)methyl)-6-(p-tolyl)imidazo[1,2-a]pyrazin-3-yl acetate
8-benzyl-2-(4-bromobenzyl)-6-phenylimidazo[1,2-a]pyrazin-3-yl acetate
8-benzyl-2-(4-chlorobenzyl)-6-phenylimidazo[1,2-a]pyrazin-3-yl acetate
8-benzyl-2-((5-methylfuran-2-yl)methyl)-6-(m-tolyl)imidazo[1,2-a]pyrazine-3-yl acetate
8-benzyl-2-(4-cyclopropylbenzyl)-6-phenylimidazo[1,2-a]pyrazin-3-yl acetate
8-benzyl-2-(3-cyclopropylbenzyl)-6-phenylimidazo[1,2-a]pyrazin-3-yl acetate
8-benzyl-2-((5-ethylfuran-2-yl)methyl)-6-(2-fluorophenyl)imidazo[1,2-a]pyrazin-3-yl acetate
8-benzyl-6-(3-methoxyphenyl)-2-((5-methylfuran-2-yl)methyl)imidazo[1,2-a]pyrazin-3-yl acetate
8-benzyl-2-(4-fluorobenzyl)-6-(2-fluorophenyl)imidazo[1,2-a]pyrazin-3-yl acetate
8-benzyl-6-(3-fluorophenyl)-2-((5-methylfuran-2-yl)methyl)imidazo[1,2-a]pyrazin-3-yl acetate
8-benzyl-2-(4-methylbenzyl)-6-phenylimidazo[1,2-a]pyrazin-3-yl acetate
8-benzyl-2-(2-fluorobenzyl)-6-phenylimidazo[1,2-a]pyrazin-3-yl acetate
8-benzyl-2-(2-methoxybenzyl)-6-phenylimidazo[1,2-a]pyrazin-3-yl acetate
8-benzyl-2-((5-ethylthiophen-2-yl)methyl)-6-phenylimidazo[1,2-a]pyrazin-3-yl acetate
8-benzyl-2-(sec-butyl)-6-phenylimidazo[1,2-a]pyrazin-3-yl acetate
8-benzyl-2-((3-methylthiophen-2-yl)methyl)-6-phenylimidazo[1,2-a]pyrazin-3-yl acetate 8-benzyl-2-((4,5-dimethylfuran-2-yl)methyl)-6-(2-fluorophenyl)imidazo[1,2-a]pyrazin-3-yl acetate
8-benzyl-2-(2-methylbenzyl)-6-phenylimidazo[1,2-a]pyrazin-3-yl acetate
2-benzylimidazo[1,2-a]quinoxalin-1-yl acetate
2,4-dibenzylimidazo[1,2-a]quinoxalin-1-yl acetate
8-benzyl-6-phenyl-2-(1-phenylethyl)imidazo[1,2-a]pyrazin-3-yl acetate
8-benzyl-2-((4,5-dimethyloxazol-2-yl)methyl)-6-phenylimidazo[1,2-a]pyrazin-3-yl acetate
8-benzyl-2-(2,4-difluorobenzyl)-6-phenylimidazo[1,2-a]pyrazin-3-yl acetate
8-benzyl-2-(cyclohexylmethyl)-6-phenylimidazo[1,2-a]pyrazin-3-yl acetate
8-benzyl-2-(cyclopentylmethyl)-6-phenylimidazo[1,2-a]pyrazin-3-yl acetate
8-benzyl-2-((4,5-dimethylthiophen-2-yl)methyl)-6-phenylimidazo[1,2-a]pyrazin-3-yl acetate
8-benzyl-2-(bicyclo[2.2.1]heptan-2-ylmethyl)-6-phenylimidazo[1,2-a]pyrazin-3-yl acetate
2-benzyl-8-(2-fluorobenzyl)-6-phenylimidazo[1,2-a]pyrazin-3-yl acetate
2-benzyl-8-(3-fluorobenzyl)-6-phenylimidazo[1,2-a]pyrazin-3-yl acetate
2-benzyl-8-(4-fluorobenzyl)-6-phenylimidazo[1,2-a]pyrazin-3-yl acetate
2,8-dibenzyl-6-(4-hydroxyphenyl)imidazo[1,2-a]pyrazin-3-yl acetate
8-benzyl-6-(4-hydroxyphenyl)-2-(3-propylbenzyl)imidazo[1,2-a]pyrazin-3-yl acetate
2,8-dibenzyl-5-methyl-6-phenylimidazo[1,2-a]pyrazin-3-yl acetate
8-benzyl-2-((5-ethylfuran-2-yl)methyl)-6-(4-hydroxyphenyl)imidazo[1,2-a]pyrazin-3-yl acetate
8-benzyl-2-((4,5-dimethylfuran-2-yl)methyl)-6-(4-hydroxyphenyl)imidazo[1,2-a]pyrazin-3-yl acetate 20
8-benzyl-2-(furan-2-ylmethyl)-6-(4-hydroxyphenyl)imidazo[1,2-a]pyrazin-3-yl acetate
8-(3-fluorobenzyl)-2-(furan-2-ylmethyl)-6-phenylimidazo[1,2-a]pyrazin-3-yl acetate
8-(2-fluorobenzyl)-2-(3-methylbenzyl)-6-phenylimidazo[1,2-a]pyrazin-3-yl acetate
8-(2-fluorobenzyl)-2-(3-methoxybenzyl)-6-phenylimidazo[1,2-a]pyrazin-3-yl acetate
8-(2-fluorobenzyl)-2-(furan-2-ylmethyl)-6-phenylimidazo[1,2-a]pyrazin-3-yl acetate
8-(2-fluorobenzyl)-2-((5-methylfuran-2-yl)methyl)-6-phenylimidazo[1,2-a]pyrazin-3-yl acetate
8-benzyl-2-(4-hydroxybenzyl)-6-(4-hydroxyphenyl)imidazo[1,2-a]pyrazin-3-yl acetate
8-(2-chlorobenzyl)-2-(furan-2-ylmethyl)-6-phenylimidazo[1,2-a]pyrazin-3-yl acetate
2-benzyl-8-(2-chlorobenzyl)-6-phenylimidazo[1,2-a]pyrazin-3-yl acetate
2,8-dibenzyl-6-(3-fluoro-4-hydroxyphenyl)imidazo[1,2-a]pyrazin-3-yl acetate
2-benzyl-8-(2-methoxybenzyl)-6-phenylimidazo[1,2-a]pyrazin-3-yl acetate
8-benzyl-2-phenethyl-6-phenylimidazo[1,2-a]pyrazin-3-yl acetate
2-benzyl-8-(2-methylbenzyl)-6-phenylimidazo[1,2-a]pyrazin-3-yl acetate
2-(furan-2-ylmethyl)-8-(2-methylbenzyl)-6-phenylimidazo[1,2-a]pyrazin-3-yl acetate
2-benzyl-8-(3-methylbenzyl)-6-phenylimidazo[1,2-a]pyrazin-3-yl acetate 2-(furan-2-ylmethyl)-8-(3-methylbenzyl)-6-phenylimidazo[1,2-a]pyrazin-3-yl acetate
2-((5-ethylfuran-2-yl)methyl)-8-(2-fluorobenzyl)-6-phenylimidazo[1,2-a]pyrazin-3-yl acetate
8-(3-fluorobenzyl)-2-((5-methylfuran-2-yl)methyl)-6-phenylimidazo[1,2-a]pyrazin-3-yl acetate
8-(2-chlorobenzyl)-2-((5-methylfuran-2-yl)methyl)-6-phenylimidazo[1,2-a]pyrazin-3-yl acetate
2-((5-ethylfuran-2-yl)methyl)-8-(3-fluorobenzyl)-6-phenylimidazo[1,2-a]pyrazin-3-yl acetate
8-(3-fluorobenzyl)-2-(3-methylbenzyl)-6-phenylimidazo[1,2-a]pyrazin-3-yl acetate
8-(3-fluorobenzyl)-2-(3-methoxybenzyl)-6-phenylimidazo[1,2-a]pyrazin-3-yl acetate
8-(2,6-difluorobenzyl)-2-(furan-2-ylmethyl)-6-phenylimidazo[1,2-a]pyrazin-3-yl acetate
8-(3,5-difluorobenzyl)-2-(furan-2-ylmethyl)-6-phenylimidazo[1,2-a]pyrazin-3-yl acetate
8-(3-chlorobenzyl)-2-(furan-2-ylmethyl)-6-phenylimidazo[1,2-a]pyrazin-3-yl acetate
8-(3-fluorobenzyl)-6-(2-fluorophenyl)-2-((5-methylfuran-2-yl)methyl)imidazo[1,2-a]pyrazin-3-yl acetate
8-(3-fluorobenzyl)-2-(4-fluorobenzyl)-6-phenylimidazo[1,2-a]pyrazin-3-yl acetate
8-(2,3-difluorobenzyl)-2-(furan-2-ylmethyl)-6-phenylimidazo[1,2-a]pyrazin-3-yl acetate
8-(2,3-difluorobenzyl)-2-((5-methylfuran-2-yl)methyl)-6-phenylimidazo[1,2-a]pyrazin-3-yl acetate 20
8-(2,5-difluorobenzyl)-2-(furan-2-ylmethyl)-6-phenylimidazo[1,2-a]pyrazin-3-yl acetate
8-(2,5-difluorobenzyl)-2-((5-methylfuran-2-yl)methyl)-6-phenylimidazo[1,2-a]pyrazin-3-yl acetate
2,12-dibenzyl-6-fluorobenzo[f]imidazo[1,2-a]quinoxalin-3-yl acetate
12-benzyl-6-fluoro-2-(furan-2-ylmethyl)benzo[f]imidazo[1,2-a]quinoxalin-3-yl acetate
8-(3,5-difluorobenzyl)-2-((5-methylfuran-2-yl)methyl)-6-phenylimidazo[1,2-a]pyrazin-3-yl acetate
8-benzyl-2-((3-methylisoxazol-5-yl)methyl)-6-phenylimidazo[1,2-a]pyrazin-3-yl acetate
8-benzyl-2-((3-ethylisoxazol-5-yl)methyl)-6-phenylimidazo[1,2-a]pyrazin-3-yl acetate
2-benzyl-8-(2,3-difluorobenzyl)-6-phenylimidazo[1,2-a]pyrazin-3-yl acetate
2-benzyl-6-phenyl-8-(2-(trifluoromethyl)benzyl)imidazo[1,2-a]pyrazin-3-yl acetate
2-benzyl-6-phenyl-8-(3-(trifluoromethyl)benzyl)imidazo[1,2-a]pyrazin-3-yl acetate
2-benzyl-6-phenyl-8-(2,3,5-trifluorobenzyl)imidazo[1,2-a]pyrazin-3-yl acetate
8-(2,6-Difluorobenzyl)-2-((5-methylfuran-2-yl)methyl)-6-phenylimidazo[1,2-a]pyrazin-3-yl acetate
8-(2,5-Difluorobenzyl)-2-((4,5-dimethylfuran-2-yl)methyl)-6-phenylimidazo[1,2-a]pyrazin-3-yl acetate
8-(2,5-Difluorobenzyl)-2-((5-ethylfuran-2-yl)methyl)-6-phenylimidazo[1,2-a]pyrazin-3-yl acetate
8-(2,3-Difluorobenzyl)-2-((4,5-dimethylfuran-2-yl)methyl)-6-phenylimidazo[1,2-a]pyrazin-3-yl acetate
8-(3,5-Difluorobenzyl)-2-((4,5-dimethylfuran-2-yl)methyl)-6-phenylimidazo[1,2-a]pyrazin-3-yl acetate
2-(furan-2-ylmethyl)-6-phenyl-8-(2,3,5-trifluorobenzyl)imidazo[1,2-a]pyrazin-3-yl acetate
8-(2,3-Difluorobenzyl)-2-((5-ethylfuran-2-yl)methyl)-6-phenylimidazo[1,2-a]pyrazin-3-yl acetate
8-(3,5-Difluorobenzyl)-2-((5-ethylfuran-2-yl)methyl)-6-phenylimidazo[1,2-a]pyrazin-3-yl acetate 8-(2,6-Difluorobenzyl)-2-((5-ethylfuran-2-yl)methyl)-6-phenylimidazo[1,2-a]pyrazin-3-yl acetate
8-(2,6-Difluorobenzyl)-2-((4,5-dimethylfuran-2-yl)methyl)-6-phenylimidazo[1,2-a]pyrazin-3-yl acetate
2-((4,5-Dimethylfuran-2-yl)methyl)-8-(2-fluorobenzyl)-6-phenylimidazo[1,2-a]pyrazin-3-yl acetate
2-((4,5-Dimethylfuran-2-yl)methyl)-8-(3-fluorobenzyl)-6-phenylimidazo[1,2-a]pyrazin-3-yl acetate
8-Benzyl-6-phenyl-2-((5-propylfuran-2-yl)methyl)imidazo[1,2-a]pyrazin-3-yl acetate
8-benzyl-6-phenyl-2-((4,5,6,7-tetrahydrobenzofuran-2-yl)methyl)imidazo[1,2-a]pyrazin-3-yl acetate
8-(2,3-difluorobenzyl)-2-((4-ethyl-5-methylfuran-2-yl)methyl)-6-phenylimidazo[1,2-a]pyrazin-3-yl acetate
8-benzyl-2-((4-ethyl-5-methylfuran-2-yl)methyl)-6-phenylimidazo[1,2-a]pyrazin-3-yl acetate
8-(2,3-difluorobenzyl)-6-phenyl-2-((4,5,6,7-tetrahydrobenzofuran-2-yl)methyl)imidazo[1,2-a]pyrazin-3-yl acetate
8-benzyl-2-((5-isopropyl-4-methylfuran-2-yl)methyl)-6-phenylimidazo[1,2-a]pyrazin-3-yl acetate
8-benzyl-2-((5-ethyl-4-methylfuran-2-yl)methyl)-6-phenylimidazo[1,2-a]pyrazin-3-yl acetate
8-(2,3-difluorobenzyl)-2-((5-ethyl-4-methylfuran-2-yl)methyl)-6-phenylimidazo[1,2-a]pyrazin-3-yl acetate
8-benzyl-2-(1-(furan-2-yl)ethyl)-6-phenylimidazo[1,2-a]pyrazin-3-yl acetate
8-(3-fluorobenzyl)-2-(4-hydroxybenzyl)-6-(4-hydroxyphenyl)imidazo[1,2-a]pyrazin-3-yl acetate
8-(2-fluorobenzyl)-2-(4-hydroxybenzyl)-6-(4-hydroxyphenyl)imidazo[1,2-a]pyrazin-3-yl acetate
8-(2,3-difluorobenzyl)-2-((5-isopropyl-4-methylfuran-2-yl)methyl)-6-phenylimidazo[1,2-a]pyrazin-3-yl acetate
8-benzyl-2-(furan-2-ylmethyl)-6-(3-hydroxyphenyl)imidazo[1,2-a]pyrazin-3-yl acetate
8-benzyl-2-(4-hydroxybenzyl)-6-(3-hydroxyphenyl)imidazo[1,2-a]pyrazin-3-yl acetate.

The present invention also relates to a compound of following formula (III):

(III)

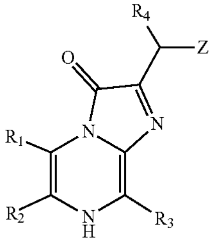

wherein:

$R_1$ represents H or a group selected from $C_1$-$C_6$ alkyl, $C_3$-$C_7$ cycloalkyl, $C_6$-$C_{10}$ aryl, aralkyl and $C_5$-$C_{10}$-membered heteroaryl groups, said $C_1$-$C_6$ alkyl, $C_3$-$C_7$ cycloalkyl, $C_6$-$C_{10}$ aryl, aralkyl and $C_5$-$C_{10}$-membered heteroaryl groups being optionally substituted by at least one $Y_2$ group;

$R_3$ represents a group selected from $C_6$-$C_{10}$ aryl and $C_5$-$C_{10}$-membered heteroaryl groups, said $C_6$-$C_{10}$ aryl and $C_5$-$C_{10}$-membered heteroaryl groups being optionally substituted by at least one $Y_2$ group;

$R_3$ represents an aralkyl group, said aralkyl group being optionally substituted by at least one $Y_3$ group;

$R_4$ represents H or a group selected from $C_1$-$C_6$ alkyl and $C_3$-$C_7$ cycloalkyl groups, said $C_1$-$C_6$ alkyl and $C_3$-$C_7$ cycloalkyl groups being optionally substituted by at least one Y group;

Z represents a group of following formula:

(Z1)

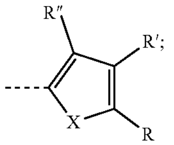

(Z2)

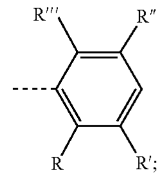

or an oxazolyl, or an oxadiazolyl;

R, R', R'' and R''' each independently represent H or a group selected from:
- a $C_1$-$C_6$ alkyl group;
- a $C_3$-$C_7$ cycloalkyl group;
- an halogen;
- a —$OR_i$ group;
- a —$CF_3$ group;

X represents O or S;

said $Y_1$, $Y_2$, $Y_3$ and $Y_4$, groups being each independently selected from:
- a $C_1$-$C_6$ alkyl group;
- a $C_3$-$C_7$ cycloalkyl group;
- an halogen;
- a —$OR_{ii}$ group;

$R_i$ and $R_{ii}$ each independently represent H, a $C_1$-$C_6$ alkyl group, a $C_3$-$C_{10}$ cycloalkyl group or an aralkyl group;

provided that:

when Z═Z1:

at least one of R, R' and R'' does not represent H; or when R, R' and R'' represent H, then $R_2$ represents a group selected from $C_6$-$C_{10}$ aryl and $C_5$-$C_{10}$-membered heteroaryl groups substituted by at least an halogen group, in particular —F, $R_2$ representing in particular a 2-F-phenyl, a 3-F-phenyl, or a 2,6-diF-phenyl group; or $R_3$ represents a group selected from $C_6$-$C_{10}$ aralkyl groups substituted by at least an halogen group, in particular —F;

when Z═Z2:

at least one of R, R', R' and R''' does not represent H; or when R, R', R'' and R''' represent H; then $R_2$ represents a group selected from $C_6$-$C_{10}$ aryl and $C_5$-$C_{10}$-membered heteroaryl groups substituted by at least a halogen group, in particular —F, $R_2$ representing in particular 2-F-phenyl, a 3-F-phenyl, or a 2,6-diF-phenyl group; or $R_3$ represents a group selected from $C_6$-$C_{10}$ aralkyl groups substituted by at least an halogen group, in particular —F; or when R, R' and R''' represent H and R'' represents a $C_1$-$C_6$ alkyl group or a —$OR_i$ group; then $R_2$ does not represent a 4-HO-Ph- group, $R_2$ representing in particular a phenyl group or a group selected from $C_6$-$C_{10}$ aryl and $C_5$-$C_{10}$-membered heteroaryl groups substituted by at least a halogen group, in particular —F, $R_2$ representing more particularly a 2-F-phenyl, a 3-F-phenyl, or a 2,6-diF-phenyl group; or $R_3$ represents a group selected from $C_6$-$C_{10}$ aralkyl groups substituted by at least an halogen group, in particular —F.

In a particular embodiment, the present invention relates to a compound of formula (III) as defined above, wherein:

Z represents a group Z2 and $R_3$ represents an aralkyl group, said aralkyl group being substituted by at least one $Y_3$ group, provided that:

at least one of R, R', R' and R''' does not represent H; or when R, R', R'' and R''' represent H; then $R_2$ represents a group selected from $C_6$-$C_{10}$ aryl and $C_5$-$C_{10}$-membered heteroaryl groups substituted by at least a halogen group, in particular —F, $R_2$ representing in particular 2-F-phenyl, a 3-F-phenyl, or a 2,6-diF-phenyl group; of $R_3$ represents a group selected from $C_6$-$C_{10}$ aralkyl groups substituted by at least a —F group; or when R, R' and R''' represent H and R'' represents a $C_1$-$C_6$ alkyl group or a —$OR_i$ group; then $R_2$ does not represent a 4-HO-Ph- group, $R_2$ representing in particular a phenyl group or a group selected from $C_6$-$C_{10}$ aryl and $C_5$-$C_{10}$-membered heteroaryl groups substituted by at least a halogen group, in particular —F, $R_2$ representing more particularly a 2-F-phenyl, a 3-F-phenyl, or a 2,6-diF-phenyl group; or $R_3$ represents a group selected from $C_6$-$C_{10}$ aralkyl groups substituted by at least an halogen group, in particular —F;

or

Z represents a group of following formula:

(Z1)

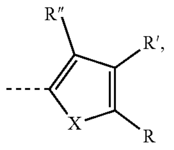

R and R' being in particular different from H.

In a more particular embodiment, the present invention relates to a compound of formula (III) as defined above, wherein:

Z represents a group Z2 and $R_3$ represents an aralkyl group, said aralkyl group being substituted by at least one —F group, or Z represents a group Z1, R and R' being in particular different from H.

In a particular embodiment, the present invention relates to a compound of formula (III) as defined above, wherein:

$R_3$ represents an aralkyl group, said aralkyl group being substituted by at least one $Y_3$ group, provided that when Z═Z2:

at least one of R, R', R'' and R''' does not represent H; or when R, R', R'' and R''' represent H; then $R_2$ represents a group selected from $C_6$-$C_{10}$ aryl and $C_5$-$C_{10}$-membered heteroaryl groups substituted by at least a halogen group, in particular —F, $R_2$ representing in particular 2-F-phenyl, a 3-F-phenyl, or a 2,6-diF-phenyl group; or $R_3$ represents a group selected from $C_6$-$C_{10}$ aralkyl groups substituted by at least a —F group; or when R, R' and R''' represent H and R'' represents a $C_1$-$C_6$ alkyl group or a —$OR_i$ group; then $R_2$ does not represent a 4-HO-Ph- group, $R_2$ representing in particular a phenyl group or a group selected from $C_6$-$C_{10}$ aryl and $C_5$-$C_{10}$-membered heteroaryl groups substituted by at least a halogen group, in particular —F, $R_2$ representing more particularly a 2-F-phenyl, a 3-F-phenyl, or a 2,6-diF-phenyl group; or $R_3$ represents a group selected from $C_6$-$C_{10}$ aralkyl groups substituted by at least an halogen group, in particular —F;

or $R_2$ represents a group selected from $C_6$-$C_{10}$ aryl and $C_5$-$C_{10}$-membered heteroaryl groups, said $C_6$-$C_{10}$ aryl and $C_5$-$C_{10}$-membered heteroaryl groups being optionally substituted by at least one $Y_2$ group;

or

Z represents a group Z1, R and R' being in particular different from H.

In a particular embodiment, $R_1$ represents H.

In a particular embodiment, $R_4$ represents H.

In a particular embodiment, $R_3$ represents a benzyl group, optionally substituted as defined above, in particular by at least one halogen, more particularly F.

In an even more particular embodiment, $R_3$ represents a benzyl, substituted by at least one halogen, more particularly F. In this case, $R_3$ may represent a benzyl, substituted one halogen, more particularly F, or a benzyl, substituted by two halogen that are identical or different, more particularly F and/or Cl, the substitution being for example in 2,3; 2,5; 2,6 or 3,5.

For example, $R_3$ is selected from the group consisting of:

(3a)

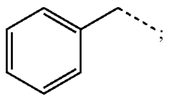

(3b)

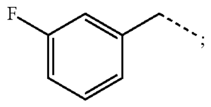

(3c)

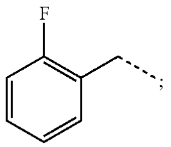

(3d)

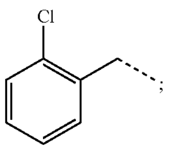

(3e)

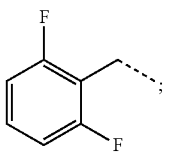

-continued (3f)

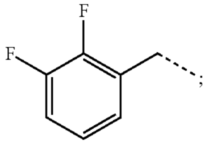

(3g)

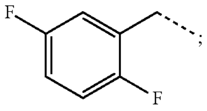

(3h)

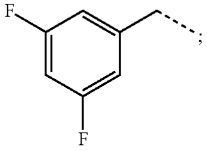

(3i)

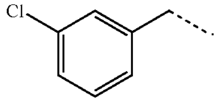

In a particular embodiment, $R_2$ represents a phenyl, optionally substituted as defined above, $R_2$ representing in particular a phenyl optionally substituted by at least a halogen, in particular F;

$R_2$ being more particularly selected from the group consisting of (2a)

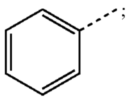

(2b)

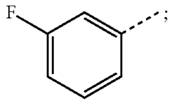

(2c)

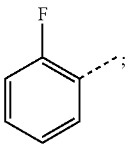

(2d)

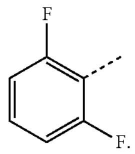

In a particular embodiment, Z is selected from Z1 and Z2,

R, R', R''' and R'''' each independently representing in particular H or a group selected from:

a $C_1$-$C_6$ alkyl group;

a $C_3$-$C_7$ cycloalkyl group;

an halogen;

a —$OR_i$ group;

a —$CF_3$ group;

Z being more particularly selected from the group consisting of;

(Za)

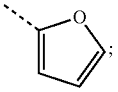

(Zb)

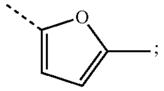

(Zc)

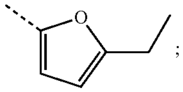

(Zd)

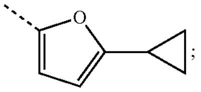

(Ze)

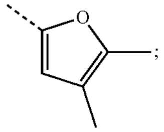

(Zf)

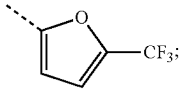

(Zh)

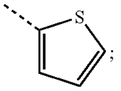

(Zi)

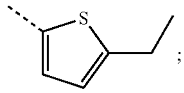

(Zk)

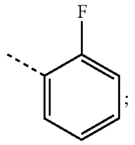

(Zl)

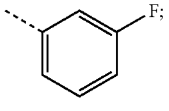

(Zo)

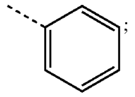

(Zp)

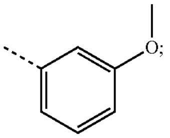

(Zv)

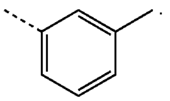

It is to be noted that the present invention includes the combination of all the embodiments listed hereabove for $R_1$, $R_2$, $R_3$, $R_4$ and/or Z.

In particular, $R_3$ represents a benzyl, optionally substituted by at least one halogen, more particularly F, and Z represents a furanyl, or thiophenyl, optionally substituted by at least one $Y_Z$ as defined above.

In a particular embodiment, the compound of formula (III) is a compound of following formula (IIIa):

(IIIa)

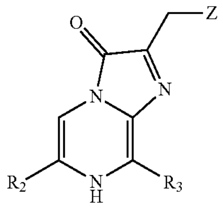

wherein:

$R_2$ being in particular selected from the group consisting of:

(2a)

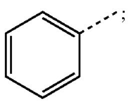

(2b)

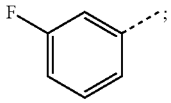

(2c)

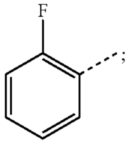

(2d)

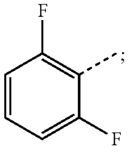

$R_3$ being in particular selected from the group consisting of:

(3a)

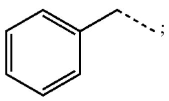

(3b)

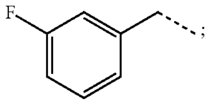

(3c)

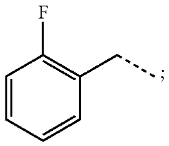

-continued (3d)

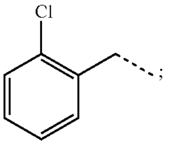

(3e)

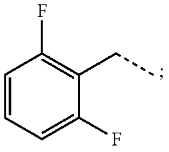

(3f)

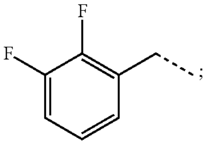

(3g)

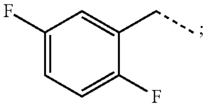

(3h)

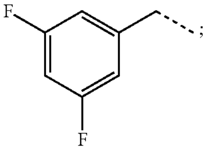

(3i)

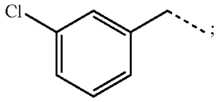

Z is selected from the group consisting of:

(Za)

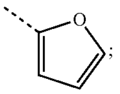

(Zb)

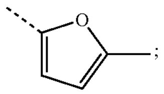

(Zc)

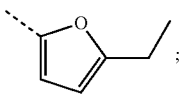

(Zd)

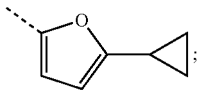

(Ze)

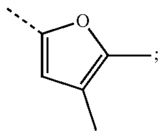

(Zf)

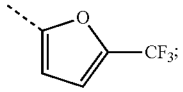

-continued (Zh)

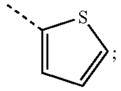

(Zi)

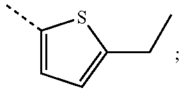

(Zk)

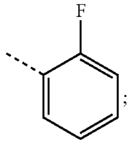

(Zl)

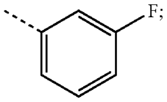

(Zo)

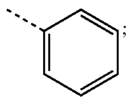

(Zp)

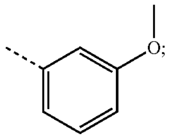

(Zv)

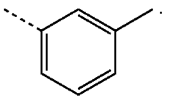

In a particular embodiment, the present invention relates to compounds with the general formula IIIa and the following names:

8-benzyl-2-((5-methylfuran-2-yl)methyl)-6-phenylimidazo [1,2-a]pyrazin-3(7H)-one 8-benzyl-2-((5-ethylfuran-2-yl)methyl)-6-phenylimidazo[1, 2-a]pyrazin-3(7H)-one 8-benzyl-2-((4,5-dimethylfuran-2-yl)methyl)-6-phenylimidazo[1,2-a]pyrazin-3(7H)-one 8-benzyl-6-(2-fluorophenyl)-2-(furan-2-ylmethyl)imidazo [1,2-a]pyrazin-3(7H)-one 8-benzyl-2-(3-methylbenzyl)-6-phenylimidazo[1,2-a] pyrazin-3(7H)-one 8-benzyl-2-(3-methoxybenzyl)-6-phenylimidazo[1,2-a] pyrazin-3(7H)-one 2,8-dibenzyl-6-(2-fluorophenyl)imidazo[1,2-a]pyrazin-3 (7H)-one 8-benzyl-6-(2,6-difluorophenyl)-2-(furan-2-ylmethyl)imidazo[1,2-a]pyrazin-3(7H)-one 8-benzyl-6-phenyl-2-((5-(trifluoromethyl)furan-2-yl) methyl)imidazo[1,2-a]pyrazin-3(7H)-one 2,8-dibenzyl-6-(2,6-difluorophenyl)imidazo[1,2-a]pyrazin-3(7H)-one 8-benzyl-6-(2-fluorophenyl)-2-((5-methylfuran-2-yl) methyl)imidazo[1,2-a]pyrazin-3(7H)-one 8-benzyl-2-((5-cyclopropylfuran-2-yl)methyl)-6-phenylimidazo[1,2-a]pyrazin-3(7H)-one 8-benzyl-2-(3-fluorobenzyl)-6-phenylimidazo[1,2-]pyrazin-3(7H)-one 8-benzyl-2-((5-ethylfuran-2-yl)methyl)-6-(2-fluorophenyl) imidazo[1,2-a]pyrazin-3(7H)-one 8-benzyl-6-(3-fluorophenyl)-2-((5-methylfuran-2-yl) methyl)imidazo[1,2-a]pyrazin-3(7H)-one 8-benzyl-2-(2-fluorobenzyl)-6-phenylimidazo[1,2-a] pyrazin-3(7H)-one 8-benzyl-2-((5-ethylthiophen-2-yl)methyl)-6-phenylimidazo[1,2-a]pyrazin-3(7H)-one 8-benzyl-2-((4,5-dimethylfuran-2-yl)methyl)-6-(2-fluorophenyl)imidazo[1,2-a]pyrazin-3(7H)-one 2-benzyl-8-(2-fluorobenzyl)-6-phenylimidazo[1,2-a] pyrazin-3(7H)-one 2-benzyl-8-(3-fluorobenzyl)-6-phenylimidazo[1,2-a] pyrazin-3(7H)-one 8-(3-fluorobenzyl)-2-(furan-2-ylmethyl)-6-phenylimidazo [1,2-a]pyrazin-3(7H)-one 8-(2-fluorobenzyl)-2-(3-methylbenzyl)-6-phenylimidazo[1, 2-a]pyrazin-3(7H)-one 8-(2-fluorobenzyl)-2-(3-methoxybenzyl)-6-phenylimidazo [1,2-a]pyrazin-3(7H)-one 8-(2-fluorobenzyl)-2-(furan-2-ylmethyl)-6-phenylimidazo [1,2-a]pyrazin-3(7H)-one 8-(2-fluorobenzyl)-2-((5-methylfuran-2-yl)methyl)-6-phenylimidazo[1,2-a]pyrazin-3(7H)-one 8-(3-fluorobenzyl)-2-(3-methoxybenzyl)-6-phenylimidazo [1,2-a]pyrazin-3(7H)-one 8-(3-fluorobenzyl)-2-(3-methylbenzyl)-6-phenylimidazo[1, 2-a]pyrazin-3(7H)-one 2-((5-ethylfuran-2-yl)methyl)-8-(3-fluorobenzyl)-6-phenylimidazo[1,2-a]pyrazin-3(7H)-one 8-(2-chlorobenzyl)-2-((5-methylfuran-2-yl)methyl)-6-phenylimidazo[1,2-a]pyrazin-3(7H)-one 8-(3-fluorobenzyl)-2-((5-methylfuran-2-yl)methyl)-6-phenylimidazo[1,2-a]pyrazin-3(7H)-one 2-((5-ethylfuran-2-yl)methyl)-8-(2-fluorobenzyl)-6-phenylimidazo[1,2-a]pyrazin-3(7H)-one 8-(3-fluorobenzyl)-6-(2-fluorophenyl)-2-((5-methylfuran-2-yl)methyl)imidazo[1,2-a]pyrazin-3(7H)-one 8-(2,3-difluorobenzyl)-2-(furan-2-ylmethyl)-6-phenylimidazo[1,2-a]pyrazin-3(7H)-one 8-(2,3-difluorobenzyl)-2-((5-methylfuran-2-yl)methyl)-6-phenylimidazo[1,2-a]pyrazin-3(7H)-one 2-benzyl-8-(2,3-difluorobenzyl)-6-phenylimidazo[1,2-a] pyrazin-3(7H)-one 8-(2,6-Difluorobenzyl)-2-((5-methylfuran-2-yl)methyl)-6-phenylimidazo[1,2-a]pyrazin-3(7H)-one 8-(2,3-Difluorobenzyl)-2-((4,5-dimethylfuran-2-yl)methyl)-6-phenylimidazo[1,2-a]pyrazin-3(7H)-one 8-(2,3-Difluorobenzyl)-2-((5-ethylfuran-2-yl)methyl)-6-phenylimidazo[1,2-a]pyrazin-3(7H)-one 8-(2,6-Difluorobenzyl)-2-((5-ethylfuran-2-yl)methyl)-6-phenylimidazo[1,2-a]pyrazin-3(7H)-one 2-((4,5-Dimethylfuran-2-yl)methyl)-8-(2-fluorobenzyl)-6-phenylimidazo[1,2-a]pyrazin-3(7H)-one 2-((4,5-Dimethylfuran-2-yl)methyl)-8-(3-fluorobenzyl)-6-phenylimidazo[1,2-a]pyrazin-3(7H)-one 8-(2,3-difluorobenzyl)-2-((4-ethyl-5-methylfuran-2-yl) methyl)-6-phenylimidazo[1,2-a]pyrazin-3(7H)-one 8-(2,3-difluorobenzyl)-2-((5-ethyl-4-methylfuran-2-yl) methyl)-6-phenylimidazo[1,2-a]pyrazin-3(7H)-one 8-benzyl-2-(furan-2-ylmethyl)-6-(3-hydroxyphenyl)imidazo[1,2-a]pyrazin-3(7H)-one.

The present invention also relates to the use of a compound of formula (III) or (IIIa) as defined above as an in vitro or ex vivo diagnostic tool.

The present invention also relates to a compound of formula (III) or (IIIa) as defined above for use as an in vivo diagnostic tool.

The present invention also relates to a method for producing luminescence, which comprises contacting a compound of formula (III) or (IIIa) as defined above with a luminogenic protein, in particular an *Oplophorus* luciferase, more particularly the nanoKAZ luciferase.

The present invention also relates to a method of detecting luminescence in a sample comprising contacting a sample with a compound of formula (III) or (IIIa) as defined above;

optionally contacting the sample with a luminogenic protein, in particular an *Oplophorus* luciferase, more particularly the nanoKAZ luciferase, if not present in the sample; and detecting luminescence.

In a particular embodiment, the sample contains live cells.

In another particular embodiment, the sample contains a luminogenic protein, in particular an *Oplophorus* luciferase, more particularly the nanoKAZ luciferase.

The present invention also relates to a method for detecting luminescence in a transgenic animal expressing a luminogenic protein, comprising:

administrating a compound of formula (III) or (IIIa) as defined above to said animal; and detecting luminescence.

The present invention also relates to a method for assaying the activity of a sequence associated with promoter regulation, which comprises using a polynucleotide encoding a luminogenic protein as a reporter gene and, as a luminescence substrate, a compound of formula (III) or (IIIa) as defined above.

In another aspect, the present invention relates to a compound of following formula (IV):

(IV)

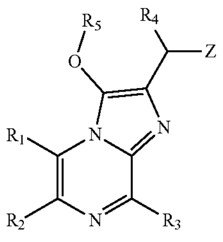

wherein:

$R_1$, $R_2$, $R_3$, $R_4$ and Z are as defined for formula (III) or (IIIa).

$R_5$ is as defined above.

It is to be noted that the present invention includes the combination of all the embodiments listed hereabove for formula (III) and/or (IIIa).

In another aspect, the present invention relates to a compound of following formula (V):

(V)

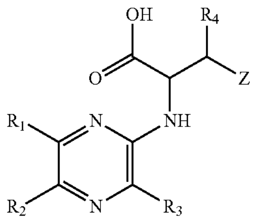

wherein $R_1$, $R_2$, $R_3$, $R_4$ and Z are as defined for formula (III) or (IIIa).

It is to be noted that the present invention includes the combination of all the embodiments listed hereabove for formula (III) and/or (IIIa).

In another aspect, the present invention relates to a compound of following formula (VI)

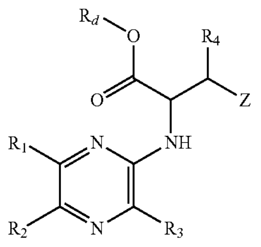

wherein:

$R_1$, $R_2$, $R_3$, $R_4$ and Z are as defined for formula (III) or (IIIa);

$R_d$ represents a group selected from $C_1$-$C_6$ alkyl, $C_3$-$C_7$ cycloalkyl and aralkyl, in particular, methyl, ethyl, or benzyl.

It is to be noted that the present invention includes the combination of all the embodiments listed hereabove for formula (III) and/or (IIIa).

In a particular embodiment, the present invention relates to compounds with the general formula (IV) and the following names:

8-benzyl-2-((5-methylfuran-2-yl)methyl)-6-phenylimidazo[1,2-a]pyrazin-3-yl acetate 8-benzyl-2-((5-ethylfuran-2-yl)methyl)-6-phenylimidazo[1,2-a]pyrazin-3-yl acetate 8-benzyl-2-((4,5-dimethylfuran-2-yl)methyl)-6-phenylimidazo[1,2-a]pyrazin-3-yl acetate 8-benzyl-6-(2-fluorophenyl)-2-(furan-2-ylmethyl)imidazo[1,2-a]pyrazin-3-yl acetate 8-benzyl-2-(3-methylbenzyl)-6-phenylimidazo[1,2-a]pyrazin-3-yl acetate 8-benzyl-2-(3-methoxybenzyl)-6-phenylimidazo[1,2-a]pyrazin-3-yl acetate 2,8-dibenzyl-6-(2-fluorophenyl)imidazo[1,2-a]pyrazin-3-yl acetate 8-benzyl-6-(2,6-difluorophenyl)-2-(furan-2-ylmethyl)imidazo[1,2-a]pyrazin-3-yl acetate 8-benzyl-6-phenyl-2-(5-(trifluoromethyl)furan-2-yl)methyl)imidazo[1,2-a]pyrazin-3-yl acetate 2,8-dibenzyl-6-(2,6-difluorophenyl)imidazo[1,2-]pyrazin-3-yl acetate 8-benzyl-6-(2-fluorophenyl)-2-((5-methylfuran-2-yl)methyl)imidazo[1,2-a]pyrazin-3-yl acetate 8-benzyl-2-((5-cyclopropylfuran-2-yl)methyl)-6-phenylimidazo[1,2-a]pyrazin-3-yl acetate 8-benzyl-2-(3-fluorobenzyl)-6-phenylimidazo[1,2-a]pyrazin-3-yl acetate 8-benzyl-2-((5-ethylfuran-2-yl)methyl)-6-(2-fluorophenyl)imidazo[1,2-a]pyrazin-3-yl acetate 8-benzyl-6-(3-fluorophenyl)-2-((5-methylfuran-2-yl)methyl)imidazo[1,2-a]pyrazin-3-yl acetate 8-benzyl-2-(2-fluorobenzyl)-6-phenylimidazo[1,2-a]pyrazin-3-yl acetate 8-benzyl-2-((5-ethylthiophen-2-yl)methyl)-6-phenylimidazo[1,2-a]pyrazin-3-yl acetate 8-benzyl-2-((4,5-dimethylfuran-2-yl)methyl)-6-(2-fluorophenyl)imidazo[1,2-a]pyrazin-3-yl acetate 2-benzyl-8-(2-fluorobenzyl)-6-phenylimidazo[1,2-a]pyrazin-3-yl acetate 2-benzyl-8-(3-fluorobenzyl)-6-phenylimidazo[1,2-a]pyrazin-3-yl acetate 8-(3-fluorobenzyl)-2-(furan-2-ylmethyl)-6-phenylimidazo[1,2-a]pyrazin-3-yl acetate 8-(2-fluorobenzyl)-2-(3-methylbenzyl)-6-phenylimidazo[1,2-a]pyrazin-3-yl acetate 8-(2-fluorobenzyl)-2-(3-methoxybenzyl)-6-phenylimidazo[1,2-a]pyrazin-3-yl acetate 8-(2-fluorobenzyl)-2-(furan-2-ylmethyl)-6-phenylimidazo[1,2-a]pyrazin-3-yl acetate 8-(2-fluorobenzyl)-2-((5-methylfuran-2-yl)methyl)-6-phenylimidazo[1,2-a]pyrazin-3-yl acetate 8-(3-fluorobenzyl)-2-(3-methoxybenzyl)-6-phenylimidazo[1,2-a]pyrazin-3-yl acetate 8-(3-fluorobenzyl)-2-(3-methylbenzyl)-6-phenylimidazo[1,2-a]pyrazin-3-yl acetate 2-((5-ethylfuran-2-yl)methyl)-8-(3-fluorobenzyl)-6-phenylimidazo[1,2-a]pyrazin-3-yl acetate 8-(2-chlorobenzyl)-2-((3-methylfuran-2-yl)methyl)-6-phenylimidazo[1,2-a]pyrazin-3-yl acetate 8-(3-fluorobenzyl)-2-((5-methylfuran-2-yl)methyl)-6-phenylimidazo[1,2-a]pyrazin-3-yl acetate 2-((5-ethylfuran-2-yl)methyl)-8-(2-fluorobenzyl)-6-phenylimidazo[1,2-a]pyrazin-3-yl acetate 8-(2,6-difluorobenzyl)-2-(furan-2-ylmethyl)-6-phenylimidazo[1,2-a]pyrazin-3-yl acetate 8-(3,5-difluorobenzyl)-2-(furan-2-ylmethyl)-6-phenylimidazo[1,2-a]pyrazin-3-yl acetate 8-(3-chlorobenzyl)-2-(furan-2-ylmethyl)-6-phenylimidazo[1,2-a]pyrazin-3-yl acetate 8-(3-fluorobenzyl)-6-(2-fluorophenyl)-2-((5-methylfuran-2-yl)methyl)imidazo[1,2-a]pyrazin-3-yl acetate 8-(2,3-difluorobenzyl)-2-(furan-2-ylmethyl)-6-phenylimidazo[1,2-a]pyrazin-3-yl acetate 8-(2,3-difluorobenzyl)-2-((5-methylfuran-2-yl)methyl)-6-phenylimidazo[1,2-a]pyrazin-3-yl acetate 8-(2,5-difluorobenzyl)-2-(furan-2-ylmethyl)-6-phenylimidazo[1,2-a]pyrazin-3-yl acetate 8-(2,5-difluorobenzyl)-2-((5-methylfuran-2-yl)methyl)-6-phenylimidazo[1,2-a]pyrazin-3-yl acetate 8-(3,5-difluorobenzyl)-2-((5-methylfuran-2-yl)methyl)-6-phenylimidazo[1,2-a]pyrazin-3-yl acetate 2-benzyl-8-(2,3-difluorobenzyl)-6-phenylimidazo[1,2-a]pyrazin-3-yl acetate 2-benzyl-6-phenyl-8-(2-(trifluoromethyl)benzyl)imidazo[1,2-a]pyrazin-3-yl acetate 2-benzyl-6-phenyl-8-(3-(trifluoromethyl)benzyl)imidazo[1,2-a]pyrazin-3-yl acetate 2-benzyl-6-phenyl-8-(2,3,5-trifluorobenzyl)imidazo[1,2-a]pyrazin-3-yl acetate 8-(2,6-Difluorobenzyl)-2-((5-methylfuran-2-yl)methyl)-6-phenylimidazo[1,2-a]pyrazin-3-yl acetate 8-(2,5-Difluorobenzyl)-2-((4,5-dimethylfuran-2-yl)methyl)-6-phenylimidazo[1,2-a]pyrazin-3-yl acetate 8-(2,5-Difluorobenzyl)-2-((5-ethylfuran-2-yl)methyl)-6-phenylimidazo[1,2-a]pyrazin-3-yl acetate 8-(2,3-Difluorobenzyl)-2-((4,5-dimethylfuran-2-yl)methyl)-6-phenylimidazo[1,2-a]pyrazin-3-yl acetate 8-(3,5-Difluorobenzyl)-2-((4,5-dimethylfuran-2-yl)methyl)-6-phenylimidazo[1,2-a]pyrazin-3-yl acetate 2-(furan-2-ylmethyl)-6-phenyl-8-(2,3,5-trifluorobenzyl)imidazo[1,2-a]pyrazin-3-yl acetate 8-(2,3-Difluorobenzyl)-2-((5-ethylfuran-2-yl)methyl)-6-phenylimidazo[1,2-a]pyrazin-3-yl acetate 8-(3,5-Difluorobenzyl)-2-((5-ethylfuran-2-yl)methyl)-6-phenylimidazo[1,2-a]pyrazin-3-yl acetate 8-(2,6-Difluorobenzyl)-2-((5-ethylfuran-2-yl)methyl)-6-phenylimidazo[1,2-a]pyrazin-3-yl acetate 8-(2,6-Difluorobenzyl)-2-((4,5-dimethylfuran-2-yl)methyl)-6-phenylimidazo[1,2-a]pyrazin-3-yl acetate 2-((4,5-Dimethylfuran-2-yl)methyl)-8-(2-fluorobenzyl)-6-phenylimidazo[1,2-a]pyrazin-3-yl acetate 2-((4,5-Dimethylfuran-2-yl)methyl)-8-(3-fluorobenzyl)-6-phenylimidazo[1,2-a]pyrazin-3-yl acetate 8-Benzyl-6-phenyl-2-((5-propylfuran-2-yl)methyl)imidazo[1,2-a]pyrazin-3-yl acetate 8-(2,3-difluorobenzyl)-2-((4-ethyl-5-methylfuran-2-yl)methyl)-6-phenylimidazo[1,2-a]pyrazin-3-yl acetate 8-benzyl-2-((4-ethyl-5-methylfuran-2-yl)methyl)-6-phenylimidazo[1,2-a]pyrazin-3-yl acetate 8-benzyl-2-((5-isopropyl-4-methylfuran-2-yl)methyl)-6-phenylimidazo[1,2-a]pyrazin-3-yl acetate 8-benzyl-2-((5-ethyl-4-methylfuran-2-yl)methyl)-6-phenylimidazo[1,2-a]pyrazin-3-yl acetate 8-(2,3-difluorobenzyl)-2-((5-ethyl-4-methylfuran-2-yl)methyl)-6-phenylimidazo[1,2-a]pyrazin-3-yl acetate 8-benzyl-2-(1-(furan-2-yl)ethyl)-6-phenylimidazo[1,2-a]pyrazin-3-yl acetate 8-(2,3-difluorobenzyl)-2-((5-isopropyl-4-methylfuran-2-yl)methyl)-6-phenylimidazo[1,2-a]pyrazin-3-yl acetate 8-benzyl-2-(furan-2-ylmethyl)-6-(3-hydroxyphenyl)imidazo[1,2-a]pyrazin-3-yl acetate;

or compounds with the general formula (V) and the following names:

2-((3-benzyl-5-phenylpyrazin-2-yl)amino)-3-(5-methylfuran-2-yl)propanoic acid 2-((3-benzyl-5-phenylpyrazin-2-yl)amino)-3-(5-ethylfuran-2-yl)propanoic acid 2-((3-benzyl-5-phenylpyrazin-2-yl)amino)-3-(4,5-dimethylfuran-2-yl)propanoic acid 2-((3-benzyl-5-(2-fluorophenyl)pyrazin-2-yl)amino)-3-(furan-2-yl)propanoic acid 2-((3-benzyl-5-phenylpyrazin-2-yl)amino)-3-(m-tolyl)propanoic acid 2-((3-benzyl-5-phenylpyrazin-2-yl)amino)-3-(3-methoxyphenyl)propanoic acid (3-benzyl-5-(2-fluorophenyl)pyrazin-2-yl)phenylalanine 2-((3-benzyl-5-(2,6-difluorophenyl)pyrazin-2-yl)amino)-3-(furan-2-yl)propanoic acid 2-((3-benzyl-5-phenylpyrazin-2-yl)amino)-3-(5-(trifluoromethyl)furan-2-yl)propanoic acid (3-benzyl-5-(2,6-difluorophenyl)pyrazin-2-yl)phenylalanine 2-((3-benzyl-5-(2-fluorophenyl)pyrazin-2-yl)amino)-3-(5-methylfuran-2-yl)propanoic acid 2-((3-benzyl-5-phenylpyrazin-2-yl)amino)-3-(5-cyclopropylfuran-2-yl)propanoic acid 2-((3-benzyl-5-phenylpyrazin-2-yl)amino)-3-(3-fluorophenyl)propanoic acid
2-((3-benzyl-5-(2-fluorophenyl)pyrazin-2-yl)amino)-3-(5-ethylfuran-2-yl)propanoic acid
2-((3-benzyl-5-(3-fluorophenyl)pyrazin-2-yl)amino)-3-(5-methylfuran-2-yl)propanoic acid
2-((3-benzyl-5-phenylpyrazin-2-yl)amino)-3-(2-fluorophenyl)propanoic acid
2-((3-benzyl-5-phenylpyrazin-2-yl)amino)-3-(5-ethylthiophen-2-yl)propanoic acid
2-((3-benzyl-5-(2-fluorophenyl)pyrazin-2-yl)amino)-3-(4,5-dimethylfuran-2-yl)propanoic acid
(3-(2-fluorobenzyl)-5-phenylpyrazin-2-yl)phenylalanine
(3-(3-fluorobenzyl)-5-phenylpyrazin-2-yl)phenylalanine
2-((3-(3-fluorobenzyl)-5-phenylpyrazin-2-yl)amino)-3-(furan-2-yl)propanoic acid
2-((3-(2-fluorobenzyl)-5-phenylpyrazin-2-yl)amino)-3-(m-tolyl)propanoic acid
2-((3-(2-fluorobenzyl)-5-phenylpyrazin-2-yl)amino)-3-(3-methoxyphenyl)propanoic acid
2-4 (3-(2-fluorobenzyl)-5-phenylpyrazin-2-yl)amino)-3-(furan-2-yl)propanoic acid
2-((3-(2-fluorobenzyl)-5-phenylpyrazin-2-yl)amino)-3-((5-methylfuran-2-yl)propanoic acid
2 ((3-(3-fluorobenzyl)-5-phenylpyrazin-2-yl)amino)-3-(3-methoxyphenyl)propanoic acid
2-((3-(3-fluorobenzyl)-5-phenylpyrazin-2-yl)amino)-3-(m-tolyl)propanoic acid
3-((5-ethylfuran-2-yl)-2-((3-(3-fluorobenzyl)-5-phenylpyrazin-2-yl)amino)propanoic acid
2-((3-(2-chlorobenzyl)-5-phenylpyrazin-2-yl)amino)-3-(5-methylfuran-2-yl)propanoic acid
2-((3-(3-fluorobenzyl)-5-phenylpyrazin-2-yl)amino)-3-(5-methylfuran-2-yl)propanoic acid
3-(5-ethylfuran-2-yl)-2-((3-(2-fluorobenzyl)-5-phenylpyrazin-2-yl)amino)propanoic acid
3-(3-(2,6-difluorobenzyl)-5-phenylpyrazin-2-yl)-2-(furan-2-ylmethyl)propanoic acid
3-(3-(3,5-difluorobenzyl)-5-phenylpyrazin-2-yl)-2-(furan-2-ylmethyl)propanoic acid
3-(3-(3-chlorobenzyl)-5-phenylpyrazin-2-yl)-2-(furan-2-ylmethyl)propanoic acid
3-(3-(3-fluorobenzyl)-5-(2-fluorophenyl)pyrazin-2-yl)-2-((5-methylfuran-2-yl)methyl)propanoic acid
3-(3-(2,3-difluorobenzyl)-5-phenylpyrazin-2-yl)-2-(furan-2-ylmethyl)propanoic acid
3-(3-(2,3-difluorobenzyl)-5-phenylpyrazin-2-yl)-2-((5-methylfuran-2-yl)methyl)propanoic acid
3-(3-(2,5-difluorobenzyl)-5-phenylpyrazin-2-yl)-2-(furan-2-ylmethyl)propanoic acid
3-(3-(2,5-difluorobenzyl)-5-phenylpyrazin-2-yl)-2-((5-methylfuran-2-yl)methyl)propanoic acid
3-(3-(3,5-difluorobenzyl)-5-phenylpyrazin-2-yl)-2-((5-methylfuran-2-yl)methyl)propanoic acid
2-benzyl-3-(3-(2,3-difluorobenzyl)-5-phenylpyrazin-2-yl)propanoic acid
2-benzyl-3-(5-phenyl-3-(2-(trifluoromethyl)benzyl)pyrazin-2-yl)propanoic acid
2-benzyl-3-(5-phenyl-3-(3-(trifluoromethyl)benzyl)pyrazin-2-yl)propanoic acid
2-benzyl-3-(5-phenyl-3-(2,3,5-trifluorobenzyl)pyrazin-2-yl)propanoic acid
3-(3-(2,6-difluorobenzyl)-5-phenylpyrazin-2-yl)-2-((5-methylfuran-2-yl)methyl)propanoic acid
3-(3-(2,5-difluorobenzyl)-5-phenylpyrazin-2-yl)-2-((4,5-dimethylfuran-2-yl)methyl)propanoic acid
3-(3-(2,5-difluorobenzyl)-5-phenylpyrazin-2-yl)-2-((5-ethylfuran-2-yl)methyl)propanoic acid
3-(3-(2,3-difluorobenzyl)-5-phenylpyrazin-2-yl)-2-((4,5-dimethylfuran-2-yl)methyl)propanoic acid
3-(3-(3,5-difluorobenzyl)-5-phenylpyrazin-2-yl)-2-((4,5-dimethylfuran-2-yl)methyl)propanoic acid
3-(furan-2-yl)-2-((5-phenyl-3-(2,3,5-trifluorobenzyl)pyrazin-2-yl)methyl)propanoic acid
3-(3-(2,3-difluorobenzyl)-5-phenylpyrazin-2-yl)-2-((5-ethylfuran-2-yl)methyl)propanoic acid
3-(3-(3,5-difluorobenzyl)-5-phenylpyrazin-2-yl)-2-((5-ethylfuran-2-yl)methyl)propanoic acid
3-(3-(2,6-difluorobenzyl)-5-phenylpyrazin-2-yl)-2-((5-ethylfuran-2-yl)methyl)propanoic acid
3-(3-(2,6-difluorobenzyl)-5-phenylpyrazin-2-yl)-2-((4,5-dimethylfuran-2-yl)methyl)propanoic acid
3-(4,5-dimethylfuran-2-yl)-2-((3-(2-fluorobenzyl)-5-phenylpyrazin-2-yl)methyl)propanoic acid
3-(4,5-dimethylfuran-2-yl)-2-((3-(3-fluorobenzyl)-5-phenylpyrazin-2-yl)methyl)propanoic acid
2-((3-(2,3-difluorobenzyl)-5-phenylpyrazin-2-yl)amino)-3-(4-ethyl-5-methylfuran-2-yl)propanoic acid
2-((3-benzyl-5-phenylpyrazin-2-yl)amino)-3-(4-ethyl-5-methylfuran-2-yl)propanoic acid
2-((3-benzyl-5-phenylpyrazin-2-yl)amino)-3-(5-isopropyl-4-methylfuran-2-yl)propanoic acid
2-((3-benzyl-5-phenylpyrazin-2-yl)amino)-3-(5-ethyl-4-methylfuran-2-yl)propanoic acid
2-((3-(2,3-difluorobenzyl)-5-phenylpyrazin-2-yl)amino)-3-(5-ethyl-4-methylfuran-2-yl)propanoic acid
2-((3-benzyl-5-phenylpyrazin-2-yl)amino)-3-(furan-2-yl)butanoic acid (144)
2-((3-(2,3-difluorobenzyl)-5-phenylpyrazin-2-yl)amino)-3-(5-isopropyl-4-methylfuran-2-yl)propanoic acid
2-((3-benzyl-5-(3-(benzyloxy)phenyl)pyrazin-2-ylamino)-3-(furan-2-yl)propanoic acid
2-((3-benzyl-5-(3-(hydroxy)phenyl)pyrazin-2-yl)amino)-3-(furan-2-yl)propanoic acid.

In another aspect, the present invention relates to a compound of following formula (VII):

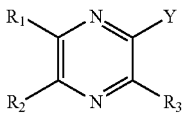

(VII)

wherein:

$R_1$ represents H or a group selected from $C_1$-$C_6$ alkyl, $C_3$-$C_7$ cycloalkyl, $C_6$-$C_{10}$ aryl, aralkyl and $C_5$-$C_{10}$-membered heteroaryl groups, said $C_1$-$C_6$ alkyl, $C_3$-$C_7$ cycloalkyl, $C_6$-$C_{10}$ aryl, aralkyl and $C_5$-$C_{10}$-membered heteroaryl groups being optionally substituted by at least one $Y_1$ group;

$R_2$ represents a group selected from $C_6$-$C_{10}$ aryl and $C_5$-$C_{10}$-membered heteroaryl groups, said $C_6$-$C_{10}$ aryl and $C_5$-$C_{10}$-membered heteroaryl groups being optionally substituted by at least one $Y_2$ group;

$R_3$ represents an aralkyl group, said aralkyl group being optionally substituted by at least one $Y_3$ group;

Y is a leaving group, in particular an halogen, more particularly a —Cl;

said $Y_1$, $Y_2$ and $Y_3$ groups being each independently selected from:

a $C_1$-$C_6$ alkyl group;

a $C_3$-$C_7$ cycloalkyl group;

an halogen;

a —$OR_{ii}$ group;

$R_{ii}$ represents H, a $C_1$-$C_6$ alkyl group, a $C_3$-$C_{10}$ cycloalkyl group or an aralkyl group;

with the proviso that said compound is not of one of the following formulae.

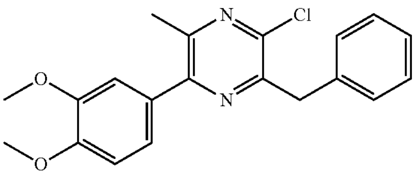

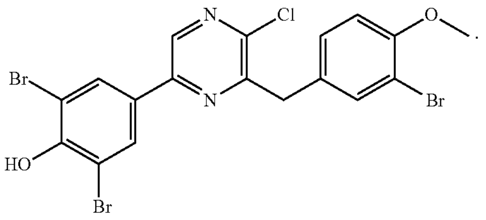

In a particular embodiment, $R_1$ represents H.

In a particular embodiment, $R_3$ represents a benzyl group, optionally substituted as defined above, in particular by at least one halogen, more particularly F, $R_3$ being more particularly selected from the group consisting of:

(3a)

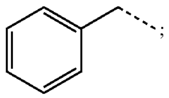

(3b)

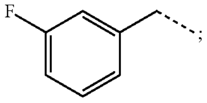

(3c)

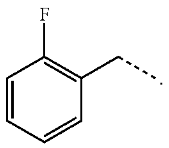

(3d)

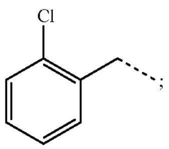

(3e)

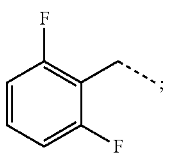

-continued (3f)

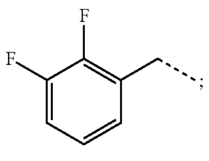

(3g)

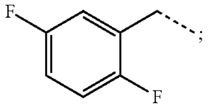

(3h)

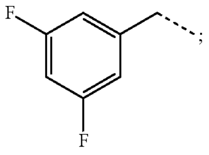

(3i)

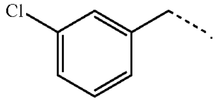

In a particular embodiment, $R_2$ represents a phenyl, optionally substituted as defined above, $R_2$ representing in particular a phenyl optionally substituted by at least an halogen, in particular F;

$R_2$ being more particularly selected from the group consisting of:

(2a)

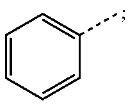

(2b)

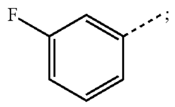

(2c)

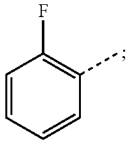

(2d)

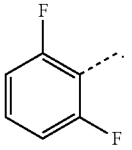

DETAILED DESCRIPTION OF THE INVENTION

Definitions

The following terms and expressions contained herein are defined as follows:

As used herein, a range of values in the form "x-y" or "x to y", or "x through y", include integers x, y, and the integers therebetween. For example, the phrases "1-6", or "1 to 6" or "1 through 6" are intended to include the integers 1, 2, 3, 4, 5, and 6. Preferred embodiments include each individual integer in the range, as well as any subcombination of integers. For example, preferred integers for "1-6" can include 1, 2, 3, 4, 5, 6, 1-2, 1-3, 1-4, 1-5, 2-3, 2-4, 2-5, 2-6, etc.

As used herein, the term "alkyl" refers to a straight-chain, or branched alkyl group having 1 to 6 carbon atoms, such as methyl, ethyl, propyl, isopropyl, butyl, isobutyl, sec-butyl, tert-butyl, pentyl, isoamyl, neopentyl, I-ethylpropyl, 3-methylpentyl, 2,2-dimethylbutyl, 2,3-dimethylbutyl, hexyl, etc. The alkyl moiety of alkyl-containing groups, such as aralkyl or O-alkyl groups, has the same meaning as alkyl defined above. Lower alkyl groups, which are preferred, are alkyl groups as defined above which contain 1 to 4 carbons. A designation such as "C1-C4 alkyl" refers to an alkyl radical containing from 1 to 4 carbon atoms.

As used herein, the term "cycloalkyl" refers to a saturated or partially saturated mono- or bicyclic alkyl ring system containing 3 to 7 carbon atoms. A designation such as "$C_5$-$C_6$ cycloalkyl" refers to a cycloalkyl radical containing from 5 to 6 ring carbon atoms. Examples of cycloalkyl groups include such groups as cyclopropyl, cyclobutyl, cyclopentyl, cyclohexyl, cycloheptyl, cyclooctyl, pinenyl, and adamantanyl. The cycloalkyl moiety of cycloalkyl-containing groups, such as O-cycloalkyl groups, has the same meaning as alkyl defined above.

As used herein, the term "aryl" refers to a substituted or unsubstituted, mono- or bicyclic hydrocarbon aromatic ring system having 6 to 10 ring carbon atoms. Examples include phenyl and naphthyl. Preferred aryl groups include unsubstituted or substituted phenyl and naphthyl groups. Included within the definition of "aryl" are fused ring systems, including, for example, ring systems in which an aromatic ring is fused to a cycloalkyl ring. Examples of such fused ring systems include, for example, indane, indene, and tetrahydronaphthalene.

As used herein, the term "aralkyl" refers to a aryl alkyl group of formula Ar-alkyl-, wherein "aryl" and "alkyl" are as defined above, Ar being in particular Ph, alkyl being in particular Me ($—CH_2—$).

As used herein, the term "heteroaryl" refers to an aromatic group containing 5 to 10 ring carbon atoms in which one or more ring carbon atoms are replaced by at least one hetero atom such as —O—, —N—, or —S—. Examples of heteroaryl groups include pyrrolyl, furanyl, thienyl, pirazolyl, imidazolyl, thiazolyl, isothiazolyl, isoxazolyl, oxazolyl, oxathiolyl, oxadiazolyl, triazolyl, oxatriazolyl, furazanyl, tetrazolyl, pyridyl, pyrazinyl, pyrimidinyl, pyridazinyl, triazinyl, indolyl, isoindolyl, indazolyl, benzofuranyl, isobenzofuranyl, purinyl, quinazolinyl, quinolyl, isoquinolyl, benzoimidazolyl, benzothiazolyl, benzothiophenyl, thianaphthenyl, benzoxazolyl, benzisoxazolyl, cinnolinyl, phthalazinyl, naphthyridinyl, and quinoxalinyl. Included within the definition of "heteroaryl" are fused ring systems, including, for example, ring systems in which an aromatic ring is fused to a heterocycloalkyl ring. Examples of such fused ring systems include, for example, phthalamide, phthalic anhydride, indoline, isoindoline, tetrahydroisoquinoline, chroman, isochroman, chromene, and isochromene.

As used herein, the term "hetaralkyl" refers to a heteroaryl alkyl group of formula Heteroaryl-alkyl-, wherein "heteroaryl" and "alkyl" are as defined above, alkyl being in particular Me ($—CH_2—$).

As used herein, the term "pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio.

As used herein, the term "luminogenic proteins" refers to luciferases and photoproteins using luciferins.

By "strong acid" is meant an acid that ionizes completely in aqueous solution by losing one proton.

By "leaving group" is meant a nucleofuge which retains the lone pair from its previous bond with another species, in particular in a nucleophilic substitution reaction. The leaving group is for example chosen from the group consisting of halogens, in particular —I, —Br, —Cl and —F, and triflate $—OS(O_2)CF_3$.

All other terms used in the description of the present invention have their meanings as is well known in the art.

In another aspect, the present invention is directed to pharmaceutically acceptable salts of the compounds described above. As used herein, "pharmaceutically acceptable salts" includes salts of compounds of the present invention derived from the combination of such compounds with non-toxic acid.

Acid addition salts include inorganic acids such as hydrochloric, hydrobromic, hydroiodic, sulfuric, nitric and phosphoric acid, as well as organic acids such as acetic, citric, propionic, tartaric, glutamic, salicylic, oxalic, methanesulfonic, para-toluenesulfonic, succinic, and benzoic acid, and related inorganic and organic acids.

In addition to pharmaceutically-acceptable salts, other salts are included in the invention. They may serve as intermediates in the purification of the compounds, in the preparation of other salts, or in the identification and characterization of the compounds or intermediates.

The pharmaceutically acceptable salts of compounds of the present invention can also exist as various solvates, such as with water, methanol, ethanol, dimethylformamide, ethyl acetate and the like. Mixtures of such solvates can also be prepared. The source of such solvate can be from the solvent of crystallization, inherent in the solvent of preparation or crystallization, or adventitious to such solvent. Such solvates are within the scope of the present invention.

It is recognized that compounds of the present invention may exist in various stereoisomeric forms. As such, the compounds of the present invention include both diastereomers and enantiomers. The compounds are normally prepared as racemates and can conveniently be used as such, but individual enantiomers can be isolated or synthesized by conventional techniques if so desired. Such racemates and individual enantiomers and mixtures thereof form part of the present invention.

It is well known in the art how to prepare and isolate such optically active forms. Specific stereoisomers can be prepared by stereospecific synthesis using enantiomerically pure or enantiomerically enriched starting materials. The specific stereoisomers of either starting materials or products can be resolved and recovered by techniques known in the art, such as resolution of racemic forms, normal, reverse-phase, and chiral chromatography, recrystallization, enzymatic resolution, or fractional recrystallization of addition salts formed by reagents used for that purpose, Useful methods of resolving and recovering specific stereoisomers described in Eliel, E. L.; Wilen, S. H. *Stereochemistry of Organic Compounds*; Wiley: New York, 1994, and Jacques, J. et al. *Enantiomers, Racemates, and Resolutions*; Wiley: New York, 1981, each incorporated by reference herein in their entireties.

Synthesis

The compounds of the present invention may be prepared in a number of methods well known to those skilled in the art, including, but not limited to those described below, or through modifications of these methods by applying standard techniques known to those skilled in the art of organic synthesis. The appropriate modifications and substitutions will be readily apparent and well known or readily obtainable from the scientific literature to those skilled in the art. In particular, such methods can be found in R. C. Larock, *Comprehensive Organic Transformations*, Wiley-VCH Publishers, 1999.

All processes disclosed in association with the present invention are contemplated to be practiced on any scale, including milligram, gram, multigram, kilogram, multikilogram or commercial industrial scale.

It will be appreciated that the compounds of the present invention may contain one or more asymmetrically substituted carbon atoms, and may be isolated in optically active or racemic forms. Thos, all chiral, diastereomeric, racemic forms, isomeric forms of a structure are intended, unless the specific stereochemistry or isomeric form is specifically indicated. It is well-known in the art how to prepare and isolate such optically active forms. For example, mixtures of stereoisomers may be separated by standard techniques including, but not limited to, resolution of racemic forms, normal, reverse-phase, and chiral chromatography, preferential salt formation, recrystallization, and the like, or by chiral synthesis cither from chiral starting materials or by deliberate synthesis of target chiral centers.

Compounds of the present invention may be prepared by a variety of synthetic routes. The reagents and starting materials are commercially available, or readily synthesized by well-known techniques by one of ordinary skill in the arts. All substituents, unless otherwise indicated, are as previously defined.

In the reactions described hereinafter, it may be necessary to protect reactive functional groups, for example hydroxy, amino, imino, thio or carboxy groups, where these are desired in the final product, to avoid their unwanted participation in the reactions. Conventional protecting groups may be used in accordance with standard practice, for examples see T. W. Greene and P. G. M. Wuts in *Protective Groups in Organic Chemistry,* 3rd ed., John Wiley and Sons, 1999; J. F. W. McOmie in *Protective Groups in Organic Chemistry*, Plenum Press, 1973.

The present invention also relates to a process of preparation of a compound of formula (III) as defined above, comprising a step of conversion of a compound of formula (IV) as defined above into a compound of formula (III).

In a particular embodiment, the process of preparation of a compound of formula (III) as defined above comprises:

i) A step of contacting a compound of formula (IV) as defined above with a strong acid in presence of a solvent of the compound of formula (IV); or ii) A step of contacting a compound of formula (IV) as defined above with a strong acid or ammonia, in particular under inert gas when ammonia is used, in presence of a solvent of the compound of formula (IV).

In a particular embodiment, the strong acid is hydrochloric acid.

In a particular embodiment, the conversion of (IV) into (III) is conducted at a temperature comprised from 40° C. to 90° C., for example at 50° C., in particular in a sealed tube.

In a particular embodiment, the strong acid used for the conversion of (IV) into (III) is hydrochloric acid, in particular in solution in ethanol.

In a particular embodiment, the conversion of (IV) into (III) is conducted at a temperature comprised from 40° C. to 90° C., in particular at 50° C.

In a particular embodiment said compound of formula (IV) is prepared according to a process comprising:

i) A step of conversion of a compound of formula (VI) as defined above into a compound of formula (V), followed by a step of conversion of the compound of formula (V) into a compound of formula (IV); or ii) A step of conversion of a compound of formula (VI) into a compound of formula (IV).

In a particular embodiment said compound of formula (IV) is prepared according to a process comprising:

i) A step of hydrolysis of the COO—Ra ester function of a compound of formula (VI) as defined above, in particular by contacting the compound of formula (VI) with a strong base in presence of a solvent of said compound of formula (VI) to give a compound of formula (V), followed by a step of contacting the compound of formula (V) with a compound selected from the group consisting of anhydrides, chlorofomates and dicarbonates; or ii) A step of contacting said compound of formula (VD) with a mixture of acetic acid and aliphatic anhydride, in particular acetic anhydride.

In a particular embodiment, the strong base used for the conversion of (VI) into (V) is sodium hydroxide, the hydrolysis being in particular conducted at a temperature comprised from 15 to 30° C.

In a particular embodiment, the compound selected from the group consisting of anhydrides, chlorofomates and dicarbonates is acetic or pivalic anhydride, the contacting with said compound being in particular conducted at a temperature comprised from 15 to 30° C.

In a particular embodiment, the conversion of (VI) into (IV) is conducted at a temperature comprised from 100° C. to 150° C., in particular at 140° C., in particular under microwave irradiation.

In a particular embodiment, said compound of formula (VI) is obtained from a process comprising:

i) a step of replacement of the hydroxyl group of a compound of following formula (VIII):

(VIII)

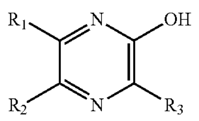

by a leaving group —Y, Y being in particular an halogen, to give a compound of following formula (VII):

(VII)

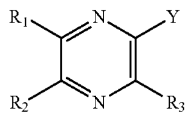

and ii) a step of contacting the compound of following formula (VII):

with a compound of following formula (IX):

(IX)

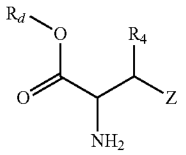

wherein $R_1$, $R_2$, $R_3$, $R_4$, Z and $R_d$ are as defined above, in presence of a catalyst comprising copper or palladium and a ligand chosen from BINAP, Xantphos, dichloro [1,3-bis(2,6-di-3-pentylphenyl)imidazol-2-ylidene](3-chloropyridyl) (PEPPSI-IPentCl), thereby obtaining a compound of formula (VI).

In a particular embodiment, Y is Cl, step vi) being a step of contacting a compound of formula (VIII) with phenylphosphonic dichloride, in particular at a temperature comprised from 60° C. and 150° C., more particularly at 100° C.

In a particular embodiment, Y is Br, step i) being a step of contacting a compound of formula (VIII) with triflic anhydride, followed by a step of contacting the product obtained in previous step with sodium bromide, in particular at a temperature comprised from 80° C. and 160° C., for example at 120° C. in particular in a sealed tube.

In a particular embodiment, step ii) is performed in presence of a base, in particular cesium carbonate.

In a particular embodiment, the catalyst and the ligand of step ii) are palladium acetate and BINAP, respectively, said step ii) being conducted at a temperature comprised from 40° C. and 80° C., more particularly at 60° C.

In a particular embodiment, said compound of formula (VIII) is obtained from a process comprising a step of dehydrogenation and aromatization of a compound of following formula (X):

(X)

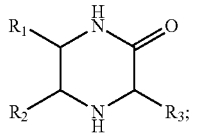

In particular from a process comprising:

i) A step of contacting the compound of formula (X) with sulfur, in presence of a solvent, at a temperature comprised from 180° C. and reflux; or ii) A step of contacting the compound of formula (X) with peroxide-based oxidants such as peracetic acid, followed by a step of thermal treatment at a temperature comprised from 150° C. to 190° C., in particular in presence of a solvent.

The general routes to prepare the examples of the present invention are shown in the schemes A-C hereafter.

The reagents and starting materials are commercially available, or readily synthesized by well-known techniques by one of ordinary skill in the arts. All the substituents of compounds A-Q depicted in schemes A-C are, unless otherwise indicated, as previously defined above for the corresponding compounds (III)-(X).

Scheme A

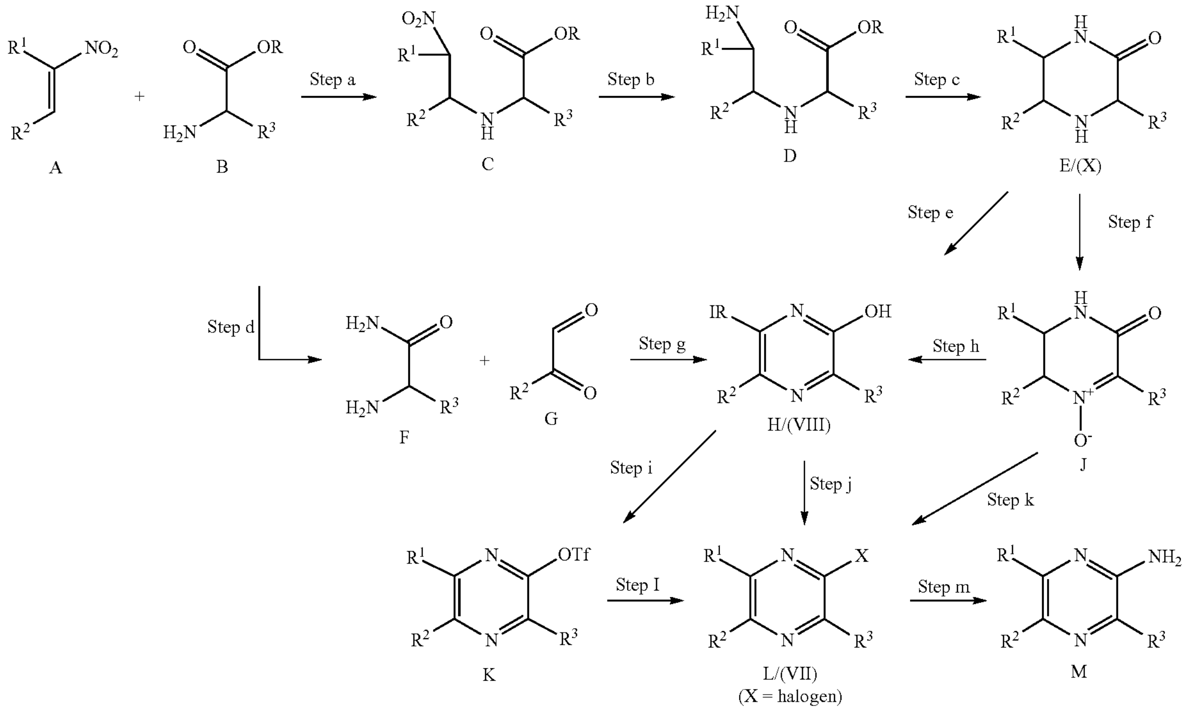

Concerning the synthetic pathways described in scheme A, step a is a 1,4-addition of aminoesters B on nitrovinyls A which is preferably achieved in the absence of solvents. Step b is the reduction of the nitro group of compounds C which is preferably achieved in acidic medium using zinc. Step e involves the heat-triggered cyclization of the resulting free diamine D into compound E. Steps a, b and e were usually telescoped in order to minimize side reactions and potential losses in the course of purification processes. Step e is a dehydrogenation/aromatization of compound E to give the hydroxypyrazine derivatives HI, which is preferably achieved using sulfur in a boiling inert solvent. An alternative was found via the preparation of 5-oxo-2,3,4,5-tetrahydropyrazine 1-oxide derivatives J using peracetic acid (step f) and its rearrangement into hydroxypyrazine derivatives H (step h). When $R^1$ is H, the 3-hydroxypyrazine H can also be prepared, via step g, using the reported (*J. Am. Chem. Soc.,* 1949, 78; U.S. Pat. No. 2,520,088, 1949*; J. Am. Chem. Soc.,* 1952, 1580; U.S. Pat. No. 4,046,763, 1977) condensation of glyoxals G and aminoamides F (made from the reaction between aminoesters B and ammonia via step d). Step j is the replacement of the hydroxyl group of compound H by a halogen to give compounds L. In the case of the group X being a chloride, the preferable reagent used to achieve this transformation is phenylphosphonic dichloride. These compounds can also be prepared in two steps (i and l) via an ester intermediate endowed with a strong leaving capacity such as the triflic esters K followed by a reaction akin to an aromatic Finkelstein reaction (*Heterocycles,* 1998, 1255; WO 2012119046, 2012). A subsequent substitution with an iodine salt to obtain iodo derivatives (X═I) is also possible via known acid-catalysed reaction (*J. Org. Chem.,* 1961, 1907; Tetrahedron, 1998, 9701; *Syntett,* 2003, 1801). Moreover, the direct conversion of the of 5-oxo-2,3,4,5-tetrahydropyrazine 1-oxide derivatives J into chloropyrazines L (step k) was also found possible for instance by using phenylphosphonic dichloride and heat. Finally, a recent publication (*Org. Process. Res. Dev.* 2017, 21, 346) is offering the possibility to prepare, from these halogenopyrazines, the corresponding aminopyrazines M, via step m, which are key intermediates in the vast majority of the previously reported preparation of imidazo[1,2-a]pyrazine-3(7H)-one luciferins (*Chem. Eur. J.* 2015, 21, 17158).

As depicted in scheme B, from halogenopyrazines L, the preparation of the Q-protected luciferins with the general formula P was found to be possible, either in two separated steps via the amino acids O or in one pot from their amino esters precursors with the general formula N. Amongst many interesting aspects, it is important to mention that our invention is answering the unmet need of disposing of a fresh solution, and thus of a reproducible titre, of any luciferin with the general formula Q. Since the O-protected luciferins (pre-luciferins), with the general formula P, can upon a simple and unprecedented acid treatment, lead to ready-to-use solutions of the corresponding luciferins Q. Indeed, these O-protected luciferins P are much more stable and can be conveniently shipped and stored for a long time at room temperature and then hydrolysed to readily generate solutions of luciferins for their immediate use. Moreover, the removal of such group is simply achieved in a vial using solutions containing a strong acid, such as hydrochloric acid, without the need of an inert atmosphere. This unprecedented use of an acid is actually instrumental in providing a degree of stability of the resulting solution as little or no product resulting from the chemoluminescence process is observed in the course of this deprotection step. This is in stark contrast with previously reported (Tetrahedron Lett., 1977, 2685*; Chemistry,* 2013, (4970) uses of a base, such as ammonia, which in the presence of oxygen does lead to much more extensive decomposition. Concerning the chemistry described in scheme B, Step n is an amination reaction using a wide variety of α-amino esters B to give compounds N. This can be achieved using copper or palladium catalysts and a variety of ligands as described in the case of many halogenated aromatic or heteroaromatic derivatives (*Acc. Chem, Res.,* 1998, 852*; J. Organomet. Chem.,* 1999, 125*; Chem. Rev.,* 2006, 2651*; Angew. Chem., In. Ed.,* 2008, 6338*; Angew. Chem., Int. Ed.,* 2008, 3096*; J. Org. Chem.,* 2013, 7930*; Org. Lett.* 2016, 4128*; Beilstein J. Org. Chem.* 2012, 2004*; Tetrahedron,* 2011, 9405). In the present cases, in order to avoid side reactions, this step was found to require a low (60° C.) temperature. Step o is a hydrolysis of the ester function of N, preferably achieved under basic conditions to give the acids O. Step p is a cyclization followed by an O-protection which is achieved by activation of the acid function of O, preferably with a variety of reagents such as anhydrides, chloroformates, or dicarbonates. This gives directly the rather more stable O-protected compounds P. Moreover, the step o and p can in many cases be performed in one pot (step q) using acetic acid along with acetic anhydride. Finally, the compounds N or O can be transformed directly into the corresponding luciferin Q using for instance hot acetic acid and/or hydrochloric acid (step r).

Scheme B

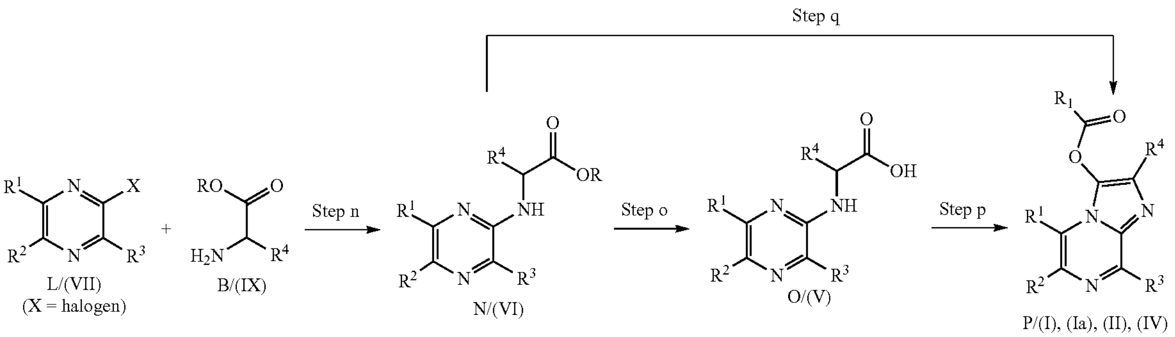

L/(VII) (X = halogen)   B/(IX)   N/(VI)   O/(V)   P/(I), (Ia), (II), (IV)

-continued

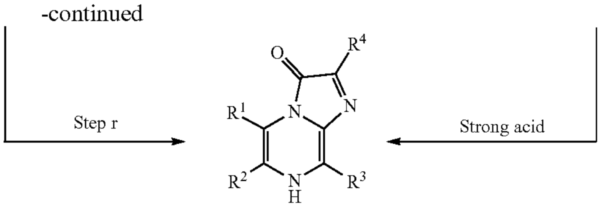

Q/(III), (IIIa)

When considering each synthetic steps individually depicted in the schemes above, step e, the dehydrogenation/aromatization of piperazin-2-ones E into 2-hydroxypyrazines H, the preparation of the N-oxides J via step f and their rearrangement into 2-hydroxypyrazines H via step h, the transformation of the N-oxides J into the halogenopyrazines L via step k and the isolation of the O-protected derivatives P obtained from compounds O via step p or from compound N via step q are the only one which have no precedents. Moreover, before or after each of these steps, further chemistry focusing on the side chains $R^1$, $R^2$, $R^3$ and $R^4$ and their various protecting groups or functions can be planned in order to alter them and/or make them compatible with the chemistry used in the next steps. For instance, the hydrogenation of eventual benzyl groups protecting OH functions present on compounds of type N or O can be undertaken before their transformations into compounds of type P via step o-q.

These synthetic pathways are making extensive uses of many aminoesters of type B. Accordingly, to prepare such intermediates; we used for instance the pathways depicted in scheme C. The first path is based on the reported (*Bull. Acad, Sci. USSR Div. Chem. Sci.* (*Engl. Transl.*), 1980, 458; *Bull. Acad. Sci. USSR Div. Chem. Sci.* (*Engl. Transl.*), 1981, 466) use of ethyl nitroacetate to prepare the corresponding nitroacrylates which are then reduced into aminoesters. A simplification of the procedure led us to telescope the first three steps of this method and only properly isolate the intermediate nitroesters R before their final reduction into aminoesters B. The second path is endowed with a larger scope and is based on the use of a Knoevenagel reaction with diethylmalonate which, after a reduction, gives the corresponding substituted malonates. From them, as reported (*Ber. Disch, Chem. Ges.*, 1902, 3772; *Org. Process. Res. Dev.*, 2007, 1069), «-oxime esters are readily prepared and can be reduced into the corresponding aminoesters. Again, telescoping the first three steps very often led us to properly isolate only the intermediate oximes S before their final reduction into aminoesters. As further described in detail below, less general methods, were also employed to prepare other types of α-oxime esters.

Scheme C.

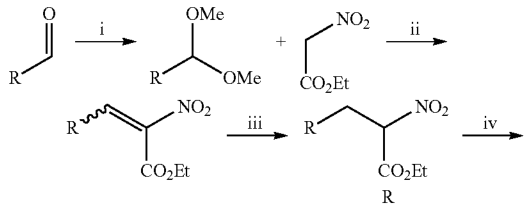

R

-continued

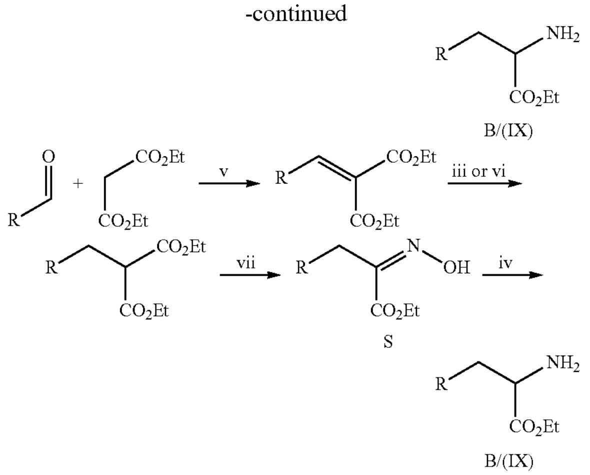

i: $HC(OMe)_3$, Dowex 50 W, MeOH. ii: $Ac_2O$, heat. iii: $NaBH_4$, iPrOH. iv: Zn, EtOH, $H_3O^+Cl^-$. v: AcOH, piperidine, EtOH, 4Å molecular sieve. vi: $H_2$, Pd/C, EtOH. EtONa, vii: a) EtOH,isoamylnitrite, b) $H_3O^+Cl^-$.

EXAMPLES

Description, Chemistry

General Experimental Procedure

Figure 1:
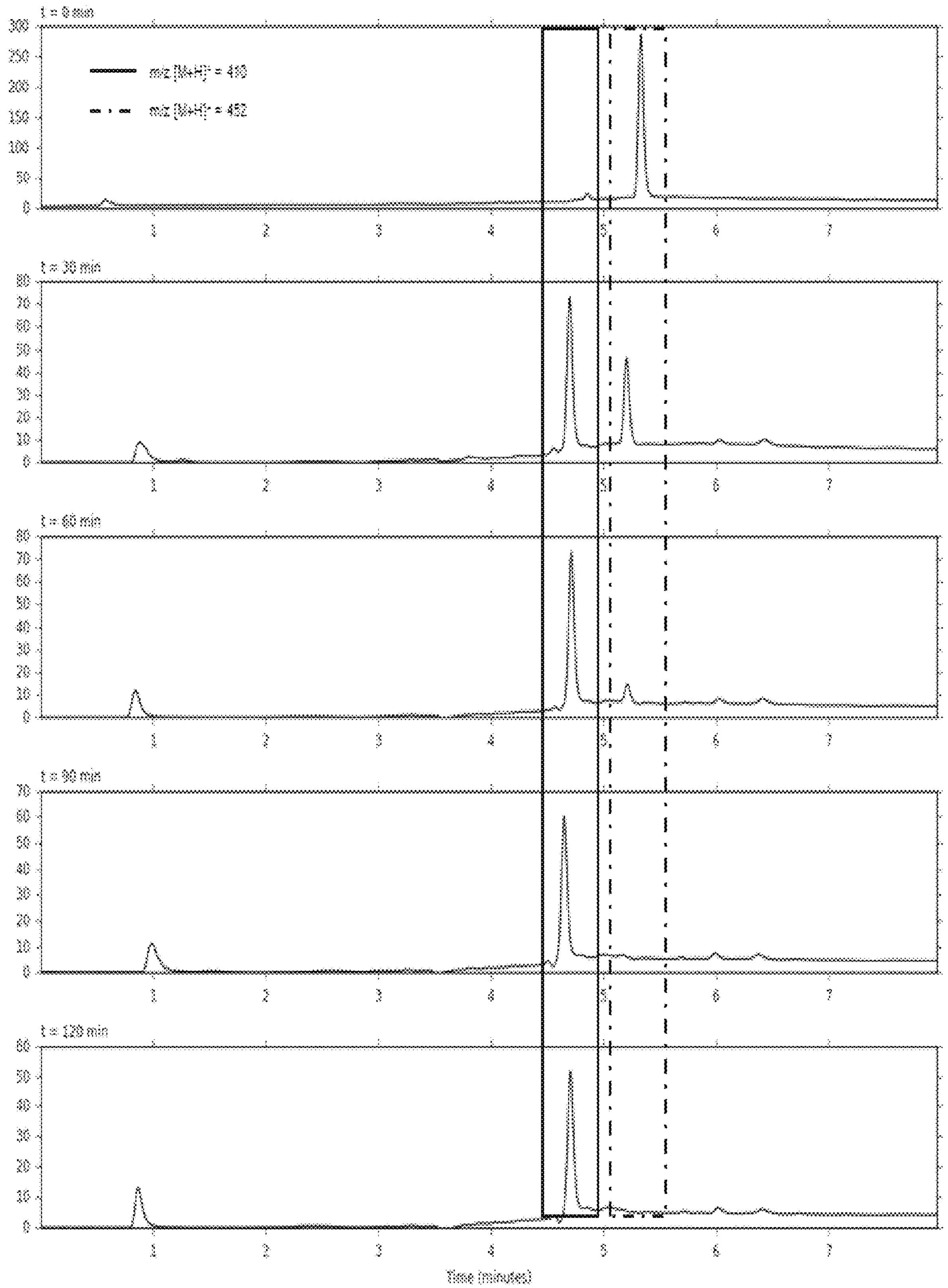
FIG. 1 illustrates the HPLC profiles over time for the acetyl hydrolysis of P-21 (M=451) into the corresponding luciferin Q-12 (M=409). Obtained on an Agilent apparatus, with a 3.5 μm XDB-C18 column and a water/methanol gradient (containing 5 mM ammonium formate, from 95-5 to 5-95 in 3.5 min, 3.5 min at 5-95, and then back at 95-5 in 0.5 min), UV monitoring set at 254 nM.

A Biotage initiator 2 microwave oven was used for reactions mentioning such heating method. $^1$H NMR spectra were recorded on a Bruker Avance 400 spectrometer at 400 MHz and 100 MHz, respectively. Shifts (δ) are given in ppm with respect to the TMS signal and coupling constants (J) are given in Hertz. Column chromatography were performed either on Merck silica gel 60 (0.035-0.070 mm) or neutral alumina using a solvent pump and an automated collecting system driven by a UV detector set to 254 nm unless required otherwise. Sample deposition was carried out by absorption of the mixture to be purified on a small amount of the solid phase followed by its deposition of the top of the column. The low resolution mass spectra were obtained on an Agilent 1100 series LC/MSD system using an atmospheric electrospray ionization system and the high resolution mass spectra (HRMS) were obtained using a Waters Micromass Q-Tof with an electrospray ion source.

General procedures for the synthesis of α-aminoesters B via α-nitroesters R, preparation of nitroesters R. Step 1: preparation of the dimethylacetal. The corresponding aldehyde (0.044 mol) and trimethylorthoformate (5.8 mL, 0.053 mol) were dissolved in methanol (7.3 mL, 0.24 mol, dried over 3 A molecular sieve). To this was added the DOWEX 50WX8-100 ion-exchange resin (0.2 g) and the solution was stirred overnight under a calcium chloride-protected atmosphere. The resin was then removed by filtration, the filter washed with dry methanol and the filtrate concentrated to dryness (at 30 mbar) to yield the corresponding volatile acetal (usually not fully stable in $CDCl_3$). Step 2-condensation with ethyl nitroacetate, preparation of the nitroacrylates. In order to remove some eventual traces of water, prior to this reaction, under a calcium chloride-protected atmosphere, the nitroacetate (5.7 g, 0.042 mol) was stirred in acetic anhydride (5 mL, 0.053 mol) for 15 minutes. To this solution was added the crude acetal described above dissolved in acetic anhydride (5.1 mL, 0.053 mol) and the solution was heated at the temperature and time described in each cases below while allowing the resulting low boiling methyl acetate to distil off. This was then thoroughly concentrated to dryness to yield the crude 3-aryl-2-nitroacrylates. Step 3: reduction with sodium borohydride, preparation of the substituted nitroesters. The crude acrylate was dispersed/dissolved in isopropanol (100 ml, dried over 4 A molecular sieve). To this was added portion-wise sodium borohydride (2 g, 0.053 mol) and the suspension was heated op to reflux before allowing it to cool back to room temperature. Acetic acid was then cautiously added (3.3 mL, 0.053 mol) and the isopropanol was removed under vacuum. The crude residue was dispersed in water (100 ml) and 10% hydrochloric acid (5.7 mL, 0.0057 mol) was added to help the hydrolysis of half reacted boron hydrides. The resulting solution was extracted with ethyl acetate, the organic layer was washed with water, brine, dried over magnesium sulfate and concentrated to dryness. The residue was then purified as described in each case below to yield the corresponding α-nitroester R.

Ethyl 3-(4-fluorophenyl)-2-nitropropanoate (R-1): Obtained as an oil (2.72 g, 23% from 4-fluorobenzaldehyde) after heating at 190° C. for 4 h in the course of the condensation step and two chromatography over silica gel (cyclohexane—ethyl acetate 9/1) and (cyclohexane—dichloromethane 2/1). $^1$H NMR ($CDCl_3$): 7.21 (m, 2H), 7.02 (m, 2H), 5.32 (dd, 1H, J=5.7, 9.4), 4.30 (m, 2H), 3.56 (dd, 1H, J=9.4, 14.7), 3.47 (dd, 1H, J=5.7, 14.7), 1.31 (m, 3H). HRMS (m/z): $[M-H]^-$ calcd for $C_{11}H_{11}FNO_4$: 240.0672; found, 240.0645.

Ethyl 3-(2-methoxyphenyl)-2-nitropropanoate (R-2): Obtained as an oil (6.12 g, 53% from 2-methoxybenzaldehyde) after heating at 150° C. for 9 h in the course of the condensation step and a chromatography over silica gel (cyclohexane—ethyl acetate 95/5 to 9/1). $^1$H NMR ($CDCl_3$): 7.28 (m, 1H), 7.14 (m, 1H), 6.91 (m, 2H), 5.57 (dd, 1H, J=6.2, 9.1, 4.28 (g, 2H, J=7.1), 3.82 (s, 3H), 3.55 (dd, 1H, J=6.2, 14.1), 3.51 (dd, 1H, J=9.1, 14.1), 1.28 (t, 3H, J=7.1) HRMS: calcd for $C_{12}H_{15}NO_5Na$: 276.0848; found, 276.0831.

Ethyl 3-(3-methoxyphenyl)-2-nitropropanoate (R-3): Obtained as an oil (2.34 g, 21% from 3-methoxybenzaldehyde) after heating at 150° C. for 9 h in the course of the condensation step and a chromatography over silica gel (cyclohexane—ethyl acetate 95/5 to 9/1). $^1$H NMR ($CDCl_3$): 7.25 (t, 1H, J=7.9), 6.81 (m, 3H), 5.35 (dd, 1H, J=5.8, 9.3), 4.31 (q, 2H, J=7.2), 3.81 (s, 3H), 3.56 (dd, 1H, J=9.3, 14.7), 3.47 (dd, 1H, J=5.8, 14.7), 1.31 (t, 3H, J=7.2). HRMS: calcd for $C_{12}H_{15}NO_5Na$: 276.0848; found, 276.0831.

Ethyl 3-(4-methoxyphenyl)-2-nitropropanoate (R-4): Obtained as an oil (6.95 g, 55% from 4-methoxybenzaldehyde) after heating at 150° C. for 9 h in the course of the condensation step and a chromatography over silica gel (cyclohexane—ethyl acetate 95/5 to 9/1). $^1$H NMR ($CDCl_3$): 7.15 (m, 2H), 6.86 (m, 2H), 5.31 (dd, 1H, J=5.9, 9.5), 4.30 (m, 2H), 3.81 (s, 3H), 3.52 (dd, 1H, J=9.5, 14.6), 3.44 (dd, 1H, J=5.9, 14.6), 1.31 (L 3H, J=7.1). HRMS: calcd for $C_{12}H_{15}NO_5Na$: 276.0848; found, 276.0840.

Ethyl 3-(4-(benzyloxy)phenyl)-2-nitropropanoste (R-5): Obtained as an yellow solid (4.08 g, 51% from 4-benzyloxybenzaldehyde) after heating at 150° C. for 9 h in the course of the condensation step and a chromatography over silica gel (cyclohexane—ethyl acetate 92/8 to 9/1). $^1$H NMR ($CDCl_3$): 7.46-7.33 (m, 5H), 7.15 (m, 2H), 6.94 (m, 2H), 5.31 (dd, 1H, J=6.0, 9.3), 5.06 (s, 2H), 4.30 (m, 2H), 3.52 (dd, 1H, J=9.3, 14.6), 3.44 (dd, 1H, J=6.0, 14.6), 1.30 (t, 3H, J=7.1). HRMS: calcd for $C_{18}H_{19}NO_5Na$: 352.1161; found, 352.1150.

Ethyl 2-nitro-3-m-tolylpropanoste (R-6): Obtained as an oil (1.05 g, 16% from 3-methylbenzaldehyde) after heating at 180° C. for 8 h in the course of the condensation step and two chromatography over silica gel (cyclohexane—dichloromethane 2/1 to 1/6) and (cyclohexane—ethyl acetate 97/3). $^1$H NMR ($CDCl_3$): 7.22 (m, 1H), 7.60 (m, 1H), 7.01 (m, 2H), 5.33 (dd, 1H, J=5.8, 9.4), 4.30 (q, 2H, J=7.1), 3.54 (dd, 1H, J=9.4, 14.6), 3.46 (dd, 1H, J=5.8, 14.6), 2.34 (s, 3H), 1.30 (t, 3H, J=7.1). HRMS (m/z): $[M-H]^-$ calcd for $C_{12}H_{14}NO_4$: 236.0923; found, 236.0983.

Ethyl 3-(furan-2-yl)-2-nitropropanoate (R-7): In the present case, the nitroacrylate was prepared directly from furfural as previously described. (*Org. Biomol. Chem.,* 2012, 524) Obtained as an oil (5.04 g, 39% from furfural) after a chromatography over silica gel (dichloromethane-methanol 99/1). $^1$H NMR ($CDCl_3$): 7.36 (m, 1H), 6.32 (m, 1H), 6.19 (m, 1H), 5.44 (dd, 1H, J=5.5, 9.3), 4.32 (q, 2H, J=7.2), 3.66 (dd, 1H, J=9.3, 15.7), 3.54 (dd, 1H, J=5.5, 15.7), 1.32 (t, 3H, J=7.2) HRMS: calcd for $C_9H_{11}NO_5Na$: 236.0535; found, 236.0522.

Ethyl 3-(5-methylfuran-2-yl)-2-nitropropanoate (R-8): Obtained as an oil (3.44 g, 60% from 5-methylfurfural) after heating at 140° C. for 2 h in the course of the condensation step and a chromatography over silica gel (cyclohexane—dichloromethane 3/2). $^1$H NMR ($CDCl_3$): 6.02 (d, 1H, J=3.0), 5.86 (dd, 1H, J=3.0, 0.9), 6.19 (m, 1H), 5.40 (dd, 1H, J=5.5, 9.3), 4.30 (q, 2H, J=7.1), 3.58 (dd, 1H, J=93, 15.7), 3.45 (dd, 1H, J=5.5, 15.7), 2.23 (s, 3H), 1.30 (t, 3H, J=7.1). HRMS: calcd for $C_{10}H_{13}NO_5Na$: 250.0691; found, 250.0682.

Ethyl 3-(4,5-dimethylfuran-2-yl)-2-nitropropanoate (R-9). As seen by $^1$H NMR, this compound was obtained after heating at 140° C. for 2 h in the course of the condensation step and a chromatography over silica gel (cyclohexane—dichloromethane 2/1) as an oil also containing 50 mol % of ethyl-3-(4,5-dimethylfuran-2-yl)acrylate (1.94 g). This was used without further purification in the next step.

Ethyl 3-(5-ethylfuran-2-yl)-2-nitropropanoate (R-10): Obtained as an oil (3.68 g, 39% from 5-ethylfurfural) after heating at 140° C. for 2 h in the course of the condensation step and two chromatography over silica gel (cyclohexane—dichloromethane 2/1 to 1/6) and (cyclohexane—ethyl acetate 97/3) $^1$H NMR ($CDCl_3$): 6.05 (d, 1H, J=3.0), 5.88 (m, 1H), 6.19 (m, 1H), 5.42 (dd, 1H, J=5.7, 9.1), 4.31 (q, 2H, J=7.0), 3.61 (dd, 1H, J=9.1, 15.7), 3.48 (dd, 1H, J=5.7, 15.7), 2.60 (q, 2H, J=7.0), 1.32 (t, 3H, J=7.0), 1.21 (t, 3H, J=7.5). HRMS (m/z): $[M-H]^-$ calcd for $C_{11}H_{14}NO_5$: 240.0872; found, 240.0857.

Ethyl 3-(furan-3-yl)-2-nitropropanoate (R-11): Obtained as an oil (0.74 g, 34% from furan-3-carbaldehyde) from ethyl (E)-3-(furan-3-yl)-2-nitroacrylate prepared as described before (Org. Biomol. Chem., 2012, 524), after a chromatography over silica gel (cyclohexane—ethyl acetate 95/5 to 9/1). $^1$H NMR ($CDCl_3$): 7.40 (m, 1H), 7.34 (m, 1H), 6.30 (m, 1H), 5.26 (dd, 1H, J=5.3, 9.4), 4.32 (q, 2H, J=7.1), 3.39 (dd, 1H, J=9.4, 15.2), 3.32 (dd, 1H, J=5.4, 15.2), 1.32 (t, 3H, J=7.1). HRMS: calcd for $C_9H_{11}NO_5Na$, 236.0559; found, 236.0567.

Ethyl 2-nitro-3-(thiophen-2-yl)propanoate (R-12): Obtained as an oil (3.43 g, 33% from thiophene-2-carbaldehyde) after heating at 140° C. for 4 h in the course of the condensation step and two chromatography over silica gel (cyclohexane—dichloromethane 3/2) and (cyclohexane—ethyl acetate 97/3 to 95/5). $^1$H NMR ($CDCl_3$): 7.23 (dd, 1H, J=1.3, 5.1), 6.96 (m, 1H), 6.92 (m, 1H), 5.35 (dd, 1H, J=5.6, 9.2), 4.32 (q, 2H, J=7.1), 3.83 (dd, 1H, J=9.2, 15.4), 3.70 (dd, 1H, J=5.6, 1534), 1.32 (t, 3H, J=7.1). HRMS (m/z): $[M-H]^-$ calcd for $C_9H_8NO_4$, 228.0331; found, 228.0348.

General procedure for the reduction of the α-nitroesters R. The considered α-nitroester (0.023 mol) was dissolved in ethanol (75 ml) and 37% hydrochloric acid (29 mL, 0.34 mol) and cooled to ° C. Powdered zinc (9.05 g, 0.13 mol, less than 10 μm size) was added by portion. This was left to stir overnight, the ethanol was removed under vacuum, the residue was dispersed in water and ethyl acetate, the suspension was made basic with 22% ammonia, this was extracted with ethyl acetate, the organic layer was washed with water, brine, dried over sodium carbonate and concentrated to dryness to yield the amino ester which was in some cases further purified as described below:

Ethyl 2-amino-3-(4-fluorophenyl)propanoate (B-1): Obtained as an oil (1.95 g, 94%). $^1$H NMR ($CDCl_3$): 7.18 (m, 3H), 7.01 (m, 1H), 4.17 (q, 2H, J=7.1), 3.68 (dd, 1H, J=5.5, 7.6), 3.04 (dd, 1H, J=5.5, 13.6), 2.86 (dd, 18, J=7.6, 13.6), 1.48 (s, 2H), 1.25 (t, 3H, J=7.1) HRMS: calcd for $C_{11}H_{15}FNO_2$: 212.1087; found, 212.1069.

Ethyl 2-amino-3-(2-methoxyphenyl)propanoate (B-2): Obtained as an oil (5.16 g, 90%). $^1$H NMR ($CDCl_3$): 7.23 (m, 1H), 7.14 (m, 1H), 6.86-6.92 (m, 2H), 4.19 (q, 2H, J=7.2), 3.84 (s, 3H), 3.81 (dd, 1H, J=5.8, 8.1), 3.10 (dd, 1H, J=5.8, 13.3), 2.84 (dd, 1H, J=8.1, 13.3), 1.51 (s, 2H), 1.31 (t, 3H, J=7.1). HRMS: calcd for $C_{12}H_{18}NO_3$: 224.1287; found, 224.1218.

Ethyl 2-amino-3-(3-methoxyphenyl)propanoate (B-3): Obtained as an oil (0.81 g, 92%). $^1$H NMR ($CDCl_3$): 7.23 (t, 1H, J=7.9), 6.77-6.82 (m, 3H), 4.19 (q, 2H, J=7.1), 3.81 (s, 3H), 3.73 (dd, 1H, J=5.2, 7.9), 3.08 (dd, 1H, J=5.2, 13.5), 2.84 (dd, 1H, J=7.9, 13.5), 1.51 (s, 2H), 1.31 (t, 3H, J=7.1). HRMS: calcd for $C_{12}H_{18}NO_3$: 224.1287; found, 224.1260.

Ethyl 2-amino-3-(4-methoxyphenyl)propanoate (B-4): Obtained as an oil (4.2 g, 95%). $^1$H NMR ($CDCl_3$): 7.15 (m, 2H), 6.88 (m, 2H), 4.19 (q, 2H, J=7.1), 3.80 (s, 3H), 3.68 (dd, 1H, J=5.3, 7.7), 3.03 (dd, 1H, J=5.3, 13.7), 2.83 (dd, 1H, J=7.7, 13.7), 1.48 (s, 2H), 1.31 (t, 3H, J=7.1). HRMS: calcd for $C_{12}H_{18}NO_3$: 224.1287; found, 224.1238.

Ethyl 2-amino-3-(4-(benzyloxy)phenyl)propanoate (B-5): Obtained as an oil (2.65 g, 67%) after a chromatography over silica gel (dichloromethane—ethanol 96/4). $^1$H NMR ($CDCl_3$): 7.46-7.33 (m, 5H), 7.13 (m, 2H), 6.93 (m, 2H), 5.06 (s, 2H), 4.18 (q, 2H, J=7.1), 3.68 (dd, 1H, J=5.3, 7.8), 3.04 (dd, 1H, J=5.3, 13.7), 2.84 (dd, 1H, J=7.8, 13.7), 1.47 (s, 2H), 1.27 (t, 3H, J=7.1). HRMS: calcd for $C_{18}H_{22}NO_3$: 300.1600; found, 300.1591.

Ethyl 2-amino-3-(m-tolyl)propanoate (B-6): Obtained as an oil (0.73 g, 80%). $^1$H NMR ($CDCl_3$): 7.22 (m, 1H), 7.02 (m, 3H), 4.19 (q, 2H, J=7.1), 3.72 (dd, 1H, J=8.0, 5.2), 3.07 (dd, 1H, J=13.6, 5.2), 2.84 (dd, 1H, J=13.6, 8.0), 2.34 (s, 3H), 1.50 (s, 2H), 1.27 (t, 3H, J=7.1). HRMS: calcd for $C_{12}H_{18}NO_2$, 208.1338; found, 208.1334.

Ethyl 2-amino-3-(furan-2-yl)propanoate (B-7): Obtained as an oil (4.84 g, 94%). $^1$H NMR ($CDCl_3$): 7.34 (dd, 1H, J=0.8, 1.9), 6.30 (dd, 1H, J=1.9, 3.2), 6.12 (m, 1H), 4.20 (m, 2H), 3.80 (dd, 1H, J=7.3, 5.2), 3.10 (dd, 1H, J=14.9, 5.2), 2.99 (dd, 1H, J=14.9, 7.3), 1.59 (s, 2H), 1.28 (t, 3H, J=7.2). HRMS: calcd for $C_9H_{14}NO_3$, 184.0974; found, 184.0955.

Ethyl 2-amino-3-(5-methylfuran-2-yl)propanoate (B-8): Obtained as an oil (1.26 g, 75%). $^1$H NMR ($CDCl_3$): 5.97 (d, 1H, J=2.9), 5.85 (dd, 1H, J=2.9, 0.9), 4.24-4.14 (m, 2H), 3.72 (dd, 1H, J=7.3, 5.0), 3.03 (dd, 1H, J=14.9, 5.0), 2.91 (dd, 1H, J=14.9, 7.3), 2.24 (s, 3H), 1.57 (s, 2H), 1.27 (t, 3H, J=7.1). HRMS: calcd for $C_{10}H_{16}NO_3$, 198.1130; found, 198.1089.

Ethyl 2-amino-3-(4,5-dimethylfuran-2-yl)propanoate (B-9): Obtained as an oil (0.6 g, 7% from 4,5-dimethylfurfural). $^1$H NMR ($CDCl_3$): 5.88 (s, 1H), 4.20 (m, 2H), 3.00 (dd, 1H, J=4.8, 14.9), 2.87 (dd, 1H, J=7.5, 14.9), 2.15 (s, 3H), 1.89 (s, 3H), 1.64 (s, 2H), 1.29 (t, 3H, J=7.1). HRMS: calcd for $C_{11}H_{18}NO_3$, 212.1287, found, 212.1246.

Ethyl 2-amino-3-(5-ethylfuran-2-yl)propanoate (B-10): Obtained as an oil (1.83 g, 56%) after a chromatography over silica gel (dichloromethane—ethanol 98/2 to 97/3). $^1$H NMR ($CDCl_3$): 6.00 (d, 1H, J=3.0), 5.87 (d, 1H, J=3.0), 4.20 (m, 2H), 3.74 (dd, 1H, J=7.2, 5.1), 3.05 (dd, 1H, J=14.9, 5.1), 2.94 (dd, 1H, J=14.9, 7.2), 2.24 (q, 2H, J=7.5), 1.58 (s, 2H), 1.29 (t, 3H, J=7.2), 1.21 (t, 3H, J=7.5). HRMS: calcd for $C_9H_{14}NO_3$, 212.1287; found, 212.1261.

Ethyl 2-amino-3-(furan-3-yl)propanoate (B-11): Obtained as an oil (1.4 g, 88%). $^1$H NMR ($CDCl_3$): 7.38 (m, 1H), 7.31 (m, 1H), 6.28 (m, 1H), 4.20 (q, 2H, J=7.2), 3.65 (dd, 1H, J=7.0, 5.3), 2.90 (dd, 1H, J=14.3, 5.3), 2.79 (dd, 1H, J=14.3, 7.0), 1.57 (s, 2H), 1.29 (t, 3H, J=7.2). HRMS: calcd for $C_9H_{14}NO_3$, 184.0974; found, 184.0951.

Ethyl 2-amino-3-(thiophen-2-yl)propanoate (B-12): Obtained as an oil (2.5 g, 58%) after dilution of the oil in ethyl acetate, extraction with 1N hydrochloric acid and, upon basification of this aqueous phase with 22% ammonia an extraction with ethyl acetate. The organic layer was then washed with brine, dried over sodium carbonate and concentrated to dryness. $^1$H NMR ($CDCl_3$): 7.19 (dd, 1H, J=1.1, 5.1), 6.96 (dd, 1H, J=33, 5.1), 6.88 (m, 1H), 4.21 (q, 2H, J=7.1), 3.72 (dd, 1H, J=7.2, 4.8) 3.30 (dd, 1H, J=14.7, 4.8), 3.17 (dd, 1H, J=14.7, 7.2), 1.57 (s, 2H), 1.29 (t, 3H, J=7.1). HRMS: calcd for CHINOS, 200.0745; found, 200.0726.

General procedures for the synthesis of α-aminoesters B via α-oxime esters S, preparation of α-oxime esters S. Step 1, Knoevenagel condensation of diethyl malonate and aldehyde, preparation of substituted diethyl 2-methylenemalonate. Under an inert atmosphere, the considered aldehyde (0.048 mol), diethyl malonate (7.54 g, 0.048 mol), acetic acid (0.14 g, 0.002 mol), piperdine (0.2 g, 0.002 mol) and 4λ molecular sieve (15 g) were heated in dry ethanol (20 mL, dried over 4 Angstrom molecular sieves) without stirring at 60° C. for 10 hours and $^1$H NMR spectra of a crude sample usually pointed out the complete disappearance of the starting aldehyde. Step 2, reduction of the substituted diethyl 2-methylenemalonate, preparation of the substituted malonate. The suspension containing the 4λ molecular sieve described above was filtered, the 4 Å molecular sieve washed with dry ethanol. To the resulting ethanol solution (160 mL total volume) 10% palladium over charcoal (1.27 g, 0.001 mol) was added and this was stirred overnight under a hydrogen atmosphere (1 atm). The resulting suspension was filtered, the filtrate concentrated to dryness to give fairly pure substituted malonate. Alternatively, as specified in some of the following examples, this hydrogenation was achieved using sodium boron hydride (1.1 eq.). Two procedures were devised, the first one proceeding by the addition of sodium borohydride at 0° C. in small portions to an ethanolic solution and stirring at 0° C. for two hours before working up, the second one by adding sodium boron hydride at 4° C. and stirring overnight at this temperature before using the following work up procedure. This was followed by its acidification with acetic acid (1.2 equivalent), dilution in an excess of water and extraction with ethyl acetate.

The organic layer was then washed with water, brine, dried over magnesium sulfate and concentrated to dryness to yield the crude substituted malonate. Step 3, preparation of α-oxime esters from the substituted malonates. The crude substituted malonate (0.0422 mol) was dissolved in ethanol (60 mL, dried over 4 Å molecular sieve) and cooled to 0° C. A 21% solution of sodium ethoxide in ethanol was added (18.4 ml, 0.0493 mol) followed by a slow addition of isoamyl nitrite (6.2 mL, 0.046 mol). This was stirred at 0° C. for two hours, made slightly acid by the addition of 1N hydrochloric acid and diluted in water (200 mL). This solution was extracted with ethyl acetate, the organic layer was washed with water, brine, dried over magnesium sulfate and concentrated to dryness to yield the crude α-oxime esters further purified as described below.

Ethyl 3-cyclopentyl-2-(hydroxyimino)propanoate (S-1): Obtained as a white solid (2.50 g, 35% from cyclopentanecarbaldehyde) after a chromatography over silica gel (cyclohexane—ethyl acetate 85/15). $^1$H NMR ($CDCl_3$): 9.51 (s, 1H), 4.32 (q, 2H, J=7.0), 2.67 (d, 2H, J=7.6), 2.20 (m, 1H), 1.70 (m, 4H), 1.53 (m, 2H), 1.36 (t, 3H, J=7.0), 1.25 (m, 2H). HRMS: calcd for $C_{10}H_{17}NO_3Na$: 222.1106; found, 222.1164.

Ethyl 3-cyclohexyl-2-(hydroxyimino)propanoate (S-2): Obtained as a white solid (4.34 g, 50% from cyclohexanecarbaldehyde) after a chromatography over silica gel (cyclohexane—ethyl acetate 9/1). $^1$H NMR ($CDCl_3$): 9.85 (s, 1H), 4.31 (q, 2H, J=7.2), 2.55 (d, 2H, J=7.1), 1.70 (m, 6H), 1.36 (t, 3H, J=7.0), 1.20 (m, 3H), 1.04 (m, 2H). HRMS: calcd for $C_{11}H_{19}NO_3Na$: 236.1263; found, 236.1291.

Ethyl 3-(bicyclo[2.2.1]heptan-2-yl)-2-(hydroxyimino)propanoate (S-3): Obtained as an oily mixture of diastereoisomers (1.39 g, 25% from the two isomers of norbornane-2-carboxaldehyde) after two chromatography over silica gel (cyclohexane—ethyl acetate 7/1 to 4/1) and (dichloromethane—ethanol 99/1). $^1$H NMR ($CDCl_3$): 4.33 (m, 4H, arbitrary value), 2.66 (m, 3.2H), 2.50 (m, 0.9H), 2.22 (m, 3.3H), 2.08 (m, 1.2H), 1.96 (m, 0.7H), 1.85 (m, 0.8H), 1.73 (m, 2.8H), 1.48 (m, 4.5H), 1.34 (m, 10.8H), 1.15 (m, 4.5H), 0.79 (m, 1.3H). HRMS: calcd for $C_{12}H_{19}NO_3Na$, 248.1263; found, 248.1265.

Ethyl 2-(hydroxyimino)-3-(tetrahydrofuran-2-yl)propanoate (S-4): This compound was obtained when using 10% Pd/C for the hydrogenation step and letting it run 48 hours, Out a 12.8 g batch, only a sample was purified by a chromatography (dichloromethane—ethanol 97/3) to give a white solid. $^1$H NMR ($CDCl_3$): 9.74 (s, 1H), 4.32 (q, 2H, J=7.2), 4.28 (m, 1H), 3.90 (m, 1H), 3.74 (m, 1H), 2.96 (dd, 1H, J=5.5, 12.8), 2.80 (dd, 1H, J=5.9, 12.8), 1.88 (m, 3H), 1.62 (m, 1H), 1.35 (t, 3H, J=7.2). HRMS: calcd for $C_9H_{15}NO_4Na$: 224.0899; found, 224.0874.

Ethyl 2-(hydroxyimino)-3-(3-methylthiophen-2-yl)propanoate (S-5): Obtained as a yellow solid (1.38 g, 32% from 3-methylthiophene-2-carbaldehyde), using sodium boron hydride at 0° C., after a chromatography over silica gel (cyclohexane—ethyl acetate 5/1). $^1$H NMR ($CDCl_3$): 9.88 (s, 1H), 7.06 (d, 1H, J=5.1), 6.77 (d, 1H, J=5.1), 4.33 (q, 2H, J=7.2), 4.09 (s, 2H), 2.28 (s, 3H), 1.36 (t, 3H, J=7.2) HRMS: calcd for $C_{10}H_{13}NO_3SNa$: 250.0514; found, 250.0513.

Ethyl 3-(5-ethylthiophen-2-yl)-2-(hydroxyimino)propanoate (S-6): Obtained as a oil (1.36 g, 29% from 5-ethylthiophene-2-carbaldehyde), using sodium boron hydride at 0° C., after a chromatography over silica gel (cyclohexane—ethyl acetate 5/1). $^1$H NMR ($CDCl_3$): 10.06 (s, 1H), 6.75 (m, 1H), 6.59 (m, 1H), 4.34 (q, 2H, J=7.2), 4.09 (s, 2H), 2.78 (m, 2H), 1.38 (t, 3H, J=7.2), 1.28 (t, 3H, J=7.5). HRMS: calcd for $C_{10}H_{13}NO_3SNa$: 264.0670; found, 264.0676.

Ethyl 3-(4,5-dimethylthiophen-2-yl)-2-(hydroxyimino)propanoate (S-7): Obtained as an oil (0.69 g, 31% from 4,5-dimethylthiophene-2-carbaldehyde), using sodium boron hydride at 0° C., after a chromatography over silica gel (cyclohexane—ethyl acetate 5/1). $^1$H NMR ($CDCl_3$): 9.77 (s, 1H), 6.62 (s, 1H), 4.34 (q, 2H, J=7.2), 4.03 (s, 2H), 2.28 (s, 3H), 2.06 (s, 3H), 1.37 (t, 3H, J=7.2). HRMS: calcd for $C_{11}H_{15}NSO_3Na$: 264.0670; found, 264.0656.

Ethyl 2-(hydroxyimino)-3-(5-(trifluoromethyl)furan-2-yl)propanoate (S-8): Obtained as a white solid (0.62 g, 36% from 5-trifluoromethylfuran-2-carbaldehyde), using sodium boron hydride at 0° C., after two chromatographies over silica gel (dichloromethane—ethanol 99/1) and (cyclohexane—ethyl acetate 5/1). $^1$H NMR ($CDCl_3$): 9.70 (s, 1H), 6.72-6.64 (m, 1H), 6.21-6.15 (m, 1H), 4.33 (q, 2H, J=7.1), 4.08 (s, 2H), 1.34 (t, 3H, J=7.1). HRMS: calcd for $C_{16}H_{11}F_3NO_4$: 266.0640; found, 266.0584.

Ethyl 2-(hydroxyimino)-3-(pyridin-2-yl)propanoate (S-9): Obtained as a solid (4.94 g, 49% from picolinaldehyde) after a chromatography (dichloromethane—ethanol 97/3). $^1$H NMR ($CDCl_3$): 10.53 (s, 1H), 8.53 (m, 1H), 7.61 (dt, 1H, J=1.8, 7.5), 7.29 (m, 1H), 7.17 (m, 1H), 4.29 (q, 2H, J=7.1), 4.23 (s, 2H), 1.30 (t, 3H, J=7.1). HRMS: calcd for $C_{10}H_{13}N_2O_3$: 209.0926; found, 209.0857.

Ethyl 2-(hydroxyimino)-3-(pyridin-3-yl)propanoate (S-10): Obtained as a tan solid (7.19 g, 43% from nicotinaldehyde) after a chromatography (dichloromethane—ethanol 97/3 to 96/4). $^1$H NMR ($CDCl_3$): 12.79 (s, 1H), 8.65 (m, 1H), 8.46 (dd, 1H, J=1.6, 4.9), 7.74 (m, 1H), 7.22 (m, 1H), 4.30 (q, 2H, J=7.1), 4.01 (s, 2H), 132 (t, 3H, J=7.1). HRMS: calcd for $C_{10}H_{13}N_2O_3$: 209.0926; found, 209.0921.

Ethyl 2-(hydroxyimino)-3-(2-(trifluoromethyl)phenyl) propanoate (S-11): Obtained as a white solid (1.05 g, 33% from 2-(trifluoromethyl)benzaldehyde), 90% pure) after a chromatography over silica gel (cyclohexane—ethyl acetate 4/1 to 3/1). $^1$H NMR ($CDCl_3$): 9.66 (s, 1H), 7.68 (d (br), 1H, J=7.5), 7.45 (m, 1H), 7.34 (m, 1H), 7.16 (d (br), 1H, J=7.7), 4.29 (q, 2H, J=7.2), 4.23 (s, 2H), 1.27 (t, 3H, J=7.2). HRMS: calcd for $C_{12}H_{12}F_3NO_3Na$: 298.0667; found, 298.0660.

Ethyl 2-(hydroxyimino)-3-(3-(trifluoromethyl)phenyl) propanoate (S-12): Obtained as a white solid (1.3 g, 41% from 3-(trifluoromethyl)benzaldehyde)) after a chromatography over silica gel (cyclohexane—ethyl acetate 4/1 to 3/1). VHI NMR ($CDCl_3$): 9.87 (s, 1H), 7.62 (s (br), 1H), 7.50 (m, 2H), 7.42 (m, 1H), 4.32 (q, 2H, J=7.0), 4.05 (s, 2H), 1.35 (t, 3H, J=7.0). HRMS: calcd for $C_{12}H_{12}F_3NO_3Na$: 298.0667; found, 298.0643.

Ethyl 2-(hydroxyimino)-3-(4-(trifluoromethyl)phenyl) propanoate (S-13): Obtained as a white solid (4.61 g, 62% from 4-(trifluoromethyl)benzaldehyde)) after a chromatography over silica gel (dichloromethane—ethanol 99/1). $^1$H NMR ($CDCl_3$): 9.76 (s, 1H), 7.55 (m, 2H), 7.45 (m, 2H), 4.32 (q, 2H, J=7.1), 4.05 (s, 2H), 1.35 (t, 3H, J=7.1). HRMS: calcd for $C_{12}H_{13}F_3NO_3$: 276.0847; found, 276.0834.

Ethyl-3-(4-chlorophenyl)-2-(hydroxyimino)propanoate (S-14): Obtained as a white solid (2.31 g, 37% from 4-chlorobenzaldehyde), using sodium boron hydride at 4° C. overnight, after a chromatography over silica gel (cyclohexane—ethyl acetate 4/1). $^1$H NMR ($CDCl_3$): 9.70 (s, 1H), 7.27 (m, 4H), 4.31 (q, 2H, J=7.1), 3.96 (s, 2H), 1.35 (t, 3H, J=7.1). HRMS: calcd for $C_{11}H_{14}ClNO_2Na$, 264.0403; found, 264.0437.

Ethyl 3-(2-chlorophenyl)-2-(hydroxyimino)propanoate (S-15): Out of a 13.1 g batch, using sodium boron hydride at 4° C., only a 0.5 g sample was purified by a chromatography over silica gel (cyclohexane—ethyl acetate 4/1) and a recrystallization in cyclohexane to give a white solid (0.36 g). $^1$H NMR ($CDCl_3$): 9.47 (s, 1H), 7.38 (m, 1H), 7.18 (m, 3H), 4.30 (q, J=7.1 Hz, 2H), 4.13 (s, 2H), 1.31 (t, J=7.1 Hz, 3H). HRMS: calcd for $C_{11}H_{12}ClNO_3Na$: 264.0403; found, 264.0401.

Ethyl-3-(4-bromophenyl)-2-(hydroxyimino)propanoate (S-16): Obtained as a white solid (1.43 g, 42% from 4-bromobenzaldehyde), using sodium boron hydride at 4° C. overnight, after a chromatography over silica gel (cyclohexane—ethyl acetate 4/1). $^1$H NMR ($CDCl_3$): 9.70 (s, 1H), 7.42 (m, 2H), 7.22 (m, 2H), 4.31 (q, 2H, J=7.1), 3.96 (s, 2H), 1.32 (t, 3H, J=7.1). HRMS: calcd for $C_{11}H_{13}BrNO_3$, 286.0079; found, 286.0056.

Ethyl 3-(2-fluorophenyl)-2-(hydroxyimino)propanoate (S-17): Obtained as a white solid (3.11 g, 57% from 2-fluorobenzaldehyde), after a chromatography over silica gel (cyclohexane—ethyl acetate 4/1). $^1$H NMR ($CDCl_3$): 10.20 (s, 1H), 7.22 (m, 2H), 7.05 (m, 2H), 4.30 (q, 2H, J=7.1), 4.04 (s, 2H), 1.31 (t, 3H, J=7.1). HRMS: calcd for $C_{11}H_{12}FNO_3Na$: 248.0699; found, 248.0704.

Ethyl 3-(3-fluorophenyl)-2-(hydroxyimino)propanoate (S-18): Obtained as a while solid (9.46 g, 65% from 3-fluorobenzaldehyde) after a chromatography (cyclohexane—ethyl acetate 5/1). $^1$H NMR ($CDCl_3$): 10.02 (s, 1H), 7.25 (m, 1H), 7.10 (m, 1H), 7.06 (m, 1H), 6.92 (m, 1H), 4.32 (q, 2H, J=7.2), 3.99 (s, 2H), 3.74 (m, 1H), 1.35 (t, 3H, J=7.2). HRMS: calcd for $C_{11}H_{12}FNO_3Na$: 248.0699; found, 248.0699.

Ethyl 3-(2,4-difluorophenyl)-2-(hydroxyimino)propanoate (S-19): Obtained as a white solid (2.21 g, 50% from 2,4-difluorobenzaldehyde) after a chromatography (cyclohexane—ethyl acetate 6/1). $^1$H NMR ($CDCl_3$): $^1$H NMR ($CDCl_3$): 9.72 (s, 1H), 7.22 (m, 1H), 6.80 (m, 2H), 4.30 (q, 2H, J=7.1), 3.98 (s, 2H), 1.33 (t, 3H, J=7.1). HRMS: calcd for $C_{11}H_{11}F_2NO_3Na$: 266.0605; found, 266.0601.

Ethyl 2-(hydroxyimino)-3-(o-tolyl)propanoate (S-20): Obtained as a white solid (3.38 g, 61% from 2-methylbenzaldehyde) after a chromatography over silica gel (cyclohexane—ethyl acetate 4/1). $^1$H NMR ($CDCl_3$): 10.09 (s, 1H), 7.16 (m, 4H), 4.28 (q, 2H, J=7.1), 4.00 (s, 2H), 2.41 (s, 3H), 1.31 (t, 3H, J=7.1). HRMS: calcd for $C_{12}H_{15}NO_3Na$: 244.0950; found, 244.0942.

Ethyl 2-(hydroxyimino)-3-(p-tolyl)propanoate (S-21): Obtained as a white solid (3.31 g, 60% from 4-methylbenzaldehyde) after a chromatography over silica gel (cyclohexane—ethyl acetate 4/1). $^1$H NMR ($CDCl_3$): 10.07 (s, 1H), 7.24 (m, 2H), 7.11 (m, 2H), 4.31 (q, 2H, J=7.1), 3.97 (s, 2H), 2.35 (s, 3H), 1.35 (t, 3H, J=7.1). HRMS: calcd for $C_{12}H_{15}NO_3Na$: 244.0950; found, 244.0944.

Ethyl 2-(hydroxyimino)-3-(4-isopropylphenyl)propanoate (S-22): Obtained as a solid (2.04 g, 48% from 4-isopropylbenzaldehyde) after a chromatography over silica gel (cyclohexane—ethyl acetate 5/1). $^1$H NMR ($CDCl_3$): 9.74 (s, 1H), 7.26-7.22 (m, 2H), 7.16-7.11 (m, 2H), 4.29 (q, 2H, J=7.1), 3.95 (s, 2H), 2.87 (hept, 1H, J=6.9), 1.32 (t, 3H, J=7.1), 1.23 (d, 6H, J=6.9). HRMS: calcd for $C_{14}H_{19}NO_3Na$, 272.1263; found, 272.1258.

Additional Synthesis α-Oxime Esters S, Via Carbon-Carbon Coupling Reactions

Preparation ethyl 3-(5-cyclopropylfuran-2-yl)-2-(hydroxyimino)propanoate (S-23). Step 1, synthesis of diethyl 2-((5-bromofuran-2-yl)methylene)malonate. Diethyl 2-(furan-2-ylmethylene)malonate (*Coll. Czech, Chem. Commun.,* 1987, 2534) (2 g, 8.39 mmol) was dispersed in acetic acid (20 mL) and N-bromosuccinimide (2.98 g, 16.78 mmol) was then added. This was stirred at room temperature overnight, diluted in ethyl acetate, washed extensively with water, brine, dried over magnesium sulfate and concentrated to dryness. The residue was purified by a chromatography over silica gel (cyclohexane—ethyl acetate 9/1) to give the brominated derivative as an orange solid (1.1 g, 41%). $^1$H NMR ($CDCl_3$): $^1$H NMR ($CDCl_3$): 7.35 (s, 1H), 6.71 (d, 1H, J=3 S), 6.44 (d, 1H, J=3.5), 4.41 (q, 2H, J=7.1), 4.29 (q, 2H, J=7.1), 1.41 (t, 3H, J=7.1), 1.33 (t, 3H, J=7.1). HRMS: calcd for $C_{12}H_{13}BrO_5Na$, 338.9844; found, 338.9868. Alternatively, a Knoevenagel condensation between 5-bromofurfural and diethylmalonate using the conditions described above also gave this compound (4.72 g, 87%). Step 2: synthesis of diethyl 2-((5-cyclopropylfuran-2-yl)methylene) malonate: Diethyl 2-((5-bromofuran-2-yl)methylene)malonate (4.7 g, 14.8 mmol), cyclopropylboronic acid (1.66 g, 19.3 mol) and cesium carbonate (18.84 g, 57.8 mmol) were dispersed in a 95/5 mixture of toluene and water (120 mL).

This was degassed by blowing a gentle stream of argon into the suspension, [1,1'-bis(diphenylphosphino)ferrocene] dichloropalladium complexed with dichloromethane (0.30 g, 0.36 mmol) was added and this was heated to reflux under argon for 50 minutes. The resulting dark solution was diluted in ethyl acetate, washed with water, brine, dried over magnesium sulfate and concentrated to dryness. The residue was purified by a chromatography over silica gel (cyclohexane—ethyl acetate 8/1) to give the cyclopropyl-bearing derivative as an oil (3.12 g, 75%). $^1$H NMR ($CDCl_3$): 7.32 (s, 1H), 6.65 (d, 1H, J=3.4), 6.09 (d, 1H, J=3.4), 4.37 (q, 2H, J=7.1), 4.25 (q, 2H, J=7.1), 1.89 (tt, 1H, J=8.4, 5.0), 1.37 (t, 3H, J=7.1), 1.30 (t, 3H, J=7.1), 1.01-0.93 (m, 2H), 0.88-0.79 (m, 2H). HRMS: calcd for $C_{15}H_{18}O_5Na$, 301.1052; found, 301.1034.

Step 3 and 4: synthesis of ethyl 3-(5-cyclopropylfuran-2-yl)-2-(hydroxyimino)propanoate (S-23): from the precedent compound, by using the general preparation of oxime esters described above, using sodium boronhydride overnight at 4° C. for the reduction step, this compound was obtained as an orange solid (1.09 g, 44% from diethyl 2-((5-cyclopropylfuran-2-yl)methylene)malonate) after a chromatography over silica gel (cyclohexane—ethyl acetate 4/1) 3H NMR ($CDCl_3$): $^1$H NMR ($CDCl_3$): 9.42 (bs, 1H), 5.97 (m, 1H), 5.84 (d, 1H, J=8.1), 4.33 (q, 2H, J=7.1), 3.97 (s, 2H), 1.84 (m, 1H), 1.36 (t, 3H, J==7.1), 0.84 (m, 2H), 0.73 (m, 2H). HRMS (m/z): HRMS: calcd for $C_{12}H_{15}NO_4Na$, 260.0899; found, 260.0892.

Preparation of ethyl-2-(hydroxyimino)-3-(3-propylphenyl)propanoate (S-24): Step 1, preparation of diethyl 2-(4-bromobenzylidene)malonate. By using a Knoevenagel condensation between 3-bromobenzaldehyde and diethylmalonate using the conditions described above this compound was obtained as an oil which was directly used in the next step. Step 2, preparation of diethyl 2-(3-cyclopropylbenzylidene)malonate. By using the protocol described above for the preparation of diethyl 2-((5-cyclopropylfuran-2-yl)methylene)malonate, this compound was obtained as an oil (4.68 g, 60% from 3-bromobenzaldehyde) after a chromatography over silica gel (cyclohexane—ethyl acetate 95/5). $^1$H NMR ($CDCl_3$): 7.72 (s, 1H), 7.27 (m, 2H), 7.17 (m, 1H), 7.11 (m, 1H), 4.36 (q, 2H, J=7.1), 4.32 (q, 2H, J=7.1), 1.90 (m, 1H), 1.35 (t, 3H, J=7.1), 1.32 (t, 3H, J=7.1). Step 3, preparation of diethyl 2-(3-propylbenzyl)malonate. A two days-long catalytic hydrogenation with 10% palladium over charcoal as described above, gave this compound which was directly used in the final step. Step 4, an oximation reaction of the crude diethyl 2-(3-propylbenzyl)malonate using the general condition described above gave S-24 (0.2 g, 14% from diethyl 2-((5-cyclopropylfuran-2-yl) methylene)malonate) as a white solid after a chromatography over silica gel (cyclohexane—ethyl acetate 5/1). $^1$H NMR ($CDCl_3$): 9.74 (bs, 1H), 7.19 (m, 3H), 7.05 (m, 1H), 4.31 (q, 2H, J=7.2), 3.99 (s, 2H), 2.58 (m, 2H), 1.63 (m, 2H), 1.34 (t, 3H, J=7.2), 0.96 (t, 3H, J=7.3). HRMS: calcd for $C_{14}H_{19}NO_3Na$, 272.1263; found, 272.1250.

Preparation of ethyl-2-(hydroxyimino)-3-(4-propylphenyl)propanoate (S-25): By using the same procedures described for the preparation of ethyl-2-(hydroxyimino)-3-(3-propylphenyl)propanoate (S-24), this isomer was obtained (2.64 g, 56% from 4-bromobenzaldehyde) as a white solid after a chromatography over silica gel (cyclohexane—ethyl acetate 6/1). $^1$H NMR ($CDCl_3$): 9.64 (s, 1H), 7.26 (m, 2H), 7.11 (m, 2H), 4.31 (q, 2H, J=7.2), 3.98 (s, 2H), 2.57 (m, 2H), 1.64 (m, 2H), 1.34 (t, 3H, J=7.2), 0.95 (t, 3H, J=7.3) HRMS: calcd for $C_{14}H_{19}NO_3Na$, 272.1263; found, 272.1276.

Ethyl 3-(3-cyclopropylphenyl)-2-(hydroxyimino)propanoate (S-26). By using the general preparation of oxime esters described above, using sodium borohydride overnight at 4° C. for the reduction step, this compound was obtained as a colourless oil (1.72 g, 50% from diethyl 2-(3-cyclopropylbenzylidene)malonate) after a chromatography over silica gel (cyclohexane—ethyl acetate 6/1). $^1$H NMR ($CDCl_3$): 9.99 (bs, 1H), 7.20 (m, 3H), 6.91 (m, 1H), 4.31 (q, J=7.2 Hz, 2H), 3.97 (s, 2H), 2.58 (m, 2H), 1.88 (m, 1H), 1.34 (t, 3H, J=7.2), 0.96 (m, 2H), 0.69 (m, 2H). HRMS: calcd for $C_{14}H_{17}NO_3Na$, 270.1106; found, 270.1112.

Ethyl 3-(4-cyclopropylphenyl)-2-(hydroxyimino)propanoate (S-27). By using the general preparation of oxime esters described above, using sodium borohydride overnight at 4° C. for the reduction step, this compound was obtained as a pale yellow solid (1.03 g, 27% from 4-bromobenzaldehyde) after a chromatography over silica gel (cyclohexane—ethyl acetate 6/1) $^1$H NMR ($CDCl_3$): 9.31 (s, 1H), 7.22 (m, 2H), 6.99 (m, 2H), 4.29 (q, J=7.2 Hz, 2H), 3.95 (s, 2H), 1.86 (m, 1H), 1.33 (t, J=7.2 Hz, 3H), 0.93 (m, 2H), 0.67 (m, 2H). HRMS: calcd for $C_{14}H_{17}NO_3Na$, 270.1106; found, 270.1109.

Additional Synthesis α-Oxime Esters Using Other Methods

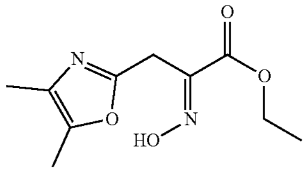 [SMILES: CCOC(=O)/C(Cc1nc(C)c(C)o1)=N/O]

Ethyl 3-(4,5-dimethyloxazol-2-yl)-2-(hydroxyimino)propanoate (S-28): Under an inert atmosphere 2,4,5-trimethyloxazole (1.05 g, 9.44 mmol) was dissolved in dry tetrahydrofuran (10 mL). The solution was cooled to −78° C. with a dry ice bath and 2N lithium diisopropylamine in tetrahydrofuran (4.7 mL, 9.44 mmol) was added. This was stirred 5 minutes and diethyloxalate (1.28 mL, 9.92 mmol) was added and the solution was allowed to warm back to 20° C. and further stirred for 10 minutes. The solution was diluted in water, extracted with ethyl acetate, the organic layer was washed with water, brine, dried over magnesium sulfate and concentrated to dryness. The resulting oil was dissolved in ethanol (100 mL), hydroxylamine hydrochloride (2.76 g, 39.7 mmol) and dry pyridine (3.3 mL, 40.8 mmol) were added and this was heated to reflux for 6 hours. The resulting suspension was diluted in water, extracted with ethyl acetate, the organic layer was washed with water, brine, dried over magnesium sulfate and concentrated to dryness. The residue was purified by a chromatography over silica gel (cyclohexane—ethyl acetate 1/1) and the corresponding fraction was dispersed in boiling cyclohexane and filtered after cooling to yield the target oxime ester as a white powder (0.15 g, 7%). $^1$H NMR ($CDCl_3$): 11.99 (s, 1H), 4.30 (q, 2H, J=7.2), 4.08 (s, 2H), 2.20 (d, 3H, J=0.8), 2.05 (d, 3H, J=0.8), 1.31 (t, 1H, J=72). Long distance correlation experiments established the regioselectivity of the reaction. HRMS: calcd for $C_{10}H_{14}N_2O_4$, 227.1032; found, 227.1035.

Ethyl 2-(hydroxyimino)-3-phenylbutanoate (S-29): Step 1: preparation of diethyl 2-(1-phenylethylmalonate: under a calcium chloride guard diethylmalonate (5.32 g, 0.033 mol) was dissolved in dry DMF (50 mL, dried over 4 Å molecular sieves) and 60% sodium hydride in mineral oil (1.39 g, 0.0348 mol) was added portion-wise while maintaining the solution temperature at 20° C. with a water bath. This was stirred until the end of hydrogen evolution and (1-chloroethyl)benzene 4.8 ml, 0.036 mol) was added. This was stirred for 7 days, diluted in water and ethyl acetate, the organic layer was washed 5 times with water, brine, dried over magnesium sulfate and concentrated to dryness under high vacuum to remove unreacted diethylmalonate and (i-chloroethyl)benzene to give an oil (6.22 g) pure enough for the next step. Step 2: reaction with isoamylnitrite. Under an inert atmosphere, 4.68 g of the resulting oil was dissolved in dry ethanol (50 mL, dried over 4 Å molecular sieves) and cooled at 0° C. with ice. A solution of 21% sodium ethanolate in ethanol (7.7 mL, 0.0207 mol) was added followed by the isoamylnitrite (2.6 mL, 0.0194 mol). This was allowed to warm to room temperature and stirred for 16 hours. The resulting solution was then treated as described above for the general preparation of α-oxime esters and obtained as an oil (1.07 g, 14% from diethylmalonate) after a chromatography over silica gel (cyclohexane—ethyl acetate 5/1). $^1$H NMR ($CDCl_3$, for once it is a separable but slowly equilibrating mixture of the two oxime isomers): 10.69 (s, 0.2H), 9.72 (s, 0.8H), 4.82 (q, 0.8H, J=7.2), 4.21 (m, 2H), 4.02 (q, 0.2H, J=7.2), 1.68 (d, 2.4H, J=72), 1.54 (d, 0.6H, J=7.2), 1.26 (t, 2.4H, J=7.3), 1.15 (t, 0.6H, J=7.3). HRMS: calcd for $C_{12}H_{15}NO_3Na$, 244.0950; found, 244.0939.

General method for the reduction of the α-oxime esters S into α-aminoesters B. The considered substituted α-oxime ester (0.065 mol) was dissolved in ethanol (70 mL) and 37% hydrochloric acid (49 mL, 0.58 mol) and the solution was cooled to ° C. Powdered zinc (12.9 g, 0.19 mol, less than 10 μm size) was added by portion. This was left to stir for 2 hours, diluted in water, made basic with 22% ammonia, extracted with ethyl acetate, washed with water, brine and concentrated to dryness to yield the pure aminoester. If a crude oxime was used, the organic layer was counter-extracted with 1N hydrochloric acid, the acidic water phase made basic again with 22% ammonia and extracted with ethyl acetate, this organic layer washed with water, brine, dried over sodium carbonate and concentrated to dryness to yield the amino ester which was in some cases further purified as described below.

Ethyl 2-amino-3-cyclopentylpropanoate (B-13): Obtained as an oil (1.16 g, 85%). $^1$H NMR ($CDCl_3$): 4.17 (q, 2H, J=7.2), 3.42 (dd, 1H, J=5.8, 8.1), 1.93 (m, 1H), 1.80 (m, 2H), 1.75-1.48 (m, 5H), 1.27 (t, 3H, J=7.2), 1.12 (m, 2H). HRMS: calcd for $CH_{10}H_{20}NO_2$: 186.1494; found, 186.1491.

Ethyl 2-amino-3-cyclohexylpropanoate (B-14): Obtained as an oil (2.35 g, 92%). $^1$H NMR ($CDCl_3$): 4.17 (m, 2H), 3.48 (dd, 1H, J=5.8, 8.7), 1.72 (m, 5H), 1.61-137 (m, 5H), 1.28 (t, 3H, J=7.3), 1.28-1.10 (m, 3H), 0.92 (m, 2H). HRMS: calcd for $C_{11}H_{22}NO_2$: 200.1651; found, 200.1648.

Ethyl 2-amino-3-(bicyclo[2.2.1]heptan-2-yl)propanoate (B-15): Obtained as an oil (1.21 g, 92%) as a mixture of four diastereoisomers (as seen by four $^{13}$C COOEt signals). $^1$H NMR ($CDCl_3$): 4.17 (m, 2H), 3.37 (m, 1H), 2.16 (m, 1.6H), 1.91 (m, 1H), 1.75 (m, 1.6H), 1.50 (m, 5H), 1.28 (m, 5.9H), 1.10 (m, 2.4H), 0.64 (m, 0.6H). HRMS: calcd for $C_{12}H_{22}NO_2$: 212.1651; found, 212.1650.

Ethyl 2-amino-3-(tetrahydrofuran-2-yl)propanoate (B-16): Obtained as an oil (5.68 g, 36% from furfural) as a mixture of two diastereoisomers in a 3/2 ratio. $^1$H NMR ($CDCl_3$): Major isomer: 4.17 (q, 2H, J=7.3), 4.01 (m, 1H), 3.85 (m, 1H), 3.72 (m, 1H), 3.62 (dd, 1H, J=8.9, 3.5), 2.03 (m, 1H), 1.89 (m, 2H), 1.68 (ddd, 2H, J=3.5, 8.9, 13.8), 1.68 (s, 2H), 1.51 (m, 1H), 1.27 (t, 3H, J=7.3). Minor isomer: 4.17 (q, 2H, J=7.2), 4.01 (m, 1H), 3.85 (m, 1H), 3.72 (m, 1H), 3.56 (dd, 1H, J=7.3, 5.4), 2.03 (m, 1H), 1.89 (m, 2H), 1.80 (m, 2H), 1.61 (s, 2H), 1.49 (m, 1H), 1.27 (t, 3H, J=7.2), HRMS: calcd for $C_9H_{18}NO_3$: 188.1287; found, 188.1258.

Ethyl 2-amino-3-(4,5-dimethylthiophen-2-yl)propanoate (B-17): Obtained as an oil (0.46 g, 87%). $^1$H NMR ($CDCl_3$): 6.54 (s, 1H), 4.22 (d, 2H, J=7.1), 3.66 (dd, 1H, J=4.8, 7.4), 3.17 (dd, 1H, J=4.8, 14.5), 3.03 (dd, 1H, J=7.4, 14.5), 2.29 (s, 3H), 2.07 (s, 3H), 1.59 (s, 2H), 1.30 (t, 3H, J=7.1). HRMS: calcd for $C_{11}H_{18}NO_2S$: 228.1058; found, 228.1053.

Ethyl 2-amino-3-(3-methylthiophen-2-yl)propanoate (B-18): Obtained as an oil (1.10 g, 89%). $^1$H NMR ($CDCl_3$): 7.08 (d, 1H, J=5.1), 6.80 (d, 1H, J=5.1), 4.20 (m, 2H), 3.70 (dd, 1H, J=5.1, 7.6), 3.23 (dd, 1H, J=5.1, 14.7), 3.04 (dd, 1H, J=7.6, 14.7), 2.20 (s, 3H), 1.59 (s, 2H), 1.28 (t, 3H, J=7.6). HRMS: calcd for $C_{10}H_{16}NO_2S$: 214.0902; found, 214.0901.

Ethyl 2-amino-3-(5-ethylthiophen-2-yl)propanoate (B-19): Obtained as an oil (1.18 g, 92%). $^1$H NMR ($CDCl_3$): 6.66 (m, 1H), 6.61 (m, 1H), 4.21 (q, 2H, J=5.1, 7.2), 3.68 (dd, 1H, J=14.8, 7.3), 3.21 (dd, 1H, J=4.8, 14.7), 3.04 (dd, 1H, J=7.3, 14.7), 2.80 (m, 2H), 1.62 (s, 2H), 1.30 (t, 3H, J=7.1), 1.29 (t, 3H, J=7.5). HRMS: calcd for $C_{11}H_{18}NO_2S$: 228.1058; found, 228.1055.

Ethyl 2-amino-3-(o-tolyl)propanoate (B-20): Obtained as an oil (2.69 g, 85%). $^1$H NMR ($CDCl_3$): 7.16 (m, 4H), 4.17 (q, 2H, J=7.2), 3.71 (dd, 1H, J=8.7, 5.6), 3.14 (dd, 1H, J=13.8, 5.6), 2.84 (dd, 1H, J=13.8, 8.7), 2.82 (s, 3H), 1.24 (t, 3H, J=7.2). HRMS: calcd for $C_{12}H_{18}NO_2$: 208.1338; found, 208.1332.

Ethyl 2-amino-3-(p-tolyl)propanoate (B-21): Obtained as an oil (2.70 g, 87%). $^1$H NMR ($CDCl_3$): 7.11 (m, 4H), 4.19 (q, 2H, J=7.1), 3.70 (dd, 1H, J=7.9, 5.3), 3.07 (dd, 1H, J=13.6, 5.3), 2.84 (dd, 1H, J=13.6, 7.9), 2.34 (s, 3H), 1.28 (t, 3H, J=7.1). HRMS: calcd for $C_{12}H_{18}NO_2$: 208.1338; found, 208.1333.

Ethyl 2-amino-3-(pyridin-2-yl)propanoate (B-22): Obtained as an oil (2.21 g, 56%). $^1$H NMR ($CDCl_3$): 8.55 (m, 1H), 7.61 (dt, 1H, J=1.9, 7.6), 7.18 (m, 1H), 7.15 (m, 1H), 4.18 (q, 2H, J=7.2), 3.98 (dd, 1H, J=4.8, 8.2), 3.28 (dd, 1H, J=4.8, 14.2), 3.04 (dd, 1H, J=8.2, 14.2), 1.70 (s, 2H), 1.24 (t, 3H, J=7.2). HRMS: calcd for $C_{10}H_{15}N_2O_2$: 195.1134; found, 195.1062.

Ethyl 2-amino-3-(pyridin-3-yl)propanoate (B-23): Obtained as an oil (4.07 g, 63%). $^1$H NMR ($CDCl_3$): 8.49 (m, 2H), 7.56 (m, 1H), 7.22 (ddd, 1H, J=0.8, 4.8, 5.6), 4.16 (q, 2H, J=7.2), 3.70 (dd, 1H, J=5.5, 7.5), 3.05 (dd, 1H, J=5.5, 13.5), 2.88 (dd, 1H, J=7.5, 13.5), 1.46 (s, 2H), 1.23 (t, 3H, J=7.2). HRMS: calcd for $C_{10}H_{15}N_2O_2$: 195.1134; found, 195.1131.

Ethyl 2-amino-3-(2-(trifluoromethyl)phenyl)propanoate (B-24): Obtained as an oil (0.72 g, 78%, 90% pure). $^1$H NMR ($CDCl_3$): 7.58 (d, 1H, J=8.1), 7.41 (m, 1H), 7.32 (d, 1H, J=7.7), 7.26 (m, 1H), 4.07 (m, 2H), 3.66 (dd, 1H, J=5.7, 8.9), 3.21 (dd, 1H, J=5.7, 14.3), 2.86 (dd, 1H, J=8.9, 14.3), 1.45 (s, 2H), 1.13 (t, 3H, J=7.1). HRMS: calcd for $C_{12}H_{15}F_3NO_2$: 262.1055, found, 262.1082.

Ethyl 2-amino-3-(3-(trifluoromethyl)phenyl)propanoate (B-25): Obtained as an oil (0.75 g, 78%). $^1$H NMR ($CDCl_3$): 7.51 (m, 1H), 7.48 (m, 1H), 7.43 (m, 2H), 4.17 (q, 2H, J=7.3), 3.74 (dd, 1H, J=5.5, 7.5), 3.13 (dd, 1H, J=5.5, 13.8), 2.96 (dd, 1H, J=7.5, 13.8), 1.51 (s, 2H), 1.24 (t, 3H, J=7.3). HRMS: calcd for $C_{12}H_{15}F_3NO_2$: 262.1055; found, 262.1054.

Ethyl 2-amino-3-(4-(trifluoromethyl)phenyl)propanoate (B-26): Obtained as an oil (1.23 g, 91%). $^1$H NMR ($CDCl_3$): 7.58 (d, 2H, J=8.3), 7.35 (d, 2H, J=8.3), 4.18 (q, 2H, J=7.3), 3.74 (dd, 1H, J=5.8, 7.8), 3.14 (dd, 1H, J=5.8, 13.4), 2.96

(da, 1H, J=7.8, 13.4), 1.50 (s, 2H), 1.25 (t, 3H, J=73). HRMS: calcd for $C_{12}H_{15}F_3NO_2$: 262.1055; found, 262.1129.

Ethyl 2-amino-3-(2-fluorophenyl)propanoate (B-27): Obtained as an oil (2.57 g, 88%). $^1$H NMR ($CDCl_3$): 7.23 (m, 2H), 7.06 (m, 2H), 4.17 (q, 2H, J=7.1), 3.76 (dd, 1H, J=7.9, 5.9), 3.11 (dd, 1H, J=13.6, 5.9), 2.93 (dd, 1H, J=13.6, 7.9), 1.24 (t, 3H, J=7.1). HRMS: calcd for $C_{11}H_{15}FNO_2$, 212.1087; found, 212.1089.

Ethyl 2-amino-3-(2,4-difluorophenyl)propanoate (B-28): Obtained as an oil (1.11 g, 85%). $^1$H NMR ($CDCl_3$): 7.19 (m, 1H), 6.80 (m, 2H), 4.15 (q, 2H, J=7.1), 3.70 (dd, 1H, J=7.9, 5.9), 3.04 (dd, 1H, J=13.7, 5.9), 2.89 (dd, 1H, J=13.7, 7.9), 1.52 (s, 2H), 1.23 (t, 3H, J=7.1). HRMS: calcd for $C_{11}H_{14}F_2NO_2$, 230.0993; found, 230.1006.

Ethyl 2-amino-3-(4-chlorophenyl)propanoate (B-29): Obtained as an oil (1.48 g, 73%). $^1$H NMR ($CDCl_3$): 7.29 (m, 2H), 7.16 (m, 2H), 4.18 (q, 2H, J=7.3), 3.69 (dd, 1H, J=5.6, 7.5), 3.05 (dd, 1H, J=5.6, 13.7), 2.84 (dd, 1H, J=7.5, 13.7), 1.47 (s (l), 2H), 1.26 (t, 3H, J=7.1) HRMS: calcd for $C_{11}H_{15}ClNO_2$, 228.0791; found, 228.0806.

Ethyl 2-amino-3-(2-chlorophenyl)propanoate (B-30): Obtained as an oil (3.73 g, 19% from 2-chlorobenzaldehyde). $^1$H NMR ($CDCl_3$): 7.38 (m, 1H), 7.22 (m, 3H), 4.16 (m, 2H), 3.84 (dd, J=8.5, 5.8 Hz, 1H), 3.24 (dd, J=13.5, 5.8 Hz, 1H), 3.96 (dd, J=13.5, 8.5 Hz, 1H), 1.23 (t, J=7.2 Hz, 1H). HRMS: calcd for $C_{11}H_{15}ClNO_2$: 228.0791; found, 228.0791.

Ethyl 2-amino-3-(4-bromophenyl)propanoate (B-31): Obtained as an oil (0.61 g, 76%). $^1$H NMR ($CDCl_3$): 7.44 (m, 2H), 7.10 (m, 2H), 4.18 (q, 2H, J=7.3), 3.69 (dd, 1H, J=5.3, 7.7), 3.04 (dd, 1H, J=5.3, 13.7), 2.84 dd, 1H, J=7.7, 13.7), 1.47 (s (l), 2H), 1.26 (t, J=7.1 Hz, 3H). HRMS: calcd for $C_{11}H_{15}BrNO_2$: 272.0286; found, 272.0296.

Ethyl 2-amino-3-(3-fluorophenyl)propanoate (B-32): Obtained as an oil (4.89 g, 89%). $^1$H NMR ($CDCl_3$): 7.27 (m, 1H), 7.01-6.92 (m, 3H), 4.18 (q, 2H, J=7.0), 3.72 (dd, 1H, J=5.4, 7.9), 3.08 (dd, 1H, J=5.4, 13.7), 2.88 (dd, 1H, J=7.9, 13.7), 1.49 (s, 2H), 1.26 (t, 3H, J=7.0). HRMS: calcd for $C_{11}H_{15}FNO_2$: 212.1087; found, 212.1088.

Ethyl 2-amino-3-(4-isopropylphenyl)propanoate hydrochloride (B-33): Obtained as an oil which was immediately treated with a solution of hydrogen chloride in dioxane and concentrated to dryness to give the hydrochloride salt as a white powder (1.9 g, 91% pure). $^1$H NMR (DMSO-$d_6$): 8.23 (s, 3H), 7.22-7.12 (m, 4H), 4.16-4.02 (m, 3H), 3.16 (dd, 1H, J=13.9, 5.8), 3.01 (dd, 1H, J=13.9, 7.8), 2.86 (hept, 1H, J=6.9), 1.18 (d, 6H, J=6.9), 1.06 (t, 3H, J=7.1). HRMS: calcd for $C_{14}H_{22}NO_2$: 236.1651; found, 236.1651.

Ethyl 2-amino-3-(4-cyclopropylphenyl)propanoate (B-34): Obtained as an oil (0.71 g, 80%). $^1$H NMR ($CDCl_3$): 7.09 (m, 210), 7.01 (m, 2H), 4.18 (q, 2H, J=7.0), 3.70 (dd, 1H, J=5.2, 7.9), 3.06 (dd, 1H, J=5.2, 13.7), 2.83 (dd, 1H, J=7.9, 13.7), 1.87 (m, 1H), 1.54 (s, 2H), 1.28 (t, 3H, J=7.0), 0.95 (m, 2H), 0.68 (m, 2H). HRMS: calcd for $C_{14}H_{20}NO_2$: 234.1494; found, 234.1490.

Ethyl 2-amino-3-(3-cyclopropylphenyl)propanoate (B-35): Obtained as an oil (1.66 g, 89%). $^1$H NMR ($CDCl_3$): 7.19 (m, 1H), 6.95 (m, 3H), 4.19 (q, 2H, J=7.0), 3.71 (dd, 1H, J=5.2, 7.9) 3.05 (dd, 1H, J=5.2, 13.5), 2.83 (dd, 1H, J=7.9, 13.5), 1.88 (m, 1H), 1.53 (s, 2H), 1.28 (t, 3H, J=7.0), 0.95 (m, 2H), 0.68 (m, 2H). HRMS: calcd for $C_{14}H_{29}NO_3$: 234.1494; found, 234.1496.

Ethyl 2-amino-3-(4-propylphenyl)propanoate hydrochloride (B-36): Obtained as an oil which was immediately treated with a solution of hydrogen chloride in dioxane and concentrated to dryness to give the hydrochloride salt as a white powder (2.46 g, 85%). $^1$H NMR (DMSO-$d_6$): 8.59 (bs, 3H), 7.15 (s, 4H), 4.20 (dd, J=7.5, 5.9 Hz, 1H), 4.10 (m, 2H), 3.16 (d, J=7.9, 5.9 Hz, 1H), 3.02 (dd, J=14.2, 7.9 Hz, 1H), 2.54 (m, 2H), 1.58 (m, 2H), 1.09 (t, J=7.2 Hz, 3H), 0.89 (t, J=7.3 Hz, 3H). HRMS: calcd for $C_{14}H_{22}NO_2$: 236.1651; found, 236.1659.

Ethyl 2-amino-3-(3-propylphenyl)propanoate hydrochloride (B-37): Obtained as an oil which was immediately treated with a solution of hydrogen chloride in dioxane and concentrated to dryness to give the hydrochloride salt as a white powder (1.89 g 90%). $^1$H NMR (DMSO-$d_6$): 8.72 (bs, 3H), 7.24 (m, 1H), 7.08 (m, 3H), 4.18 (dd, J=7.9, 5.6 Hz, 1H), 4.08 (q, J=7.2 Hz, 2H), 3.21 (dd, J=13.9, 5.6 Hz, 1H), 3.03 (dd, J=13.9, 7.9 Hz, 1H), 2.53 (m, 2H), 1.58 (m, 2H), 1.08 (t, J=7.2 Hz, 3H), 0.89 (t, J=7.3 Hz, 3H). HRMS: calcd for $C_{14}H_{22}NO_2$: 236.1651; found, 236.1637.

Ethyl 2-amino-3-(5-(trifluoromethyl furan-2-yl)propanoate (B-38): Obtained as a 95% pure oil (0.53 g, 93%). $^1$H NMR ($CDCl_3$): 6.66 (dd, 1H, J=3.3, 1.2), 6.20-6.15 (m, 1H), 4.20-4.10 (m, 2H), 3.79-3.73 (m, 1H), 3.08 (dd, 1H, J=15.0, 5.4), 2.99 (ad, 1H, J=15.0, 7.1), 1.60 (bs, 2H), 1.22 (t, 3H, J=7.1). HRMS: calcd for $C_{10}H_{13}F_3NO_3$, 252.0847; found, 252.0852.

Ethyl 2-amino-3-(5-cyclopropylfuran-2-yl)propanoate (B-39): Obtained as an oil (0.70 g, 88%) $^1$H NMR ($CDCl_3$): 5.99 (d, J=3.1 Hz, 1H), 5.85 (d, J=3.1 Hz, 1H), 4.20 (q, 2H, J=7.2), 3.74 (dd, 1H, J=7.1, 5.1), 3.03 (dd, 1H, J=14.8, 3.1), 2.93 (dd, 1H, J=14.8, 7.1), 1.84 (m, 1H), 1.36 (t, 3H, J=7.2), 0.84 (m, 2H), 0.73 (m, 2H). HRMS: calcd for $C_{12}H_{17}NO_3$, 224.1287; found, 224.1282.

Ethyl 2-amino-3-(4,5-dimethyloxazol-2-yl)propanoate (B-40): Obtained as an oil (0.23 g, 74%). $^1$H NMR ($CDCl_3$): 4.19 (m, 2H), 3.90 (dd, 1H, J=4.5, 8.1), 3.14 (dd, 1H, J=4.5, 15.0), 2.96 (dd, 1H, J=8.1, 15.0), 2.27 (s, 3H), 2.05 (s, 3H), 1.84 (s (l), 2H), 1.26 (t, 3H, J=7.3). HRMS: calcd for $C_{16}H_{17}N_2O_3$, 213.1229; found, 213.1230.

Ethyl 2-amino-3-phenylbutanoate (B-41): Obtained as an oil (0.76 g, 88%) containing a 1/2 mixture of two diastereoisomers. $^1$H NMR ($CDCl_3$): 7.39-7.21 (m, 5H), 4.20 (q, 1.3H, J=7.1), 4.20 (q, 0.7H, J=7.1), 3.62 (d, 0.3H, J=6.0), 3.56 (d, 0.7H, J=7.2), 3.18 (m, 0.3H), 3.12 (m, 0.3H), 1.44 (s, 2H), 1.36 (d, 2H, J=7.2), 1.34 (d, 1H, J=6.0), 1.29 (t, 2H, J=7.1), 1.16 (t, 1H, J=7.1). HRMS: calcd for $C_{12}H_{18}NO_2$, 208.1338; found, 208.1331.

Preparation of 2-Amino-4-phenylbutanoate (B-42): Ethyl 5-phenyl-4,5-dihydroisoxazole-3-carboxylate (WO20100142801, 2010) (0.47 g, 2.14 mmol), ammonium formate (2.7 g, 21.4 mmol) and 10% palladium over charcoal (0.11 g, 0.10 mmol) were heated to reflux in ethanol (50 mL) for one hour. This was filtered, the insoluble washed with a small amount of ethanol and 37% hydrochloric acid (1.6 mL, 13.6 mmol) was added before adding powdered zinc (0.42 g, 6.3 mmol) by portions. This was stirred for 90 mmn, the resulting solution was diluted in water made basic with 22% ammonia and extracted with ethyl acetate. The organic layer was washed wirth water, brine, dried over sodium carbonate and concentrated to dryness to yield the amino ester as an oil (0.32 g, 72%). $^1$H NMR ($CDCl_3$): 7.31 (m, 2H), 7.22 (m, 3H), 4.19 (m, 2H), 3.46 (dd, 1H, J=5.3, 7.9), 2.76 (m, 2H), 2.07 (m, 1H), 1.87 (m, 1H), 1.65 (s, 2H), 1.30 (t, 3H, J=7.1).

Preparation of ethyl 2-amino-3-(1,3-dioxolan-2-yl)propanoate (B-43): Step 1: the previously described (J. Org. Chem., 2006, 360) diethyl 2-((1,3-dioxolan-2-yl)methyl) malonate (7.8 g, 0.317 mol) was dissolved in ethanol (40 ml) and potassium hydroxide (1.78 g, 0.0317 mol) dissolved in ethanol (60 mL) was added drop wise. The solution was stirred overnight at room temperature and then briefly heated to reflux. This was concentrated, dissolved in water which was made more basic with 22% ammonia. The aqueous phase was washed with dichloromethane, made acid with 37% hydrochloric acid, extracted with ethyl acetate, the organic layer was washed with water, brine, dried over magnesium sulfate and concentrated to dryness to yield pure 2-((1,3-dioxolan-2-yl)methyl)-3-ethoxy-3-oxopropanoic acid (3.85 g, 55%). $^1$H NMR ($CDCl_3$): 5.05 (t, 1H, J=3.7), 4.24 (q, 2H, J=7.1), 3.98 (m, 2H), 3.82 (m, 2H), 3.64 (t, 1H, J=6.9), 2.40 (m, 2H), 1.30 (t, 3H, J=7.1). Step 2: Under argon, this compound (3.85 g, 0.0176 mol) was dissolved in toluene (50 mL, dried over 4 Å molecular). Triethylamine (2.95 mL, 0.021 mol) was added and then diphenylphosphoryl azide (4.18 mL, 0.021 mol). This was stirred at 80° C. for 1 h 30, the toluene was removed under vacuum and the resulting oil repeatedly extracted with cyclohexane. Concentration to dryness of this extract led to an oil which was stirred at room temperature in 4% hydrochloric acid (50 mL) overnight. The resulting solution was diluted in more acid, washed with ethyl acetate, the aqueous phase was made basic with 22% ammonia, extracted with ethyl acetate, and this organic layer was washed with water brine, dried over sodium carbonate and concentrated to dryness to yield the amino ester as an oil (0.14 g, 16%). $^1$H NMR ($CDCl_3$): 5.05 (dd, 1H, J=4.3, 5.0), 4.0 (m, 2H), 3.87 (m, 2H), 3.66 (dd, 1H, J=4.6, 8.2), 2.15 (ddd, 1H, J=4.6, 5.0, 14.2), 1.94 (ddd, 1H, J=4.3, 8.2, 14.2), 1.57 (s, 2H), 1.29 (t, 3H, J=7.1). HRMS: calcd for $C_8H_{16}NO_4$, 190.1079; found, 190.1061.

Synthesis of piperazin-2-ones E, representative preparation of (3S,5S) and (3S,5R)-3-benzyl-5-phenylpiperazin-2-ones. Step a, preparation of ethyl (2-nitro-1-phenylethyl)-L-phenylalaninate: 2-nitrovinylbenzene (3.78 g, 0.025 mol) was added to a freshly extracted free base of L-phenylalanine ethyl ester (4.9 g, 0.025 mol). Upon stirring on a rotatory evaporator at room temperature the suspension homogenised in about 10 minutes to give the 1,4 adduct C. Step b, preparation of ethyl (2-amino-1-phenylethy)phenylalaninate: this oil was dispersed in a cold solution of dioxane (100 mL) and 37% hydrochloric acid (38.7 mL, 0.33 mol). Zinc dust (7.45 g, 0.11 g, <10 μm) was added portion-wise in the course of 10 minutes. The temperature was then allowed to rise to room temperature and the suspension was stirred for 2 hours. This was diluted in water, made basic with an excess of 22% ammonia and extracted with ethyl acetate. The organic layer was washed with brine, dried over sodium carbonate and concentrated to dryness to give the crude compound D as an oil Step c, preparation of 3-benzyl-5-phenylpiperazin-2-ones E: under an argon atmosphere, this oil was heated at 140° C. for 3 hours. The ethanol was removed under vacuum and the resulting solid was subjected to purification procedures as described below. Note: when separated, the structure attribution of these pairs of diastereoisomers can be made by checking for the existence (or not) of a nOe effect between H-3 and H-5.

(3S,5R)-3-benzyl-5-phenylpiperazin-2-one (E-1): The crude mixture of diastereoisomers was dispersed in boiling cyclohexane to remove unreacted L-phenylalanine ester and the resulting solid purified by a chromatography over silica gel (dichloromethane/ethanol 96/4 to 95/5) to yield this compound as a white solid (2.05 g, 35%). $^1$H NMR ($CDCl_3$): 7.42-7.29 (m, 9H), 7.26-7.20 (m, 1H), 6.27 (s, 1H), 4.06 (dd, 1H, J=9.7, 4.7), 3.84 (di, 1H, J=10.1, 3.4), 3.60 (dd, 1H, J=13.6, 3.1), 3.41-3.25 (m, 2H), 2.91 (dd, 1H, J=13.6, 10.1), 1.78 (s, 1H) HRMS: calcd for $C_{17}H_{19}N_2O$, 267.1497; found: 267.1459.

(3S,5S)-3-benzyl-5-phenylpiperazin-2-one (E-2): A second chromatographic fraction gave this isomer as a white solid (1.29 g, 22%). $^1$H NMR ($CDCl_3$): 7.46-7.18 (m, 10H), 6.44 (s, 1H), 4.27 (dd, 1H, J=9.6, 4.0), 3.89 (dd, 1H, J=10.7, 3.6), 3.34-3.44 (m, 1H), 3.41 (dt, 1H, J=11.5, 4.0), 3.32 (dd, 1H, J=13.8, 3.6), 3.18 (dd, 1H, J=13.8, 10.7), 1.79 (s, 1H). HRMS: calcd for $C_{17}H_{19}N_2O$, 267.1497; found: 267.1435.

3-Benzyl-5-(p-tolyl)piperazin-2-one (E-3): This compound was obtained as a crude mixture of the two diastereoisomers (5.40 g) by dispersing the resulting solid in boiling cyclohexane and filtration at 20° C. and was used directly in the aromatization step. HRMS: calcd for $C_{18}H_{20}N_2O$, 281.1654; found: 281.1649.

3-Benzyl-5-(m-tolyl)piperazin-2-one (E-4): An analytical sample of a mixture of the the two diastereoisomers was obtained by a recrystallization in cyclohexane but most of the solid and the filtrate were used directly in the in the aromatization step. HRMS: calcd for $C_{18}H_{20}N_2O$, 281.1654; found: 281.1645.

Cis-3-(2-methylbenzyl)-5-phenylpiperazin-2-one (E-5): This compound was obtained as a white powder (4.04 g, 26%) after a chromatography over silica gel (dichloromethane/ethanol 98/2 to 95/5) and a dispersion in boiling cyclohexane. $^1$H NMR ($CDCl_3$): 7.40-7.27 (m, 6H), 7.14 (m, 3H), 6.58 (s (br), 1H), 4.03 (dd, 1H, J=4.1, 10.5), 3.82 (d (br), 1H, J=10.5), 3.68 (dd, 1H, J=2.7, 14.0), 3.36 (m, 2H), 2.92 (dd, 1H, J=10.8, 13.7), 2.45 (s, 3H), 1.77 (s, 1H). HRMS: calcd for $C_{18}H_{21}N_2O$, 281.1654; found: 281.1652.

Trans-3-(2-methylbenzyl)-5-phenylpiperazin-2-one (B-6): This compound was obtained as a white powder (2.77 g, 17%) after a chromatography over silica gel (dichloromethane/ethanol 98/2 to 95/5) and a dispersion in boiling cyclohexane. $^1$H NMR ($CDCl_3$): 7.41-7.30 (m, 5H), 7.14 (m, 4H), 6.80 (s (br), 1H), 4.35 (dd, 1H, J=5.0, 9.8), 3.89 (dd, 1H, J=3.3, 11.2), 3.43 (m, 2H), 3.39 (dd, 1H, J=3.3, 13.9), 3.16 (dd, 1H, J=11.2, 13.9), 2.40 (s, 3H), 1.76 (s, 1H). HRMS: calcd for $C_{18}H_{21}N_2O$, 281.1654; found: 281.1652.

Cis-3-(3-methylbenzyl)-5-phenylpiperazin-2-one (E-7). This compound was obtained as a white powder (3.70 g, 26%) after a chromatography over silica gel (dichloromethane/ethanol 98/2 to 95/5) and a dispersion in boiling cyclohexane. $^1$H NMR ($CDCl_3$): 7.40-7.28 (m, 5H), 7.20 (m, 1H), 7.13 (m, 2H), 7.04 (m, 1H), 6.72 (s (br), 1H), 4.05 (dd, 1H, J=5.4, 9.5) 3.83 (d (br), 1H, J=10.4), 3.58 (dd, 1H, J=3.0, 13.6), 3.35 (m, 2H), 2.86 (dd, 1H, J=10.4, 13.6), 2.34 (s, 3H), 1.80 (s, 1H). HRMS: calcd for $C_{18}H_{21}N_2O$, 281.1654; found: 281.1649.

Trans-3-(3-methylbenzyl)-5-phenylpiperazin-2-one (E-8): This compound was obtained as a white powder (2.73 g, 19%) after a chromatography over silica gel (dichloromethane/ethanol 98/2 to 95/5) and a recrystallization in cyclohexane. $^1$H NMR ($CDCl_3$): 7.39-7.30 (m, 5H), 7.19 (m, 1H), 7.05 (m, 3H), 6.8) (s (br), 1H), 4.26 (dd, 1H, J=4.0, 9.9), 3.87 (dd, 1H, J=3.8, 10.7), 3.45 (m, 2H), 3.28 (dd, 1H, J=3.5, 13.7), 3.14 (dd, 1H, J=10.7, 13.7), 2.31 (s, 3H), 1.81 (s, 1H). HRMS: calcd for $C_{18}H_{21}N_2O$, 281.1654; found: 281.1656.

(3S,5R)-3-benzyl-5-(2-methoxyphenyl)piperazin-2-one (E-9): This isomer was obtained as a glass (1.06 g, 25%) after two chromatography over silica gel (dichloromethane—ethanol 96/4 to 95/5) and (cyclohexane—ethyl acetate 1/2 to 1/3). $^1$H NMR ($CDCl_3$): 7.40-7.22 (m, 7H), 6.98 (m, 1H), 6.84 (m, 1H), 6.69 (s (br), 1H), 4.39 (ad, 11, J=3.7, 10.7), 3.74 (s, 3H), 3.85 (dd, 1H, J=3.2, 9.2), 3.53 (dd, 1H, J=3.5, 13.7), 3.44 (ddd, 1H, J=4.0, 8.0, 11.0), 3.28 (t, 1H, J=11.0), 3.01 (dd, 1H, J=8.3, 13.7), 1.90 (s (br), 1H). HRMS: calcd for $C_{18}H_{21}N_2O$: 297.1603, found: 297.1591.

(3S,5S)-3-benzyl-5-(2-methoxyphenyl)piperazin-2-one (E-10): This isomer was obtained as a white solid (0.52 g, 12%) after two chromatography over silica gel (dichloromethane/ethanol 96/4 to 95) and (ethyl acetate-ethanol 1/0 to 99/1). $^1$H NMR ($CDCl_3$): 7.36-7.20 (m, 7H), 6.94 (m, 1H), 6.88 (m, 1H), 6.65 (s (br), 1H), 4.64 (dd, 1H, J=4.2, 8.1), 3.77 (s, 3H), 3.71 (dd, 1H, J=3.3, 10.8), 3.59 (m, 1H), 3.47 (ddd, 1H, J=1.0, 11.2), 3.36 (dd, 1H, J=3.3, 13.7), 3.09 (dd, 1H, J=10.8, 13.7), 2.08 (s (br), 1H). HRMS: calcd for $C_{18}H_{21}N_2O$: 297.1603, found: 297.1589.

(3S,5R)-3-benzyl-5-(3-methoxyphenyl)piperazin-2-one (E-11): This isomer was obtained as a glass (1.33 g, 30%) after two chromatography over silica gel (dichloromethane—ethanol 97/3 to 95/5) and (cyclohexane—ethyl acetate 1/4). $^1$H NMR ($CDCl_3$): 7.34-7.20 (m, 6H), 6.94 (m, 2H), 6.83 (m, 1H), 6.72 (s (br), 1H), 4.02 (dd, 1H, J=6.3, 8.7), 3.83 (m, 1H), 3.81 (s, 3H), 3.58 (dd, 1H, J=3.3, 13.4), 3.34 (m, 2H), 2.91 (dd, 1H, J=10.3, 13.4), 1.90 (s (br), 1H). HRMS: calcd for $C_{18}H_{21}N_2O$: 297.1603, found: 297.1582.

(3S,5S)-3-benzyl-5-(3-methoxyphenyl)piperazin-2-one (E-12): This isomer was obtained as a glass (0.84 g, 19%) after two chromatography over silica gel (dichloromethane—ethanol 97/3 to 95/5) and (ethyl acetate-ethanol 1/0 to 99/1). $^1$H NMR ($CDCl_3$): 7.33-7.22 (m, 6H), 6.94 (m, 2H), 6.85 (m, 1H), 6.76 (s (br), 1H), 4.22 (dd, 1H, J=4.1, 9.5), 3.88 (dd, 1H, J=3.6, 10.6), 3.80 (s, 3H), 3.45 (m, 2H), 3.31 (dd, 1H, J=3.6, 13.8), 3.16 (dd, 1H, J=10.7, 13.8), 1.81 (s (br), 1H). HRMS: calcd for $C_{18}H_{21}N_2O$: 297.1603, found: 297.1584.

(3S,5R)-3-benzyl-5-(4-methoxyphenyl)piperazin-2-one (E-13): This isomer was obtained as a glass (1.37 g, 27%) after two chromatography over silica gel (dichloromethane—ethanol 97/3 to 95/5) and (cyclohexane—ethyl acetate 1/4). $^1$H NMR ($CDCl_3$): 7.28 (m, 7H), 6.87 (m, 2H), 6.38 (s (br), 1H), 3.99 (dd, 1H, J=4.3, 10.3), 3.82 (m, 1H), 3.80 (s, 3H), 3.58 (dd, 1H, J=3.8, 13.6), 3.31 (m, 2H), 2.89 (dd, 1H, J=10.2, 13.6), 1.90 (s (br), 1H). HRMS: calcd for $C_{18}H_{21}N_2O$: 297.1603, found: 297.1585.

(3S,5S)-3-benzyl-5-(4-methoxyphenyl)piperazin-2-one (B-14): This isomer was obtained as a white powder (0.81 g, 16%) after two chromatography over silica gel (dichloromethane-ethanol 97/3 to 95/5) and (ethyl acetate-ethanol 1/0 to 99/1). $^1$H NMR ($CDCl_3$): 7.28 (m, 7H), 6.81 (m, 2H), 6.73 (s (br), 1H), 4.19 (dd, 1H, J=4.0, 9.8), 3.86 (dd, 1H, J=3.6, 10.6), 3.80 (s, 3H), 3.44 (m, 1H), 3.31 (m, 2H), 3.36 (td, 1H, J=3.8, 11.5), 3.30 (dd, 1H, J=3.8, 13.9), 3.17 (dd, 1H, J=10.6, 13.9), 1.85 (s (br), 1H). HRMS: calcd for $C_{18}H_{21}N_2O$: 297.1603, found: 297.1533.

(3S,5R)-3-benzyl-5-(2-fluorophenyl)piperazin-2-one (E-15); This isomer was obtained as a white powder (4.06 g, 39%) after two chromatography over silica gel (dichloromethane-ethanol 96/4 to 94/6) and (cyclohexane—ethyl acetate 2/3 to 1/3) followed by a dispersion in boiling cyclohexane and extensive drying at 70° C. under vacuum. $^1$H NMR ($CDCl_3$): 7.49 (m, 1H), 7.31 (m, 4H), 7.26 (m, 2H), 7.16 (m, 1H), 7.02 (m, 1H), 6.65 (s (br), 1H), 4.42 (m, 1H), 3.87 (m, 1H), 3.57 (dd, 1H, J=3.3, 13.8), 3.29 (t, 1H, J=10.9), 2.95 (dd, 1H, J=9.1, 13.8), 1.73 (s (br), 1H). HRMS: calcd for $C_{17}H_{18}FN_2O$: 285.1403, found: 285.1391.

(3S,5S)-3-benzyl-5-(2-fluorophenyl)piperazin-2-one (E-16): This isomer was obtained as a white powder (2.16 g, 20%) after a chromatography over silica gel (dichloromethane/ethanol 96/4 to 94/6). $^1$H NMR ($CDCl_3$): 7.44 (m, 1H), 7.27 (m, 6H), 7.13 (m, 1H), 7.08 (m, 1H), 6.74 (s (br), 1H), 4.65 (dd, 1H, J=4.3, 9.1), 3.84 (dd, 1H, J=3.5, 10.8), 3.48 (m, 2H), 3.34 (dd, 1H, J=3.8, 13.7), 3.15 (dd, 1H, J=10.7, 13.7), 1.78 (s (br), 1H). HRMS: calcd for $C_{17}H_{18}FN_2O$: 285.1403, found: 285.1367.

3-benzyl-5-(2,6-difluorophenyl)piperazin-2-one (E-17). This compound was obtained as a 1/1 mixture of diastereoisomers after a recrystallization in cyclohexane (1.97 g, 62%). HRMS: calcd for $C_{17}H_{17}F_2N_2O$: 303.1309, found: 303.1323.

(3S,5R)-3-benzyl-5-(4-fluorophenyl)piperazin-2-one (E-18): This isomer was obtained as a white powder (1.26 g, 29%) after two chromatography over silica gel (dichloromethane-ethanol 97/3 to 95/5) and (cyclohexane—ethyl acetate 1/2 to 1/3). $^1$H NMR ($CDCl_3$): 7.28 (m, 7H), 7.01 (m, 2H), 6.61 (s (br), 1H), 4.05 (t, 1H, J=7.3), 3.82 (d, 1H, J=9.3), 3.58 (dd, 1H, J=3.0, 13.6), 3.31 (m, 2H), 2.89 (dd, 1H, J=9.8, 13.6), 1.72 (s (br), 1H). HRMS: calcd for $C_{17}H_{18}FN_2O$: 285.1403, found: 285.1342.

(3S,5S)-3-benzyl-5-(4-fluorophenyl)piperazin-2-one (E-19): This isomer was obtained as a white powder (1.26 g, 29%) after two chromatography over silica gel (dichloromethane/ethanol 97/3 to 95/5) and (ethyl acetate-ethanol 99/1). $^1$H NMR ($CDCl_3$): 7.29 (m, 7H), 7.05 (m, 2H), 6.79 (s (br), 1H), 4.21 (dd, 1H, J=4.5, 9.5), 3.86 (dd, 1H, J=3.7, 10.6), 3.40 (m, 2H), 3.16 (dd, 1H, J=10.7, 13.9), 1.74 (s (br), 1H). HRMS: calcd for $C_{17}H_{18}FN_2O$: 285.1403, found: 285.1315.

3-benzyl-5-(3-fluorophenyl)piperazin-2-one (E-20): This mixture of isomers was obtained as an oil, after washing it with cyclohexane to remove unreacted ethyl phenylalanine ester, and used directly in the aromatization step.

(3S,5R)-3-benzyl-5-(4-(benzyloxy)phenyl)piperazin-2-one (E-21): This isomer was obtained as a white powder (0.92 g, 17%) after two chromatography over silica gel (dichloromethane-ethanol 95/5 to 92/8) and (cyclohexane—ethyl acetate 1/2) and a recrystallization in cyclohexane. $^1$H NMR ($CDCl_3$): 7.45-7.21 (m, 12H), 6.94 (m, 2H), 6.47 (s (br), 1H), 5.06 (s, 2H), 4.00 (dd, 1H, J=4.3, 10.1), 3.83 (dd, 1H, J=3.0, 10.1), 3.59 (dd, 1H, J=3.0, 13.6), 3.32 (m, 2H), 2.90 (dd, 1H, J=10.1, 13.6), 1.73 (s (br), 1H). HRMS: calcd for $C_{25}H_{25}NO_3$: 373.1916, found: 373.1932.

(3S,5S)-3-benzyl-5-(4-(benzyloxy)phenyl)piperazin-2-one (E-22): This isomer was obtained as a white powder (0.59 g, 11%) after two chromatography over silica gel (dichloromethane-ethanol 95/5 to 92/8) and (ethyl acetate—ethanol 1/0 to 99/1). $^1$H NMR ($CDCl_3$): 7.45-7.23 (m, 12H), 6.96 (m, 2H), 6.67 (s (br), 1H), 5.07 (s, 2H), 4.21 (dd, 1H, J=4.0, 9.6), 3.85 (dd, 1H, J=35, 10.7), 3.40 (m, 2H), 3.31 (dd, 1H, J=3.5, 13.8), 3.18 (dd, 1H, J=10.7, 13.7), 1.76 (s (br), 1H), HRMS: calcd for $C_{25}H_{25}N_2O_3$: 373.1916, found: 373.1907.

(3S,5R)-3-benzyl-5-(4-(benzyloxy)-3-fluorophenyl)piperazin-2-one (E-23): This isomer was obtained as a powder (2.47 g, 54%, 90% pure) after a chromatography over silica gel (dichloromethane—ethanol 98/2 to 95/5). $^1$H NMR ($CDCl_3$): 7.44-7.21 (m, 10H), 7.15 (m, 1H), 7.01 (m, 1H), 6.95 (m, 1H), 6.19 (s (br), 1H), 5.13 (s, 2H), 3.96 (m, 1H), 3.81 (dd, 1H, J=3.0, 10.1), 3.58 (dd, 1H, J=3.0, 13.8), 3.28 (m, 2H), 2.88 (dd, 1H, J=10.2, 13.8), 1.71 (s (br), 1H). HRMS: calcd for $C_{24}H_{25}FN_2O_3$: 391.1822, found: 391.1828.

(3S,5S)-3-Benzyl-5-(4-(benzyloxy)-3-fluorophenyl)piperazin-2-one (E-24): This isomer was obtained as as a powder (0.5 g, 11%) after a chromatography over silica gel (dichloromethane—ethanol 98/2 to 95/5). $^1$H NMR ($CDCl_3$): 7.45-7.22 (m, 10H), 7.13 (m, 1H), 7.02 (m, 1H), 6.96 (m, 1H), 6.19 (s (br), 1H), 5.14 (s, 2H), 4.15 (dd, 1H, J=4.1, 9.3), 3.86 (dd, 1H, J=3.6, 10.4), 3.45-3.33 (m, 2H), 3.29 (dd, 1H, J=4.1, 14.4), 3.16 (dd, 1H, J=10.8, 13.8), 1.71 (s (br), 1H). HRMS: calcd for $C_{24}H_{25}FN_2O_3$: 391.1822, found: 391.1828.

Cis-3-(2-fluorobenzyl)-5-phenylpiperazin-2-one (B-25): This racemic isomer was obtained from B-27 as a white powder (2.85 g, 31%) after a chromatography over silica gel (dichloromethane—ethanol 97/3 to 95/5) and a dispersion in boiling cyclohexane. $^1H$ NMR ($CDCl_3$): 7.35 (m, 6H), 7.21 (m, 1H), 7.07 (m, 2H), 6.60 (s (br), 1H), 4.08 (dd, 1H, J=6.4, 8.3), 3.92 (dd, 1H, J=3.1, 9.6), 3.65 (dd, 1H, J=3.0, 34.0), 3.34 (m, 2H), 2.97 (dd, 1H, J=9.6, 14.0), 1.78 (s (br), 1H). HRMS: calcd for $C_{17}H_{18}FN_2O$: 285.1403. found: 285.1412.

Trans-3-(2-fluorobenzyl)-5-phenylpiperazin-2-one (E-26): This racemic isomer was obtained from B-27 as a white powder (2.15 g, 23%) after a chromatography over silica gel (dichloromethane—ethanol 97/3 to 95/5) and a recrystallization of a sample in cyclohexane for analytical purposes, $^1H$ NMR ($CDCl_3$): 7.40-7.26 (m, 6H), 7.21 (m, 1H), 7.09 (m, 1H), 7.03 (m, 1H), 6.92 (s (br), 1H), 4.33 (dd, 1H, J=3.9, 9.8), 3.92 (dd, 1H, J=3.9, 10.6), 3.51-3.33 (m, 3H), 3.27 (dd, 1H, J=4.0, 14.0), 1.72 (s (br), 1H). HRMS: calcd for $C_{17}H_{18}FN_2O$): 285.1403, found: 285.1410.

3-(2-Chlorobenzyl)-5-phenylpiperazin-2-one (E-27): This compound was obtained from B-30 as a white powder containing a mixture of the two diastereoisomers after a recrystallization in cyclohexane (2.21 g, 45%). $^1H$ NMR ($CDCl_3$): 7.42-7.29 (m, 7H), 7.25-7.14 (m, 2H), 6.85 (bs, 0.4H), 6.69 (bs, 0.6H), 4.37 (dd, J=9.8, 4.2 Hz, 0.4H), 4.10-3.98 (m, 1.4H), 3.83 (dd, J=13.8, 3.4 Hz, 0.6H), 3.51-3.30 (m, 3H), 3.02 (dd, J=13.8, 9.8 Hz, 0.6H). HRMS: calcd for $C_{17}H_{18}ClN_2O$: 301.1108; found, 301.1117.

Cis-3-(2-methoxybenzyl)-5-phenylpiperazin-2-one (E-28): This isomer was obtained as a powder (4.03 g, still containing 5% of the aminoester) after a chromatography over silica gel (dichloromethane—ethanol 97.5/2.5). H. NMR ($CDCl_3$): 7.39-7.27 (m, 6H), 7.21 (m, 1H), 6.89 (m, 2H), 6.38 (s (br), 1H), 4.05 (dd, 1H, J=5.3, 9.3), 3.92 (m, 1H), 3.84 (s, 3H), 3.75 (dd, 1H, J=3.3, 13.7), 3.35 (m, 2H), 2.88 (dd, 1H, J=10.3, 13.7), 1.81 (s (br), 1H). HRMS: calcd for $C_{18}H_{21}N_2O$: 297.1603, found: 297.1607.

Trans-3-(2-methoxybenzyl)-5-phenylpiperazin-2-one (E-29): This isomer was obtained as a powder (2.23 g, 24%) after a chromatography over silica gel (dichloromethane—ethanol 97.5/2.5). $^1H$ NMR ($CDCl_3$): 7.39-7.30 (m, 5H), 7.21 (m, 2H), 6.92 (m, 1H), 6.82 (m, 1H), 6.70 (s (br), 1H), 4.36 (dd, 1H, J=3.9, 9.9), 3.97 (dd, 1H, J=3.9, 10.7), 3.68 (s, 3H), 3.46-3.32 (m, 4H), 3.26 (dd, 1H, J=3.8, 13.5), 1.83 (s (br), 1H). HRMS: calcd for $C_{18}H_{21}N_2O$: 297.1603, found: 297.1604.

Cis-3-(3-fluorobenzyl)-5-phenylpiperazin-2-one (E-30): This isomer was obtained as a powder (2.25 g, 13%) after a chromatography over silica gel (dichloromethane—ethanol 97.5/2.5) and a recrystallization in a mixture of toluene and cyclohexane. $^1H$ NMR ($CDCl_3$): 7.40-7.24 (m, 6H), 7.10 (m, 1H), 7.05 (m, 1H), 6.92 (m, 1H), 6.62 (s (br), 1H), 4.07 (m, 1H), 3.85 (dd, 1H, J=2.9, 10.0), 3.55 (dd, 1H, J=2.9, 13.5), 3.34 (m, 2H), 2.93 (dd, 1H, J=10.0, 13.5), 1.74 (s (br), 1H). HRMS: calcd for $C_{17}H_{19}FN_2O$: 285.1403, found: 285.1400.

Trans-3-G-fluorobenzyl)-5-phenylpiperazin-2-one (E-31): This isomer was obtained as #powder (2.49 g, 15%) after a chromatography over silica gel (dichloromethane—ethanol 97.5/2.5). $^1H$ NMR ($CDCl_3$): 7.35 (m, 5H), 7.26 (m, 3H), 6.70 (s (br), 1H), 4.21 (dd, 1H, J=4.2, 9.3 Hz, 1H), 3.87 (dd, 1H, J=3.8, 10.3), 3.54-3.41 (m, 2H), 3.30 (dd, 1H, J=3.8, 14.0), 3.30 (dd, 1H, J=10.3, 14.0), 1.77 (s (br), 1H). HRMS: calcd for $C_{17}H_{19}FN_2O$: 285.1403, found: 285.1409.

3-(4-fluorobenzyl)-5-phenylpiperazin-2-one (E-32): This compound was obtained as white powder (0.9 g, 59% from phenylnitrostyrene), as a mixture of diastereoisomers after a recrystallization in cyclohexane. HRMS: calcd for $C_{17}H_{18}FN_2O$: 285.1403, found: 285.1408.

(3S,5S)-3-methyl-5-phenylpiperazin-2-one (E-33): This isomer was obtained as a white powder (0.2 g, 12%) after a chromatography over silica gel (dichloromethane—ethanol 97/3 to 9/1) and a recrystallization in a toluene-cyclohexane mixture. Note: by a simple recrystallization of the crude reaction product, a far better overall yield (7.49 g, 47%) of a 1/1 mixture of these isomers was obtained in two batches. $^1H$ NMR ($CDCl_3$): 7.37 (m, 5H), 6.47 (s, 1H), 4.16 (dd, 1H, J=4.2, 10.3), 3.75 (d, 1H, J=6.9), 3.41 (m, 2H), 1.46 (d, 3H, J=6.9) HRMS calcd for $C_{11}H_{14}N_2O$+H: 191.1184 Found: 191.1109.

(3S,5R)-3-methyl-5-phenylpiperazin-2-one (E-34): This isomer was obtained as a white powder (0.19 g, 11%) after a chromatography over silica gel (dichloromethane—ethanol 97/3 to 9/1) and a recrystallization in a toluene-cyclohexane mixture. Note: by simply recrystallizing the crude reaction product, a far better yield (7.49 g, 47%) of a 1/1 mixture of these isomers was obtained in two recrystallization batches. $^1H$ NMR ($CDCl_3$): 7.38 (m, 5H), 6.86 (s, 1H), 4.29 (dd, 1H, J=4.2, 10.3), 3.78 (q, 1H, J=7.0), 3.47 (m, 2H), 1.51 (d, 3H, J=7.0). HRMS calcd for $C_{11}H_{14}N_2O$+H: 191.1184 Found: 191.1138.

3-Benzyl-6-methyl-5-phenylpiperazin-2-one (E-35): Mixture of various diastereoisomers of this compound were obtained after removal of unreacted phenylalanine ethyl ester under high vacuum at 180° C. and a chromatography over silica gel (dichloromethane-methanol 98/2 to 95/5). One of these fractions could be recrystallized in cyclohexane to give the single diastereoisomer (0.8 g, 7%) described below (with an undetermined configuration). In any case, this compound as well, as the other fractions containing different diastereoisomers, were used in the next step. $^1H$ NMR ($CDCl_3$): 7.38-7.28 (m, 7H), 7.24-7.20 (m, 3H), 6.62 (s, 1H), 3.90-3.87 (dd, 1H, J=10.2, 3.8), 3.70-3.63 (m, 2H), 3.30-3.16 (m, 2H), 1.73 (s, 1H), 1.03-0.98 (m, 3H). HRMS: calcd for $C_{18}H_{21}N_2O$: 281.1654, found: 281.1659.

2-Benzyl-1,4a,5,10b-tetrahydro-2H-chromeno[3,4-b]pyrazin-3(4H)-one (E-36); This compound was prepared as described above from 3-nitro-2H-chromene (*Synthesis,* 1984, 348; *Bioorg. Med. Chem.,* 2011, 5420) but running the addition step at 0° C. overnight and obtained, upon refluxing the resulting solid in cyclohexane, as an inseparable mixture containing one major diastereoisomer (4.75 g, 76%). $^1H$ NMR ($CDCl_3$): 7.38-7.29 (m, 16H), 7.20 (m, 1H), 7.02 (s (br), 1H), 6.97 (m, 1H), 6.85 (m, 1H), 4.31 (dd, 1H, J=4.3, 10.3), 3.99 (m, 2H), 3.90 (dd, 1H, J=3.8, 10.0), 3.68 (ddd, 1H, J=3.9, 9.6, 11.1), 3.30 (dd, 1H, J=3.9, 13.6), 3.12 (dd, 1H, J=10.0, 13.6), 1.79 (s (br), 1H). HRMS calcd for $C_{18}H_{19}N_2O_2$: 295.1447, found: 295.1402.

General procedure for the synthesis of pyrazin-2-ols H using sulfur. The considered piperazin-2-one (0.011 mol) and sulfur (0.72 g, 0.0225 mol) were heated to reflux in 1,3-dichlorobenzene (40 mL) for 10 hours. This was concentrated to dryness and the residue purified as described below.

3-Methyl-5-phenylpyrazin-2-ol (H-1): Obtained from E-33 and/or E-34 as a beige powder (1.33 g, 69%) after a chromatography over silica gel (cyclohexane/ethyl acetate 1:2). $^1H$ NMR (DMSO-$d_6$) 12.31 (s, 1H), 7.83 (m, 3H), 7.39 (m, 2H), 7.28 (m, 1H), 2.36 (s, 3H). HRMS: calcd for $C_{11}H_{11}N_2O$: 187.0871; found, 187.0808.

3-(2-Fluorobenzyl)-5-phenylpyrazin-2-ol (H-2): Obtained from B-25 and/or E-26 as a white powder (3.66 g, 88%) after a chromatography over silica gel (dichloromethane/ethanol 97.7:2.5). $^1$H NMR (DMSO-$d_6$) 12.45 (s, 1H), 7.89 (s, 1H), 7.73 (m, 2H), 7.38-7.22 (m, 5H), 7.19-7.12 (m, 2H), 4.12 (s, 2H). HRMS: calcd for $C_{17}H_{17}FN_2O$: 281.1090; found, 281.1087.

3-(2-Chlorobenzyl)-5-phenylpyrazin-2-ol (H-3): Obtained from E-27 as a powder (2.06 g, 68%) after a chromatography over silica gel (dichloromethane/ethanol 98:2) and a dispersion in a boiling mixture of toluene and cyclohexane. $^1$H NMR (DMSO): 12.47 (bs, 1H), 7.90 (s, 1H), 7.70 (m, 2H), 7.46 (m, 1H), 7.32 (m, 5H), 7.25 (m, 1H), 4.22 (s, 2H). HRMS: calcd for $C_{17}H_{14}ClN_2O$: 297.0795; found, 297.0795.

3-(2-Methoxybenzyl)-5-phenylpyrazin-2-ol (H-4): Obtained from (E-28) and/or (E-29) as a white powder (1.7 g, 30%) after a chromatography over silica gel (dichloromethane/ethanol 98.5:1.5 to 97.5:2.5) and a dispersion in a boiling mixture of cyclohexane and toluene. $^1$H NMR (DMSO-$d_6$) 12.35 (s (br), 1H), 7.86 (s, 1H), 7.73 (m, 2H), 7.34 (m, 2H), 7.23 (m, 2H), 7.11 (m, 1H), 6.98 (m, 1H), 6.87 (m, 1H), 4.04 (s, 2H), 3.75 (s, 3H). HRMS: calcd for $C_{18}H_{17}N_2O_2$: 293.1290; found, 293.1280.

3-(3-Fluorobenzyl)-5-phenylpyrazin-2-ol (H-5): Obtained from E-30 and/or E-31 as a white powder (3.92 g, 88%) after a chromatography over silica gel (dichloromethane/ethanol 98:2). A sample was recrystallized in a mixture of cyclohexane and toluene for analytical purposes. $^1$H NMR (DMSO-do) 12.45 (s (br), 1H), 7.89 (s, 1H), 7.82 (m, 2H), 7.41-7.26 (m, 4H), 7.17 (m, 2H), 7.04 (m, 1H), 4.10 (s, 2H). HRMS; calcd for $C_{17}H_{14}FN_2O$: 281.1090; found, 281.1650.

3-(4-Fluorobenzyl)-5-phenylpyrazin-2-ol (H-6): This crude compound was obtained from E-32 after evaporation to dryness and was directly used in the chlorination step without any purification.

3-Benzyl-5-phenylpyrazin-2-ol (H-7): This compound was obtained from E-1 and/or E-2 as a white powder (2.28 g, 73%) after a chromatography over silica gel (dichloromethane—ethanol 98/2 to 97/3). $^1$H NMR (DMSO-6) 12.41 (s, 1H), 7.85 (m, 3H), 7.40 (m, 4H), 7.30 (m, 3H), 7.20 (m, 1H), 4.07 (s, 2H). HRMS: calcd for $C_{17}H_{15}N_2O$: 263.1184; found, 263.1118.

3-Benzyl-5-(p-toly)pyrazin-2-ol (H-8): A pure sample (1.48 g) of this compound (obtained from E-3) was isolated as a white solid by a dispersion of the crude mixture in dichloromethane, the concentrated filtrate and most of this solid were used directly in the next step. $^1$H NMR (DMSO-$d_6$) 12.35 (s, 1H), 7.82 (s, 1H), 7.72 (m, 2H), 7.40-7.17 (m, 7H), 4.06 (s, 2H), 2.30 (s, 3H). HRMS: calcd for $C_{18}H_{16}N_2ONa$: 299.1160; found, 299.1177.

3-Benzyl-5-(m-tolyl)pyrazin-2-ol (H-9): A crude fraction was obtained from E-4 and isolated by a filtration of the resulting precipitate and washing with toluene. An analytical sample was obtained from a recrystallization in toluene of the concentrated filtrate. $^1$H NMR (DMSO-$d_6$) 12.35 (s, 1H), 7.85 (s, 1H), 7.66 (m, 1H), 7.62 (m, 2H), 7.33-7.17 (m, 5H), 7.08 (m, 1H), 4.07 (s, 2H), 2.33 (s, 3H). HRMS: calcd for $C_{18}H_{16}N_2ONa$: 299.1160; found, 299.1172.

3-(2-Methylbenzyl)-5-phenylpyrazin-2-ol (H-10): This compound was obtained from E-5 and/or E-6 as a powder (5.65 g, 88%) after a chromatography over silica gel (dichloromethane—ethanol 99/1-98/2). $^1$H NMR (DMSO-$d_6$) 12.40 (s, 1H), 7.87 (s, 1H), 7.77 (m, 1H), 7.37 (m, 2H), 7.24 (m, 2H), 7.16 (m, 1H), 7.10 (m, 1H), 4.08 (s, 2H), 2.37 (s, 3H). HRMS: calcd for $C_{18}H_{17}N_2ON$: 277.1341; found, 277.1392.

3-(3-Methylbenzyl)-5-phenylpyrazin-2-ol (H-11): This compound was obtained from E-7 and/or E-8 as a powder (5.52 g, 88%) after a chromatography over silica gel (dichloromethane—ethanol 99/1-98/2) and a sample (0.29 g) was recrystallized in a mixture of toluene and cyclohexane (0.27 g). $^1$H NMR (DMSO-$d_6$) 12.38 (s, 1H), 7.87 (s, 1H), 7.84 (m, 2H), 7.40 (m, 2H), 7.28 (m, 1H), 7.16 (m, 3H), 7.01 (m, 1H), 4.03 (s, 2H), 2.26 (s, 3H). HRMS: calcd for $C_{18}H_{17}N_2ON$: 277.1341; found, 277.1395.

3-Benzyl-5-(2-methoxyphenyl)pyrazin-2-ol (H-12); This compound was obtained from E-9 and/or E-10 as a powder (0.54 g, 79%) after a chromatography over silica gel (dichloromethane—ethanol 97/3) $^1$H NMR ($CDCl_3$): 13.33 (s (br), 1H), 8.05 (s, 1H), 8.02 (dd, J=7.7, 1.7 Hz, 1H), 7.51-7.42 (m, 2H), 7.37-7.28 (m, 3H), 7.25-7.19 (m, 1H), 7.08 (td, J=7.7, 1.0 Hz, 1H), 7.02-6.94 (m, 1H), 4.27 (s, 2H), 3.92 (s, 3H). HRMS: calcd for $C_{18}H_{17}N_2O_2$, 293.1290; found, 293.1253.

3-Benzyl-5-(4-methoxyphenyl)pyrazin-2-ol (H-13): This compound was obtained from E-13 and/or E-14 as a powder (0.9 g, 45%) after a chromatography over silica gel (dichloromethane—ethanol 98/2). $^1$H NMR (DMSO-$d_6$) 12.30 (s, 1H), 7.77 (m, 3H), 7.30 (m), 2H), 7.27 (m, 2H), 7.21 (m, 1H), 6.96 (m, 2H), 4.06 (s, 2H), 3.77 (s, 3H). HRMS: calcd for $C_{18}H_{17}N_2O_2$: 293.1290, found, 293.1284.

3-Benzyl-5-(3-methoxyphenyl)pyrazin-2-ol (H-14): An analytical sample of this compound was obtained as a white powder after a recrystallization of the resulting residue in toluene, the rest was used directly in the next step. $^1$H NMR (DMSO-$d_6$) 12.41 (s, 1H), 7.90 (s, 1H), 7.41 (m, 8H), 6.85 (m, 1H), 4.07 (s, 2H), 3.77 (s, 3H). HRMS; calcd for $C_{18}H_{17}N_2O_2$: 293.1290; found, 293.1279.

3-Benzyl-5-(4-(benzyloxy)phenyl)pyrazin-2-ol (H-15): This compound was obtained from (E-21) and/or (E-22) as a powder (0.8 g, 62%) after a chromatography over silica gel (dichloromethane—ethanol 98/2). $^1$H NMR ($CDCl_3$) 12.31 (s, 1H), 7.78 (m, 2H), 7.40 (n), 4H), 7.37 (m, 9H), 7.19 (m, 1H), 7.03 (m, 2H), 5.13 (s, 2H), 4.06 (s, 2H). HRMS: calcd for $C_{24}H_{22}N_2O_2$: 369.1603; found, 369.1603.

3-Benzyl-5-(4-(benzyloxy)-3-fluorophenyl)pyrazin-2-ol (H-16): This compound was obtained from E-23 and/or E-24 as a powder (2 g) after a chromatography over silica gel (dichloromethane—ethanol 985/15) and a sample was recrystallized in toluene for analytical purposes. $^1$H NMR (DMSO-$d_6$) 12.40 (s, 1H), 7.87 (s, 1H), 7.68 (m, 1H), 7.60 (m, 1H), 7.48-7.12 (m, 11H), 5.20 (s, 2H), 4.06 (s, 2H). HRMS: calcd for $C_{24}H_{20}FN_2O_2$: 387.1509; found, 387.1514.

3-benzyl-5-(2-fluorophenyl)pyrazin-2-ol (H-17): This compound was obtained from E-15 and/or E-16 as a white powder (3.38 g, 62%) after a chromatography over silica gel (dichloromethane—ethanol 975/25) and a recrystallization in toluene. $^1$H NMR (DMSO-$d_6$) 12.38 (s, 1H), 7.88 (m, 1H), 7.68 (s, 1H), 7.28 (m, 8H), 4.06 (s, 2H). HRMS: calcd for $C_{17}H_{14}FN_2O$: 281.1090; found, 281.1050.

3-benzyl-5-(2,6-difluorophenyl)pyrazin-2-ol (H-18): This compound was obtained from E-17 as a white powder (1.45 g, 83%) after a chromatography over silica gel (dichloromethane-ethanol 99/1), 12.49 (s, 1H), 7.57 (s, 1H), 7.47 (m, 1H), 7.27 (m, 4H), 7.19 (m, 3H), 4.01 (s, 2H). HRMS: calcd for $C_{17}H_{13}F_2N_2O$: 299.0996; found, 299.0994.

3-benzyl-5-(4-fluorophenyl)pyrazin-2-ol (H-19): This compound was obtained from E-18 and/or E-19 as a white powder (0.43 g, 72%) after a chromatography over silica gel (cyclohexane—ethyl acetate 1/1). $^{1}$H NMR (DMSO-$d_6$) 12.4 (s, 1H), 7.87 (m, 3H), 7.22 (m, 7H), 4.06 (s, 2H). HRMS: calcd for $C_{17}H_{14}FN_2O$): 281.1090; found, 281.1030.

3-Benzyl-5-(3-fluorophenyl)pyrazin-2-ol (H-20): This compound was obtained from E-20 as a 90% pure orange powder (1.69 g) after a chromatography over silica gel (dichloromethane—ethanol 98/2). $^{1}$H NMR (DMSO-$d_6$) 12.50 (s, 1H), 7.98 (s, 1H), 7.69 (m, 1H), 7.64 (m, 1H), J=7.42-7.17 (m, 6H), 7.08 (m, 1H), 4.07 (s, 2H). LCMS (m/z)=281.

Synthesis of pyrazin-2-ol H via step d through of 5-oxo-2,3,4,5-tetrahydropyrazine 1-oxides J, representative preparation of 3-benzyl-5-phenylpyrazin-2-ol (H-7). Step 1, preparation of 6-benzyl-5-oxo-2-phenyl-2,3,4,5-tetrahydropyrazine 1-oxide (J-1): The 3-benzyl-5-phenylpiperazin-2-one (intermediates E-1/E2) (0.44 g, 1.65 mmol) was dissolved in acetic acid (5 mL) and a 36% solution of peracetic acid in acetic acid (0.77 g, 3.63 mmol) was added. This was stirred overnight, diluted in ethyl acetate, washed with water, brine, dried over molecular sieve and concentrated to dryness. The residue was purified by a chromatography over silica gel (cyclohexane—ethyl acetate 1/1 to 1/2) to yield the N-oxide (0.26 g, 56%) as a white powder. Nota, COSY correlations firmly established the structures of this compound. $^{1}$H NMR ($CDCl_3$): 7.43 (m, 2H), 7.35-7.20 (m, 6H), 7.15 (m, 2H), 6.84 (s (br), 1H), 5.12 (t, 1H, J=4.4), 4.13 (s, 2H), 4.00 (dd, 1H, J=4.4, 13.3), 3.63 (dt, 1H, J=4.4, 13.3). HRMS: calcd for $C_{17}H_{17}N_2O_2$: 281.1190; found, 281.1234. Step 2: thermal rearrangement of the N-oxide. In a microwave-adapted vial, crude J-1 (0.41 g, 1.46 mmol) was dissolved in chlorobenzene (5 mL). This was sealed and heated in a microwave oven at 190° C. for two hours. The solvent were removed in vacuum and the residue purified by a chromatography over silica gel (cyclohexane—ethyl acetate 3/2) to give 3-benzyl-5-phenylpyrazin-2-ol (H-7) (0.20 g, 52% from intermediates E-1/E2) with analytical data identical with the one described above.

3-Benzyl-6-methyl-5-phenylpyrazin-2-ol (H-21): Obtained from E-35, or the other diastereoisomers, via 6-benzyl-3-methyl-5-oxo-2-phenyl-2,3,4,5-tetrahydropyrazine 1-oxide, as described above after a chromatography over silica gel (cyclohexane—ethyl acetate 2/1) and a recrystallization in cyclohexane to obtain an analytically pure sample. $^{1}$H NMR ($CDCl_3$) 13.33 (s, 1H), 7.48 (m, 6H), 7.39 (m, 1H), 7.28 (m, 2H), 7.20 (m, 1H), 4.19 (s, 2H), 2.37 (#, 3H). HRMS calcd for $C_{18}H_{17}N_2O$: 277.1341; found, 277.1344.

Synthesis of 2-benzyl-5H-chromeno[3,4-b]pyrazin-3-ol (H-22): Under an inert atmosphere, in a tube fitted with a Teflon cap, (E-36) (0.1 g, 0.34 mmol) and N-iodosuccinimide (0.16 g, 0.69 mmol) were stirred in dry DMF (4 mL) at 60° C. for 90 minute and then 24 hours at 20° C. The resulting solution was diluted in ethyl acetate, washed with water, brine, dried over magnesium sulfate and concentrated to dryness. The resulting residue was purified by a chromatography over silica gel (cyclohexane—ethyl acetate 3/1) to give the expected compound as a powder (0.03 g, 30%). $^{1}$H NMR (DMSO-$d_6$): 12.33 (6, 1H), 7.78 (dd, 1H, J=1.6 et 7.6), 7.37-7.25 (m, 4H), 7.23-7.16 (m, 2H), 7.05 (dt, 1H, J=1.0, 8.5), 6.91 (dd, 1H, J=0.8, 8.1), 5.13 (s, 2H), 4.07 (s, 2H). HRMS: calcd for $C_{18}H_{15}N_2O_2$: 291.1133, found, 291.1066.

General preparation of α-aminosmides F from α-amino esters B. In a steel reactor, the considered α-amino ester (0.065 mol, either as a free base or as a hydrochloride) was dispersed in 7 N methanolic ammonia (50 mL). This was heated at 70° C. for 16-19 hours, concentrated to dryness and the residue was purified as further described below.

2-Amino-3-phenylpropanamide (F-1): Obtained from the hydrochloride of phenylalanine ethyl ester as a white solid (10.29 g, 78%) after 19 hours of heating and a dispersion of the residue in boiling isopropanol (three crops). $^{1}$H NMR (DMSO-$d_6$): 7.71 (s (br), 1H), 7.29 (m, 6H), 6.47 (s (br), 3H), 3.74 (dd, 1H, J=5.9, 7.6), 3.04 (dd, 1H, J=5.9, 13.7), 2.87 (dd, 1H, J=7.6, 13.7), note: signals shifts are dependent on the sample concentration as well as its water content.

2-Amino-3-(tetrahydrofuran-2-yl)propanamide (F-2): Obtained from B-16 as a solid which was not further purified. $^{1}$H NMR ($CDCl_3$): mixture of isomer: 7.23 (s, 1H), 5.63 (s, 1H), 4.02 (m, 2H), 3.88 (m, 1H), 3.74 (m, 1H), 3.56 (m, 1H), 2.07 (m, 1H), 1.89 (m, 5H), 1.54 (m, 1H). HRMS: calcd for $C_7H_{15}N_2O$: 159.1134; found, 139.1122.

2-Amino-3-(pyridin-3-yl)propanamide (F-3): Obtained from B-23 as an orange solid (3.46 g, 99%). $^{1}$H NMR (DMSO-$d_6$): 8.42 (m, 1H), 8.40 (dd, 1H, J=1.9, 4.6), 7.62 (m, 1H), 7.26 (m, 2H), 6.95 (s (br), 1H), 4.02 (m, 2H), 3.35 (dd, 1H, J=5.3, 8.0), 2.90 (dd, 1H, J=5.2, 13.6), 2.64 (dd, 1H, J=8.0, 13.6), 1.75 (m, 2H). HRMS: calcd for $C_8H_{12}N_3O$: 166.0980; found, 166.0984.

General procedure for the synthesis pyrazin-2-ol H vis a condensation between glyoxal and α-aminoamides F. These compounds were prepared by following the protocols previously described (J. Am. Chem. Soc., 1949, 78; U.S. Pat. No. 4,046,763, 1977).

5-Phenylpyrazin-2-ol (H-23): Obtained from phenyl glyoxal and glycine amide hydrochloride as a beige powder (1.69 g, 48%). $^{1}$H NMR (DMSO-$d_6$) 12.43 (s, 1H), 8.12 (d, 1H, J=1.3), 8.06 (s, 1H), 7.85 (m, 2H), 7.42 (m, 2H), 7.30 (m, 1H). HRMS: calcd for $C_{10}H_9N_2O$: 173.0715; found, 173.0654.

5-phenyl-3-((tetrahydrofuran-2-yl)methyl)pyrazin-2-ol (H-24): Obtained from phenyl glyoxal and F-2 as a pink solid (1.02 g, 45%). $^{1}$H NMR ($CDCl_3$): 13.22 (s (br), 1H), 7.8) (m, 2H), 7.63 (s (br), 1H), 7.44 (m, 2H), 7.35 (m, 1H), 4.60 (p, 1H, J=6.6), 3.99 (m, 1H), 3.80 (m, 1H), 3.30 (dd, 1H, J=7.0, 14.8), 3.05 (dd, 1H, J=6.1, 14.8), 2.17 (m, 1H), 1.98 (m, 2H), 1.76 (m, 1H). HRMS; calcd for $C_{15}H_{17}N_2O_2$, 257.1290; found, 257.1281.

5-phenyl-3-(pyridin-3-ylmethyl)pyrazin-2-ol (H-25): Obtained from phenyl glyoxal and F-3 as a white solid (0.57 g, 11.5%) after a dispersion of the crude ethyl acetate extract in dichloromethane and a chromatography over silica gel (dichloromethane—ethanol 95/5 to 9/1). $^{1}$H NMR (DMSO-$d_6$): 12.47 (s (br), 1H), 8.57 (d, 1H, J=1.7), 8.43 (dd, 1H, J=1.7, 4.8), 7.89 (s, 1H), 7.92 (m, 2H), 7.74 (m, 1H), 7.40-7.25 (m, 4H), 4.10 (s, 2H). HRMS: calcd for $C_{16}H_{14}N_3O$, 264.1137; found, 264.1122.

General procedure for the synthesis of chloropyrazines L vis steps j. Under a calcium-protected atmosphere, the considered 2-hydroxypyrazine H (0.02 mol) was dispersed in phenylphosphonic dichloride (10 mL) and the suspension was heated at 100° C. for, unless stated otherwise, 12 h. The resulting solution was diluted in ethyl acetate and poured onto an excess of crushed ice and stirred for 15 min. This was made basic with 22% ammonia and extracted with ethyl acetate. The organic layer was washed with water, brine, dried over magnesium sulfate and concentrated to dryness and purified as described below.

2-Chloro-5-phenylpyrazine (L-1): Obtained from H-23 as a yellow solid (1.42 g, 82%) after healing at 100° C. for 4 hours and a chromatography over silica gel (cyclohexane—dichloromethane 1/1). $^{1}$H NMR ($CDCl_3$): 8.80 (d, 1H, J=1.5), 8.64 (d, 1H, J=1.5), 8.00 (m, 2H), 7.51 (m, 3H). HRMS: calcd for $C_{10}H_8ClN_2$, 191.0376; found, 191.0322.

2-Chloro-3-methyl-5-phenylpyrazine (L-2): Obtained from H-1 as a yellow solid (1.18 g, 74%) after heating only at 80° C. for 12 hours and a chromatography over silica gel (cyclohexane—dichloromethane 1/1). $^1H$ NMR ($CDCl_3$): 8.63 (s, 1H), 8.01 (m, 2H), 7.50 (m, 3H), 2.75 (s, 3H). HRMS: calcd for $C_{11}H_{10}ClN_2$, 205.0533; found, 205.0464.

2-Chloro-3-(2-fluorobenzyl)-5-phenylpyrazine (L-3): Obtained from H-2 as a white solid (3.01 g, 79%) after a chromatography over silica gel (cyclohexane—ethyl acetate 94/6). $^1H$ NMR ($CDCl_3$): 1H NMR (CDC), 400 MHz): 8.70 (s, 1H), 7.98-7.94 (m, 2H), 7.53-7.45 (m, 3H), 7.31-7.25 (m, 2H), 7.14-7.09 (m, 2H), 4.44 (s, 2H). HRMS: calcd for $C_{17}H_{13}ClFN_2$, 299.0751; found, 299.0749.

2-Chloro-3-(2-chlorobenzyl)-5-phenylpyrazine (L-4): Obtained from H-3 as a white solid (1.58 g, 73%) after a recrystallization in ethanol. $^1H$ NMR ($CDCl_3$): 8.70 (s, 1H), 7.93 (m, 2H), 7.46 (m, 4H), 7.22 (m, 3H), 4.52 (s, 2H). HRMS: calcd for $C_{17}H_{13}Cl_2N_2$: 315.0456; found, 315.0466.

2-Chloro-3-(2-methoxybenzyl)-5-phenylpyrazine (L-5): Obtained from H-4 as a white solid (0.73 g, 63%) after a recrystallization in ethanol. $^1H$ NMR ($CDCl_3$): $^1H$ NMR (CDC), 400 MHz): 8.66 (s, 1H), 7.96 (m, 2H), 7.48 (m, 3H), 7.27 (m, 1H), 7.14 (m, 1H), 6.93 (m, 2H), 4.40 (s, 2H), 3.83 (s, 2H) HRMS: calcd for $C_{18}H_{16}ClN_2O$, 311.0951; found, 311.0949.

2-Chloro-3-(3-fluorobenzyl)-5-phenylpyrazine (L-6): Obtained from H-5 as an oil (3.19 g, 86%) after a chromatography over silica gel (cyclohexane—ethyl acetate 97/3). $^1H$ NMR ($CDCl_3$): 8.69 (s, 1H), 8.03 (m, 2H), 7.52 (m, 3H), 7.29 (m, 1H), 7.18 (m, 1H), 7.12 (m, 1H), 6.96 (m, 1H), 4.39 (s, 2H). HRMS: calcd for $C_{17}H_{13}ClFN_2$, 299.0751; found, 299.0749.

2-Chloro-3-(4-fluorobenzyl)-5-phenylpyrazine (L-7): Obtained from H-6 as a white solid (0.25 g, 29% from E-32) after a chromatography over silica gel (cyclohexane—ethyl acetate 97/3) $^1H$ NMR ($CDCl_3$): 8.68 (s, 1H), 8.02 (m, 2H), 7.52 (m, 3H), 7.36 (m, 2H), 7.02 (m, 2H), 4.36 (s, 2H) HRMS: calcd for $C_{17}H_{13}ClFN_2$, 299.0751; found, 299.0746.

3-benzyl-2-chloro-5-phenylpyrazine (L-8): Obtained from H-7 as a yellowish solid (1.60 g, 82%) after a chromatography over silica gel (cyclohexane—dichloromethane 3:2). Alternatively, this compound was obtained in 36% yield under the same reaction conditions but using the N-oxide J=1. $^1H$ NMR ($CDCl_3$): 8.68 (s, 1H), 8.08-8.00 (m, 2H), 7.58-7.47 (m, 3H), 7.44-7.40 (m, 2H), 7.37-7.32 (m, 2H), 7.30-7.25 (m, 1H), 4.41 (s, 2H). HRMS: calcd for $C_{17}H_{14}ClN_2$: 281.0846; found, 281.0730.

2-Benzyl-3-chloro-5-methyl-6-phenylpyrazine (L-9): Obtained from H-21 as an oil (0.38 g, 20% overall from 6-benzyl-3-methyl-5-oxo-2-phenyl-2,3,4,5-tetrahydropyrazine 1-oxide) after a chromatography over silica gel (cyclohexane—ethylacetate 97:3). $^1H$ NMR ($CDCl_3$, 400 MHz): 7.62-7.59 (m, 2H), 7.53-7.45 (m, 3H), 7.40-7.37 (m, 2H), 7.33-7.22 (m, 4H), 4.36 (s, 2H), 2.61 (s, 3H). HRMS: calcd for $C_{18}H_{16}ClN_2$, 295.1002; found, 295.1003.

3-Benzyl-2-chloro-5-(p-tolyl)pyrazine (L-10): Obtained from H-8 as a yellow solid (1.83 g, 22% from 1-methyl-4-(2-nitrovinyl)benzene) after a chromatography over silica gel (cyclohexane—dichloromethane 3/2). $^1H$ NMR ($CDCl_3$): 8.64 (s, 1H), 7.94 (m, 2H), 7.48-7.23 (m, 7H), 4.39 (s, 2H), 2.45 (s, 3H). HRMS: calcd for $C_{18}H_{16}ClN_2$: 295.1002; found, 295.0999.

3-Benzyl-2-chloro-5-(m-tolyl)pyrazine (L-11): This compound was obtained from H-9 as a white solid (3.02 g, 33% from 1-methyl-3-(2-nitrovinyl)benzene) after heating for 18 hours and a chromatography over silica gel (cyclohexane—ethyl acetate 965/35). $^1H$ NMR ($CDCl_3$): 8.66 (s, 1H), 7.84 (m, 1H), 7.82 (m, 2H), 7.43-7.24 (m, 6H), 4.40 (s, 2H), 2.48 (s, 3H). HRMS: calcd for $C_{18}H_{16}ClN_2$, 295.1002; found, 295.1014.

2-Chloro-3-(2-methylbenzyl)-5-phenylpyrazine (L-12): This compound was obtained from H-10 as a solid (5.12 g, 89%) after a chromatography over silica gel (cyclohexane—ethyl acetate 95/5). $^1H$ NMR ($CDCl_3$): 8.69 (s, 1H), 7.98 (m, 2H), 7.50 (m, 3H), 7.20 (m, 4H), 4.39 (s, 2H) 2.46 (s, 3H). HRMS: calcd for $C_{18}H_{16}ClN_2$, 295.1002; found, 295.1009.

2-Chloro-3-(3-methylbenzyl)-5-phenylpyrazine (L-13): This compound was obtained from H-11 as a solid (5.03 g, 90%) after a chromatography over silica gel (cyclohexane—ethyl acetate 96/4). $^1H$ NMR ($CDCl_3$): 8.68 (s, 1H), 8.05 (m, 2H), 7.51 (m, 3H), 7.22 (m, 3H), 7.08 (m, 1H), 4.37 (s, 2H), 2.36 (s, 3H). HRMS: calcd for $C_{18}H_{16}ClN_2$, 295.1002; found, 295.0997.

3-Benzyl-2-chloro-5-(2-methoxyphenyl)pyrazine (L-14): Obtained from H-12 as a yellow solid (1.82 g, 81%) after heating for 18 hours and a chromatography over silica gel (cyclohexane—dichloromethane 3/2). $^1H$ NMR ($CDCl_3$): 8.86 (s, 1H), 7.91 (dd, 1H, J=7.6, 1.8), 7.48-7.36 (m, 3H), 7.34-7.28 (m, 2H), 7.26-7.18 (m, 1H), 7.11 (td, 1H, J=7.6, 0.8), 7.03 (d, 1H, J=8.3), 4.37 (s, 2H), 3.90 (s, 3H). HRMS: calcd for $C_{18}H_{16}ClN_2O$, 311.0951; found, 311.0965.

3-Benzyl-2-chloro-5-(2-fluorophenyl)pyrazine (L-15): Obtained from H-17 as a yellow solid (3.30 g, 67%) after heating for 16 hours and a chromatography over silica gel (cyclohexane-dichloromethane 2/1). $^1H$ NMR ($CDCl_3$): 8.78 (d, 1H, J=2.2), 8.04 (dt, 1H, J=7.6, 1.8), 7.30 (m, 8H), 4.40 (s, 2H). HRMS: calcd for $C_{17}H_{13}ClFN_2$, 299.0751; found, 299.0818.

3-Benzyl-2-chloro-5-(3-fluorophenyl)pyrazine (L-16): Obtained as a powder from H-20 after a chromatography over silica gel (cyclohexane—ethyl acetate 98/2) (0.98 g, 8% from 1-fluoro-3-(2-nitrovinyl)benzene). $^1H$ NMR ($CDCl_3$): 8.66 (s, 1H), 7.78 (m, 2H), 7.48 (m, 1H), 7.41-7.24 (m, 4H), 7.18 (m, 1H), 4.40 (s, 2H). HRMS: calcd for $C_{17}H_{13}ClFN_2$, 299.0751; found, 299.0749.

3-benzyl-2-chloro-5-(2,6-difluorophenyl)pyrazine (L-17): Obtained from H-18 as a white solid (0.75 g, 56%) after a chromatography over silica gel (cyclohexane—dichloromethane 3/1). $^1H$ NMR ($CDCl_3$): 8.44 (m, 1H), 7.43 (m, 3H), 7.27 (m, 2H), 7.25 (m, 1H), 7.05 (m, 2H), 4.40 (s, 2H). HRMS: calcd for $C_{17}H_{11}ClF_2N_2$, 317.0657; found, 317.0648.

3-benzyl-2-chloro-5-(4-fluorophenyl)pyrazine (L-18): Obtained from H-19 as a white solid (0.84 g, 52%) after heating for 14 hours and a chromatography over silica gel (cyclohexane—dichloromethane 3/1). $^1H$ NMR ($CDCl_3$): 8.63 (s, 1H), 8.02 (m, 2H), 7.39 (m, 2H), 7.34 (m, 2H), 7.28 (m, 1H), 7.19 (m, 2H), 4.39 (s, 2H). HRMS: calcd for $C_{17}H_{13}ClFN_2$, 299.0751; found, 299.0763.

3-Benzyl-2-chloro-5-(4-methoxyphenyl)pyrazine (L-19): Obtained from (H-13) as a yellow solid (0.33 g, 35%) after a chromatography over silica gel (cyclohexane—dichloromethane 3/2). H. NMR ($CDCl_3$): 8.61 (s, 1H), 7.97 (m, 2H), 7.40 (m, 2H), 7.31 (m, 2H), 7.27 (m, 1H), 7.02 (m, 2H), 4.37 (s, 2H), 3.89 (s, 3H), HRMS: calcd for $C_{18}H_{16}ClN_2O$, 311.0951; found, 311.0955.

3-Benzyl-2-chloro-5-(3-methoxyphenyl)pyrazine (L-20): This compound was obtained from the crude H-14 as a white powder (0.4 g, 32% from E-11/E-12), after a chromatography over silica gel (cyclohexane—ethyl acetate 95/5). $^1H$ NMR ($CDCl_3$): 8.66 (s, 1H), 7.97 (m, 2H), 7.58 (m, 2H), 7.41 (m, 3H), 7.33 (m, 2H), 7.25 (m, 1H), 7.03 (m, 1H), 4.39 (s, 2H), 3.90 (s, 3H). HRMS: calcd for $C_{18}H_{16}ClN_2O$, 311.0951; found, 311.0962.

3-Benzyl-5-(4-(benzyloxy)phenyl)-2-chloropyrazine (L-21); Obtained from H-15 as a yellow solid (5.66 g, 62%) after heating for 18 hours and a chromatography over silica gel (cyclohexane—dichloromethane 1/1). $^1$H NMR ($CDCl_3$): 8.61 (s, 1H), 8.0 (m, 2H), 7.47-7.20 (m, 10H), 7.11 (m, 2H), 5.17 (s, 2H), 4.38 (s, 2H). HRMS: calcd for $C_{24}H_{20}ClN_2O$, 387.1264; found, 387.1266.

3-Benzyl-5-(4-(benzyloxy)-3-fluorophenyl)-2-chloropyrazine (L-22): Obtained from H-16 as a yellow solid (1.39 g, 29% from the nitrovinyl) after a chromatography over silica gel (cyclohexane—dichloromethane 1/1). $^1$H NMR ($CDCl_3$): 8.58 (s, 1H), 7.84 (m, 1H), 7.70 (m, 1H), 7.50-7.24 (m, 10H), 7.11 (m, 1H), 5.24 (s, 2H), 4.37 (s, 2H). HRMS: calcd for $C_{24}H_{19}ClFN_2O$, 405.1170; found, 405.1154.

2-benzyl-3-chloro-5H-chromeno[4,3-b]pyrazine (L-23): Obtained from H-22 as a white powder (0.01 g, 10%) after a chromatography over silica gel (cyclohexane—dichloromethane 3/2). $^1$H NMR ($CDCl_3$): 8.15 (dd, 1H, J=2.0, 7.8), 7.41-7.31 (m, 5H), 7.28-7.24 (m, 1H), 7.13 (dt, 1H, J=1.0, 8.1), 7.00 (dd, 1H, J=1.0, 8.3), 5.31 (s, 2H), 4.37 (s, 2H). HRMS: calcd for $C_{18}H_{14}ClN_2O$, 309.0795; found, 309.0804.

2-chloro-5-phenyl-3-(pyridin-3-ylmethyl)pyrazine (L-24); obtained from H-25 as an oil (0.42 g, 83%) after a chromatography over silica gel (dichloromethane—ethanol 98/2). $^1$H NMR ($CDCl_3$): 8.70 (m, 1H), 8.69 (s, 1H), 8.52 (dd, 1H, J=1.6, 4.9), 7.99 (m, 2H), 7.71 (m, 1H), 7.50 (m, 3H), 7.26 (ddd, 1H, J=0.8, 4.9, 8.0), 4.38 (s, 2H). HRMS: calcd for $C_{16}H_{13}ClN_3$, 282.0798; found, 282.0795.

General procedure for the synthesis of bromopyrazines L (X═Br) via steps i and l. Step i: preparation of the trifluoromethanesulfonate K. At room temperature, the considered hydroxypyrazine (3 mmol) was dissolved in dry dichloromethane (20 mL, stabilized by amylene, dried over 4 Å sieve). Triethylamine (0.142 mL, 3.15 mmol) and triflic anhydride (0.51 mL, 3.06 mmol) were then added. The resulting solution was stirred for 40 minutes, diluted in ethyl acetate, washed with water, brine, dried over magnesium sulfate and concentrated to dryness. The resulting residue was purified as described below. Step 1: Exchange reaction with sodium bromide. In a tube featuring a Teflon-coated screw cap, one of these purified triflate esters (2 mmol) and dry sodium bromide (0.51 g, 5 mmol) were dispersed in dry dimethylformamide (4 ml). Triflic acid (0.16 mL, 1.8 mmol) was added, the tube was closed and heated at 120° C. overnight. The resulting solution was diluted in diluted in ethyl acetate, washed with water, brine, dried over magnesium sulfate and concentrated to dryness. The resulting residue was then further purified as described below.

3-Benzyl-5-phenylpyrazin-2-yl trifluoromethanesulfonate (K-1): Obtained from H-7 as a white powder (0.34 g, 30%) after a chromatography over silica gel (cyclohexane—dichloromethane 4/1 to 1/1) H NMR ($CDCl_3$): 8.60 (s, 1H), 8.05-7.97 (m, 2H), 7.57-7.49 (m, 3H), 7.39-7.30 (m, 4H), 7.29-7.23 (m, 1H), 4.32 (s, 2H). HRMS: calcd for $C_{18}H_{14}F_3N_2O_3S$, 395.0677; found, 395.0695.

3-Benzyl-2-bromo-5-phenylpyrazine (L-25); Obtained from K-1 as white crystals (0.02 g, 30%) after a chromatography over silica gel (cyclohexane—dichloromethane 3:2). $^1$H NMR ($CDCl_3$), 8.63 (s, 1H), 8.05-7.97 (m, 2H), 7.56-7.47 (m, 3H), 7.43-7.37 (m, 2H), 7.35-7.29 (m, 2H), 7.28-7.21 (m, 1H), 4.41 (s, 2H). HRMS: calcd for $C_{17}H_{14}BrN_2$, 325.0340; found, 325.0319.

5-phenyl-3-((tetrahydrofuran-2-yl)methyl)pyrazin-2-yl trifluoromethanesulfonate (K-2): Obtained from (H-24) as an oil (0.37 g, 43%) after a chromatography over silica gel (cyclohexane—dichloromethane 1/3). $^1$H NMR ($CDCl_3$): 8.60 (s, 1H), 8.01 (m, 2H), 7.53 (m, 3H), 4.51 (m, 1H), 3.95 (m, 1H), 3.77 (m, 1H), 3.27 (dd, 1H, J=7.8, 14.1), 3.10 (dd, 1H, J=5.4, 14.1), 2.17 (m, 1H), 1.96 (m, 2H), 1.76 (m, 1H). HRMS: calcd for $C_{16}H_{16}F_3N_2O_4S$, 389.0783; found, 389.0808.

2-Bromo-5-phenyl-3-((tetrahydrofuran-2-yl)methyl)pyrazine (L-26): Obtained from K-2 as an oil (0.19 g, 62%) after a chromatography over silica gel (cyclohexane—dichloromethane 1/4 to dichloromethane—ethanol 99/1). $^1$H NMR ($CDCl_3$): 8.62 (s, 1H), 8.02 (m, 2H), 7.50 (m, 3H), 4.57 (p, 1H, J=6.7), 3.99 (m, 1H), 3.80 (m, 1H), 3.42 (dd, 1H, J=6.7, 14.6), 3.14 (dd, 1H, J=6.7, 14.6), 2.12 (m, 1H), 1.99 (m, 2H), 1.76 (m, 1H). HRMS: calcd for $C_{15}H_{16}BrN_2O$, 319.0446; found, 319.0464.

2-benzyl-5H-chromeno[4,3-b]pyrazin-3-yl trifluoromethanesulfonate (K-3): Obtained from H-22, as an oil and a sample was purified by a chromatography over silica gel (cyclohexane—dichloromethane 2/1). $^1$H NMR ($CDCl_3$): 8.15 (dd, 1H, J=1.7, 7.8), 7.44-7.30 (m, 6H), 7.14 (dt, 1H, J=1.1, 8.0), 7.02 (dd, 1H, J=0.9, 8.3), 5.31 (s, 2H), 4.30 (s, 2H). HRMS: calcd for $C_{18}H_{13}F_3N_2O_4S$, 423.0627; found, 423.0638.

2-benzyl-3-bromo-5H-chromeno[4,3-b]pyrazine (L-27): Obtained from K-3, as white solid (0.04 g, 24%) after a chromatography over silica gel (cyclohexane—dichloromethane 2/1). Nota: an improved yield (0.075 g, 40%) was achieved when using a 10 equivalent excess of sodium bromide under the same reaction conditions. $^1$H NMR ($CDCl_3$): 8.15 (dd, 1H, J=1.6, 7.8), 7.44-7.23 (m, GH), 7.12 (dt, 1H, J=1.0, 8.1), 7.02 (dd, 1H, J=0.7, 8.1), 5.32 (s, 2H), 4.39 (s, 2H). HRMS: calcd for $C_{18}H_{13}BrN_2O$, 353.0290; found, 353.0295.

General procedure for the synthesis N-aryl α-aminoesters N from halogenopyrazines L and α-aminoesters B via steps n. In a 20 mL sealable vial, the considered 2-halogenopyrazine L (0.001 mol), the considered amino ester B (0.0011 mol, either as a free base or as a hydrochloride salt), cesium carbonate (0.0022 mol or 0.0032 mol, 0.69 g or 1.04 g) and a 1/1 mixture of palladium acetate and 2,2-bis(diphenylphosphanyl)-1,1'-binaphthalene (BINAP) (0.05 mmol, 47 mg) were weighted. The air was replaced by argon and, under an inert atmosphere, dry acetonitrile (8 mL) was injected (dry dimethyl formamide can also be used). This was heated at 60° C. for 12 hours using either an oil bath along with very fast stirring to break up the clumps of caesium hydrogen carbonate forming, or an ultra sound bath featuring a temperature regulation. The resulting dark red or black suspension was dispersed in dichloromethane; this was filtered and concentrated to dryness prior further purification as described below.

Ethyl 2-((3-benzyl-5-phenylpyrazin-2-yl)amino)-3-methylpentanoate (N-1): Obtained from L-8 and IleOEt as an oil (0.25 g, 52%) after a chromatography over silica gel (cyclohexane—ethyl acetate 95/5). N.B.: A degree of racemization (about 30%) was observed, either upon storage of IleOEt as a free base or upon the N-arylation reaction. $^1$H NMR (diastereoisomeric mixture, 0.30/0.70 ratio, $CDCl_3$): 8.41 (s, 1H), 7.95 (m, 2H), 7.47 (m, 2H), 7.38-7.32 (m, 5H), 7.29-7.26 (m, 1H), 4.84 (m, 0.7H), 4.75 (m, 0.3H), 4.65 (m, 1H), 4.31 (m, 2H), 4.15 (m, 2H), 1.83 (m, 1H), 1.35 (m, 1H), 1.24 (m, 3H), 1.02 (m, 1H), 0.85 (m, 3H), 0.75 (m, 3H). HRMS: calcd for $C_{25}H_{30}N_3O_2$, 404.2338; found, 404.2348.

Ethyl 2-(3-benzyl-5-phenylpyrazin-2-yl)amino)-3-cyclopentylpropanoate (N-2); Obtained from L-8 and B-13 as an oil (0.26 g, 58%) after a chromatography over silica gel (cyclohexane—ethyl acetate 95/5). $^{1}$H NMR ($CDCl_3$): 8.42 (s, 1H), 7.95 (m, 2H), 7.47 (m, 2H), 7.38-7.32 (m, 5H), 7.29-7.26 (m, 1H), 4.78 (d, 1H, J=7.4), 4.60 (m, 2H), 4.30 (d, 1H, J=15.1), 4.21 (d, 1H, J=15.1), 4.16 (q, 2H, J=7.2), 1.83 (m, 1H), 1.70-1.39 (m, 7H), 1.24 (t, 3H/=7.2), 1.01 (m, 2H). HRMS: calcd for $C_{27}H_{32}N_3O_2$, 430.2495; found, 430.2485.

Ethyl 2-((3-benzyl-5-phenylpyrazin-2-yl)amino)-3-cyclohexylpropanoate (N-3): Obtained from L-8 and B-14 as an oil (0.36 g, 78%) after a chromatography over silica gel (cyclohexane—ethyl acetate 95/5). $^{1}$H NMR ($CDCl_3$): 8.41 (s, 1H), 7.95 (m, 2H), 7.47 (m, 2H), 7.38-7.32 (m, 5H), 7.29-7.26 (m, 1H), 4.60 (m, 4H), 4.30 (d, 1H, J=15.5), 4.20 (d, 1H. J=15.5), 4.16 (m, 2H), 1.60 (m, 6H), 1.48 (m, 1H), 1.24 (t, 3H, J=7.2), 1.08 (m, 4H), 0.86 (m, 2H). HRMS: calcd for $C_{28}H_{34}N_3O_2$, 444.2651; found, 444.2647.

Ethyl 2-((3-benzyl-5-phenylpyrazin-2-yl)amino)-3-(bicyclo[2.2.1]heptan-2-yl)propanoate (N-4): Obtained from (L-8) and (B-15) as an oil (1.48 g, 82%) as a mixture of 4 diastereoisomers (as seen by the number of CO signals in the $^{13}$C spectrum) after a chromatography over silica gel (cyclohexane—ethyl acetate 95/5). $^{1}$H NMR ($CDCl_3$): 8.41 (s, 1H), 7.95 (m, 2H), 7.46 (m, 2H), 7.38-7.25 (m, 6H), 4.77 (m, 1H), 4.56 (m, 1H), 4.31-4.16 (m, 4H), 2.17 (m, 0.4H), 2.10 (m, 0.6H), 2.02 (m, 0.4H), 1.90-0.88 (m, 14H), 0.50 (m, 0.6H). HRMS: calcd for $C_{29}H_{34}N_3O_2$, 456.2651; found, 456.2661.

Ethyl (3-benzyl-5-phenylpyrazin-2-yl)phenylalaninate (N-5): Obtained from L-8 and PheOEt, HCl as an oil (1.07 g, 69%) after a chromatography over silica gel (dichloromethane), $^{1}$H NMR ($CDCl_3$): 8.43 (s, 1H), 7.96 (m, 2H), 7.53-7.43 (m, 1H), 7.41-7.34 (m, 1H), 7.33-7.20 (m, 8H), 7.05-6.95 (m, 2H), 4.97 (m, 2H), 4.14 (s, 2H), 4.13 (q, J=7.1 Hz, 2H), 3.18 (dd, J=13.8, 5.4 Hz, 1H), 3.09 (dd, J=13.8, 5.9 Hz, 1H), 1.20 (t, J=7.1 Hz, 3H). HRMS: calcd for $C_{28}H_{28}N_3O_2$, 438.2182; found, 438.2185.

Ethyl (3-benzyl-6-methyl-5-phenylpyrazin-2-yl)phenylalaninate (N-6): Obtained from 1-9 and PheOEt, HCl as an oil (0.4 g, 84%) after a chromatography over silica gel (cyclohexane—ethyl acetate 94/6). $^{1}$H NMR (CDC), 400 MHz): 7.60-7.57 (m, 2H), 7.48-7.44 (m, 2H), 7.39-7.35 (m, 1H), 7.31-7.20 (m, 5H), 7.03-7.00 (m, 2H), 5.00-4.95 (q, 1H, J=7.0), 4.80-4.78 (m, 1H), 4.18-4.09 (m, 4H), 3.17-3.12 (m, 1H), 3.08-3.03 (m, 1H), 2.46 (s, 3H), 1.22-1.18 (t, J=7.9 Hz, 3H). HRMS: calcd for $C_{29}H_{30}N_3O_2$, 452.2338; found, 452.2347.

Ethyl 2-((3-benzyl-5-phenylpyrazin-2-yl)amino)-3-phenylbutanoate (N-7): Obtained from L-8 and B-41 as an oil (0.3 g, 67%) after a a chromatography over silica gel (cyclohexane—ethyl acetate 96/4). $^{1}$H NMR (diastereoisomeric mixture, 0.6/0.4 ratio) ($CDCl_3$): 8.40 (s, 0.6H), 8.34 (s, 0.3H), 7.94 (m, 2H), 7.46 (m, 2H), 7.39-7.19 (m, 7H), 7.21 (m, 1H), 7.16 (m, 1H), 7.05 (m, 2H), 4.95 (m, 1H), 4.89 (d, 0.4H, J=7.7), 4.69 (d, 0.6H, J=8.3), 4.20 (m, 0.8H), 4.08 (m, 0.8H), 4.08 (m, 2.6H), 3.37 (m, 0.6H), 3.0 (m, 0.4H), 1.28 (d, 1.8H, J=7.1), 1.24 (d, 0.8H, J=7.3), 1.16 (t, 1.8H, J=7.5), 1.08 (t, 0.8H, J=7.3). HRMS: calcd for $C_{29}H_{30}N_3O_2$, 452.2338; found, 452.2378.

Methyl 2-((3-benzyl-5-(4-(benzyloxy)phenyl)pyrazin-2-yl)amino)-3-(4-(benzyloxy)phenyl)propanoate (N-8): Obtained from L-21 PheOMe, HCl (0.53 g, 86%) after a chromatography over silica gel (dichloromethane). $^{1}$H NMR ($CDCl_3$): 8.39 (s, 1H), 7.98-7.87 (m, 2H), 7.53-7.47 (m, 4H), 7.47-7.4) (m, 4H), 7.41-7.35 (m, 2H), 7.34-7.27 (m, 3H), 7.25-7.21 (m, 2H), 7.15-7.07 (m, 2H), 6.94-6.82 (m, 4H), 5.17 (s, 2H), 5.09 (s, 2H), 5.03-4.94 (m, 1H), 4.86 (d, 1H, J=7.4), 4.15 (s, 2H), 3.70 (s, 3H), 3.15 (dd, 1H, J=13.9, 5.3), 3.05 (dd, 1H, J=13.9, 6.0). HRMS: calcd for $C_{41}H_{38}N_3O_4$, 636.2863; found, 636.2897.

Ethyl 2-((3-benzyl-5-(4-(benzyloxy)phenyl)pyrazin-2-yl)amino)-3-(4-(benzyloxy)phenyl)propanoate (N-9): Obtained as an oil (1.17 g, 70%) from L-21 and B-5 after a chromatography over silica gel (cyclohexane—ethyl acetate 91/9 to 9/1). $^{1}$H NMR ($CDCl_3$): 8.34 (s, 1H), 7.92-7.83 (m, 2H), 7.49-7.43 (m, 4H), 7.43-7.37 (m, 4H), 7.37-7.31 (m, 2H), 7.30-7.22 (m, 3H), 7.22-7.17 (m, 2H), 7.11-7.02 (m, 2H), 6.91-6.77 (m, 4H), 5.13 (s, 2H), 5.05 (s, 2H), 4.95-4.87 (m, 1H), 4.86-4.79 (m, 1H), 4.15-4.09 (m, 4H), 3.10 (dd, 1H, J=13.9, 5.4), 3.01 (dd, 1H, J=13.9, 5.9), 1.19 (t, 3H, J=7.1). HRMS; calcd for $C_{42}H_{40}N_3O_4$, 650.3019; found, 650.3049.

Ethyl (3-benzyl-5-(4-(benzyloxy)-3-fluorophenyl)pyrazin-2-yl)phenylalaninate (N-10): Obtained as an oil (0.66 g, 83%) from L-22 and PheOEt, HCl after a chromatography over silica gel (cyclohexane—ethyl acetate 96/4 to 93/7). $^{1}$H NMR ($CDCl_3$): 8.33 (s, 1H), 7.75 (m, 1H), 7.60 (m, 1H), 7.49 (m, 2H), 7.41 (m, 2H), 7.37-7.18 (m, 9H), 7.07 (m, 1H), 7.98 (m, 2H), 5.21 (s, 2H), 4.12 (m, 4H), 3.16 (dd, 1H, J=5.4, 14.1), 3.08 (dd, 1H, J=5.7, 14.1), 1.19 (t, 3H, J=7.1). HRMS: calcd for $C_{35}H_{33}FN_3O_3$, 562.2506; found, 562.2506.

Ethyl 2-((3-benzyl-5-phenylpyrazin-2-yl)amino)-3-(tetrahydrofuran-2-yl)propanoate (N-11): Obtained from L-8 and B-16 as an oil (0.50 g, 60%) after a chromatography over silica gel (cyclohexane—ethyl acetate 9/1). $^{1}$H NMR (diastereoisomeric mixture, 0.53/0.47 ratio) ($CDCl_3$): 8.39 (s, 1H), 7.96 (m, 2H), 7.45 (m, 2H), 7.35 (m, 5H), 7.25 (m, 1H), 4.78 (m, 0.6H), 4.59 (m, 0.4H), 4.20 (m, 4H), 3.81 (m, 1.6H), 3.70 (m, 1.4H), 2.1 (m, 1H), 1.88 (m, 4H), 1.46 (m, 1H), 1.25 (t, 1.4H, J=7.2), 1.18 (t, 1.6H, J=7.2). HRMS: calcd for $C_{26}H_{30}N_3O_2$, 432.2287; found, 432.2253.

Ethyl 2-(3-benzyl-5-phenylpyrazin-2-ylamino)-3-(1,3-dioxolan-2-yl)propanoate (N-12): Obtained from L-8 and B-43 as an oil (0.61 g, 67%) after a chromatography over silica gel (cyclohexane—ethyl acetate 9/1 to 7/3). $^{1}$H NMR ($CDCl_3$): 8.41 (s, 1H), 7.94 (m, 2H), 7.46 (m, 2H), 7.37-7.31 (m, 5H), 7.25 (m, 1H), 5.66 (m, 1H), 4.85 (t, 2H, J=4.3), 4.77 (m, 1H), 4.23 (m, 2H), 4.18 (q, 2H, J=7.1), 3.83 (m, 2H), 3.75 (m, 2H), 2.25 (m, 2H), 1.25 (t, 3H, J=7.1). HRMS: calcd for $C_{25}H_{28}N_3O_4$, 434.2080; found, 434.2117.

Ethyl 2-((3-benzyl-5-phenylpyrazin-2-yl)amino)-3-(2-methoxyphenyl)propanoate (N-13): Obtained from L-8 and B-2 as a yellow solid (0.32 g, 77%) after a chromatography over silica gel (cyclohexane—ethyl acetate 95/5). $^{1}$H NMR ($CDCl_3$): 8.38 (s, 1H), 7.90 (m, 2H), 7.44 (m, 2H), 7.34 (m, 1H), 7.26 (m, 3H), 7.22 (m, 6H), 7.04 (dd, 1H, J=7.4, 1.7), 6.88 (td, 1H, J=7.4, 1.0), 6.83 (m, 1H), 5.30 (d, 1H, J=7.0), 4.85 (m, 1H), 4.11 (m, 4H), 3.75 (s, 3H), 3.20 (dd, 1H, J=13.6, 5.6), 3.15 (dd, 1H, J=13.6, 7.6), 1.20 (t, 3H, J=7.1). HRMS: calcd for $C_{29}H_{30}N_3O_3$, 468.2287; found, 468.2281.

Ethyl 2-((3-benzyl-5-phenylpyrazin-2-yl)amino)-3-(3-methoxyphenyl)propanoate (N-14): Obtained from L-8 and B-3 as an oil (0.30 g, 95% pure) after a chromatography over silica gel (cyclohexane—ethyl acetate 95/5). $^{1}$H NMR ($CDCl_3$): 8.42 (s, 1H), 7.95 (m, 2H), 7.46 (m, 2H), 7.36 (m, 1H), 7.30-7.13 (m, 6H), 6.79 (m, 2H), 6.65 (m, 1H), 6.58 (m, 1H), 4.96-4.90 (m, 2H), 4.14 (m, 4H), 3.78 (s, 3H), 3.15 (dd, 1H, J=5.6, 13.8), 3.07 (dd, 1H, J=6.0, 13.8), 1.19 (t, 3H, J=7.1). HRMS: calcd for $C_{29}H_{30}N_3O_3$, 468.2287; found, 468.2301.

Ethyl 2-((3-benzyl-5-phenylpyrazin-2-yl)amino)-3-(4-methoxyphenyl)propanoate (N-15): Obtained from L-8 and B-4 as an oil (0.16 g, 35%) after a chromatography over silica gel (cyclohexane—ethyl acetate 93/7). $^1$H NMR ($CDCl_3$): 8.42 (s, 1H), 7.95 (m, 2H), 7.46 (m, 2H), 7.39-7.21 (m, 6H), 6.89 (m, 2H), 6.76 (m, 1H), 4.96-4.90 (m, 2H), 4.15 (m, 4H), 3.81 (s, 3H), 3.12 (dd, 1H, J=4.8, 13.7), 3.03 (dd, 1H, J=5.2, 13.7), 1.21 (t, 3H, J=7.1). HRMS: calcd for $C_{29}H_{30}N_3O_3$, 468.2287; found, 468.2271.

Ethyl 2-((3-benzyl-5-phenylpyrazin-2-yl)amino)-3-(2-(trifluoromethyl)phenyl)propanoate (N-16): Obtained from L-8 and B-24 as an oil (0.08 g, 18%) after a chromatography over silica gel (cyclohexane—ethyl acetate 95/5). $^1$H NMR ($CDCl_3$): 8.36 (s, 1H), 7.93 (m, 2H), 7.62 (m, 1H), 7.45 (m, 2H), 7.37-7.18 (m, 9H), 5.01-4.93 (m, 2H), 4.17 (s, 2H), 4.12 (m, 2H), 3.31 (m, 1H), 3.15 (m, 1H), 1.17 (m, 3H). HRMS: calcd for $C_{29}H_{27}F_3N_3O_2$, 506.2055; found, 506.2053.

Ethyl 2-((3-benzyl-5-phenylpyrazin-2-yl)amino)-3-(3-(trifluoromethyl)phenyl)propanoate (N-17): Obtained from L-8 and B-25 as an oil (0.14 g, 31%) after a chromatography over silica gel (cyclohexane—ethyl acetate 95/5). $^1$H NMR ($CDCl_3$): 8.44 (s, 1H), 7.99 (m, 2H), 7.62 (m, 1H), 7.49 (m, 3H), 7.40-7.26 (m, 5H), 7.10 (m, 1H), 5.02 (m, 2H), 4.17 (s, 2H), 4.13 (m, 2H), 3.25 (m, 1H), 3.14 (m, 1H), 1.19 (m, 3H). HRMS: calcd for $C_{29}H_{27}F_3N_3O_2$: 506.2055; found, 506.2063.

Ethyl 2-((3-benzyl-5-phenylpyrazin-2-yl)amino)-3-(4-(trifluoromethyl)phenyl)propanoate (N-18): Obtained from L-8 and B-26 as an oil (0.12 g, 26%) after a chromatography over silica gel (cyclohexane—ethyl acetate 95/5). $^1$H NMR ($CDCl_3$): 8.44 (s, 1H), 7.98 (m, 2H), 7.48 (m, 2H), 7.40 (m, 3H), 7.29-7.26 (m, 5H), 7.03 (m, 2H), 5.02 (m, 2H), 4.19 (m, 2H), 4.14 (s, 2H), 3.26 (dd, 1H, J=5.6, 13.6), 3.14 (dd, 1H, J=5.7, 13.6), 1.22 (t, 3H, J=7.0), HRMS: calcd for $C_{29}H_{27}F_3N_3O_2$, 506.2055; found, 506.2002.

Ethyl (3-benzyl-5-(2-fluorophenyl)pyrazin-2-yl)phenylalaninate (N-19): Obtained from L-15 and PheOEt, HCl as an oil (0.47 g, 81%) after a chromatography over silica gel (cyclohexane—ethyl acetate 91/9). $^1$H NMR ($CDCl_3$): 8.53 (d, 1H, J=2.3), 8.04 (dt, 1H, J=1.9, 7.9), 7.24 (m, 11H), 6.99 (m, 2H), 5.00 (m, 2H), 4.13 (m, 4H), 3.18 (dd, 1H, J=5.1, 13.7), 3.10 (dd, 1H, J=5.5, 13.7), 1.20 (t, 3H, J=7.2). HRMS: calcd for $C_{28}H_{27}FN_3O_2$, 456.2087; found, 456.2079.

Ethyl 2-((3-benzyl-5-(2-fluorophenyl)pyrazin-2-yl)amino)-3-(4-fluorophenyl)propanoate (N-20): Obtained from L-15 and B-1 as an oil (0.18 g, 90% pure) after a chromatography over silica gel (cyclohexane—ethyl acetate 95/5). $^1$H NMR ($CDCl_3$): 8.53 (d, 1H, J=2.3), 8.05 (dt, 1H, J=19, 7.9), 7.37-7.14 (m, 8H), 6.88 (m, 2H), 6.86 (m, 2H), 4.99 (m, 2H), 4.15 (m, 4H), 3.16 (m, 1H), 3.07 (m, 1H), 1.20 (t, 3H, J=7.1). HRMS: calcd for $C_{28}H_{26}F_2N_3O_2$, 474.1993; found, 474.1991.

Ethyl 2-((3-benzyl-5-(2-fluorophenyl)pyrazin-2-yl)amino)-3-(furan-2-yl)propanoate (N-21): Obtained from L-15 and B-7 as an oil (0.42 g, 72%) after a chromatography over silica gel (cyclohexane—ethyl acetate 91/9). $^1$H NMR ($CDCl_3$): 8.52 (d, 1H, J=2.3), 8.03 (dt, 1H, J=1.9, 7.9), 7.41-7.24 (m, 5H), 7.17 (ddd, 1H, J=1.3, 8.0, 11.4), 6.22 (dd, 1H, J=1.8, 3.0), 5.84 (m, 1H), 5.19 (d (br), 1H, J=7.6), 4.97 (m, 1H), 4.17 (m, 4H), 3.21 (m, 2H), 1.22 (t, 3H, J=7.1). HRMS: calcd for $C_{26}H_{25}FN_3O_3$, 446.1880; found, 446.1870.

Ethyl 2-((3-benzyl-5-(2-fluorophenyl)pyrazin-2-yl)amino)-3-(5-methylfuran-2-yl)propanoate (N-22): Obtained from L-15 and B-8 as an oil (0.11 g, 30%) after a chromatography over silica gel (cyclohexane—ethyl acetate 98/2 to 95/5). $^1$H NMR ($CDCl_3$): 8.52 (d, 1H, J=2.3), 8.03 (dt, 1H, J=1.9, 7.8), 7.35-7.24 (m, 7H), 7.16 (ddd, 1H, J=1.2, 8.1, 11.1), 5.82 (m, 1H), 5.75 (d, 1H, J=3.0), 5.19 (d (br), 1H, J=7.5), 4.95 (m, 1H), 4.18 (m, 4H), 3.16 (d, 2H, J=5.4), 2.24 (s, 3H), 1.24 (t, 3H, J=7.2). HRMS: calcd for $C_{27}H_{27}FN_3O_3$, 460.2036; found, 460.2039.

Ethyl 2-((3-benzyl-5-(2-fluorophenyl)pyrazin-2-yl)amino)-3-(5-ethylfuran-2-yl)propanoate (N-23): Obtained from L-15 and B-10 as an oil (0.2 g, 46%) after a chromatography over silica gel (cyclohexane—ethyl acetate 95/5). $^1$H NMR ($CDCl_3$): 8.51 (d, 1H, J=2.3), 8.03 (dt, 1H, J=1.9, 7.8), 7.35-7.23 (m, 7H), 7.16 (ddd, 1H, J=1.3, 8.1, 9.4), 5.82 (m, 1H), 5.75 (d, 1H, J=3.0), 5.19 (d (br), 1H, J=7.5), 4.95 (m, 1H), 4.18 (m, 4H), 3.15 (d, 2H, J=5.3), 2.58 (q, 2H, J=7.6), 1.24 (t, 3H, J=7.2), 1.21 (t, 3H, J=7.6), HRMS; calcd for $C_{28}H_{29}FN_3O_3$, 474.2193; found, 474.2186.

Ethyl 2-((3-benzyl-5-(2-fluorophenyl)pyrazin-2-yl)amino)-3-(4,5-dimethylfuran-2-yl)propanoate (N-24): Obtained from L-15 and B-9 as an oil (0.48 g, 86%) after a chromatography over silica gel (cyclohexane—ethyl acetate 95/5). $^1$H NMR ($CDCl_3$): 8.51 (d, 1H, J=2.4), 8.02 (dt, 1H, J=1.9, 7.8), 7.35-7.23 (m, 7H), 7.16 (add, 1H, J=1.3, 8.1, 9.4), 5.65 (s, 1H), 5.19 (d (br), 1H, J=7.5), 4.92 (m, 1H), 4.16 (m, 4H), 3.11 (d, 2H, J=5.1), 2.13 (s, 3H), 1.88 (s, 3H), 1.25 (t, 3H, J=7.2). HRMS: calcd for $C_{28}H_{29}FN_3O_3$, 474.2193; found, 474.2203.

Ethyl 2-((3-benzyl-5-(3-fluorophenyl)pyrazin-2-yl)amino)-3-(5-methylfuran-2-yl)propanoate (N-25): Obtained from L-16 and B-8 as an oil (0.14 g, 90% pure) after a chromatography over silica gel (cyclohexane . . . ethyl acetate 95/5). $^1$H NMR ($CDCl_3$): 8.73 (s, 1H), 7.70 (m, 2H), 7.45-7.23 (m, 6H), 7.02 (m, 1H), 5.82 (m, 1H), 5.74 (d (br), 1H, J=3.1), 5.18 (d (br), 1H, J=7.5), 4.92 (m, 1H), 4.17 (m, 4H), 3.15 (d, 2H, J=5.5), 2.22 (m, 3H), 1.24 (t, 3H, J=7.2). HRMS: calcd for $C_{27}H_{27}FN_3O_3$, 460.2036; found, 460.2040.

Ethyl 2-((3-benzyl-5-(4-fluorophenyl)pyrazin-2-yl)amino)-3-(5-methylfuran-2-yl)propanoate (N-26): Obtained from L-18 and B-8 as an oil (0.12 g, 21%) after a chromatography over silica gel (cyclohexane—ethyl acetate 96/4). $^1$H NMR ($CDCl_3$): 8.36 (s, 1H), 7.91 (m, 2H), 7.34-7.23 (m, 5H), 7.15 (m, 2H), 5.82 (m, 1H), 5.75 (d, 1H, J=3.0), 5.13 (d (br), 1H, J=7.6), 4.92 (m, 1H), 4.17 (m, 4H), 3.15 (d, 2H, J=5.3), 2.22 (s, 3H), 1.23 (t, 3H, J=7.2). HRMS: calcd for $C_{27}H_{27}FN_3O_3$, 460.2036; found, 460.2039.

Ethyl 2-((3-Benzyl-5-(4-methoxyphenyl)pyrazin-2-yl)amino)-3-(5-methylfuran-2-yl)propanoate (N-27): Obtained, using DMF as the reaction solvent, from L-19 and B-8 as an oil (0.16 g, 44%) after a chromatography over silica gel (cyclohexane—ethyl acetate 95/5 to 94/6). $^1$H NMR ($CDCl_3$): 8.35 (s, 1H), 7.90 (m, 2H), 7.33-7.23 (m, 5H), 7.01 (m, 2H), 5.82 (m, 1H), 5.75 (d, 1H, J=2.6), 5.06 (d (br), 1H, J=7.5), 4.91 (m, 1H), 4.21 (m, 4H), 3.87 (s, 3H), 3.14 (d, 2H, J=5.5), 2.22 (s, 3H), 1.23 (t, 3H, J=7.2) HRMS: calcd for $C_{28}H_{30}N_3O_4$, 472.2236; found, 472.2230.

2-((3-Benzyl-5-(3-methoxyphenyl)pyrazin-2-yl)amino)-3-(5-methylfuran-2-yl)propanoate (N-28): Obtained from L-20 and B-8 as oil (0.07 g, 20%) after a chromatography over silica gel (cyclohexane—ethyl acetate 95/5 to 94/6). $^1$H NMR ($CDCl_3$): 8.41 (s, 1H), 7.51 (m, 2H), 7.40-7.23 (m, 6H), 6.91 (m, 1H), 5.82 (m, 1H), 5.75 (d, 1H, J=2.9), 5.06 (d (br), 1H, J=7.3), 4.93 (m, 1H), 4.17 (m, 4H), 3.89 (s, 3H), 3.14 (d, 2H, J=5.4), 2.23 (s, 3H), 1.24 (t, 3H. J=7.2). HRMS: calcd for $C_{28}H_{30}N_3O_4$, 472.2236; found, 472.2250.

Ethyl 2-((3-benzyl-5-(4-(benzyloxy)phenyl)pyrazin-2-yl)amino)-3-(5-methylfuran-2-yl)propanoate (N-29): Obtained, using DMF as the reaction solvent, from L-21 and B-8 as an oil (0.31 g, 50%) after a chromatography over silica gel (cyclohexane—ethyl acetate 95/5). $^1$H NMR $(CDCl_3)$: 8.36 (s, 1H), 7.89 (m, 2H), 7.50-7.23 (m, 10H), 7.01 (m, 2H), 5.81 (m, 1H), 5.76 (d, 1H, J=2.6), 5.15 (s, 2H), 5.07 (d (br), 1H, J=7.5), 4.91 (m, 1H), 4.19 (m, 4H), 3.15 (d, 2H, J=5.5), 2.24 (s, 3H), 1.23 (t, 3H, J=7.2). HRMS: calcd for $C_{34}H_{34}N_3O_4$, 548.2549; found, 548.2533.

Ethyl (3-benzyl-5-(2,6-difluorophenyl)pyrazin-2-yl)phenylalaninate (N-30): Obtained from L-17) and PheOEt, HCL as an oil (0.24 g, 65%) after a chromatography over silica gel (cyclohexane—ethyl acetate 9/1). $^1H$ NMR $(CDCl_3)$: 8.14 (s, 1H), 7.30-7.19 (m, 9H), 7.04-6.96 (m, 4H), 5.01 (m, 2H), 4.12 (m, 2H), 4.11 (s, 2H), 3.16 (dd, 1H, J=5.2, 13.8), 3.08 (dd, 1H, J=5.9, 13.8), 1.18 (t, 3H, J=7.1). HRMS: calcd for $C_{28}H_{25}F_2N_3O_2$: 474.1993; found, 474.2011.

Ethyl 2-((3-benzyl-5-(2,6-difluorophenyl)pyrazin-2-yl) amino)-3-(furan-2-yl)propanoate (N-31): Obtained from L-17 and B-7 as an oil (0.19 g, 52%) after a chromatography over silica gel (cyclohexane—ethyl acetate 9/1). $^1H$ NMR $(CDCl_3)$: 8.13 (s, 1H), 7.36-7.19 (m, 7H), 7.04-6.98 (m, 2H), 6.23 (m, 1H), 5.84 (m, 1H), 5.22 (d, 1H, J=7.3), 4.96 (m, 1H), 4.16 (s, 2H), 4.15 (m, 2H), 3.20 (d, 2H, J=5.3), 1.12 (t, 3H, J=7.0). HRMS: calcd for $C_{26}H_{23}F_2N_3O_3$, 464.1786; found, 464.1799.

Isopropyl (5-phenylpyrazin-2-yl)phenylalaninate (N-32): Obtained from L-1 and PheOiPr, HCl as a solid, using dimethyl formamide as a solvent, after a chromatography over silica gel (cyclohexane—ethyl acetate 5/1). $^1H$ NMR $(CDCl_3)$: 8.48 (m, 1H), 8.01 (m, 1H), 7.89 (m, 2H,), 7.46 (m, 2H), 7.39-7.19 (m, 6H), 5.15 (d (br), 1H, J=7.7), 5.07 (sept, 1H, J=6.3), 4.92 (m, 1H), 3.29 (dd, 1H, J=6.2, 13.8), 3.22 (dd, 1H, J=6.0, 13.8), 1.27 (d, 3H, J=6.3), 1.22 (d, 3H, J=6.3). HRMS: calcd for $C_{22}H_{24}N_3O_2$, 362.1869; found, 362.1851.

Isopropyl (3-methyl-5-phenylpyrazin-2-yl)phenylalaninate (N-33): Obtained from 1-2 and PheOiPr, HCl as a solid, using dimethyl formamide, after a chromatography over silica gel (cyclohexane—ethyl acetate 6/1). $^1H$ NMR $(CDCl_3)$: 8.36 (s, 1H), 7.90 (m, 2H), 7.46 (m, 2H), 7.37-7.18 (m, 6H), 5.06 (sept, 1H, J=6.3), 5.01 (m, 1H), 4.88 (d (br), 1H, J=7.3), 3.31 (dd, 1H, J=6.2, 13.7), 3.22 (dd, 1H, J=6.0, 13.7), 1.27 (d, 3H, J=6.3), 1.22 (d, 3H, J=6.3) HRMS: calcd for $C_{23}H_{26}N_3O_2$, 376.2025; found, 376.2027.

Ethyl 2-((3-benzyl-5-phenylpyrazin-2-yl)amino)-3-(furan-2-yl)propanoate (N-34): Obtained from L-8 and B-7 as an oil (6.31 g, 89%) after a chromatography over silica gel (cyclohexane—ethyl acetate 95:5). $^1H$ NMR $(CDCl_3)$: 8.42 (s, 1H), 7.99-7.92 (m, 2H), 7.52-7.42 (m, 2H), 7.39-7.28 (m, 5H), 7.28-7.24 (m, 2H), 6.22 (dd, J=3.2, 1.9 Hz, 1H), 5.85 (dd, J=3.2, 0.7 Hz, 1H), 5.13 (d, J=7.5 Hz, 1H), 4.95 (dt, J=7.5, 5.3 Hz, 1H), 4.23-4.11 (m, 4H), 3.24-3.18 (m, 2H), 1.22 (t, J=7.1 Hz, 3H), HRMS: calcd for $C_{26}H_{26}N_3O_3$, 428.1974; found: 428.1965.

Ethyl 2-(3-benzyl-5-phenylpyrazin-2-ylamino)-3-(furan-3-yl)propanoate (N-35): Obtained from L-8 and B-11 as an oil (1.2 g, 89%) after a chromatography over silica gel (cyclohexane—ethyl acetate 95/5 to 9/1). $^1H$ NMR $(CDCl_3)$: 8.43 (s, 1H), 7.97 (m, 2H), 7.48 (m, 2H), 7.40-7.24 (m, 7H), 6.96 (m, 1H), 5.96 (m, 1H), 5.00 (m, 1H), 4.93 (m, 1H), 4.24-4.14 (m, 4H), 3.02 (dd, 1H, J=5.1, 14.7), 2.95 (dd, 1H, J=5.4, 14.7), 1.22 (t, 3H, J=7.2). HRMS: calcd for $C_{26}H_{26}N_3O_3$, 428.1974; found: 428.2006.

Ethyl 2-((3-benzyl-5-phenylpyrazin-2-yl)amino)-3-(5-methylfuran-2-yl)propanoate (N-36): Obtained from L-8 and B-8 as an oil (0.69 g, 74%) after a chromatography over silica gel (dichloromethane). $^1H$ NMR $(CDCl_3)$: 8.38 (s, 1H), 7.96-7.89 (m, 2H), 7.48-7.40 (m, 2H), 7.38-7.26 (m, 5H), 7.25-7.19 (m, 1H), 5.83-5.77 (m, 1H), 5.72 (d, J=3.0 Hz, 1H), 5.11 (d, J=7.5 Hz, 1H), 4.89 (dt, J=7.5, 5.3 Hz, 1H), 4.21-4.08 (m, 4H), 3.12 (d, J=5.3 Hz, 2H), 2.20 (s, 3H), 1.21 (t, J=7.1 Hz, 3H). HRMS: calcd for $C_{27}H_{28}N_3O_3$, 442.2131; found, 442.2121.

Ethyl 2-((3-benzyl-5-(p-tolyl)pyrazin-2-yl)amino)-3-(5-methylfuran-2-yl)propanoate (N-37): Obtained from L-10 and B-8 as an oil (0.23 g, 45%) after a chromatography over silica gel (cyclohexane—ethyl acetate 95:5). $^1H$ NMR $(CDCl_3)$: 8.38 (s, 1H), 7.83 (m, 2H), 7.28 (m, 2H), 7.26-7.17 (m, 7H), 5.81 (m, 1H), 5.74 (d, 1H, J=3.0), 5.07 (d, 1H, J=7.9), 4.91 (m, 1H), 4.15 (m, 4H), 3.13 (d, 2H, J=5.3), 2.41 (s, 3H), 2.22 (s, 3H), 1.24 (t, 3H, J=7.2). HRMS: calcd for $C_{28}H_{30}N_3O_3$, 456.2287; found, 456.2274.

Ethyl 2-((3-benzyl-5-(m-tolyl)pyrazin-2-yl)amino)-3-(5-methylfuran-2-yl)propanoate (N-38): Obtained from L-11 and B-8 as an oil (0.20 g, 26%) after a chromatography over silica gel (cyclohexane—ethyl acetate 96:4). $^1H$ NMR $(CDCl_3)$: 8.39 (s, 1H), 7.77 (m, 1H), 7.72 (m, 1H), 7.37-7.23 (m, 6H), 7.17 (m, 1H), 5.81 (m, 1H), 5.74 (d, 1H, J=3.0), 5.09 (d, 1H, J=7.5), 4.91 (m, 1H), 4.17 (m, 4H), 3.12 (d, 2H, J=5.3), 2.45 (s, 3H), 2.22 (s, 3H), 1.22 (t, 3H, J=7.2). HRMS: calcd for $C_{28}H_{30}N_3O_3$, 456.2287; found, 456.2253.

Ethyl (3-benzyl-5-(2-methoxyphenyl)pyrazin-2-yl)phenylalaninate (N-39): Obtained from L-14 and PheOEt, HCl as an oil (0.42 g, 72%) after a chromatography over silica gel (cyclohexane—ethyl acetate 90:10). $^1H$ NMR $(CDCl_3)$: 8.59 (s, 1H), 7.87 (m, 1H), 7.37-7.26 (m, 2H), 7.26-7.17 (m, 7H), 7.08 (m, 1H), 7.03-6.92 (m, 3H), 5.01-4.93 (m, 1H), 4.86 (d, J=7.5 Hz, 1H), 4.11 (s, 2H), 4.10 (q, J=7.1 Hz, 2H), 3.89 (s, 3H), 3.15 (dd, J=13.8, 5.5 Hz, 1H), 3.06 (dd, J=13.8, 6.0 Hz, 1H), 1.16 (t, J=7.1 Hz, 3H). HRMS: calcd for $C_{29}H_{30}N_3O_3$, 468.2287; found, 468.2282.

Ethyl 2-((3-benzyl-5-(2-methoxyphenyl)pyrazin-2-yl) amino)-3-(furan-2-yl)propanoate (N-40): Obtained from L-14 and B-7 as an oil (0.40 g, 64%) after a chromatography over silica gel (cyclohexane—ethyl acetate 90:10). $^1H$ NMR $(CDCl_3)$: 8.58 (s, 1H), 7.87 (dd, J=7.7, 1.8 Hz, 1H), 7.37-7.27 (m, 5H), 7.25-7.19 (m, 2H), 7.08 (td, J=7.5, 1.0 Hz, 1H), 7.00 (dd, J=8.3, 0.6 Hz, 1H), 6.20 (dd, J=3.1, 1.8 Hz, 1H), 5.82 (dd, J=3.1, 0.5 Hz, 1H), 5.07 (d, J=7.6 Hz, 1H), 5.00-4.91 (m, 1H), 4.15 (s, 2H), 4.13 (qd, J=7.1, 1.4 Hz, 2H), 3.89 (s, 3H), 3.19 (d, J=5.3 Hz, 2H), 1.19 (t, J=7.1 Hz, 3H). HRMS: calcd for $C_{27}H_{28}N_3O_4$, 458.2080; found, 458.2083.

Ethyl 2-((3-benzyl-5-(2-methoxyphenyl)pyrazin-2-yl) amino)-3-(furan-3-yl)propanoate (N-41): Obtained from L-14 and B-11 as an oil (0.53 g, 84%) after a chromatography over silica gel (cyclohexane—ethyl acetate 90:10). $^1H$ NMR $(CDCl_3)$: 8.60 (s, 1H), 7.89 (dd, J=7.6, 1.7 Hz, 1H), 7.38-7.19 (m, 7H), 7.13-7.04 (m, 1H), 7.00 (d, J=8.3 Hz, 1H), 6.94 (s, 1H), 5.97-5.91 (m, 1H), 5.02-4.87 (m, 2H), 4.24-4.07 (m, 4H), 3.89 (s, 3H), 2.97 (qd, J=14.7, 4.8 Hz, 2H), 1.21 (t, J=7.1 Hz, 3H). HRMS: calcd for $C_{27}H_{28}N_3O_4$, 458.2080; found, 458.2095.

Ethyl 2-((3-benzyl-5-phenylpyrazin-2-yl)amino)-3-(pyridin-2-yl)propanoate (N-42): Obtained from 1-8 and B-22 as an oil (0.45 g, 64%) after a chromatography over silica gel (cyclohexane—ethyl acetate 95:5 to 75:25). $^1H$ NMR $(CDCl_3)$: 8.42-8.39 (m, 1H), 8.38 (s, 1H), 7.95-7.89 (m, 2H), 7.52 (td, J=7.6, 1.8 Hz, 1H), 7.47-7.39 (m, 2H), 7.36-7.29 (m, 3H), 7.29-7.23 (m, 2H), 7.23-7.18 (m, 1H), 7.11 (ddd, J=7.6, 4.9, 1.0 Hz, 1H), 7.01 (d, J=7.8 Hz, 1H), 6.30 (d, J=7.3 Hz, 1H), 5.03 (dt, J=7.3, 5.4 Hz, 1H), 4.20 (s, 2H), 4.08 (qd, J=7.1, 1.1 Hz, 2H), 3.39-3.27 (m, 2H), 1.11 (t, J=7.1 Hz, 3H). HRMS: calcd for $C_{27}H_{27}N_4O_2$, 439.2134; found, 439.2152.

Ethyl (5-phenyl-3-((tetrahydrofuran-2-yl)methyl) pyrazin-2-yl)phenylalaninate (N-42'): Obtained as a mixture of two diastereoisomers from L-26 and PheOEt, HCl as an oil (0.06 g, 21%) after a chromatography over silica gel (cyclohexane—ethyl acetate 93:7). $^{1}$H NMR ($CDCl_3$): 8.34 (s, 0.5H), 8.33 (s, 0.5H), 7.89-7.84 (m, 2H), 7.45-7.40 (m, 2H), 7.35-7.21 (m, 6H), 6.62 (d, J=7.5 Hz, 0.5H), 6.44 (d, J=7.1 Hz, 0.5H), 4.95 (dd, J=13.0, 6.8 Hz, 0.5H), 4.86 (td, J=7.4, 5.9 Hz, 0.5H), 4.37-4.30 (m, 0.5H), 4.30-4.23 (m, 0.5H), 4.22-4.13 (m, 2H), 3.89-3.79 (m, 0.5H), 3.77-3.58 (m, 1.5H), 3.31-2.88 (m, 4.5H), 2.17-2.00 (m, 1H), 1.92-1.61 (m, 3.5H), 1.22 (t, J=7.1 Hz, 1.5H), 1.21 (t, J=7.1 Hz, 1.5H). HRMS: calcd for $C_{26}H_{30}N_3O_3$, 432.2287; found, 432.2273.

Ethyl 2-((3-benzyl-5-phenylpyrazin-2-yl)amino)-3-(4,5-dimethylfuran-2-yl)propanoate (N-43): Obtained from L-8 and B-9 as an oil (0.20 g, 49%) after a chromatography over silica gel (cyclohexane—ethyl acetate 95:5). $^{1}$H NMR ($CDCl_3$): 8.39 (s, 1H), 7.97-7.90 (m, 2H), 7.50-7.40 (m, 2H), 7.39-7.19 (m, 6H), 5.65 (s, 1H), 5.11 (d, J=7.5 Hz, 1H), 4.88 (dt, J=7.5, 5.4 Hz, 1H), 4.19-4.12 (m, 4H), 3.09 (d, J=5.4 Hz, 2H), 2.12 (s, 3H), 1.87 (s, 3H), 1.21 (t, J=7.1 Hz, 3H). HRMS: calcd for $C_{28}H_{30}N_3O_3$, 456.2287; found, 456.2337.

Ethyl 2-((3-benzyl-5-phenylpyrazin-2-yl)amino)-3-(4,5-dimethylthiophen-2-yl)propanoate (N-44): Obtained from L-8 and B-17 as an oil (0.24 g, 47%) after a chromatography over silica gel (cyclohexane—ethyl acetate 96:4). $^{1}$H NMR ($CDCl_3$): 8.42 (s, 1H), 7.95 (m, 2H), 7.47 (m, 2H), 7.36 (m, 1H), 7.28 (m, 5H), 6.33 (s, 1H), 5.12 (d, J=7.3 Hz, 1H), 4.92 (dt, 1H, J=7.2, 5.0), 4.18 (m, 4H), 3.32 (dd, 1H, J=4.7, 14.8), 3.26 (dd, 1H, J=5.4, 14.8), 2.28 (s, 3H), 2.06 (s, 3H), 1.24 (t, J=7.1 Hz, 3H). HRMS: calcd for $C_{28}H_{30}N_3O_2S$, 472.2059; found, 472.2054.

Ethyl 2-((3-benzyl-5-phenylpyrazin-2-yl)amino)-3-(4,5-dimethyloxazol-2-yl)propanoate (N-45): Obtained from L-8 and B-40 as an oil (0.20 g, 49%) after a chromatography over silica gel (cyclohexane—ethyl acetate 97:3 to 3/1). $^{1}$H NMR ($CDCl_3$) 8.39 (s, 1H), 7.93 (m, 2H), 7.46 (m, 2H), 7.37-7.21 (m, 6H), 5.75 (d, J=7.8 Hz, 1H), 5.07 (m, 1H), 4.20 (m, 2H), 4.15 (q, J=7.1 Hz, 2H), 3.30 (dd, J=5.6 and 15.3 Hz, 1H), 3.22 (dd, J=5.4 and 15.3 Hz, 1H), 2.17 (s, 3H), 2.05 (s, 3H), 1.18 (t, J=7.1 Hz, 3H). HRMS: calcd for $C_{27}H_{29}N_4O_3$, 457.2240; found, 457.2234.

Ethyl 2-((3-benzyl-5-phenylpyrazin-2-yl)amino)-3-(4-fluorophenyl)propanoate (N-46): Obtained from (L-8) and (B-1) as an oil (0.45 g, 69%) after a chromatography over silica gel (cyclohexane—ethyl acetate 95:5). $^{1}$H NMR ($CDCl_3$): 8.41 (s, 1H), 7.99-7.91 (m, 2H), 7.51-7.41 (m, 2H), 7.40-7.32 (m, 1H), 7.31-7.25 (m, 3H), 7.23-7.17 (m, 2H), 6.91-6.79 (m, 4H), 4.99-4.84 (m, 2H), 4.21-4.06 (m, 4H), 3.15 (dd, J=13.9, 5.1 Hz, 1H), 3.03 (dd, J=13.9, 5.5 Hz, 1H), 1.20 (t, J=7.1 Hz, 3H), HRMS: calcd for $C_{28}H_{27}FN_3O_2$, 456.2087; found, 456.2110.

Ethyl 2-((3-benzyl-5-phenylpyrazin-2-yl)amino)-3-(3-fluorophenyl)propanoate (N-46'): Obtained from L-8 and B-32 as an oil (0.25 g, 64%) after a chromatography over silica gel (cyclohexane—ethyl acetate 95:5). $^{1}$H NMR ($CDCl_3$): 8.44 (s, 1H), 7.97 (m, 2H), 7.48 (m, 2H), 7.38 (m, 1H), 7.32-7.23 (m, 5H), 7.17 (m, 1H), 6.92 (m, 1H), 6.73 (m, 1H), 4.98 (m, 2H), 4.16 (m, 4H), 3.18 (dd, J=5.5, 13.8 Hz, 1H), 3.03 (dd, J=5.1, 13.8 Hz, 1H), 1.21 (t, J=7.1 Hz, 3H) HRMS: calcd for $C_{28}H_{27}FN_3O_2$, 456.2087; found, 456.2065.

Ethyl 2-((3-benzyl-5-phenylpyrazin-2-yl)amino)-3-(2-fluorophenyl)propanoate (N-47): Obtained from L-8 and B-27 as an oil (0.32 g, 79%) after a chromatography over silica gel (cyclohexane—ethyl acetate 95:5). $^{1}$H NMR ($CDCl_3$): 8.42 (s, 1H), 7.96 (m, 2H), 7.47 (m, 2H), 7.37 (m, 1H), 7.27 (m, 6H), 6.98 (m, 3H), 4.99 (m, 2H), 4.15 (m, 4H), 3.22 (dd, 1H, J=13.9, 5.5), 3.16 (dd, 1H, J=13.9, 6.3), 1.20 (t, 3H, J=7.1). HRMS: calcd for $C_{28}H_{27}FN_3O_2$, 456.2087; found, 456.2084.

Ethyl 2-((3-benzyl-5-phenylpyrazin-2-yl)amino)-3-(2,4-difluorophenyl)propanoate (N-48): Obtained from L-8 and B-28 as an oil (0.27 g, 61%) after a chromatography over silica gel (cyclohexane—ethyl acetate 96:4). $^{1}$H NMR ($CDCl_3$): 8.42 (s, 1H), 7.96 (m, 2H), 7.47 (m, 2H), 7.37 (m, 1H), 7.27 (m, 5H), 6.98 (m, 1H), 6.70 (m, 2H), 4.97 (m, 2H), 4.16 (m, 4H), 3.22 (dd, 1H, J=5.4, 14.3), 3.10 (dd, 1H, J=6.1, 14.3), 1.22 (t, 3H, J=7.1). HRMS: calcd for $C_{28}H_{26}F_2N_3O_2$, 474.1993; found, 474.1988.

Ethyl 2-((3-benzyl-5-phenylpyrazin-2-yl)amino)-3-(4-chlorophenyl)propanoate (N-49): Obtained from L-8 and B-29 as an oil (0.38 g, 64%) after a chromatography over silica gel (cyclohexane—ethyl acetate 97:3 to 96:4). $^{1}$H NMR ($CDCl_3$): 8.43 (s, 1H), 7.97 (m, 2H), 7.48 (m, 2H), 7.37 (m, 1H), 7.30 (m, 3H) 7.22 (m, 2H), 7.14 (m, 2H) 6.85 (m, 2H), 4.95 (m, 2H), 4.15 (m, 4H), 3.16 (m, 1H), 3.03 (m, 1H), 1.23 (t3H, J=7.2 Hz,). HRMS: calcd for $C_{28}H_{27}ClN_3O_2$, 472.1792; found, 472.1782.

Ethyl 2-((3-benzyl-5-phenylpyrazin-2-yl)amino)-3-(4-bromophenyl)propanoate (N-50): Obtained from L-8 and B-31 as an oil (0.37 g, 57%) after a chromatography over silica gel (cyclohexane—ethyl acetate 97:3 to 96:4). $^{1}$H NMR ($CDCl_3$): 8.43 (s, 1H), 7.97 (m, 2H), 7.48 (m, 2H), 7.37 (m, 1H), 7.29 (m, 5H), 7.22 (m, 2H), 6.79 (m, 2H), 4.95 (m, 2H), 4.15 (m, 4H), 3.16 (m, 1H), 3.03 (m, 1H), 1.23 (t, 3H, J=7.2). HRMS: calcd for $C_{28}H_{27}BrN_3O_2$, 516.1287; found, 516.1267.

Ethyl 2-((3-benzyl-5-phenylpyrazin-2-yl)amino)-3-(o-tolyl)propanoate (N-51): Obtained from L-8 and B-20 as an oil (0.48 g, 90%) after a chromatography over silica gel (cyclohexane—ethyl acetate 95:5). $^{1}$H NMR ($CDCl_3$): 8.40 (s, 1H), 7.94 (m, 2H), 7.48-7.42 (m, 2H), 7.38-7.24 (m, 6H), 7.15 (m, 2H), 7.06 (m, 1H), 6.93 (m, 1H), 4.92 (m, 2H), 4.16 (m, 4H), 3.14 (dd, 1H, J=6.1, 14.0), 3.02 (dd, 1H, J=7.1, 14.0), 2.29 (s, 3H), 1.16 (t, 3H, J=7.1). HRMS: calcd for $C_{29}H_{29}N_3O_2$, 452.2338; found, 452.2352.

Ethyl 2-((3-benzyl-5-phenylpyrazin-2-yl)amino)-3-(m-tolyl)propanoate (N-52): Obtained from L-8 and B-6 as an oil (0.28 g, 61%) after a chromatography over silica gel (cyclohexane—ethyl acetate 95:5). $^{1}$H NMR ($CDCl_3$): 8.41 (s, 1H), 8.07-7.90 (m, 2H), 7.48-7.42 (m, 2H), 7.38-7.32 (m, 1H), 7.30-7.26 (m, 1H), 7.26-7.23 (m, 1H), 7.21-7.16 (m, 2H), 7.15-7.08 (m, 1H), 7.07-7.01 (m, 1H), 6.88 (s, 1H), 6.78 (d, 1H, J=7.5), 4.93 (t, 1H, J=5.9), 4.92 (t, 1H, J=6.5), 4.88-4.79 (m, 2H), 4.11 (q, 2H, J=7.1), 4.11 (q, 2H, J=15.4), 3.1.1 (dd, 1H, J=13.8, 5.5), 3.03 (dd, 1H, J=13.8, 6.1), 2.30 (s, 3H), 1.17 (t, 3H, J=7.1). HRMS: calcd for $C_{29}H_{29}N_3O_2$, 452.2338; found, 452.2408.

Ethyl 2-((3-benzyl-5-phenylpyrazin-2-yl)amino)-3-(p-tolyl)propanoate (N-53): Obtained from L-8 and B-21 as an oil (0.35 g, 87%) after a chromatography over silica gel (cyclohexane—ethyl acetate 94:6), H NMR ($CDCl_3$): 8.43 (s, 1H), 7.97 (m, 2H), 7.48 (m, 2H), 7.37 (m, 1H), 7.28 (m, 3H), 7.22 (m, 2H), 7.04 (m, 2H), 6.89 (m, 2H), 4.93 (m, 2H), 4.15 (m, 4H), 3.15 (dd, 1H, J=13.8, 5.2), 3.06 (dd, 1H, J=13.8, 5.8), 2.35 (s, 3H), 1.21 (t, 3H, J=7.2). HRMS: calcd for $C_{29}H_{29}N_3O_2$, 452.2338; found, 452.2325.

Ethyl 2-((3-benzyl-5-phenylpyrazin-2-yl)amino)-3-(3-propylphenyl)propanoate (N-54): Obtained from L-8 and B-37 as an oil (0.27 g, 79%) after a chromatography over silica gel (cyclohexane—ethyl acetate 95:5). $^{1}$H NMR ($CDCl_3$): 8.42 (s, 1H), 7.95 (m, 2H), 7.47 (m, 2H), 7.37 (m, 1H), 7.26 (m, 5H), 7.16 (m, 1H), 7.07 (m, 1H), 6.92 (m, 1H), 6.82 (m, 1H), 4.93, (m, 2H), 4.14 (m, 4H), 3.15 (dd, 1H, J=13.7, 5.6), 3.07 (dd, 1H, J=13.7, 6.1), 2.56 (m, 2H), 1.63 (m, 2H), 1.18 (t, 3H, J=7.2), 0.95 (L 3H, J=7.3). HRMS: calcd for $C_{31}H_{34}N_3O_2$, 480.2651; found, 480.2661.

Ethyl 2-((3-benzyl-5-phenylpyrazin-2-yl)amino)-3-(4-propylphenyl)propanoate (N-55): Obtained from L-8 and B-36 as an oil (0.25 g, 73%) after a chromatography over silica gel (cyclohexane—ethyl acetate 95:5). $^1$H NMR ($CDCl_3$): 8.42 (s, 1H), 7.96 (m, 2H), 7.47 (m, 2H), 7.37 (m, 1H), 7.26 (m, 5H), 7.05 (m, 2H), 6.91 (m, 2H), 4.93, (m, 2H), 4.13 (m, 4H), 3.14 (dd, 1H, J=13.9, 5.5), 3.06 (dd, 1H, J=13.9, 6.0), 2.59 (m, 2H), 1.65 (m, 2H), 1.19 (t, 3H, J=7.2), 0.97 (t, 3H, J=7.3). HRMS: calcd for $C_{31}H_{34}N_3O_2$, 480.2651; found, 480.2671.

Ethyl 2-((3-benzyl-5-phenylpyrazin-2-yl)amino)-3-(4-isopropylphenyl)propanoate (N-56): Obtained from L-8 and B-33 as an oil (0.25 g, 73%) after a chromatography over silica gel (cyclohexane—ethyl acetate 95:5). $^1$H NMR ($CDCl_3$): 8.40 (s, 1H), 7.97-7.90 (m, 2H), 7.49-7.40 (m, 2H), 7.38-7.32 (m, 1H), 7.32-7.23 (m, 3H), 7.23-7.17 (m, 2H), 7.12-7.05 (m, 2H), 6.94-6.88 (m, 2H), 4.99-4.84 (m, 2H), 4.18-4.06 (m, 4H), 3.08 (qd, 2H, J=13.8, 5.7), 2.96-2.84 (m, 1H), 1.25 (d, 6H, J=6.9), 1.16 (t, 3H, J=7.1). HRMS: calcd for $C_{31}H_{34}N_3O_2$, 480.2683; found, 480.2690.

Ethyl 2-((3-benzyl-5-phenylpyrazin-2-yl)amino)-3-(4-cyclopropylphenyl)propanoate (N-57): Obtained from L-8 and B-34 as an oil (0.46 g, 76%) after a chromatography over silica gel (cyclohexane—ethyl acetate 95:5). $^1$H NMR ($CDCl_3$): 8.42 (s, 1H), 7.96 (m, 2H), 7.47 (m, 2H), 7.36 (m, 1H), 7.31-7.23 (m, 3H), 7.20 (m, 2H), 6.94 (m, 2H), 6.86 (m, 2H), 4.93, (m, 2H), 4.13 (m, 4H), 3.13 (dd, 1H, J=5.3, 13.9), 3.04 (dd, 1H, J=5.9, 13.9), 1.89 (m, 1H), 1.19 (t, 3H, J=7.2), 0.98 (m, 2H), 0.69 (m, 2H). HRMS: calcd for $C_{31}H_{32}N_3O_2$, 478.2495; found, 478.2487.

Ethyl 2-((3-benzyl-5-phenylpyrazin-2-yl)amino)-3-(3-cyclopropylphenyl)propanoate (N-58): Obtained from L-8 and B-35 as an oil (0.46 g, 79%) after a chromatography over silica gel (cyclohexane—ethyl acetate 95:5). $^1$H NMR ($CDCl_3$): 8.42 (6, 1H), 7.95 (m, 2H), 7.47 (m, 2H), 7.36 (m, 1H), 7.28-7.19 (m, 5H), 7.13 (m, 1H), 6.95 (m, 1H), 6.82 (m, 1H), 6.77 (m, 1H), 4.93, (m, 2H), 4.13 (m, 4H), 3.13 (dd, 1H, J=5.5, 13.7), 3.05 (dd, J=6.0, 13.7 Hz, 1H), 1.86 (m, 1H), 1.18 (t, 3H, J=7.2), 0.96 (m, 2H), 0.67 (m, 2H). HRMS: calcd for $C_{31}H_{32}N_3O_2$, 478.2495; found, 478.2480.

Ethyl 2-((3-benzyl-5-phenylpyrazin-2-yl)amino)-3-(thiophen-2-yl)propanoate (N-59): Obtained from L-8 and B-12 as an oil (0.51 g, 80%) after a chromatography over silica gel (cyclohexane—ethyl acetate 95:5). $^1$H NMR ($CDCl_3$): 8.42 (s, 1H), 8.00-7.89 (m, 2H), 7.50-7.42 (m, 2H), 7.40-7.32 (m, 1H), 7.32-7.26 (m, 3H), 7.26-7.21 (m, 2H), 7.14-7.08 (m), 1H), 6.85 (dd, J=5.2, 3.4 Hz, 1H), 6.58-6.50 (m, 1H), 5.12 (d, J=7.1 Hz, 1H), 4.99 (dt, J=7.1, 5.0 Hz, 1H), 4.17 (s, 2H), 4.14 (q, J=7.1 Hz, 2H), 3.44 (dd, J=14.6, 4.7 Hz, 1H), 3.37 (dd, J=14.9, 4.9 Hz, 1H), 1.22 (t, J=7.1 Hz, 3H). HRMS: calcd for $C_{26}H_{26}N_3O_2S$, 444.1746; found, 444.1766.

Ethyl 2-((3-benzyl-5-phenylpyrazin-2-yl)amino)-3-(3-methylthiophen-2-yl)propanoate (N-60): Obtained from L-8 and B-18 as an oil (0.41 g, 76%) after a chromatography over silica gel (cyclohexane—ethyl acetate 95:5). $^1$H NMR ($CDCl_3$): 8.44 (s, 1H), 7.97 (m, 2H), 7.47 (m, 2H), 7.37 (m, 1H), 7.33-7.23 (m, 5H), 7.05 (d, 1H, J=4.8), 6.75 (d, 1H, J=4.8), 5.15 (d, 1H, J=7.1), 4.96 (m, 1H), 4.15 (m, 4H), 3.41 (dd, 1H, J=5.1, 15.1), 3.31 (dd, 1H, J=5.1, 15.1), 2.0 (s, 3H), 1.23 ((, J=7.3 Hz, 3H). HRMS: calcd for $C_{27}H_{28}N_3O_2S$, 458.1902; found, 458.1910.

Ethyl 2-((3-benzyl-5-phenylpyrazin-2-yl)amino)-3-(5-ethylthiophen-2-yl)propanoate (N-61): Obtained from L-8 and B-19 as an oil (0.47 g, 84%) after a chromatography over silica gel (cyclohexane—ethyl acetate 95:5). $^1$H NMR ($CDCl_3$): 8.43 (s, 1H), 7.97 (m, 2H), 7.47 (m, 2H), 7.37 (m, 1H), 7.33-7.23 (m, 5H), 6.55 (m, 1H), 6.39 (m, 1H), 5.13 (d, 1H, J=7.1), 4.91 (m, 1H), 4.17 (m, 4H), 3.34 (m, 2H), 2.79 (qd, 2H, J=0.8, 7.5), 1.30 (t, J=7.5 Hz, 3H), 1.24 (t, J=7.3 Hz, 3H). HRMS: calcd for $C_{28}H_{30}N_3O_2S$, 472.2059; found, 472.2055.

Ethyl 2-(3-benzyl-5-phenylpyrazin-2-yl)amino)-3-(5-ethylfuran-2-yl)propanoate (N-62): Obtained from L-8 and B-10 as a yellow solid (0.48 g, 74%) after a chromatography over silica gel (cyclohexane—ethyl acetate 95:5). $^1$H NMR ($CDCl_3$): 8.39 (s, 1H), 7.96-7.89 (m, 2H), 7.50-7.40 (m, 2H), 7.37-7.26 (m, 4H), 726-7.20 (m, 2H), 5.80 (d, J=2.0, 10 Hz, 1H), 5.74 (d, J=3.0 Hz, 1H), 5.09 (d, J=7.5 Hz, 1H), 4.91 (dt, J=7.5, 5.4 Hz, 1H), 4.22-4.08 (m, 4H), 3.14 (d, J=5.3 Hz, 2H), 2.56 (qd, J=7.5, 0.6 Hz, 2H), 1.21 (t, J=7.3 Hz, 3H), 1.19 (t, J=7.3 Hz, 3H). HRMS: calcd for $C_{28}H_{30}N_3O_3$, 457.2319; found, 457.2314.

Ethyl 2-((3-benzyl-5-phenylpyrazin-2-yl)amino)-3-(5-cyclopropylfuran-2-yl)propanoate (N-63): Obtained from L-8 and B-39 as an oil (0.31 g, 67%) after a chromatography over silica gel (cyclohexane—ethyl acetate 95/5). $^1$H NMR ($CDCl_3$): 8.39 (s, 1H), 7.97-7.90 (m, 2H), 7.48-7.41 (m, 2H), 7.38-7.20 (m, 6H), 5.78 (dd, J=3.1, 0.5 Hz, 1H), 5.72 (d, J=3.1 Hz, 1H), 5.08 (d, 1H, J=7.6), 4.90 (dt, 1H, J=7.6, 5.3), 4.20-4.11 (m, 4H), 3.12 (d, 2H, J=5.3), 1.81 (tt, 1H, J=8.5, 5.1), 1.22 (t, 3H, J=7.1), 0.88-0.80 (m, 2H), 0.73-0.65 (m, 2H) HRMS: calcd for $C_{29}H_{30}N_3O_3$, 468.2287; found, 468.2291.

Ethyl 2-((3-benzyl-5-phenylpyrazin-2-yl)amino)-3-(5-(trifluoromethyl)furan-2-yl)propanoate (N-64): Obtained from L-8 and B-38 as an oil (0.17 g, 44%) after a chromatography over silica gel (cyclohexane—ethyl acetate 93/7). $^1$H NMR ($CDCl_3$): 8.40 (s, 1H), 7.99-7.92 (m, 2H), 7.50-7.42 (m, 2H), 7.40-7.33 (m, 1H), 7.33-7.20 (m, 5H), 6.55 (dd, J=3.3, 1.2 Hz, 1H), 5.74 (dd, J=3.3, 0.6 Hz, 1H), 5.12 (d, J=7.1 Hz, 1H), 4.98 (dt, J=7.1, 5.2 Hz, 1H), 4.26-4.09 (m, 4H), 3.29 (dd, J=15.2, 5.2 Hz, 1H), 3.19 (dd, J=15.2, 5.2 Hz, 1H), 1.24 (t, J=7.1 Hz, 3H) HRMS: calcd for $C_{27}H_{25}F_3N_3O_3$, 496.1848; found, 496.1847.

Ethyl 2-((3-benzyl-5-phenylpyrazin-2-yl)amino)-3-(4-(benzyloxy)phenyl)propanoate (N-65): Obtained from L-8 and B-5 as an oil (0.68 g, 70%) after a chromatography over silica gel (cyclohexane—ethyl acetate 95/5). $^1$H NMR ($CDCl_3$): 8.41 (s, 1H), 8.00-7.86 (m, 2H), 7.50-7.16 (m, 13H), 6.90-6.84 (m, 2H), 6.84-6.79 (m, 2H), 5.05 (s, 2H), 4.99-4.84 (m, 2H), 4.12 (qd, 2H, J=7.1, 0.6), 4.12 (s, 2H), 3.11 (dd, 1H, J=13.9, 5.0), 3.01 (dd, 1H, J=13.9, 5.5), 1.19 (t, 3H, J=7.1). HRMS: calcd for $C_{35}H_{33}N_3O_3$, 544.2600; found, 544.2654.

Ethyl (3-benzyl-5-(4-(benzyloxy)phenyl)pyrazin-2-yl) phenylalaninate (N-66): Obtained, from L-21 and PheOEt, HCl as white solid (4.47 g, 87%) after a chromatography over silica gel (cyclohexane—ethyl acetate 95/5 to 94/6). $^1$H NMR ($CDCl_3$): 8.36 (s, 1H), 7.89 (m, 2H), 7.49 (m, 2H), 7.42 (m, 2H), 7.35 (m, 1H), 7.32-7.20 (m, 8H), 7.08 (m, 2H), 7.00 (m, 2H), 5.15 (s, 2H), 4.97 (m, 1H), 4.86 (d (br), 1H, J=8.1), 4.14 (m, 4H), 3.17 (dd, 1H, J=5.5, 13.8), 3.08 (dd, 1H, J=6.0, 13.8), 1.19 (t, 3H, J=7.2), HRMS: calcd for $C_{35}H_{34}N_3O_3$, 544.2600; found, 544.2609.

Ethyl 2-((3-benzyl-5-(4-(benzyloxy)phenyl)pyrazin-2-yl) amino)-3-(furan-2-yl)propanoate (N-67): Obtained, from L-21 and B-7 as an oil (0.83 g, 79%) after a chromatography over silica gel (cyclohexane—ethyl acetate 94/6 to 93/7). $^1$H NMR ($CDCl_3$): 8.35 (s, 1H), 7.89 (m, 2H), 7.48 (m, 2H), 7.42 (m, 2H), 7.36 (m, 1H), 7.32-7.20 (m, 5H), 7.08 (m, 2H), 6.22 (dd, 1H, J=2.0, 3.0), 5.85 (dd, 1H, J=0.7, 3.0), 5.15 (s, 2H), 5.07 (d (br), 1H, J=7.6), 4.94 (m, 1H), 4.16 (m, 4H), 3.20 (d, 2H, J=5.3), 1.21 (t, 3H, J=7.2). HRMS: calcd for $C_{33}H_{32}N_3O_4$, 534.2393; found, 534.2410.

Ethyl 2-((3-benzyl-5-(4-(benzyloxy)phenyl)pyrazin-2-yl) amino)-3-(5-ethylfuran-2-yl)propanoate (N-68): Obtained, from L-21 and B-10 as an oil (0.65 g, 60%) after a chromatography over silica gel (cyclohexane—ethyl acetate 94/6). $^1$H NMR ($CDCl_3$): 8.34 (s, 1H), 7.88 (m, 2H), 7.48 (m, 2H), 7.42 (m, 2H), 7.36 (m, 1H), 7.32-7.20 (m, 5H), 7.08 (m, 2H), 5.82 (m, 1H), 5.76 (d, 1H, J=3), 5.14 (s, 2H), 5.06 (d (br), 1H, J=7.5), 4.91 (m, 1H), 4.16 (m, 4H), 3.15 (d, 2H, J=5.4), 2.57 (q, 2H, J=7.8), 1.23 (t, 3H, J=7.2), 1.21 (t, 3H, J=7.8). HRMS: calcd for $C_{35}H_{36}N_3O_4$, 562.2706; found, 562.2716.

Ethyl 2-((3-benzyl-5-(4-(benzyloxy)phenyl)pyrazin-2-yl) amino)-3-(4,5-dimethylfuran-2-yl)propanoate (N-69): Obtained, from L-21 and B-9 as an oil (0.62 g, 56%) after a chromatography over silica gel (cyclohexane—ethyl acetate 94/6). $^1$H NMR ($CDCl_3$): 8.34 (s, 1H), 7.88 (m, 2H), 7.48 (m, 2H), 7.42 (m, 2H), 7.36 (m, 1H), 7.32-7.20 (m, 5H), 7.07 (m, 2H), 5.66 (s, 1H), 5.14 (s, 2H), 5.06 (d (br), 1H, J=7.4), 4.88 (m, 1H), 4.17 (m, 4H), 3.10 (d, 2H, J=5.4), 2.14 (s, 3H), 1.89 (s, 3H), 1.23 (t, 3H, J=7.8). HRMS: calcd for $C_{35}H_{36}N_3O_4$, 562.2706; found, 562.2690.

Ethyl 2-((3-benzyl-5-(4-(benzyloxy)phenyl)pyrazin-2-yl) amino)-3-(3-propylphenyl)propanoate (N-70): Obtained, from L-21 and B-37 (0.97 g, 85%) after a chromatography over silica gel (cyclohexane—ethyl acetate 98/2). $^1$H NMR ($CDCl_3$): 8.36 (s, 1H), 7.89 (m, 2H), 7.32 (m, 11H), 7.07 (m, 3H), 6.92 (m, 1H), 6.82 (m, 1H), 5.15 (s, 2H), 4.95 (m, 1H), 4.84 (d, 1H, J=7.5), 4.12 (m, 4H), 3.14 (dd, 1H, J=13.7, 5.7), 3.07 (dd, 1H, J=13.7, 6.2), 2.56 (m, 2H), 1.64 (m, 2H), 1.18 (t, 3H, J=7.1), 0.96 (t, 3H, J=7.3). HRMS: calcd for $C_{38}H_{40}N_3O_3$: 586.3069; found, 586.3096.

Ethyl 2-(3-benzyl-5-phenylpyrazin-2-ylamino)-4-phenylbutanoate (N-71): Obtained from L-8 and B-42 as an oil (0.36 g, 80%) after a chromatography over silica gel (cyclohexane/ethyl acetate 95:5). $^1$H NMR ($CDCl_3$): 8.42 (s, 1H), 7.97 (m, 2H), 7.48 (m, 1H), 7.38 (m, 5H), 7.28 (m, 3H), 7.20 (m, 1H), 7.06 (m, 2H), 4.97 (d (br), 1H, J=7.0), 4.73 (m, 1H), 4.27 (d, 1H, J=15.4), 4.21 (d, 1H, J=15.4), 4.16 (q, 2H, J=7.1), 2.43 (m, 2H), 2.21 (m, 1H), 1.99 (m, 1H), 1.26 (t, 3H, J=7.1). HRMS: calcd for $C_{29}H_{30}N_3O_2$, 452.2338; found, 452.2335.

Ethyl (2-benzyl-5H-chromeno[3,4-b]pyrazin-3-yl)phenylalaninate (N-72): Obtained from L-27 and PheOEt, HCl as an orange oil (0.05 g, 33%) after a chromatography over silica gel (cyclohexane—ethyl acetate 93/7). $^1$H NMR ($CDCl_3$): 8.07 (dd, 1H, J=1.6, 7.7), 7.38-7.18 (m, 9H), 7.12 (dt, 1H, J=1.0, 7.8), 7.01-6.93 (m, 3H), 5.18 (s, 2H), 5.01-4.91 (m, 2H), 4.20-4.06 (m, 4H), 3.15 (dd, 1H, J=5.2, 13.9), 3.05 (dd, 1H, J=5.9, 13.9), 1.22 (t, 3H, J=7.8). HRMS: calcd for $C_{29}H_{28}N_3O_3$, 466.2131; found, 466.2117.

Ethyl (5-phenyl-3-(pyridin-3-ylmethyl)pyrazin-2-yl)phenylalaninate (N-73): Obtained from L-24 and PheOEt, HCl as an oil (0.28 g, 62%) after a chromatography over silica gel (cyclohexane—ethyl acetate 2/1). $^1$H NMR ($CDCl_3$): 8.52 (m, 3H), 8.44 (s, 1H), 7.90 (m, 2H), 7.46 (m, 3H), 7.35 (m, 1H), 7.26 (m, 3H), 7.19 (ddd, 1H, J=0.9, 4.9, 5.6), 7.03 (m, 2H), 5.01 (m, 1H), 4.84 (d (br, 1H, J=7.4), 4.17 (q, 2H, J=7.0), 4.08 (s, 2H), 3.24 (dd, 1H, J=5.9, 13.5), 3.16 (dd, 1H, J=5.9, 13.6), 1.23 (t, 3H, J=7.0). HRMS: calcd for $C_{27}H_{27}N_4O_2$, 439.2134; found, 439.2137.

Ethyl (3-(2-Methylbenzyl)-5-phenylpyrazin-2-yl)phenylalaninate (N-74): Obtained from L-12 and PheOEt, HCl as an oil (0.40 g, 86%) after a chromatography over silica gel (cyclohexane—ethyl acetate 95:5). $^1$H NMR ($CDCl_3$): 8.43 (s, 1H), 7.92 (m, 2H), 7.43 (m, 2H), 7.35 (m, 1H), 7.20 (m, 5H), 7.11 (m, 1H), 6.98 (m, 3H), 5.01 (m, 1H), 4.86 (d (br), 1H. J=7.1), 4.14 (m, 4H), 3.17 (dd, 1H, J=5.6, 13.8), 3.07 (dd, 1H, J=6.0, 13.8), 2.33 (s, 3H), 1.21 (t, 3H, J=7.1). HRMS: calcd for $C_{29}H_{29}N_3O_2$, 452.2338; found, 452.2338.

Ethyl 3-(furan-2-yl)-2-((3-(2-methylbenzyl)-5-phenylpyrazin-2-yl)amino)propanoate (N-75): Obtained from L-12 and B-7 as an oil (0.30 g, 71%) after a chromatography over silica gel (cyclohexane—ethyl acetate 95:5). $^1$H NMR ($CDCl_3$): 8.43 (s, 1H), 7.93 (m, 2H), 7.47 (m, 2H), 7.35 (m, 1H), 7.20 (m, 3H), 7.13 (m, 1H), 7.06 (m, 1H), 6.21 (dd, 1H, J=1.8, 3.1), 5.85 (m, 1H), 5.09 (d (br), 1H, J=7.6), 4.98 (m, 1H), 4.18 (m, 4H), 3.20 (m, 2H), 2.39 (s, 3H), 1.23 (t, 3H, J=7.1). HRMS: calcd for $C_{27}H_{28}N_3O_3$, 442.2131; found, 442.2137.

Ethyl (3-(3-methylbenzyl)-5-phenylpyrazin-2-yl)phenylalaninate (N-76): Obtained from L-13 and PheOEt, HCl as an oil (0.41 g, 89%) after a chromatography over silica gel (cyclohexane—ethyl acetate 95:5). $^1$H NMR ($CDCl_3$): 8.43 (s, 1H), 7.97 (m, 2H), 7.48 (m, 2H), 7.37 (m, 1H), 7.21 (m, 4H), 7.08-6.96 (m, 4H), 4.97 (m, 2H), 4.14 (m, 4H), 3.17 (dd, 1H, J=5.0, 13.7), 3.07 (dd, 1H, J=5.7, 13.7), 2.31 (s, 3H), 1.20 (t, 3H, J=7.1). HRMS: calcd for $C_{29}H_{29}N_3O_2$, 452.2338; found, 452.2337.

Ethyl 3-(furan-2-yl)-2-((3-(3-methylbenzyl)-5-phenylpyrazin-2-yl)amino)propanoate (N-77): Obtained from L-13 and B-7 as an oil (0.35 g, 75%) after a chromatography over silica gel (cyclohexane—ethyl acetate 95:5). $^1$H NMR ($CDCl_3$): 8.42 (s, 1H), 7.96 (m, 2H), 7.48 (m, 2H), 7.38 (m, 1H), 7.21 (m, 2H), 7.08 (m, 3H), 6.22 (dd, 1H, J=2.0, 3.3), 5.83 (m, 1H), 5.16 (d (br), 1H, J=7.6), 4.96 (m, 1H), 4.17 (m, 4H), 3.21 (m, 2H), 2.33 (s, 3H), 1.21 (t, 3H, J=7.1). HRMS: calcd for $C_{27}H_{28}N_3O_3$, 442.2131; found, 442.2133.

Ethyl (3-(2-fluorobenzyl)-5-phenylpyrazin-2-yl)phenylalaninate (N-78): Obtained from L-3 and PheOEt, HCl as an oil (0.19 g, 40%) after a chromatography over silica gel (cyclohexane—ethyl acetate 94/6). $^1$H NMR (CDC), 400 MHz): 8.44 (s, 1H), 7.94-7.91 (m, 2H), 7.48-7.44 (m, 2H), 7.38-7.34 (m, 1H), 7.28-7.22 (m, 5H), 7.11-7.05 (m, 4H), 5.10-5.08 (m, 1H), 5.04-4.99 (m, 1H), 4.20-4.09 (m, 4H), 3.28-3.23 (m, 1H), 3.18-3.13 (m, 1H), 1.23-1.20 (L 3H, J=7.9). HRMS: calcd for $CH_{28}F_{27}FN_3O_2$, 456.2087; found, 456.2096.

Ethyl 2-((3-(2-fluorobenzyl)-5-phenylpyrazin-2-yl) amino)-3-(m-tolyl)propanoate (N-79): Obtained from L-3 and B-6 as an oil (0.34 g, 69%) after a chromatography over silica gel (cyclohexane—ethyl acetate 95/5). $^1$H NMR ($CDCl_3$, 400 MHz): 8.42 (s, 1H), 7.91 (m, 2H), 7.45 (m, 2H), 7.36 (m, 1H), 7.23 (m, 2H), 7.16-7.04 (m, 4H), 6.95 (m, 1H), 6.88 (m, 1H), 5.06 (d (br), 1H, J=7.3), 4.97 (m, 1H), 4.15 (m, 4H), 3.20 (dd, 1H, J=5.5, 13.7), 3.10 (dd, 1H, J=6.7, 13.7), 2.31 (s, 3H), 1.21 (t, 3H, J=7.1). HRMS: calcd for $C_{29}H_{29}FN_3O_2$, 470.2244, found, 470.2253.

Ethyl 2-((3-(2-fluorobenzyl)-5-phenylpyrazin-2-yl) amino)-3-(3-methoxyphenyl)propanoate (N-80): Obtained from L-3 and B-3 as an oil (0.32 g, 63%) after a chromatography over silica gel (cyclohexane—ethyl acetate 94/6) $^1$H NMR ($CDCl_3$, 400 MHz): 8.42 (s, 1H), 7.91 (m, 2H), 7.45 (m, 2H), 7.36 (m, 1H), 7.23 (m, 2H), 7.16 (m, 1H), 7.06 (m, 2H), 6.78 (m, 1H), 6.68 (m, 2H), 5.08 (d (br), 1H, J=7.2), 4.99 (m, 1H), 4.16 (m, 4H), 3.77 (s, 3H), 3.23 (dd, 1H, w/=5.6, 13.9) 3.12 (dd, 1H, J=6.4, 13.9), 1.22 (t, 3H, J=7.1). HRMS: calcd for $C_{29}H_{29}FN_3O_3$, 486.2193, found, 486.2182.

Ethyl 2-((3-(2-fluorobenzyl)-5-phenylpyrazin-2-yl) amino)-3-(furan-2-yl)propanoate (N-81): Obtained from L-3 and B-7 as an oil (0.29 g, 62%) after a chromatography over silica gel (cyclohexane—ethyl acetate 95/5). $^1$H NMR (CDC), 400 MHz): 8.42 (s, 1H), 7.92 (m, 2H), 7.45 (m, 2H), 7.36 (m, 1H), 7.26 (m, 3H), 7.09 (m, 2H), 6.24 (dd, 1H, J=1.9, 3.2), 5.95 (d, 1H, J=3.1), 5.28 (d (br), 1H, J=7.6), 5.01 (m, 1H), 4.19 (m, 4H), 3.77 (s, 3H), 3.26 (m, 2H), 1.24 (t, 3H, J=7.1). HRMS: calcd for $C_{26}H_{25}FN_3O_3$, 446.1880, found, 446.1873.

Ethyl 2-((3-(2-fluorobenzyl)-5-phenylpyrazin-2-yl)amino)-3-(5-methylfuran-2-yl)propanoate (N-82): Obtained from L-3 and B-8 as an oil (0.23 g, 48%) after a chromatography over silica gel (cyclohexane—ethyl acetate 95/5). $^1$H NMR ($CDCl_3$, 400 MHz): 8.42 (s, 1H), 7.91 (m, 2H), 7.45 (m, 2H), 7.36 (m, 1H), 7.25 (m, 2H), 7.08 (m, 2H), 5.82 (m, 2H), 5.27 (d (br), 1H, J=7.6), 4.97 (m, 1H), 4.19 (m, 4H), 3.77 (s, 3H), 3.20 (d, 2H, J=5.8), 2.23 (s, 3H), 1.24 (t, 3H, J=7.1). HRMS: calcd for $C_{27}H_{27}FN_3O_3$, 460.2036, found, 460.2044.

Ethyl 3-(5-ethylfuran-2-yl)-2-((3-(2-fluorobenzyl)-5-phenylpyrazin-2-yl)amino)propanoate (N-83): Obtained from L-3 and B-10 as an oil (0.19 g, 46%) after a chromatography over silica gel (cyclohexane—ethyl acetate 95/5). $^1$H NMR ($CDCl_3$, 400 MHz): 8.41 (s, 1H), 7.91 (m, 2H), 7.46 (m, 2H), 7.34 (m, 1H), 7.25 (m, 2H), 7.07 (m, 2H), 5.82 (m, 2H), 5.27 (d (br), 1H, J=7.3), 4.97 (m, 1H), 4.20 (m, 4H), 3.77 (s, 3H), 3.20 (d, 2H, J=5.1), 2.57 (q, 2H, J=7.5), 1.25 (t, 3H, J=7.1), 1.20 (t, 3H, J=7.5). HRMS: calcd for $C_{28}H_{29}FN_3O_3$, 474.2193, found, 474.2198.

Ethyl (3-(2-chlorobenzyl)-5-phenylpyrazin-2-yl)phenylalaninate (N-84): Obtained from L-4 and PheOEt, HCl as an oil (0.19 g, 68%) after a chromatography over silica gel (cyclohexane—ethyl acetate 96/4) H NMR ($CDCl_3$): 8.44 (s, 1H), 7.91 (m, 2H), 7.44 (m, 3H), 7.35 (m, 1H), 7.26-7.16 (m, 6H), 7.05 (m, 2H), 5.00 (m, 2H), 4.24 (m, 2H), 4.16 (dq, J=7.2, 1.0 Hz, 2H), 3.22 (dd, J=13.7, 5.4 Hz, 1H), 3.13 (dd, J=13.7, 6.3 Hz, 1H), 1.22 (t, J=7.2 Hz, 3H). HRMS: calcd for $C_{28}H_{27}ClN_3O_2$: 472.1792; found, 472.1784.

Ethyl 2-((3-(2-chlorobenzyl)-5-phenylpyrazin-2-yl)amino)-3-(furan-2-yl)propanoate (N-85): Obtained from L-4 and B-7 as an oil (0.44 g, 65%) after a chromatography over silica gel (cyclohexane—ethyl acetate 96/4). $^1$H NMR ($CDCl_3$): 8.44 (s, 1H), 7.91 (m, 2H), 7.45 (m, 3H), 7.35 (m, 1H), 7.25-7.15 (m, 4H), 6.22 (m, 1H), 5.92 (m, 1H), 5.18 (m, 1H), 5.00 (m, 1H), 4.28 (m, 2H), 4.19 (q, J=7.1 Hz, 2H), 3.24 (d, J=5.5 Hz, 2H), 1.24 (t, J=7.1 Hz, 3H). HRMS: calcd for $C_{26}H_{25}ClN_3O_3$: 462.1584; found, 462.1576.

Ethyl 2-((3-(2-chlorobenzyl)-5-phenylpyrazin-2-yl)amino)-3-(5-methylfuran-2-yl)propanoate (N-86): Obtained from L-4 and B-8 as an oil (0.11 g, 36%) after a chromatography over silica gel (cyclohexane—ethyl acetate 95/5). $^1$H NMR ($CDCl_3$): 8.43 (s, 1H), 7.91 (m, 2H), 7.43 (m, 3H), 7.35 (m, 1H), 7.20 (m, 3H), 6.22 (m, 1H), 5.80 (m, 2H), 5.19 (d (br), 1H, J=7.6), 4.98 (m, 1H), 4.28 (m, 2H), 4.20 (m, 2H), 3.19 (m, 2H), 2.21 (s, 3H), 1.25 (t, J=7.1 Hz, 3H). HRMS: calcd for $C_{27}H_{27}ClN_3O_3$: 476.1741; found, 476.1744.

Ethyl (3-(3-fluorobenzyl)-5-phenylpyrazin-2-yl)phenylalaninate (N-87): Obtained from L-6 and PheOEt, HCl as an oil (0.40 g, 57%) after a chromatography over silica gel (cyclohexane—ethyl acetate 94:6). $^1$H NMR ($CDCl_3$): 8.45 (s, 1H), 7.95 (m, 2H), 7.48 (m, 2H), 7.38 (m, 1H), 7.36-7.21 (m, 4H), 7.10-6.92 (m, 5H), 5.02 (m, 1H), 4.85 (d (br), 1H, J=7.5), 4.16 (q, 2H, J=7.2), 4.11 (s, 2H), 3.21 (dd, 1H, J=5.4, 13.8), 3.13 (dd, 1H, J=5.9, 13.8), 1.22 (t, J=7.1 Hz 3H). HRMS: calcd for $C_{28}H_{27}FN_3O_2$, 456.2087; found, 456.2067.

Ethyl 2-((3-(3-fluorobenzyl)-5-phenylpyrazin-2-yl)amino)-3-(furan-2-yl)propanoate (N-88): Obtained from L-6 and B-7 as an oil (0.22 g, 57%) after a chromatography over silica gel (cyclohexane—ethyl acetate 95:5). $^1$H NMR ($CDCl_3$): 8.44 (s, 1H), 7.95 (m, 2H), 7.48 (m, 2H), 7.37 (m, 1H), 7.28 (m, 2H), 7.06 (m, 1H), 6.96 (m, 2H), 6.24 (dd, 1H, J=2.0, 3.2), 5.89 (dd, 1H, J=0.7, 3.2), 5.08 (d (br), 1H, J=7.5), 4.87 (m, 1H), 4.18 (m, 4H), 3.24 (d, 2H, J=5.3), 1.23 (t, J=7.1 Hz, 3H). HRMS: calcd for $C_{26}H_{25}FN_3O_3$, 446.1880; found, 446.1883.

Ethyl 2-((3-(3-fluorobenzyl)-5-phenylpyrazin-2-yl)amino)-3-(5-methylfuran-2-yl)propanoate (N-89): Obtained from L-6 and B-8 as an oil (0.24 g, 57%) after a chromatography over silica gel (cyclohexane—ethyl acetate 95:5). $^1$H NMR ($CDCl_3$): 8.43 (s, 1H), 7.93 (m, 2H), 7.47 (m, 2H), 7.37 (m, 1H), 7.28 (m, 1H), 7.06 (m, 1H), 6.96 (m, 2H), 5.82 (m, 1H), 5.78 (m, 1H), 5.06 (d (br), 1H, J=7.9), 4.93 (m, 1H), 4.18 (m, 4H), 3.20 (d, 2H, J=5.2), 2.22 (s, 3H), 1.24 (t, 3H, J=7.1). HRMS: calcd for $C_{27}H_{27}FN_3O_3$, 460.2036; found, 460.2039.

Ethyl 3-(5-ethylfuran-2-yl)-2-((3-(3-fluorobenzyl)-5-phenylpyrazin-2-yl)amino)propanoate (N-90): Obtained from L-6 and B-10 as an oil (0.20 g, 90% pure) after a chromatography over silica gel (cyclohexane—ethyl acetate 95:5). $^1$H NMR ($CDCl_3$): 8.43 (s, 1H), 7.94 (m, 2H), 7.47 (m, 2H), 7.37 (m, 1H), 7.27 (m, 1H), 7.06 (m, 1H), 6.96 (m, 2H), 5.82 (m, 1H), 5.78 (m, 1H), 5.06 (d (br), 1H, J=7.7), 4.94 (m, 1H), 4.18 (m, 4H), 3.20 (d, 2H, J=5.1), 2.57 (q, 2H, J=7.6), 1.22 (m, 6H). HRMS: calcd for $C_{28}H_{29}FN_3O_3$, 474.2193; found, 474.2199.

Ethyl 2-((3-(3-fluorobenzyl)-5-phenylpyrazin-2-yl)amino)-3-(m-tolyl)propanoate (N-91): Obtained from L-6 and B-6 as an oil (0.35 g, 74%) after a chromatography over silica gel (cyclohexane—ethyl acetate 95:5). $^1$H NMR ($CDCl_3$): 8.45 (s, 1H), 7.94 (m, 2H), 7.47 (m, 2H), 7.37 (m, 1H), 7.23 (m, 1H), 7.14 (m, 1H), 7.07 (m, 1H), 6.93 (m, 3H), 6.81 (m, 1H), 4.96 (m, 1H), 4.82 (d (br), 1H, J=7.4), 4.18 (m, 4H), 3.17 (dd, 1H, J=5.5, 13.7), 3.09 (dd, 1H, J=6.2, 13.7), 2.32 (s, 3H), 1.21 (t, 3H J=7.1). HRMS: calcd for $C_{29}H_{29}FN_3O_3$: 470.2244; found, 470.2249.

Ethyl 2-((3-(3-fluorobenzyl)-5-phenylpyrazin-2-yl)amino)-3-(3-methoxyphenyl)propanoate (N-92): Obtained from L-6 and B-3 as an oil (0.22 g, 45%) after a chromatography over silica gel (cyclohexane—ethyl acetate 95:5). $^1$H NMR ($CDCl_3$): 8.44 (s, 1H), 7.94 (m, 2H), 7.47 (m, 2H), 7.36 (m, 1H), 7.19 (m, 2H), 6.93 (m, 3H), 6.79 (m, 1H), 6.60 (m, 2H), 4.97 (m, 1H), 4.81 (d (br), 1H, J=7.7), 4.18 (m, 4H), 3.77 (s, 3H), 3.19 (dd, 1H, J=5.7, 13.8), 3.10 (dd, 1H, J=5.9, 13.8), 1.21 (t, 3H, J=7.1). HRMS: calcd for $C_{29}H_{29}FN_3O_3$, 486.2193; found, 486.2209.

Ethyl (3-(4-fluorobenzyl)-5-phenylpyrazin-2-yl)phenylalaninate (N-93): Obtained from L-7 and PheOEt, HCl as an oil (0.12 g, 80% pure) after a chromatography over silica gel (cyclohexane—ethyl acetate 94:6). $^1$H NMR ($CDCl_3$): 8.44 (s, 1H), 7.96 (m, 2H), 7.48 (m, 2H), 7.38 (m, 1H), 7.27-7.22 (m, 3H), 7.16 (m, 2H), 7.01-6.94 (m, 4H), 5.02 (m, 1H), 4.88 (d (br), 1H, J=7.5), 4.16 (q, 2H, J=7.0), 4.10 (s, 2H), 3.24 (dd, 1H, J=5.5, 13.8), 3.14 (dd, 1H, J=5.9, 13.8), 1.24 (t, J=7.1 Hz, 3H). HRMS: calcd for $C_{28}H_{27}FN_3O_2$, 456.2087, found, 456.2072.

Ethyl 2-(3-(2-methoxybenzyl)-5-phenylpyrazin-2-ylamino)-3-phenylpropanoate (N-94): Obtained from L-5 and PheOEt, HCl as an oil (0.1 g, 28%) after a chromatography over silica gel (cyclohexane—ethyl acetate 96:4). $^1$H NMR ($CDCl_3$): 8.37 (s, 1H), 7.97 (m, 2H), 7.47 (m, 2H), 7.37 (m, 2H), 7.21 (m, 4H), 7.02 (m, 2H), 6.93 (m, 1H), 6.85 (m, 1H), 6.03 (d (br), 1H, J=7.7), 5.08 (m, 1H), 4.17 (m, 4H), 3.72 (s, 3H), 3.20 (dd, 1H, J=6.0, 13.9), 3.12 (dd, 1H, J=6.2, 13.9), 1.21 (t, 3H, J=7.2). HRMS: calcd for $C_{29}H_{29}N_3O_3$, 468.2287; found, 468.2298.

General procedure for the debenzylation of O-benzyl-bearing N-aryl α-aminoesters N. The considered compound (0.53 mmol), ammonium formate (0.17 g, 2.64 mmol) and 10% palladium over charcoal (30 mg, 0.026 mmol) were heated to reflux in ethanol (15 mL) for two hours. The suspension was filtered, the filtrate concentrated to dryness to give fairly clean deprotected products as described below.

Ethyl (3-benzyl-5-(4-hydroxyphenyl)pyrazin-2-yl)tyrosinate (N-95): Obtained from N-9 as a white solid (0.18 g, 72%) after a chromatography over silica gel (dichloromethane—ethanol 97/3). $^1$H NMR ($CDCl_3$): 8.28 (s, 1H), 7.79-7.72 (m, 2H), 7.29-7.19 (m, 3H), 7.19-7.12 (m, 2H), 6.88-6.75 (m, 4H), 6.66-6.59 (m, 2H), 4.92-4.75 (m, 2H), 4.13 (q, J=7.1 Hz, 2H), 4.09 (s, 2H), 3.06 (dd, J=14.0, 5.4 Hz, 1H), 2.97 (dd, J=14.0, 6.0 Hz, 1H), 1.19 (t, J=7.1 Hz, 3H). HRMS: calcd for $C_{28}H_{28}N_3O_4$, 470.2080; found, 470.2104.

Ethyl 2-((3-benzyl-5-(4-hydroxyphenyl)pyrazin-2-yl)amino)-3-(5-methylfuran-2-yl)propanoate (N-96): Obtained from N-29 as a glass (0.21 g, 81%) after a chromatography over silica gel (cyclohexane—ethyl acetate 3/1). $^1$H NMR ($CDCl_3$): 8.29 (s, 1H), 7.76 (m, 2H), 7.28 (m, 5H), 6.84 (m, 2H), 5.98 (m, 1H), 5.76 (d (br), 1H, J=3), 5.69 (s (br), 1H), 5.69 (d (br), 1H), 4.88 (m, 1H), 4.17 (m, 2H), 4.14 (s, 2H), 3.13 (dd, 2H, J=3.0, 5.6), 2.23 (s, 3H), 1.23 (t, J=7.1 Hz, 3H). HRMS: calcd for $C_{27}H_{28}N_3O_4$, 459.2112; found, 459.2108.

Ethyl (3-benzyl-s-phenylpyrazin-2-yl)tyrosinate (N-97): Obtained from N-65 as a white solid (0.24 g, 46%) after a chromatography over silica gel (dichloromethane—ethanol 98.5/1.5). $^1$H NMR ($CDCl_3$): 8.39 (s, 1H), 7.98-7.88 (m, 2H), 7.50-7.40 (m, 2H), 7.38-7.31 (m, 1H), 7.31-7.22 (m, 3H), 7.22-7.17 (m, 2H), 6.84-6.76 (m, 2H), 6.67-6.59 (m, 2H), 4.96 (s, 1H), 4.94-4.86 (m, 2H), 4.12 (s, 2H), 4.19-4.07 (m, 2H), 3.13-3.03 (m, 1H), 3.03-2.92 (m, 1H), 1.19 (t, 3H, J=7.1). HRMS: calcd for $C_{28}H_{28}N_3O_3$, 454.2131; found, 454.2104.

General procedure for the hydrolysis of N-aryl α-aminoesters N into the corresponding N-aryl α-aminoacids O. In a round bottomed flask, the considered ester (0.0046 mol) and powdered sodium hydroxide (0.54 g, 0.0137 mol) were mixed. The atmosphere was replaced with argon and dry tetrahydrofuran (30 mL) was added. This was stirred overnight under an inert atmosphere, made acid with 1N hydrochloric acid and extracted with ethyl acetate. The 20 organic layer was washed with water, brine, dried over magnesium sulfate and concentrated to dryness to yield the corresponding acid as described below.

(3-Benzyl-5-phenylpyrazin-2-yl)phenylalanine (O-1): Obtained from N-5 as a hard foam (1.7 g, 91%). $^1$H NMR (DMSO-$d_6$): 12.61 (s, 1H), 8.44 (s, 1H), 7.90 (m, 2H), 7.40 (m, 2H), 7.32-7.15 (m, 11H), 6.84 (m, 1H), 4.66 (m, 1H), 4.30 (d, 1H, J=14.5), 4.06 (d, 1H, J=14.5), 3.21 (m, 2H). HRMS: calcd for $C_{26}H_{24}N_3O_2$, 410.1869; found, 410.1875.

2-((3-Benzyl-5-(4-(benzyloxy)phenyl)pyrazin-2-yl)amino)-3-(4-(benzyloxy)phenyl)propanoic acid (O-2): Obtained from intermediates N-8 or N-9 as a hard foam (0.42 g, 87%). $^1$H NMR ($CDCl_3$): 8.31 (s, 1H), 7.88-7.81 (m, 2H), 7.49-7.29 (m, 11H), 7.24-7.16 (m, 3H), 7.13-7.08 (m, 2H), 7.08-7.01 (m, 2H), 6.95-6.87 (m, 2H), 6.86-6.79 (m, 2H), 5.11 (s, 2H), 5.03 (s, 2H), 4.86-4.76 (m, 1H), 4.71 (d, 1H, J=6.3), 4.06 (d, 1H, J=15.4), 4.00 (d, 1H, J=15.5), 3.19 (dd, 1H, J=14.2, 5.2), 3.01 (dd, 1H, J=14.2, 6.9). HRMS: calcd for $C_{40}H_{36}N_3O_4$, 622.2706; found, 622.2763.

(3-Benzyl-5-(4-(benzyloxy)phenyl)pyrazin-2-yl)phenylalanine (O-3): Obtained from N-60 as a foam still containing some ethyl acetate (3.73 g). $^1$H NMR (DMSO-$d_6$): 12.60 (s, 1H), 8.36 (s, 1H), 7.83 (m, 2H), 7.46 (m, 2H), 7.40 (m, 2H), 7.32 (m, 1H), 7.29-7.15 (m, 9H), 7.04 (m, 2H), 6.71 (m, 1H), 5.13 (s, 2H), 4.64 (m, 1H), 4.28 (d, 1H, J=14.6), 4.03 (d, 1H, J=14.5), 3.21 (m, 2H). HRMS: calcd for $C_{33}H_{30}N_3O_3$, 516.2287; found, 516.2273.

2-((3-Benzyl-5-(4-(benzyloxy)phenyl)pyrazin-2-yl)amino)-3-(3-propylphenyl)propanoic acid (O-4): This compound was obtained from N-70 as a glass (0.76 g) still containing some ethyl acetate. $^1$H NMR ($CDCl_3$): 8.33 (s, 1H), 7.86 (m, 2H), 7.34 (m, 11H), 7.09 (m, 5H), 6.96 (s, 1H), 6.87 (m, 1H), 4.81 (m, 1H), 4.69 (m, 1H), 4.07 (d, 1H, J=15.4), 3.93 (d, 1H, J=15.4), 3.27 (dd, 1H, J=14.2, 5.2), 3.05 (dd, 1H, J=14.2, 7.6), 2.56 (m, 2H), 1.62 (m, 2H), 0.93 (t, 3H, J=7.3). HRMS: calcd for $C_{36}H_{36}N_3O_3$: 558.2757; found, 558.2746.

2-((3-Benzyl-5-(4-(benzyloxy)phenyl)pyrazin-2-yl)amino)-3-(furan-2-yl)propanoic acid (O-5): Obtained from N-67 as a foam still containing some ethyl acetate (0.8 g). $^1$H NMR ($CDCl_3$): 10.29 (s (br), 1H), 8.33 (s, 1H), 7.87 (m, 2H), 7.49 (m, 2H), 7.41 (m, 2H), 7.37-7.23 (m, 7H), 7.08 (m, 2H), 6.25 (dd, 1H, J=1.9, 3.4), 5.95 (dd, 1H, J=0.5, 3.4), 5.14 (s, 2H), 5.0 (d (br), 1H, J=7.4), 4.85 (m, 1H), 4.15 (m, 2H), 3.28 (dd, 1H, J=5.0, 15.4), 3.20 (dd, 1H, J=6.5, 15.0). HRMS: calcd for $C_{31}H_{28}N_3O_4$, 506.2080; found, 516.2109.

2-((3-benzyl-5-(4-(benzyloxy)phenyl)pyrazin-2-yl)amino)-3-(4,5-dimethylfuran-2-yl)propanoic acid (O-6): Obtained from N-69 as a foam still containing some ethyl acetate (0.61 g). $^1$H NMR ($CDCl_3$); 9.16 (s (br), 1H), 8.32 (s, 1H), 7.87 (m, 2H), 7.49-7.22 (m, 10H), 7.08 (m, 2H), 5.77 (s, 1H), 5.14 (s, 2H), 5.01 (d (br), 1H, J=6.6), 4.76 (m, 1H), 4.15 (m, 2H), 3.18 (dd, 1H, J=4.9, 15.3), 3.10 (dd, 1H, J=7.1, 15.3), 2.14 (s, 3H), 1.89 (s, 3H). HRMS: calcd for $C_{33}H_{32}N_3O_4$, 534.2393; found, 534.2410.

2-((3-Benzyl-5-(4-(benzyloxy)phenyl)pyrazin-2-yl)amino)-3-(5-ethylfuran-2-yl)propanoic acid (O-7): Obtained from N-68 as a foam still containing some ethyl acetate (0.59 g), H NMR ($CDCl_3$): 9.16 (s (br), 1H), 8.32 (s, 1H), 7.87 (m, 2H), 7.47 (m, 2H), 7.41 (m, 2H), 7.37-7.22 (m, 9H), 7.08 (m, 2H), 5.89 (m, 2H), 5.14 (s, 2H), 4.96 (d (br), 1H, J=6.4), 4.80 (m, 1H), 4.12 (m, 2H), 3.23 (dd, 1H, J=4.9, 15.2), 3.14 (dd, 1H, J=7.1, 15.2), 2.57 (q, 2H, J=7.6), 1.19 (t, 3H, J=7.6). HRMS: calcd for $C_{33}H_{32}N_3O_4$, 534.2393; found, 534.2405.

(3-Benzyl-5-(4-(benzyloxy)-3-fluorophenyl)pyrazin-2-yl)phenylalanine (O-8): Obtained from N-10 as a hard foam (0.56 g, 92%). $^1$H NMR (DMSO-$d_6$): 12.61 (s, 1H), 8.42 (s, 1H), 7.73 (m, 1H), 7.67 (m, 1H), 7.47 (m, 2H), 7.40 (m, 2H), 7.34 (m, 1H), 7.29-7.16 (m, 11H), 6.82 (d (br), 1H, J=8.2), 5.20 (s, 2H), 4.66 (m, 1H), 4.27 (d, 1H, J=15.0), 4.02 (d, 1H, J=15.0), 3.19 (m, 2H). HRMS: calcd for $C_{33}H_{29}FN_3O_3$, 535.2225; found, 535.2239.

General procedure for the debenzylation of O-benzyl-bearing N-aryl-aminoacids O. The considered O-benzyl derivative (1.5 mmol) and ammonium formate (2.8 g, 0.044 mol) were dissolved in isopropanol (50 mL). To this was added 10% palladium over charcoal (0.16 g, 0.15 mmol) and the suspension was heated to reflux for one hour. This was cooled, filtered and concentrated to dryness under high vacuum. This led to a foam still containing some isopropanol. In some cases some unreacted compound was detected and the crude residue was then subjected to a second round of hydrogenation. As described below some attempts were made to further purify the resulting amino acids (with rather big losses) but it turned out that as long as the crude compound has been subject to a thorough drying under high vacuum (to remove all the ammonium formate) it is suitable for use in the next step.

(3-Benzyl-5-(4-hydroxyphenyl)pyrazin-2-yl)tyrosine (O-9): The residue was obtained from O-2, dispersed in water and filtered and the solid obtained was dried and dispersed again in 0.5 M hydrochloric acid, filtered and thoroughly dried again to give the pure compound (0.37 g, 45%). $^1$H NMR (DMSO-$d_6$): 8.31 (s, 1H), 7.72 (m, 2H), 7.22 (m, 5H), 7.02 (m, 2H), 6.82 (m, 2H), 6.61 (m, 2H), 6.54 (bs, 1H), 4.54 (m, 1H), 4.28 (d, 1H, J=14.6), 4.02 (d, 1H, J=14.6), 3.06 (m, 2H) HRMS: calcd for $C_{26}H_{24}N_3O_4$: 442.1767; found, 442.1773.

(3-Benzyl-5-(4-hydroxyphenyl)pyrazin-2-yl)phenylalanine (O-10): The residue was obtained from O-3, dispersed in water and filtered and the solid obtained was dried and dispersed again in 0.5 M hydrochloric acid, filtered and thoroughly dried again to give the pure compound (2.06 g, 70% from the corresponding ester). $^1$H NMR (DMSO-$d_6$): 8.34 (s, 1H), 7.72 (m, 2H), 7.20 (m, 5H), 7.08 (m, 5H), 6.82 (m, 2H), 6.34 (bs, 1H), 4.36 (m, 1H), 4.05 (d, 1H, J=14.8), 3.92 (d, 1H, J=14.8), 3.25 (dd, 1H, J=13.4, 4.7), 3.10 (dd, 1H, J=13.4, 6.2). HRMS: calcd for $C_{26}H_{24}N_3O_3$: 426.1818; found, 426.1806.

2-((3-Benzyl-5-(4-hydroxyphenyl)pyrazin-2-yl)amino)-3-(3-propylphenyl)propanoic acid (O-11): The residue was obtained from O-4, dispersed in water, made basic with ammonia and extracted with ethyl acetate. The organic layer was dried over magnesium sulfate and concentrated to dryness to yield this compound as a glass (0.5 g, 71% from the initial ester) still containing a small amount of ethyl acetate. $^1$H NMR (DMSO-$d_6$): 9.56 (s (br), 1H), 8.38 (s, 1H), 7.70 (m, 2H), 7.20 (m, 6H), 7.04 (m, 5H), 6.80 (m, 2H), 6.52 (m, 1H), 4.61 (m, 1H), 4.20 (d, 1H, J=14.9), 3.98 (d, 1H, J=14.9), 3.14 (m, 2H), 2.44 (m, 2H), 1.50 (m, 2H), 0.83 (t, 3H, J=7.3). HRMS: calcd for $C_{29}H_{30}N_3O_3$: 468.2287; found, 468.2286.

2-((3-Benzyl-5-(4-hydroxyphenyl)pyrazin-2-yl)amino)-3-(furan-2-yl)propanoic acid (O-12): This compounds was obtained from O-5 as a hard foam (0.54 g, 85% from the initial ester N-67) still containing a small amount of isopropanol after extensive drying under high vacuum. $^1$H NMR (DMSO-$d_6$): 9.56 (s (br), 1H), 8.34 (s, 1H), 7.73 (m, 2H), 7.46 (dd, 1H, J=0.7, 1.8), 7.31-7.14 (m, 6H), 6.80 (m, 2H), 6.61 (d, 1H, J=7.3), 6.30 (dd, 1H, J=1.8, 3.1), 6.07 (dd, 1H, J=0.7, 3.1), 4.67 (m, 1H), 4.20 (d, 1H, J=14.8), 4.04 (d, 1H, J=14.9) 3.24 (m, 2H). HRMS: calcd for $C_{24}H_{22}N_3O_4$: 416.1610; found, 416.1606.

2-((3-Benzyl-5-(4-hydroxyphenyl)pyrazin-2-yl)amino)-3-(4,5-dimethylfuran-2-yl)propanoic acid (O-13): The residue was obtained from O-6, dispersed in water, made basic with ammonia and extracted with ethyl acetate. The organic layer was dried over magnesium sulfate and concentrated to dryness and purified by a chromatography over silica gel (cyclohexane—ethyl acetate 1/1 to 0/1) to give the compound as a glass still containing some ethyl acetate (0.21 g, 42% from ester N-69). $^1$H NMR (DMSO-$d_6$): 12.4 (s, 1H), 9.49 (s (br), 1H), 8.33 (s, 1H), 7.75 (m, 2H), 7.32-7.16 (m, 6H), 6.80 (m, 2H), 6.54 (d, 1H, J=8.0), 5.82 (s, 1H), 4.60 (m, 1H), 4.23 (d, 1H, J=14.8), 4.04 (d, 1H, J=14.8), 3.10 (m, 2H), 2.07 (s, 3H), 1.81 (s, 3H). HRMS: calcd for $C_{26}H_{26}N_3O_4$: 444.1923; found, 444.1937.

2-((3-Benzyl-5-(4-hydroxyphenyl)pyrazin-2-yl)amino)-3-(5-ethylfuran-2-yl)propanoic acid (O-14): The residue was obtained from O-7, dispersed in water, made basic with ammonia and extracted with ethyl acetate. The organic layer was dried over magnesium sulfate and concentrated to dryness to yield the compound 80% pure as a glass still containing some ethyl acetate (0.11 g). $^1$H NMR (DMSO-$d_6$), 9.54 (s (br), 1H), 8.29 (s, 1H), 7.75 (m, 2H), 7.41-7.16 (m, 6H), 6.80 (m, 2H), 5.79 (s (br), 2H), 4.37 (m, 1H), 4.08 (d, 1H, J=14.5), 3.98 (d, 1H, J=14.5), 3.24 (dd, 1H, J=4.6, 15.2), 3.07 (dd, 1H, J=6.6, 15.2), 2.45 (q, 2H, J=7.6) 1.06 (t, 3H, J=7.6). HRMS: calcd for $C_{26}H_{29}N_3O_4$: 444.1923; found, 444.1930.

(3-Benzyl-5-(3-fluoro-4-hydroxyphenyl)pyrazin-2-yl) phenylalanine (O-15): This compounds was obtained from O-8, using ethanol as a solvent, as a hard foam (0.43 g, 92%) still containing a small amount of ethanol after extensive drying under high vacuum. $^1$H NMR (DMSO-$d_6$): 8.37 (s, 1H), 7.64 (m, 1H), 7.54 (m, 1H), 7.26-7.13 (m, 11H), 6.99 (m, 1H), 6.61 (d (br), 1H, J=7.4), 4.55 (m, 1H), 4.18 (d, 1H, J=14.7), 3.98 (d, 1H, J=14.7), 3.23 (dd, 1H, J=4.7, 13.6), 3.13 (dd, 1H, J=8.9, 13.6). HRMS: calcd for $C_{26}H_{23}F_3N_3O_3$: 444.1723; found, 444.1732.

General procedure for the synthesis of O-protected imidazo[1,2-a]pyrazines P from α-aminoesters N via steps o and p. In a sealable vessel, the considered N-pyrazyl α-aminoester (1.0 mmol) and sodium hydroxide (0.06 g, 1.5 mmol) were weighted. The air was replaced with argon and anhydrous THF (5 mL) was injected. This was stirred at 20° C. under an inert atmosphere overnight. Depending on the O-protecting group wanted, acetic anhydride (0.28 mL, 3.0 mmol) or the corresponding equivalents of pivalic anhydride was added. After stirring an additional three hours at room temperature, this was diluted in ethyl acetate, washed with water, brine and concentrated to dryness. The traces of acetic acid and acetic anhydride were removed by co-evaporation with toluene and then cyclohexane and the residue further purified as described below.

8-Benzyl-2-(sec-butyl)-6-phenylimidazo[1,2-a]pyrazin-3-yl acetate (P-1): Obtained from N-1 as a white solid (0.11 g, 48%) after a recrystallization in t-heptane. $^1$H NMR ($CDCl_3$): 7.92 (m, 2H), 7.79 (s, 1H), 7.66 (m, 2H), 7.47 (m, 2H), 7.39 (m, 1H), 7.32 (m, 2H), 7.23 (m, 1H), 4.63 (s, 2H), 2.89 (six, 1H, J=7.5), 2.49 (s, 3H), 1.89 (m, 1H), 1.74 (m, 1H), 1.39 (d, 3H, J=7.5), 0.93 (t, 3H, J=7.5). HRMS: calcd for $C_{25}H_{26}N_3O_2$: 400.2025; found, 400.2024.

8-Benzyl-2-(cyclopentylmethyl)-6-phenylimidazo[1,2-a]pyrazin-3-yl acetate (P-2); Obtained from N-2 as a powder (0.21 g, 88%) after a concentration to dryness. $^1$H NMR ($CDCl_3$): 7.92 (m, 2H), 7.80 (s, 1H), 7.65 (m, 2H), 7.47 (m, 2H), 7.39 (m, 1H), 7.32 (m, 2H), 7.23 (m, 1H), 4.63 (s, 2H), 2.78 (d, 2H, J=7.4), 2.50 (s, 3H), 2.38 (m, 1H), 1.80 (m, 2H), 1.64 (m, 4H), 1.29 (m, 2H), HRMS: calcd for $C_{27}H_{28}N_3O_2$, 426.2181; found, 426.2180.

8-Benzyl-2-(cyclohexylmethyl)-6-phenylimidazo[1,2-a]pyrazin-3-yl acetate (P-3): Obtained from N-3 as a powder (0.24 g, 72%) after a recrystallization in n-heptane. $^1$H NMR ($CDCl_3$): 7.92 (m, 2H), 7.80 (s, 1H), 7.65 (m, 2H), 7.47 (m, 2H), 7.39 (m, 1H), 7.32 (m, 2H), 7.23 (m, 1H), 4.63 (s, 2H), 2.78 (d, 2H, J=7.2), 2.50 (s, 3H), 1.87 (m, 1H), 1.75 (m, 5H), 1.27 (m, 3H), 1.05 (m, 2H). HRMS: calcd for $C_{28}H_{30}N_3O_2$, 440.2338; found, 440.2326.

8-Benzyl-2-(bicyclo[2.2.1]heptan-2-ylmethyl)-6-phenylimidazo[1,2-a]pyrazin-3-yl acetate (P-4): Obtained from N-4 as a powder (0.58 g, 52%) as a mixture of two diastereoisomers after a recrystallization in n-heptane. $^1$H NMR ($CDCl_3$): 7.92 (m, 2H), 7.80 (s, 0.4H), 7.79 (s, 0.6H), 7.65 (m, 2H), 7.47 (m, 2H), 7.39 (m, 1H), 7.32 (m, 2H), 7.23 (m, 1H), 4.63 (m, 2H), 2.85-2.57 (m, 2H), 2.51 and 2.50 (2s, 3H), 2.42 (m, 0.6H), 2.26 (m, 1H), 2.11 (m, 1H), 2.04 (m, 0.4H), 1.84 (m, 0.6H), 1.73 (m, 0.8H), 1.63-1.15 (m, 6H), 0.82 (m, 0.6H). HRMS: calcd for $C_{29}H_{30}N_3O_2$, 452.2338; found, 452.2355.

2,8-dibenzyl-5-methyl-6-phenylimidazo[1,2-a]pyrazin-3-yl acetate (P-5): Obtained as a glass from N-6 (0.3 g, 76%).

$^1$H NMR ($CDCl_3$): $^1$H NMR ($CDCl_3$): 7.62 (m, 2H), 7.51-7.38 (m, 5H), 7.33-7.23 (m, 8H), 4.58 (s, 2H), 4.15 (s, 2H), 2.56 (s, 3H), 2.14 (s, 3H). HRMS: calcd for $C_{29}H_{26}N_3O_2$, 448.2025; found, 448.2020.

8-benzyl-2-(furan-2-ylmethyl)-6-phenylimidazo[1,2-a] pyrazin-3-yl acetate (P-6): Obtained from N-34 as a beige solid (0.10 g, 36%) after a chromatography over silica gel (cyclohexane—ethyl acetate 4:1). $^1$H NMR ($CDCl_3$): 7.92 (m, 2H), 7.83 (s, 1H), 7.63 (m, 2H), 7.47 (m, 2H), 7.42-7.30 (m, 4H), 7.23 (m, 1H), 6.35 (m, 1H), 6.16 (m, 1H), 4.64 (s, 2H), 4.24 (s, 2H), 2.36 (s, 3H). HRMS: calcd for $C_{26}H_{22}N_3O_3$, 424.1661; found, 424.1607.

2,8-Dibenzyl-6-phenylimidazo[1,2-a]pyrazin-3-yl acetate (P-7): Obtained from N-5 as a yellowish solid (0.17 g, 50%) after a recrystallization from cyclohexane. $^1$H NMR ($CDCl_3$): 7.92 (m, 2H), 7.80 (s, 1H), 7.64 (m, 2H), 7.47 (m, 2H), 7.40 (m, 1H), 7.33 (m, 5H), 7.25 (m, 2H), 4.65 (s, 2H), 4.23 (s, 2H), 2.18 (s, 3H). HRMS: calcd for $C_{28}H_{24}N_3O_2$, 434.1869; found, 434.1825.

8-Benzyl-6-phenyl-2-(1-phenylethyl)imidazo[1,2-a] pyrazin-3-yl acetate (P-8): Obtained from N-7 as a white powder after a recrystallization from n-heptane (0.12 g, 44%). $^1$H NMR ($CDCl_3$): 7.90 (m, 2H), 7.74 (s, 1H), 7.68 (m, 2H), 7.46 (m, 2H), 7.40 (m, 1H), 7.33 (m, 5H), 7.25 (m, 2H), 4.68 (d, 1H, J=13.8), 4.63 (d, 1H, J=13.8), 4.34 (q, 1H, J=6.7), 2.14 (s, 3H), 1.83 (d, 3H, J=6.7). HRMS: calcd for $C_{29}H_{26}N_3O_2$, 448.2025; found, 448.2031.

8-Benzyl-2-phenethyl-6-phenylimidazo[1,2-a]pyrazin-3-yl acetate (P-9): Obtained from N-71 as a white powder after a recrystallization from n-heptane (0.22 g, 67%). $^1$H NMR ($CDCl_3$); 7.92 (m, 2H), 7.81 (s, 1H), 7.64 (m, 2H), 7.47 (m, 2H), 7.40 (m, 1H), 7.35-7.21 (m, 8H), 4.65 (s, 2H), 3.12 (m, 4H), 2.42 (s, 3H). HRMS calcd for $C_{29}H_{26}N_3O_2$, 448.2025; found, 448.2026.

8-Benzyl-2-((5-methylfuran-2-yl)methyl)-6-phenylimidazo[1,2-a]pyrazin-3-yl acetate (P-10): Obtained from N-36 as a white solid (0.14 g, 24%) after a chromatography over silica gel (cyclohexane—ethyl acetate 5:1) and a recrystallization from cyclohexane. $^1$H NMR ($CDCl_3$): 7.93-7.86 (m, 2H), 7.82 (s, 1H), 7.64-7.57 (m, 2H), 7.49-7.41 (m, 2H), 7.41-7.35 (m, 1H), 7.35-7.27 (m, 2H), 7.25-7.16 (m, 1H), 6.03-5.97 (m, 1H), 5.93-5.86 (m, 1H), 4.62 (s, 2H), 4.17 (s, 2H), 2.34 (s, 3H), 2.26 (s, 3H). HRMS: calcd for $C_{27}H_{24}N_3O_3$, 438.1818; found, 438.1828.

8-Benzyl-2-((5-methylfuran-2-yl)methyl)-6-(p-tolyl)imidazo[1,2-a]pyrazin-3-yl acetate (P-11): Obtained from N-37 as a white solid (0.15 g, 70%) after a recrystallization from n-heptane. $^1$H NMR ($CDCl_3$): 7.82-7.79 (m, 3H), 7.62 (m, 2H), 7.33-7.20 (m, 5H), 6.01 (d, 1H, J=1), 5.90 (m, 1H), 4.62 (s, 2H), 4.17 (s, 2H), 2.41 (s, 3H), 2.35 (s, 3H), 2.28 (s, 2H). HRMS: calcd for $C_{28}H_{26}N_3O_3$, 452.1974; found, 452.1960.

8-Benzyl-2-((5-methylfuran-2-yl)methyl)-6-(m-tolyl) imidazo[1,2-a]pyrazin-3-yl acetate (P-12): Obtained from N-38 as a white solid (0.1 g, 53%) after a (slow) recrystallization from n-heptane. $^1$H NMR ($CDCl_3$): 7.82 (s, 1H), 7.73 (m, 1H), 7.79 (m, 1H), 7.37-7.20 (m, 5H), 6.01 (d, 1H, J=3), 5.91 (m, 1H), 4.62 (s, 2H), 4.18 (s, 2H), 2.45 (s, 3H), 2.36 (s, 3H), 2.28 (s, 2H). HRMS: calcd for $C_{28}H_{26}N_3O_3$, 452.1974; found, 452.1981.

8-Benzyl-2-(furan-3-ylmethyl)-6-phenylimidazo[1,2-a] pyrazin-3-yl acetate (P-13): Obtained from N-35 as a beige solid (0.74 g, 67%) after a recrystallization from n-heptane. $^1$H NMR ($CDCl_3$): 7.92 (m, 2H), 7.83 (s, 1H), 7.63 (m, 2H), 7.47 (m, 2H), 7.40 (m, 2H), 7.36-7.30 (m, 3H), 7.24 (m, 1H), 6.38 (m, 1H), 4.64 (s, 2H), 4.00 (m, 2H), 2.34 (s, 3H). HRMS: calcd for $C_{26}H_{22}N_3O_3$, 424.1661; found, 424.1688.

2-((1,3-Dioxolan-2-yl)methyl)-8-benzyl-6-phenylimidazo[1,2-a]pyrazin-3-yl acetate (P-14): Obtained from N-12 as a white solid (0.46 g, 76%) after recrystallization from n-heptane. $^1$H NMR ($CDCl_3$): 7.92 (m, 2H), 7.85 (s, 1H), 7.62 (m, 2H), 7.47 (m, 2H), 7.40 (m, 1H), 7.32 (m, 2H), 7.23 (m, 1H), 5.29 (t, 1H, J=4.5), 4.64 (s, 2H), 3.97-3.86 (m, 4H), 3.22 (d, 2H, J=4.5), 2.49 (s, 3H). HRMS: calcd for $C_{25}H_{24}N_3O_3$, 430.1767; found, 430.1762.

8-Benzyl-2-(4-(benzyloxy)benzyl)-6-(4-(benzyloxy)phenyl)imidazo[1,2-a]pyrazin-3-yl acetate (P-15): Obtained from N-9 as a brown solid (0.27 g, 66%) after a recrystallization from cyclohexane. $^1$H NMR ($CDCl_3$): 7.84 (m, 2H), 7.71 (s, 1H), 7.61 (m, 2H), 7.48-7.29 (m, 12H), 7.25-7.20 (m, 3H), 7.06 (m, 2H), 6.94 (m, 2H), 5.14 (s, 2H), 5.09 (s, 2H), 4.62 (s, 2H), 2.17 (s, 3H), HRMS: calcd for $C_{42}H_{36}N_3O_4$, 646.2706; found, 646.2728.

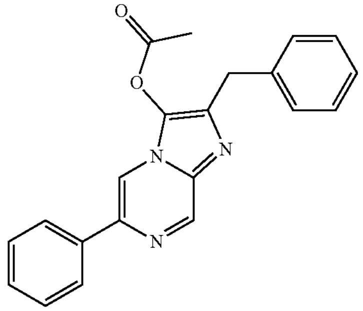 [SMILES: CC(=O)Oc1c(Cc2ccccc2)nc2cnc(-c3ccccc3)cn12]

2-Benzyl-6-phenylimidazo[1,2-a]pyrazin-3-yl acetate (P-16): Obtained from N-32 as a yellow solid (0.22 g, 48%) after a recrystallization from n-heptane. $^1$H NMR ($CDCl_3$): 9.08 (m, 1H), 7.94-7.90 (m, 3H), 7.50 (m, 2H), 7.43 (m, 1H), 7.36-7.24 (m, 5H), 4.19 (s, 2H), 2.27 (s, 3H). HRMS: calcd for $C_{21}H_{18}N_3O_2$, 344.1399; found, 344.1389.

2-Benzyl-8-methyl-6-phenylimidazo[1,2-a]pyrazin-3-yl acetate (P-17): Obtained from N-33 as a yellow solid (0.59 g, 88%) after a recrystallization from n-heptane. $^1$H NMR ($CDCl_3$): 7.91 (m, 2H), 7.80 (m, 1H), 7.48 (m, 2H), 7.41 (m, 1H), 7.35-7.23 (m, 5H), 4.21 (s, 2H), 2.96 (m, 3H), 2.18 (s, 3H). HRMS: calcd for $C_{27}H_{24}N_3O_2$, 358.1556; found, 358.1544.

8-Benzyl-2-(furan-2-ylmethyl)-6-(2-methoxyphenyl)imidazo[1,2-a]pyrazin-3-yl acetate (P-18): Obtained from N-40 as a beige solid (0.27 g, 68%) after a recrystallization from n-heptane. $^1$H NMR ($CDCl_3$): 8.21 (s, 1H), 8.05 (dd, J=7.7, 1.8 Hz, 1H), 7.59 (dd, J=7.9, 0.9 Hz, 2H), 7.39-7.27 (m, 4H), 7.23-7.18 (m, 1H), 7.09 (td, J=7.6, 1.1 Hz, 1H), 6.99 (dd, J=8.3, 0.9 Hz, 1H), 6.33 (dd. J=3.2, 1.9 Hz, 1H), 6.16-6.10 (m, 1H), 4.60 (s, 2H), 4.22 (s, 2H), 3.87 (s, 3H), 2.32 (s, 3H). HRMS: calcd for $C_{27}H_{24}N_3O_4$, 454.1767; found, 454.1785.

8-benzyl-2-(furan-3-ylmethyl)-6-(2-methoxyphenyl)imidazo[1,2-a]pyrazin-3-yl acetate (P-19): Obtained from N-41 as a beige solid (0.15 g, 29%) after a recrystallization from n-heptane. $^1$H NMR ($CDCl_3$): 8.21 (s, 1H), 8.07 (dd, J=7.7, 1.8 Hz, 1H), 7.61 (d, J=7.4 Hz, 2H), 7.41-7.27 (m, 5H), 7.22 (d, J=7.4 Hz, 1H), 7.15-7.06 (m, 1H), 6.99 (d, J=8.2 Hz, 1H), 6.40-6.34 (m, 1H), 4.61 (s, 2H), 3.98 (s, 2H), 3.88 (s, 3H), 2.30 (s, 3H). HRMS: calcd for $C_{27}H_{24}N_3O_4$, 454.1767; found, 454.1786.

2,8-Dibenzyl-6-(2-methoxyphenyl)imidazo[1,2-a] pyrazin-3-yl acetate (P-20): Obtained from N-39 as a beige solid (0.22 g, 53%) after a recrystallization from n-heptane. $^1$H NMR ($CDCl_3$): 8.17 (s, 1H), 8.05 (dd, J=7.7, 1.8 Hz, 1H), 7.65-7.58 (m, 2H), 7.38-7.27 (m, 7H), 7.26-7.16 (m, 2H), 7.09 (td, J=7.6, 1.0 Hz, 1H), 6.98 (dd, J=8.3, 0.7 Hz, 1H), 4.62 (s, 2H), 4.21 (s, 2H), 3.86 (s, 3H), 2.15 (s, 3H), HRMS: calcd for $C_{29}H_{26}N_3O_3$, 464.1974; found, 464.1979.

8-Benzyl-2-((5-ethylfuran-2-yl)methyl)-6-phenylimidazo[1,2-a]pyrazin-3-yl acetate (P-21): Obtained from N-62 as white solid (0.27 g, 57%) after a recrystallization from n-heptane. $^1$H NMR ($CDCl_3$): 7.93-7.86 (m, 2H), 7.81 (s, 1H), 7.64-7.57 (m, 2H), 7.49-7.41 (m, 2H), 7.41-7.35 (m, 1H), 7.33-7.27 (m, 2H), 7.24-7.18 (m, 1H), 6.01 (d, J=3.0 Hz, 1H), 5.93-5.87 (m, 1H), 4.62 (s, 2H), 4.17 (s, 2H), 2.61 (q, J=7.5 Hz, 2H), 2.33 (s, 3H), 1.22 (t, J=7.5 Hz, 3H). HRMS: calcd for $C_{28}H_{26}N_3O_3$, 452.1974; found, 452.2014.

8-Benzyl-6-phenyl-2-(thiophen-2-ylmethyl)imidazo[1,2-a]pyrazin-3-yl acetate (P-22): Obtained from N-59 as a white solid (0.37 g, 73%) after a recrystallization from n-heptane. $^1$H NMR ($CDCl_3$): 7.92-7.87 (m, 2H), 7.80 (s, 1H), 7.65-7.58 (m, 2H), 7.49-7.42 (m, 2H), 7.42-7.34 (m, 1H), 7.34-7.27 (m, 2H), 7.25-7.20 (m, 1H), 7.19 (dd, J=5.1, 1.3 Hz, 1H), 6.95 (dd, J=5.1, 3.5 Hz, 1H), 6.93-6.88 (m, 1H), 4.62 (s, 2H), 4.38 (d, J=0.8 Hz, 2H), 2.30 (s, 3H). HRMS: calcd for $C_{26}H_{22}N_3O_2S$, 440.1433; found, 440.1486.

8-Benzyl-2-((3-methylthiophen-2-yl)methyl)-6-phenylimidazo[1,2-a]pyrazin-3-yl acetate (P-23): Obtained from N-60 as a solid (0.37 g, 95%). $^1$H NMR ($CDCl_3$): 7.92 (m, 2H), 7.79 (s, 1H), 7.64 (m, 2H), 7.47 (m, 2H), 7.39 (m, 1H), 7.32 (m, 2H), 7.23 (m, 1H), 7.10 (d, 1H, J=5.2), 6.83 (d, 1H, J=5.2), 4.64 (s, 2H), 4.32 (s, 2H), 2.27 (s, 3H), 2.22 (s, 3H). HRMS: calcd for $C_{27}H_{24}N_3O_2S$, 454.1589; found, 454.1591.

8-Benzyl-2-((5-ethylthiophen-2-yl)methyl)-6-phenylimidazo[1,2-a]pyrazin-3-yl acetate (P-24): Obtained from N-61 as a white solid (0.25 g, 56%) after a recrystallization from n-heptane. $^1$H NMR ($CDCl_3$): 7.93 (m, 2H), 7.83 (s, 1H), 7.65 (m, 2H), 7.47 (m, 2H), 7.40 (m, 1H), 7.32 (m, 2H), 7.24 (m, 1H), 6.72 (m, 1H), 6.63 (m, 1H), 4.64 (s, 2H), 4.32 (s, 2H), 2.82 (q, 2H, J=7.6), 2.33 (s, 3H), 1.31 (t, 3H, J=7.6). HRMS: calcd for $C_{28}H_{26}N_3O_2S$, 468.1746; found, 468.1757.

8-Benzyl-6-phenyl-2-((5-(trifluoromethyl)furan-2-yl)methyl)imidazo[1,2-a]pyrazin-3-yl acetate (P-25): Obtained from N-64 as a white solid (0.07 g, 43%) after a recrystallization from n-heptane. $^1$H NMR ($CDCl_3$): 7.94-7.87 (m, 2H), 7.83 (s, 1H), 7.63-7.57 (m, 2H), 7.49-7.42 (m, 2H), 7.42-7.35 (m, 1H), 7.33-7.27 (m, 2H), 7.24-7.17 (m, 1H), 6.73 (dd, 1H, J=3.3, 1.2), 6.21 (dd, 1H, J=3.4, 0.7), 4.61 (s, 2H), 4.23 (s, 2H), 2.40 (s, 3H). HRMS: calcd for $C_{27}H_{21}F_3N_3O_3$, 492.1535; found, 492.1566.

8-benzyl-2-(2-methylbenzyl)-6-phenylimidazo[1,2-a]pyrazin-3-yl acetate (P-26): Obtained from N-51 as a white solid (0.44 g, 96%): $^1$H NMR ($CDCl_3$): 7.91 (m, 2H), 7.76 (s, 1H), 7.64 (m, 2H), 7.48-7.18 (m, 10H), 4.64 (s, 2H), 4.24 (s, 2H), 2.32 (s, 3H), 2.06 (s, 3H). HRMS: calcd for $C_{29}H_{26}N_3O_2$, 448.2025, found, 448.2032.

8-Benzyl-2-(3-methylbenzyl)-6-phenylimidazo[1,2-a]pyrazin-3-yl acetate (P-27): Obtained from N-52 as a beige solid (0.17 g, 61%) after a recrystallization from n-heptane. $^1$H NMR ($CDCl_3$): 7.92-7.85 (m, 2H), 7.77 (s, 1H), 7.66-7.58 (m, 2H), 7.49-7.35 (m, 3H), 7.35-7.27 (m, 2H), 7.24-7.16 (m, 2H), 7.15-7.01 (m, 3H), 4.62 (s, 2H), 4.16 (s, 2H), 2.33 (s, 3H), 2.17 (s, 3H) HRMS: calcd for $C_{31}H_{30}N_3O_2$, 448.2025; found, 448.2053.

8-Benzyl-2-(4-methylbenzyl)-6-phenylimidazo[1,2-a]pyrazin-3-yl acetate (P-28): Obtained from N-53 as a white solid (0.21 g, 60%) after a recrystallization from n-heptane. $^1$H NMR ($CDCl_3$): 7.91 (m, 2H), 7.80 (s, 1H), 7.64 (m, 2H), 7.49-7.13 (m, 10H), 4.65 (s, 2H), 4.18 (s, 2H), 2.36 (s, 3H), 2.20 (s, 3H). HRMS: calcd for $C_{31}H_{28}N_3O_2$, 448.2025; found, 448.2034.

8-Benzyl-6-phenyl-2-(3-propylbenzyl)imidazo[1,2-a]pyrazin-3-yl acetate (P-29): Obtained from N-54 as a white solid (0.14 g, 54%) after a recrystallization from n-heptane. $^1$H NMR ($CDCl_3$): 7.91 (m, 2H), 7.80 (s, 1H), 7.64 (m, 2H), 7.47 (m, 2H), 7.40 (m, 1H), 7.33 (m, 2H), 7.24 (m, 2H), 7.10 (m, 3H), 4.65 (s, 2H), 4.20 (s, 2H), 2.59 (m, 2H), 2.17 (s, 3H), 1.66 (m, 2H), 0.97 (t, 3H, J=7.3). HRMS: calcd for $C_{31}H_{30}N_3O_2$, 476.2338, found, 476.2346.

8-Benzyl-2-(3-cyclopropylbenzyl)-6-phenylimidazo[1,2-a]pyrazin-3-yl acetate (P-30): Obtained from N-58 as a white solid (0.29 g, 65%) after a recrystallization from n-heptane. $^1$H NMR ($CDCl_3$): 7.91 (m, 2H), 7.79 (s, 1H), 7.64 (m, 2H), 7.46 (m, 2H), 7.39 (m, 1H), 7.33 (m, 2H), 7.23 (m, 2H), 7.06 (m, 2H), 6.96 (m, 1H), 4.64 (s, 2H), 4.18 (s, 2H), 2.18 (s, 3H), 1.89 (m, 1H), 0.95 (m, 2H), 0.70 (m, 2H). HRMS: calcd for $C_{31}H_{28}N_3O_2$, 474.2181; found, 474.2189.

8-Benzyl-6-phenyl-2-(4-propylbenzyl)imidazo[1,2-a]pyrazin-3-yl acetate (P-31): Obtained from N-55 as a white solid (0.25 g, 73%) after a recrystallization from n-heptane. $^1$H NMR ($CDCl_3$): 7.91 (m, 2H), 7.80 (s, 1H), 7.64 (m, 2H), 7.47 (m, 2H), 7.40 (m, 1H), 7.33 (m, 2H), 7.24 (m, 3H), 7.15 (m, 2H), 4.65 (s, 2H), 4.20 (s, 2H), 2.60 (m, 2H), 2.18 (s, 3H), 1.66 (m, 2H), 0.98 (t, J=7.3 Hz, 3H). HRMS: calcd for $C_{31}H_{30}N_3O_2$, 476.2338; found, 476.2332.

8-Benzyl-2-(4-cyclopropylbenzyl)-6-phenylimidazo[1,2-a]pyrazin-3-yl acetate (P-32): Obtained from N-57 as a white solid (0.29 g, 68%) after a recrystallization from it-heptane. $^1$H NMR ($CDCl_3$): 7.91 (m, 2H), 7.80 (s, 1H), 7.64 (m, 2H), 7.46 (m, 2H), 7.40 (m, 1H), 7.33 (m, 2H), 7.22 (m, 3H), 7.04 (m, 2H), 4.64 (s, 2H), 4.17 (s, 2H), 2.18 (s, 3H), 1.92 (m, 1H), 0.94 (m, 2H), 0.68 (m, 2H). HRMS: calcd for $C_{31}H_{28}N_3O_2$, 474.2181; found, 474.2183.

8-Benzyl-2-(4-isopropylbenzyl)-6-phenylimidazo[1,2-a]pyrazin-3-yl acetate (P-33): Obtained from N-56 as a white solid (0.16 g, 70%) after a recrystallization from n-heptane. $^1$H NMR ($CDCl_3$): 7.93-7.84 (m, 2H), 7.77 (s, 1H), 7.65-7.59 (m, 2H), 7.49-7.41 (m, 2H), 7.41-7.33 (m, 1H), 7.33-7.28 (m, 2H), 7.24-7.14 (m, 5H), 4.62 (s, 2H), 4.17 (s, 2H), 2.90 (hept, 1H, J=6.9), 2.13 (s, 3H), 1.25 (d, 6H, J=6.9). HRMS: calcd for $C_{31}H_{30}N_3O_2$: 476.2338; found, 476.2337.

8-Benzyl-2-(4-fluorobenzyl)-6-phenylimidazo[1,2-a]pyrazin-3-yl acetate (P-34): Obtained from N-46 as a beige solid (0.31 g, 70%) after a recrystallization from n-heptane. $^1$H NMR ($CDCl_3$): 7.94-7.86 (m, 2H), 7.79 (s, 1H), 7.65-7.58 (m, 2H), 7.50-7.36 (m, 3H), 7.35-7.17 (m, 5H) 7.00 (dd, J=9.8, 7.7 Hz, 2H), 4.62 (s, 2H), 4.15 (s, 2H), 2.25 (s, 3H). HRMS: calcd for $C_{28}H_{23}FN_3O_2$, 452.1774; found, 452.1776.

8-Benzyl-2-(3-fluorobenzyl)-6-phenylimidazo[1,2-a]pyrazin-3-yl acetate (P-35): Obtained from N-46' as a white solid (0.13 g, 57%) after a recrystallization from n-heptane. $^1$H NMR ($CDCl_3$): 7.92 (m, 2H), 7.81 (s, 1H), 7.63 (m, 2H), 7.47 (m, 2H), 7.40 (m, 1H), 7.33-7.22 (m, 4H), 7.06 (m, 2H), 6.95 (m, 1H), 4.64 (s, 2H), 4.19 (s, 2H), 2.29 (s, 3H). HRMS: calcd for $C_{28}H_{23}FN_3O_2$, 452.1774; found, 452.1778.

8-Benzyl-2-(2-fluorobenzyl)-6-phenylimidazo[1,2-a]pyrazin-3-yl acetate (P-36): Obtained from N-47 as a white solid (0.22 g, 71%) after a recrystallization from n-heptane. $^1$H NMR ($CDCl_3$): 7.90 (m, 2H), 7.81 (s, 1H), 7.63 (m, 2H), 7.48-7.21 (m, 8H), 7.10 (m, 2H), 4.63 (s, 2H), 4.23 (s, 2H), 2.29 (s, 3H). HRMS: calcd for $C_{28}H_{23}FN_3O_2$, 452.1774; found, 452.1769.

8-Benzyl-2-(2,4-difluorobenzyl)-6-phenylimidazo[1,2-a]pyrazin-3-yl acetate (P-37): Obtained from N-48 as a white solid (0.13 g, 52%) after a recrystallization from n-heptane. $^1H$ NMR ($CDCl_3$): 7.90 (m, 2H), 7.81 (s, 1H), 7.63 (m, 2H), 7.47 (m, 2H), 7.40 (m, 1H), 7.32 (m, 2H), 7.23 (m, 1H), 6.84 (m, 2H), 4.62 (s, 2H), 4.16 (s, 2H), 2.36 (s, 3H). HRMS: calcd for $C_{28}H_{22}F_2N_3O_2$, 470.1680; found, 470.1686.

8-benzyl-2-(4-chlorobenzyl)-6-phenylimidazo[1,2-a] pyrazin-3-yl acetate (P-38): Obtained from N-49 as a white solid (0.23 g, 62%) after a recrystallization from n-heptane. $^1H$ NMR ($CDCl_3$): 7.92 (m, 2H), 7.81 (s, 1H), 7.62 (m, 2H), 7.48 (m, 2H), 7.40 (m, 1H), 7.28 (m, 7H), 4.63 (s, 2H), 4.14 (s, 2H), 2.27 (s, 3H). HRMS: calcd for $C_{28}H_{23}ClN_3O_2$, 468.1479; found, 468.1485.

8-benzyl-2-(4-bromobenzyl)-6-phenylimidazo[1,2-a] pyrazin-3-yl acetate (P-39): Obtained from 50 as a white solid (0.18 g, 49%) after a recrystallization from n-heptane. $^1H$ NMR ($CDCl_3$): 7.92 (m, 2H), 7.80 (s, 1H), 7.62 (m, 2H), 7.44 (m, 5H), 7.32 (m, 2H), 7.24 (m, 1H), 7.18 (m, 1H), 4.63 (s, 2H), 4.14 (s, 2H), 2.27 (s, 3H). HRMS: calcd for $C_{28}H_{26}BrN_3O_2$, 512.0974; found, 512.0950.

8-Benzyl-2-((4,5-dimethylfuran-2-yl)methyl)-6-phenylimidazo[1,2-a]pyrazin-3-yl acetate (P-40): Obtained from N-43 as a beige solid (0.09 g, 45%) after a recrystallization from n-heptane $^1H$ NMR ($CDCl_3$): 7.94-7.86 (m, 2H), 7.82 (s, 1H), 7.65-7.58 (m, 2H), 7.50-7.41 (m, 2H), 7.41-7.35 (m, 1H), 7.34-7.27 (m, 2H), 7.25-7.16 (m, 1H), 5.90 (s, 1H), 4.62 (s, 2H), 4.13 (s, 2H), 2.34 (s, 3H), 2.17 (s, 3H), 1.91 (s, 3H). HRMS: calcd for $C_{28}H_{26}N_3O_3$, 452.1974; found, 452.1990.

8-Benzyl-2-(4,5-dimethylthiophen-2-yl)methyl)-6-phenylimidazo[1,2-a]pyrazin-3-yl acetate (P-41): Obtained from N-44 as a white solid (0.14 g, 59%) after a recrystallization from n-heptane. $^1H$ NMR ($CDCl_3$): 7.91 (m, 2H), 7.82 (s, 1H), 7.64 (m, 2H), 7.47 (m, 2H), 7.40 (m, 1H), 7.33 (m, 2H), 7.24 (m, 1H), 6.59 (s, 1H), 4.64 (s, 2H), 4.26 (s, 2H), 2.35 (s, 3H), 2.31 (s, 3H), 2.09 (s, 3H). HRMS: calcd for $C_{28}H_{26}N_3O_2S$, 468.1746; found, 468.1758.

8-Benzyl-2-((4,5-dimethyloxazol-2-yl)methyl)-6-phenylimidazo[1,2-a]pyrazin-3-yl acetate (P-42): Obtained from N-45 as a white crystals (0.1 g, 34%) after a recrystallization from n-heptane. $^1H$ NMR ($CDCl_3$): 7.91 (m, 2H), 7.85 (s, 1H), 7.47 (m, 2H), 7.39 (m, 1H), 7.31 (m, 2H), 7.24 (m, 1H), 4.62 (s, 2H), 4.28 (s, 2H), 2.41 (s, 3H), 2.21 (s, 3H), 2.08 (s, 3H). HRMS: calcd for $C_{27}H_{25}N_4O_3$, 453.1927, found, 453.1915.

8-benzyl-2-((4,5-dimethylfuran-2-yl)methyl)-6-(2-fluorophenyl)imidazo[1,2-a]pyrazin-3-yl acetate (P-43): Obtained from N-24 as a wax (0.44 g, 95%). $^1H$ NMR ($CDCl_3$): 8.20 (dt, 1H, J=1.8, 8.0), 8.09 (s, 1H), 7.61 (m, 2H), 7.37-7.24 (m, 5H), 7.15 (ddd, 1H, J=1.8, 8.1, 9.4), 5.91 (s, 1H), 4.63 (s, 2H), 4.41 (s, 2H), 2.35 (s, 3H), 2.19 (s, 3H), 1.92 (s, 3H). HRMS: calcd for $C_{28}H_{25}FN_3O_3$, 470.1880; found, 470.1890.

8-Benzyl-6-phenyl-2-(pyridin-2-ylmethyl)imidazo[1,2-a] pyrazin-3-yl acetate (P-44): Obtained from N-42 as an oil (0.41 g, 91%). $^1H$ NMR ($CDCl_3$): 8.56 (m, 1H), 7.92 (m, 1H), 7.90 (m, 1H), 7.83 (s, 1H), 7.62 (m, 2H), 7.46 (m, 2H), 7.40 (m, 1H), 7.32 (m, 3H), 7.17 (m, 3H), 4.63 (s, 2H), 4.38 (s, 2H), 2.35 (s, 3H). HRMS: calcd for $C_{27}H_{23}N_4O_2$, 435.1821; found, 435.1823.

8-Benzyl-2-(2-methoxybenzyl)-6-phenylimidazo[1,2-a] pyrazin-3-yl acetate (P-45): Obtained from N-13 as a white solid (0.23 g, 72%) after a recrystallization from n-heptane. $^1H$ NMR ($CDCl_3$): 7.90 (m, 2H), 7.78 (s, 1H), 7.64 (m, 2H), 7.46 (m, 2H), 7.39 (m, 1H), 7.32 (m, 2H), 7.24 (m, 3H), 6.92 (m, 2H), 4.63 (s, 2H), 4.22 (s, 2H), 3.82 (s, 3H), 2.16 (s, 3H). HRMS: calcd for $C_{29}H_{26}N_3O_3$, 464.1974; found, 464.1978.

8-Benzyl-2-(3-methoxybenzyl)-6-phenylimidazo[1,2-a] pyrazin-3-yl acetate (P-46): Obtained from N-14 as a white solid (0.20 g, 56%) after a recrystallization from n-heptane. $^1H$ NMR ($CDCl_3$): 7.92-7.86 (m, 2H), 7.78 (s, 1H), 7.65-7.58 (m, 2H), 7.49-7.41 (m, 2H), 7.41-7.34 (m, 1H), 7.33-7.27 (m, 2H), 7.25-7.18 (m, 2H), 6.91-6.86 (m, 1H), 6.86-6.83 (m, 1H), 6.81-6.75 (m, 1H), 4.63 (s, 2H), 4.17 (s, 2H), 3.77 (s, 3H), 2.21 (s, 3H). HRMS: calcd for $C_{29}H_{26}N_3O_3$: 464.1974; found, 464.1982.

8-Benzyl-2-(4-methoxybenzyl)-6-phenylimidazo[1,2-a] pyrazin-3-yl acetate (P-47): Obtained from N-15 as a white solid (0.04 g, 28%) after a recrystallization from n-heptane. $^1H$ NMR ($CDCl_3$): 7.91 (m, 2H), 7.80 (s, 1H), 7.63 (m, 2H), 7.45 (m, 2H), 7.40 (m, 1H), 7.33 (m, 3H), 7.23 (m, 2H), 6.87 (m, 2H), 4.63 (s, 2H), 4.17 (s, 2H), 3.77 (s, 3H), 2.21 (s, 3H). HRMS: calcd for $C_{29}H_{26}N_3O_3$, 464.1974; found, 464.1990.

8-Benzyl-6-phenyl-2-((tetrahydrofuran-2-yl)methyl)imidazo[1,2-a]pyrazin-3-yl acetate (P-48): Obtained from N-11 as an oil (0.36 g, 81%). $^1H$ NMR ($CDCl_3$): 7.93-7.87 (m, 2H), 7.82 (s, 1H), 7.62-7.57 (m, 2H), 7.48-7.41 (m, 2H), 7.40-7.34 (m, 1H), 7.32-7.27 (m, 2H), 7.23-7.17 (m, 1H), 4.66-4.55 (m, 2H), 4.32-4.23 (m, 1H), 3.89-3.69 (m, 2H), 3.10-2.95 (m, 2H), 2.46 (s, 3H), 2.09-1.98 (m, 1H), 1.92-1.82 (m, 2H), 1.77-1.66 (m, 1H). HRMS: calcd for $C_{26}H_{26}N_3O_3$, 428.1974; found, 428.1956.

2,8-Dibenzyl-6-(2-fluorophenyl)imidazo[1,2-a]pyrazin-3-yl acetate (P-49): Obtained from N-19 as a solid (0.21 g, 45%) after a recrystallization from n-heptane. $^1H$ NMR ($CDCl_3$): 8.20 (m, 1H), 8.05 (s, 1H), 7.62 (m, 2H), 7.32 (m, 10H), 7.15 (m, 1H), 4.63 (s, 2H), 4.22 (s, 2H), 2.18 (s, 3H). HRMS: calcd for $C_{28}H_{23}FN_3O_2$, 452.1774; found, 452.1838.

8-Benzyl-2-(4-fluorobenzyl)-6-(2-fluorophenyl)imidazo [1,2-a]pyrazin-3-yl acetate (P-50): Obtained from N-20 as a solid (0.1 g, 63%) after a recrystallization from n-heptane. $^1H$ NMR ($CDCl_3$): 8.20 (dt, 1H, J=2.0, 7.9), 8.06 (s, 1H), 7.60 (m, 2H), 7.38-7.21 (m, 7H), 7.15 (m, 1H), 7.01 (m, 2H), 4.62 (s, 2H), 4.16 (s, 2H), 2.26 (s, 3H). HRMS: calcd for $C_{28}H_{22}F_2N_3O_2$, 470.1680; found, 470.1670.

8-Benzyl-6-(2-fluorophenyl)-2-(furan-2-ylmethyl)imidazo[1,2-a]pyrazin-3-yl acetate (P-51): Obtained from N-21 as a solid (0.15 g, 36%) after a recrystallization from n-heptane. $^1H$ NMR ($CDCl_3$): 8.20 (m, 1H), 8.10 (s, 1H), 7.61 (m, 2H), 7.31 (m, 6H), 7.14 (m, 1H), 6.35 (m, 1H), 6.16 (m, 1H), 4.63 (s, 2H), 4.24 (s, 2H), 2.35 (s, 3H). HRMS: calcd for $C_{26}H_{21}FN_3O_3$, 442.1567; found, 442.1631.

8-Benzyl-6-(2-fluorophenyl)-2-((5-methylfuran-2-yl) methyl)imidazo[1,2-a]pyrazin-3-yl acetate (P-52): Obtained from N-22 as a glass (0.08 g, 72%). $^1H$ NMR ($CDCl_3$): 8.19 (dt, 1H, J=1.8, 7.8), 8.09 (s, 1H), 7.61 (m, 2H), 7.37-7.21 (m, 5H), 7.15 (add, 1H, J=1.2, 8.1, 12.0), 6.02 (d, 1H, J=3.0), 5.90 (m, 1H), 4.63 (s, 2H), 4.18 (s, 2H), 2.35 (s, 3H), 2.27 (s, 3H). HRMS: calcd for $C_{27}H_{23}FN_3O_3$, 456.1723; found, 456.1734.

8-Benzyl-2-((5-ethylfuran-2-yl)methyl)-6-(2-fluorophenyl)imidazo[1,2-a]pyrazin-3-yl acetate (P-53): Obtained from N-23 as a wax (0.18 g, 95%). $^1H$ NMR ($CDCl_3$): 8.19 (di, 1H, J=1.8, 7.8), 8.10 (6, 1H), 7.62 (m, 2H), 7.39-7.22 (m, 5H), 7.15 (ddd, 1H, J=1.2, 8.1, 12.0), 6.04 (d, 1H, J=3.0), 5.93 (m, 1H), 4.64 (s, 2H), 4.21 (s, 2H), 2.65 (q, 2H, J=7.6), 2.34 (s, 3H), 1.24 (t, 3H, J=7.6). HRMS: calcd for $C_{28}H_{25}FN_3O_3$, 470.1880; found, 470.1884.

8-Benzyl-6-(3-fluorophenyl)-2-((5-methylfuran-2-yl) methyl)imidazo[1,2-a]pyrazin-3-yl acetate (P-34): Obtained from N-25 as white powder after a recrystallization in n-heptane (0.018 g, 14%). $^1H$ NMR ($CDCl_3$): 7.85 (s, 1H), 7.68 (m, 2H), 7.60 (m, 2H), 7.46-7.37 (m, 2H), 7.34-7.21

(m, 3H), 6.02 (d, 1H, J=3.1), 5.90 (m, 1H), 4.62 (s, 2H), 4.18 (s, 2H), 2.37 (s, 3H), 2.26 (s, 3H). HRMS: calcd for $C_{27}H_{23}FN_3O_3$, 456.1723; found, 456.1732.

8-Benzyl-6-(4-fluorophenyl)-2-((5-methylfuran-2-yl)methyl)imidazo[1,2-a]pyrazin-3-yl acetate (P-55): Obtained from N-26 as a glass (0.1 g, 83%). $^1$H NMR ($CDCl_3$): 7.88 (m, 2H), 7.78 (s, 1H), 7.59 (m, 2H), 7.34-7.12 (m, 6H), 6.02 (d, 1H, J=3.0), 5.90 (m, 1H), 4.61 (%, 2H), 4.18 (s, 2H), 2.36 (s, 3H), 2.27 (s, 3H). HRMS: calcd for $C_{27}H_{23}FN_3O_3$, 456.1723; found, 456.1721.

2,8-dibenzyl-6-(2,6-difluorophenyl)imidazo[1,2-a]pyrazin-3-yl acetate (P-56): Obtained from N-30 as a solid (0.16 g, 61%) after a recrystallization from n-heptane. $^1$H NMR ($CDCl_3$): 7.66 (s, 1H), 7.63 (m, 2H), 7.31 (m, 9H), 7.02 (m, 2H), 4.62 (s, 2H), 4.21 (s, 2H), 2.13 (s, 3H). HRMS: calcd for $C_{28}H_{21}F_2N_3O_2$, 470.1680; found, 470.1630.

8-benzyl-6-(2,6-difluorophenyl)-2-(furan-2-ylmethyl)imidazo[1,2-a]pyrazin-3-yl acetate (P-57): Obtained from N-31 as wax (0.19 g, 95%). $^1$H NMR ($CDCl_3$): 7.70 (s, 1H), 7.60 (m, 2H), 7.37-7.19 (m, 6H), 7.02 (m, 2H), 6.35 (m, 1H), 6.15 (m, 1H), 4.62 (s, 2H), 4.24 (s, 2H), 2.31 (s, 3H). HRMS: calcd for $C_{26}H_{19}F_2NO_3$, 460.1473; found, 460.1430.

8-Benzyl-6-phenyl-2-(2-(trifluoromethyl)benzyl)imidazo[1,2-a]pyrazin-3-yl acetate (P-58): Obtained from N-16 as wax (0.07 g, 95%) $^1$H NMR ($CDCl_3$): 7.93 (m, 2H), 7.80 (s, 1H), 7.65 (m, 3H), 7.45 (m, 2H), 7.53-7.21 (m, 9H), 4.65 (s, 2H), 4.38 (s, 2H), 2.28 (s, 3H). HRMS: calcd for $C_{29}H_{23}F_3N_3O_2$, 502.1742; found, 502.1722.

8-Benzyl-6-phenyl-2-(3-(trifluoromethyl)benzyl)imidazo[1,2-a]pyrazin-3-yl acetate (P-59): Obtained from N-17 as white solid after a recrystallization in n-heptane (0.08 g, 57%) $^1$H NMR ($CDCl_3$): 7.91 (m, 2H), 7.81 (s, 1H), 7.63 (m, 3H), 7.54-7.38 (m, 6H), 7.34-7.21 (m, 3H), 4.63 (s, 2H), 4.25 (s, 2H), 2.27 (s, 3H). HRMS: calcd for $C_{29}H_{23}F_3N_3O_2$, 502.1742; found, 502.1795.

8-Benzyl-6-phenyl-2-(4-(trifluoromethyl)benzyl)imidazo[1,2-a]pyrazin-3-yl acetate (P-60): Obtained from N-18 as white solid after a recrystallization in n-heptane (0.08 g, 66%). $^1$H NMR ($CDCl_3$): 7.92 (m, 2H), 7.81 (s, 1H), 7.60 (m, 4H), 7.49-7.38 (m, 5H), 7.33-7.22 (m, 3H), 4.63 (s, 2H), 4.24 (s, 2H), 2.27 (s, 3H). HRMS: calcd for $C_{29}H_{23}F_3N_3O_2$, 502.1742; found, 502.1730.

2,12-dibenzyl-5H-chromeno[4,3-e]imidazo[1,2-a]pyrazin-3-yl acetate (P-61). Obtained from N-72 as a wax (0.06 g, 95%). $^1$H NMR ($CDCl_3$): 8.14 (dd, 1H, J=1.6, 7.8), 7.61 (s, 1H), 7.60 (s, 1H), 7.38-7.20 (m, 9H), 7.10 (dt, 1H, J=1.0, 8.4), 6.90 (d, 1H, J=8.0), 5.58 (s, 2H), 4.61 (s, 2H), 4.15 (s, 2H), 2.14 (s, 3H). HRMS: calcd for $C_{29}H_{24}N_3O_5$, 462.1818; found, 462.1812.

8-benzyl-6-(4-methoxyphenyl)-2-((5-methylfuran-2-yl)methyl)imidazo[1,2-a]pyrazin-3-yl acetate (P-62): Obtained from N-27 as white solid after a recrystallization in n-heptane (0.11 g, 69%). $^1$H NMR ($CDCl_3$): 7.84 (m, 2H), 7.75 (s, 1H), 7.61 (m, 2H), 7.32 (m, 2H), 7.24 (m, 1H), 7.0 (m, 2H), 6.02 (m, 1H), 591 (m, 1H), 4.62 (s, 2H), 4.17 (s, 2H), 3.87 (s, 3H), 2.35 (s, 3H), 2.28 (s, 3H). HRMS: calcd for $C_{29}H_{26}N_3O_4$, 468.1923; found, 468.1919.

8-benzyl-6-(3-methoxyphenyl)-2-((5-methylfuran-2-yl)methyl)imidazo[1,2-a]pyrazin-3-yl acetate (P-63): Obtained from N-28 as a wax (0.08 g, 95%). $^1$H NMR ($CDCl_3$): 7.84 (s, 1H), 7.61 (m, 2H), 7.52 (m, 1H), 7.45 (m, 1H), 7.38-7.29 (m, 3H), 7.23 (m, 1H), 6.93 (m, 1H), 6.02 (d, 1H, J=3), 5.91 (m, 1H), 4.63 (s, 2H), 4.18 (s, 2H), 3.88 (s, 3H), 2.35 (s, 3H), 2.28 (s, 3H). HRMS: calcd for $C_{29}H_{26}N_3O_4$, 468.1923; found, 468.1928.

8-benzyl-2-((5-cyclopropylfuran-2-yl)methyl)-6-phenylimidazo[1,2-a]pyrazin-3-yl acetate (P-64): Obtained from N-63 as a white solid after a recrystallization in n-heptane (0.13 g, 42%). $^1$H NMR ($CDCl_3$): 7.93-7.86 (m, 2H), 7.81 (s, 1H), 7.64-7.57 (m, 2H), 7.48-7.41 (m, 2H), 7.41-7.35 (m, 1H), 7.34-7.27 (m, 2H), 7.24-7.17 (m, 1H), 5.98 (d, 1H, J=3.1), 5.86 (d, 1H, J=3.1), 4.61 (s, 2H), 4.15 (s, 2H), 2.34 (s, 3H), 1.84 (tt, 1H, J=8.4, 5.1), 0.89-0.80 (m, 2H), 0.76-0.69 (m, 2H). HRMS: calcd for $C_{29}H_{26}N_3O_3$, 464.1974; found, 464.1990.

2-Benzyl-6-phenyl-8-(pyridin-3-ylmethyl)imidazo[1,2-a]pyrazin-3-yl (P-65); Obtained from N-73 as white solid after a recrystallization in n-heptane (0.1 g, 37%). $^1$H NMR ($CDCl_3$): 8.87 (d, 1H, J=2.0), 8.50 (dd, 1H, J=1.7, 5.0), 7.92 (m, 1H), 7.87 (m, 2H), 7.82 (s, 1H), 7.48-7.22 (m, 9H), 4.63 (s, 2H), 4.21 (s, 2H), 2.19 (s, 3H). HRMS: calcd for $C_{27}H_{22}N_4O_2$, 435.1821; found, 435.1805.

2-Benzyl-8-(2-methylbenzyl)-6-phenylimidazo[1,2-a]pyrazin-3-yl acetate (P-66): Obtained from N-74 as a white solid (0.29 g, 77%) after a recrystallization from n-heptane. $^1$H NMR ($CDCl_3$): 7.87 (m, 2H), 7.82 (s, 1H), 7.57 (m, 1H), 7.44 (m, 2H), 7.37 (m, 1H), 7.33 (m, 4H), 7.27 (m, 1H), 7.22 (m, 1H), 7.17 (m, 2H), 4.67 (s, 2H), 4.22 (s, 2H), 2.61 (s, 3H), 2.20 (s, 3H). HRMS: calcd for $C_{29}H_{26}N_3O_2$: 448.2025; found, 448.2031.

2-(Furan-2-ylmethyl)-8-(2-methylbenzyl)-6-phenylimidazo[1,2-a]pyrazin-3-yl acetate (P-67): Obtained from N-75 as a white solid (0.18 g, 64%) after a recrystallization in n-heptane. $^1$H NMR ($CDCl_3$): 7.88 (m, 2H), 7.85 (s, 1H), 7.54 (m, 2H), 7.45 (m, 2H), 7.38 (m, 2H), 7.23 (m, 1H), 7.16 (m, 2H), 6.36 (dd, 1H, J=1.9, 3.4), 6.17 (m, 1H), 4.66 (s, 2H), 4.24 (s, 2H), 2.60 (s, 3H), 2.36 (s, 3H). HRMS: calcd for $C_{27}H_{24}N_3O_3$, 438.1818; found, 438.1823.

2-Benzyl-8-(3-methylbenzyl)-6-phenylimidazo[1,2-a]pyrazin-3-yl acetate (P-68): Obtained from N-76 as a white solid (0.27 g, 70%) after a recrystallization from n-heptane. $^1$H NMR ($CDCl_3$): 7.92 (m, 2H), 7.80 (s, 1H), 7.57 (m, 1H), 7.50-7.37 (m, 5H), 7.32 (m, 4H), 7.28-7.20 (m, 2H), 7.05 (m, 1H), 4.61 (s, 2H), 4.22 (s, 2H), 2.35 (s, 3H), 2.19 (s, 3H). HRMS: calcd for $C_{29}H_{26}N_3O_2$: 448.2025; found, 448.2026.

2-(Furan-2-ylmethyl)-8-(3-methylbenzyl)-6-phenylimidazo[1,2-a]pyrazin-3-yl acetate (P-69): Obtained from N-77 as a white solid (0.23 g, 70%) after a recrystallization in n-heptane. $^1$H NMR ($CDCl_3$): 7.93 (m, 2H), 7.84 (s, 1H), 7.49-7.37 (m, 6H), 7.22 (m, 1H), 7.05 (m, 1H), 6.35 (dd, 1H, J=1.7, 3.1), 6.16 (m, 1H), 4.60 (s, 2H), 4.24 (s, 2H), 2.36 (s, 3H), 2.35 (s, 3H). HRMS: calcd for $C_{27}H_{24}N_3O_3$, 438.1818; found, 438.1820.

2-Benzyl-8-(2-fluorobenzyl)-6-phenylimidazo[1,2-a]pyrazin-3-yl acetate (P-70): Obtained from N-78 as white solid after a recrystallization in n-heptane (0.12 g, 61%). $^1$H NMR ($CDCl_3$): 7.86-7.83 (m, 3H), 7.52-7.48 (dt, 1H, J=7.4, 1.9), 7.47-7.23 (m, 8H), 7.14-7.08 (m, 2H), 4.72 (s, 2H), 4.23 (s, 2H), 2.19 (s, 3H). HRMS; calcd for $C_{28}H_{22}FN_3O_2$, 452.1774, found, 452.1774.

8-(2-Fluorobenzyl)-2-(3-methylbenzyl)-6-phenylimidazo[1,2-a]pyrazin-3-yl acetate (P-71): Obtained from N-79 as white solid after a recrystallization in n-heptane (0.18 g, 58%). $^1$H NMR ($CDCl_3$): 7.84 (m, 2H), 7.83 (s, 1H), 7.50 (m, 1H), 7.42 (m, 2H), 7.36 (m, 1H), 7.23 (m, 2H), 7.13-7.06 (m, 5H), 4.72 (s, 2H), 4.19 (s, 2H), 2.35 (s, 3H), 2.19 (s, 3H). HRMS: calcd for $C_{29}H_{25}FN_3O_2$, 466.1931, found, 466.1938.

8-(2-Fluorobenzyl)-2-(3-methoxybenzyl)-6-phenylimidazo[1,2-a]pyrazin-3-yl acetate (P-72): Obtained from N-80 as white solid after a recrystallization in n-heptane (0.26 g, 87%). $^1$H NMR ($CDCl_3$): 7.85 (m, 2H), 7.83 (s, 1H), 7.48 (m, 1H), 7.42 (m, 2H), 7.36 (m, 1H), 7.25 (m, 2H), 7.10 (m, 2H), 6.90 (m, 2H), 6.81 (m, 1H), 4.71 (s, 2H), 4.19 (s, 2H), 3.80 (s, 3H), 2.23 (s, 3H). HRMS: calcd for $C_{29}H_{25}FN_3O_3$, 482.1880, found, 482.1873.

8-(2-fluorobenzyl)-2-(furan-2-ylmethyl)-6-phenylimidazo[1,2-a]pyrazin-3-yl acetate (P-73): Obtained from N-81 as white solid after a recrystallization in n-heptane (0.19 g, 73%). $^1$H NMR ($CDCl_3$): 7.87 (s, 1H), 7.85 (m, 2H), 7.50-7.34 (m, 5H), 7.24 (m, 1H), 7.10 (m, 2H), 6.35 (dd, 1H, J=1.9, 3.2), 6.17 (dd, 1H, J=0.7, 3.2), 4.70 (s, 2H), 4.24 (s, 2H), 2.37 (s, 3H). HRMS: calcd for $C_{26}H_{21}FN_3O_3$, 442.1567, found, 442.1567.

8-(2-fluorobenzyl)-2-((5-methylfuran-2-yl)methyl)-6-phenylimidazo[1,2-a]pyrazin-3-yl acetate (P-74): Obtained from N-82 as white solid after a recrystallization in n-heptane (0.08 g, 38%). $^1$H NMR ($CDCl_3$): 7.87 (s, 1H), 7.85 (m, 2H), 7.50-7.34 (m, 4H), 7.24 (m, 1H), 7.10 (m, 2H), 6.04 (d, 1H, J=3.0), 5.91 (m, 1H), 4.70 (6, 2H), 4.19 (s, 2H), 2.37 (s, 3H), 2.28 (s, 3H). HRMS: calcd for $C_{27}H_{23}FN_3O_3$, 456.1723, found, 456.1719.

2-((5-Ethylfuran-2-yl)methyl)-8-(2-fluorobenzyl)-6-phenylimidazo[1,2-a]pyrazin-3-yl acetate (P-75): Obtained from N-83 as white solid after a recrystallization in n-heptane (0.05 g, 28%). $^1$H NMR ($CDCl_3$): 7.87 (s, 1H), 7.85 (m, 2H), 7.50-7.34 (m, 4H), 7.24 (m, 1H), 7.10 (m, 2H), 6.04 (d, 1H, J=3.1), 5.92 (m, 1H), 4.70 (s, 2H), 4.20 (s, 2H), 2.64 (q, 2H, J=7.2), 2.36 (s, 3H), 1.24 (t, 3H, J=7.2). HRMS: calcd for $C_{28}H_{25}FN_3O_3$, 470.1880, found, 470.1881.

2-Benzyl-8-(2-chlorobenzyl)-6-phenylimidazo[1,2-a]pyrazin-3-yl acetate (P-76): Obtained from N-84 as a white solid after a recrystallization in n-heptane (0.12 g, 67%). $^1$H NMR ($CDCl_3$): 7.84 (s, 1H), 7.83 (m, 2H), 7.50-7.20 (m, 12H), 4.82 (s, 2H), 4.23 (s, 2H), 2.20 (s, 3H). HRMS: calcd for $C_{28}H_{23}ClN_3O_2$: 468.1479; found, 468.1489.

8-(2-Chlorobenzyl)-2-(furan-2-ylmethyl)-6-phenylimidazo[1,2-a]pyrazin-3-yl acetate (P-77): Obtained from N-85 as a white solid after a recrystallization in n-heptane (0.27 g, 70%), $^1$H NMR ($CDCl_3$): 7.88 (s, 1H), 7.83 (m, 2H), 7.46-7.34 (m, 6H), 7.23 (m, 2H), 6.36 (m, 1H), 6.18 (m, 1H), 4.81 (s, 2H), 4.25 (s, 2H), 2.38 (s, 3H). HRMS: calcd for $C_{26}H_{26}ClN_3O_3$: 458.1271; found, 458.1266.

8-(2-chlorobenzyl)-2-((5-methylfuran-2-yl)methyl)-6-phenylimidazo[1,2-a]pyrazin-3-yl acetate (P-78): Obtained from N-86 as a solid after a recrystallization in n-heptane (0.03 g, 27%) $^1$H NMR ($CDCl_3$): 7.88 (s, 1H), 7.83 (m, 2H), 7.46-7.33 (m, 5H), 7.21 (m, 2H), 6.04 (m, 1H), 5.91 (m, 1H), 4.81 (s, 2H), 4.19 (s, 2H), 2.38 (s, 3H), 2.28 (s, 3H). HRMS: calcd for $C_{27}H_{24}ClN_3O_3$: 472.1428; found, 472.1408.

2-Benzyl-8-(3-fluorobenzyl)-6-phenylimidazo[1,2-a]pyrazin-3-yl acetate (P-79): Obtained from N-87 as a solid (0.19 g, 50%) after a recrystallization from n-heptane. $^1$H NMR ($CDCl_3$): 7.90 (m, 2H), 7.82 (s, 1H), 7.47 (m, 2H), 7.42-7.25 (m, 9H), 6.95 (m, 1H), 4.63 (s, 2H), 4.22 (s, 2H), 2.20 (s, 3H). HRMS: calcd for $C_{28}H_{23}FN_3O_2$, 452.1774; found, 452.1775.

8-(3-Fluorobenzyl)-2-(3-methylbenzyl)-6-phenylimidazo[1,2-a]pyrazin-3-yl acetate (P-80): Obtained from N-91 as a solid (0.16 g, 50%) after a recrystallization from n-heptane. $^1$H NMR ($CDCl_3$): 7.91 (m, 2H), 7.82 (s, 1H), 7.47 (m, 2H), 7.38 (m, 3H), 7.28 (m, 1H), 7.22 (m, 1H), 7.09 (m, 3H), 6.95 (m, 1H), 4.63 (s, 2H), 4.18 (s, 2H), 2.35 (s, 3H), 2.20 (s, 3H). HRMS: calcd for $C_{29}H_{25}FN_3O_2$, 466.1931; found, 466.1926.

8-(3-Fluorobenzyl)-2-(3-methoxybenzyl)-6-phenylimidazo[1,2-a]pyrazin-3-yl acetate (P-81): Obtained from N-92 as a solid (0.12 g, 60%) after a recrystallization from n-heptane. $^1$H NMR ($CDCl_3$): 7.90 (m, 2H), 7.82 (s, 1H), 7.47 (m, 2H), 7.38 (m, 3H), 7.26 (m, 2H), 6.95 (m, 3H), 6.80 (m, 1H), 4.63 (s, 2H), 4.19 (s, 2H), 3.79 (s, 3H), 2.24 (s, 3H). HRMS: calcd for $C_{29}H_{25}FN_3O_3$, 482.1880; found, 482.1879.

8-(3-Fluorobenzyl)-2-(furan-2-ylmethyl)-6-phenylimidazo[1,2-a]pyrazin-3-yl acetate (P-82): Obtained from N-88 as a solid (0.13 g, 59%) after a recrystallization from n-heptane. $^1$H NMR ($CDCl_3$): 7.91 (m, 2H), 7.85 (s, 1H), 7.49 (m, 2H), 7.42-7.33 (m, 4H), 7.26 (m, 1H), 6.93 (m, 1H), 6.36 (dd, 1H, J=2.0, 3.2), 6.17 (dd, 1H, J=0.8, 3.2), 4.62 (s, 2H), 4.24 (s, 2H), 2.36 (s, 3H). HRMS: calcd for $C_{26}H_{21}FN_3O_3$, 442.1567; found, 442.1549.

8-(3-Fluorobenzyl)-2-((5-methylfuran-2-yl)methyl)-6-phenylimidazo[1,2-a]pyrazin-3-yl acetate (P-83): Obtained from N-89 as a solid (0.10 g, 45%) after a recrystallization from n-heptane. $^1$H NMR ($CDCl_3$): 7.91 (m, 2H), 7.85 (s, 1H), 7.47 (m, 2H), 7.42-7.24 (m, 4H), 6.92 (m, 1H), 6.03 (d, 1H, J=3.0), 5.91 (m, 1H), 4.62 (s, 2H), 4.18 (s, 2H), 2.37 (s, 3H), 2.28 (s, 3H). HRMS: calcd for $C_{27}H_{23}FN_3O_3$, 456.1723; found, 456.1732.

2-((5-Ethylfuran-2-yl)methyl)-8-(3-fluorobenzyl)-6-phenylimidazo[1,2-a]pyrazin-3-yl acetate (P-84): Obtained from N-90 as a white solid (0.05 g, 11% from the chloropyrazine) after a chromatography over silica gel (cyclohexane ethyl acetate 6/1) and recrystallization from n-heptane. $^1$H NMR ($CDCl_3$): 7.91 (m, 2H), 7.85 (s, 1H), 7.48 (m, 2H), 7.42-7.24 (m, 4H), 6.92 (m, 1H), 6.03 (d, 1H, J=3.1), 5.92 (m, 1H), 4.62 (s, 2H), 4.19 (s, 2H), 2.63 (q, 2H, J=7.5), 2.36 (s, 3H), 2.63 (t, 3H, J=7.5). HRMS; calcd for $C_{28}H_{25}FN_3O_3$, 470.1880; found, 470.1888.

2-Benzyl-8-(4-fluorobenzyl)-6-phenylimidazo[1,2-a]pyrazin-3-yl acetate (P-85): Obtained from N-93 as a solid (0.04 g, 33%) after a recrystallization in two crops from n-heptane. $^1$H NMR ($CDCl_3$): 7.90 (m, 2H), 7.81 (s, 1H), 7.58 (m, 2H), 7.47 (m, 2H), 7.40 (m, 1H), 7.36-7.24 (m, 5H), 7.00 (m, 2H), 4.60 (s, 2H), 4.21 (s, 2H), 2.19 (s, 3H). HRMS: calcd for $C_{28}H_{23}FN_3O_2$, 452.1774; found, 452.1789.

2-Benzyl-8-(2-methoxybenzyl)-6-phenylimidazo[1,2-a]pyrazin-3-yl acetate (P-86): Obtained from N-94 as a white solid (0.06 g, 70%) after a recrystallization from n-heptane. $^1$H NMR ($CDCl_3$): 7.84 (m, 2H), 7.82 (s, 1H), 7.43-7.23 (m, 10H), 6.93 (m, 2H), 4.69 (s, 2H), 4.22 (s, 2H), 3.83 (s, 3H), 2.18 (s, 3H). HRMS: calcd for $C_{29}H_{26}N_3O_3$: 464.1974; found, 464.1983.

2-benzyl-6-phenyl-8-((tetrahydrofuran-2-yl)methyl)imidazo[1,2-a]pyrazin-3-yl acetate (P-87): Obtained from N-42' as a solid (0.03 g, 30%) after a recrystallization from n-heptane and #small amount of toluene. $^1$H NMR ($CDCl_3$): 7.90 (m, 2H), 7.78 (s, 1H), 7.48-7.41 (m, 2H), 7.40-7.35 (m, 1H), 7.34-7.20 (m, 5H), 4.85-4.75 (m, 1H), 4.18 (s, 2H), 3.98 (id, J=7.7, 6.2 Hz, 1H), 3.78 (td, J=7.8, 6.1 Hz, 1H), 3.64 (dd, J=14.3, 7.4 Hz, 1H), 3.38 (dd, J=14.3, 6.1 Hz, 1H), 2.14 (s, 3H), 2.21-1.74 (m, 5H). HRMS: calcd for $C_{26}H_{26}H_3O_3$, 428.1974; found, 428.1936.

8-Benzyl-2-(4-(benzyloxy)benzyl)-6-(4-(benzyloxy)phenyl)imidazo[1,2-a]pyrazin-3-yl pivalate (P-88): Obtained from N-9 as a solid (1.06 g, 48%) after a recrystallization from cyclohexane. $^1$H NMR ($CDCl_3$): δ 7.86-7.72 (m, 2H), 7.61 (s, 1H), 7.60-7.55 (m, 2H), 7.47-7.36 (m, 8H), 7.36-7.32 (mi, 2H), 7.32-7.29 (m, 1H), 7.29-7.27 (m, 1H), 7.23-7.19 (m, 1H), 7.19-7.14 (m, 2H), 7.08-7.01 (m, 2H), 6.93-6.86 (m, 2H), 5.12 (s, 2H), 5.04 (s, 2H), 4.60 (s, 2H), 4.09 (s, 2H), 1.33 (s, 9H). HRMS: calcd for $C_{45}H_{42}N_3O_4$, 688.3175; found, 688.3148.

2,8-Dibenzyl-6-phenylimidazo[1,2-a]pyrazin-3-yl pivalate (P-89): Obtained from N-5 as a solid (0.12 g, 42%) after two chromatography over silica gel (dichloromethane—ethanol 99:1) and (cyclohexane—ethyl acetate 90:10). $^1$H NMR ($CDCl_3$): 7.93-7.86 (m, 2H), 7.72 (s, 1H), 7.68-7.60 (m, 2H), 7.52-7.44 (m, 2H), 7.44-7.37 (m, 1H), 7.37-7.20 (m, 8H), 4.66 (s, 2H), 4.20 (s, 2H), 1.36 (s, 9H). HRMS: calcd for $C_{31}H_{29}N_3O_2$, 476.2338; found, 476.2362.

Representative synthesis of 2,8-dibenzyl-6-phenylimidazo[1,2-a]pyrazin-3(7H)-one (Q-2) directly from the α-aminoesters N-5. Under an inert atmosphere, N-5 (0.41 g, 0.93 mmol) was dissolved in ethanol (10 ml) and 37% hydrochloric acid (0.4 mL). This was sealed and heated at 90° C. overnight. The solution was then left to crystallize at 0° C., the resulting precipitate was filtered, rinsed with ethanol and dried under vacuum to yield compound Q-2 as an orange powder (0.11 g, 30%). $^1$H NMR (DMSO-$d_6$): 8.68 (s (br), 1H), 8.01 (m, 2H), 7.52-7.17 (m, 14H), 4.58 (s, 2H), 4.31 (s, 2H). HRMS: calcd for $C_{26}H_{22}N_3O$, 392.1763; found, 392.1776.

8-benzyl-2-(furan-2-ylmethyl)-6-phenylimidazo[1,2-a]pyrazin-3(7H)-one (Q-1): By using similar reaction conditions, compound Q-1 (aka furimazine) was obtained as a brown powder (0.03 g, 30%). $^1$H NMR (DMSO-$d_6$): 8.38 (s, 1H), 7.96 (d, 2H, J=7.6), 7.56 (dd, 1H, J=1.8, 0.8), 7.54-7.41 (m, 5H), 7.34-7.19 (m, 3H), 6.39 (dd, 1H, J=3.2, 1.8), 6.17 (dd, 1H, J=3.2, 0.8), 4.46 (s, 2H), 4.21 (s, 2H). HRMS: $C_{24}H_{20}N_3O_2$, 382.1556; found: 382.1531.

Representative synthesis of poly O-acetylated derivatives P from α-aminoesters N via step q. The considered ester (0.3 mmol) and a 1/1 mixture of acetic acid and acetic anhydride (10 mL) were heated in a microwave oven at 140° C. for four and half hours. The resulting solution was concentrated to dryness and further purified as described below.

4-((3-Acetoxy-8-benzyl-6-phenylimidazo[1,2-a]pyrazin-2-yl)methyl)phenyl acetate (P90): Obtained from N-97 as an oil containing traces of acetic acid after co-evaporation with toluene (0.26 g). $^1$H NMR ($CDCl_3$): 7.90 (m, 2H), 7.80 (s, 1H), 7.62 (m, 2H), 7.39 (m, 5H), 7.22 (m, 3H), 7.04 (m, 2H), 4.63 (6, 2H), 4.21 (s, 2H, J=10.6), 2.31 (s, 3H), 2.21 (s, 3H), HRMS: calcd for $C_{30}H_{26}N_3O_4$, 492.1923; found, 492.1927.

4-(3-Acetoxy-2-(4-acetoxybenzyl)-8-benzylimidazo[1,2-a]pyrazin-6-yl)phenyl acetate (P-91): Obtained from N-95 as a white powder (0.018 g, 10%) after a recrystallization in a mixture of toluene and cyclohexane (two crops). $^1$H NMR ($CDCl_3$): 7.92-7.86 (m, 2H), 7.75 (s, 1H), 7.62-7.55 (m, 2H), 7.33-7.26 (m, 4H), 7.25-7.14 (m, 3H), 7.05-6.99 (m, 2H), 4.60 (s, 2H), 4.19 (s, 2H), 2.32 (s, 3H), 2.29 (s, 3H), 2.19 (s, 3H). HRMS: calcd for $C_{32}H_{28}N_3O_6$, 550.1978; found, 550.1995.

4-(3-Acetoxy-8-benzyl-2-((5-methylfuran-2-yl)methyl)imidazo[1,2-a]pyrazin-6-yl)phenyl acetate (P-92): Obtained as a purple powder (0.13 g, 63%) from N-96 after a recrystallization in a mixture of dichloromethane and cyclohexane. $^1$H NMR ($CDCl_3$): 7.92 (m, 2H), 7.80 (s, 1H), 7.62 (m, 2H), 7.33-7.17 (m, 7H), 6.02 (d, 1H, J=2.9), 5.91 (m, 1H), 4.62 (s, 2H), 4.18 (s, 2H), 2.35 (s, 1H), 2.34 (s, 3H), 2.27 (s, 3H). HRMS: calcd for $C_{29}H_{26}N_3O_5$, 496.1873; found, 496.1859.

Preparation of 8-Benzyl-2-(4-hydroxybenzyl)-6-(4-hydroxyphenyl)imidazo[1,2-a]pyrazin-3-yl pivalate (P-93): The bisbenzylated O-pivaloate P-88 (0.18 g, 0.26 mmol) and 10% palladium over charcoal (0.25 mg, 0.026 mmol) were suspended in ethanol (15 ml). This was stirred under one atmosphere of hydrogen for 24 hours, filtered. The filtrate was concentrated to dryness and purified by a chromatography over silica gel (dichloromethane—ethanol 97/3) to give deprotected compound as a red solid (0.06 g, 45%). $^1$H NMR (DMSO-$d_6$): 9.65 (s, 1H), 9.18 (s, 1H), 8.10 (s, 1H), 7.87-7.80 (m, 2H), 7.51-7.43 (m, 2H), 7.34-7.24 (m, 2H), 7.24-7.15 (m, 1H), 7.07-6.99 (m, 2H), 6.93-6.83 (m, 2H), 6.77-6.64 (m, 2H), 4.47 (s, 2H), 3.92 (s, 2H), 1.36 (s, 9H) HRMS: calcd for $C_{31}H_{30}N_3O_4$, 508.2236; found, 508.2269.

General protocol for the cyclization and mono-acetylation of OH-bearing α-aminoacids O. This reaction makes good use of the difference of reactivity of the acid function and of the resulting hydroxyimidazole in comparison with the phenolic function(s) present elsewhere in these starting materials. Moreover, the variable amount of water which is present has led us to systematically proceed by the step-wise addition of initially two equivalents of acetic anhydride followed by monitoring the reaction by $^1$H NMR analysis of a sample before adding more acetic anhydride or working up the reaction. All this said, here is a "typical" procedure. The considered deprotected acid (0.4 mmol) was dispersed in either ethyl acetate or toluene. To this was added an initial acetic anhydride (95 microL, 0.9 mmol) and the mixture heated to reflux for 30 mn. An $^1$H NMR analysis of sample was made and depending on the degree of disappearance of the starting material more acetic anhydride. Care should be taken in not adding too much of this as the polyacetylation will take place quite quickly, especially in refluxing toluene. In few, unfortunate cases, this reaction was run at room temperature in acetic anhydride and along with small amount of the target mono acetylation produce, polyacetylation was the main results. When relevant, the resulting solution was concentrated to dryness and purified as described below. The compounds obtained usually contained less than 5% of bis acetylated material.

2,8-Dibenzyl-6-(4-hydroxyphenyl)imidazo[1,2-a]pyrazin-3-yl acetate (P-94): This compound was obtained from O-10 as a beige solid (0.11 g, 52%) using toluene as a solvent and a chromatography over silica gel (dichloromethane—ethanol 98/2). $^1$H NMR (DMSO-$d_6$): 9.64 (s, 1H), 8.54 (s, 1H), 7.89 (m, 2H), 7.48 (m, 2H), 7.26 (m, 8H), 6.87 (m, 2H), 4.46 (s, 2H), 4.08 (s, 2H), 2.37 (s, 3H). HRMS: calcd for $C_{28}H_{24}N_3O_4$: 450.1818; found, 450.1825.

8-Benzyl-6-(4-hydroxyphenyl)-2-(3-propylbenzyl)imidazo[1,2-a]pyrazin-3-yl acetate (P-95): The reaction was run, using O-11, in acetic anhydride at room temperature for 30 mn. The resulting solution was dispersed in water, extracted with ethyl acetate, the organic layer was washed with water, brine, dried over magnesium sulfate and concentrated to dryness. A chromatography of the residue over silica gel (cyclohexane—ethyl acetate 4/1) gave the target compound as a beige solid (0.02 g, 10%) along with the corresponding diacetylated product (0.13 g, 65%). $^1$H NMR ($CDCl_3$): 7.76 (m, 2H), 7.70 (s, 1H), 7.61 (m, 2H), 7.30 (m, 2H), 7.22 (m, 2H), 7.07 (m, 3H), 6.00 (m, 2H), 4.62 (s, 2H), 4.19 (s, 2H), 2.56 (m, 2H), 2.16 (s, 3H), 1.65 (m, 2H), 0.96 (t, J=7.3 Hz, 3H). HRMS: calcd for $C_{31}H_{30}N_3O_3$: 492.2287; found, 492.2260.

8-Benzyl-2-(furan-2-ylmethyl)-6-(4-hydroxyphenyl)imidazo[1,2-a]pyrazin-3-yl acetate (P-97): This compound was obtained from O-12 as a beige solid (0.33 g, 60%) using ethyl acetate as a solvent and a chromatography over silica gel (cyclohexane—ethyl acetate 2/1). $^1$H NMR (DMSO-$d_6$): 9.65 (s, 1H), 8.55 (s, 1H), 7.90 (m, 2H), 7.55 (m, 1H), 7.47 (m, 2H), 7.27 (m, 2H), 7.22 (m, 1H), 6.88 (m, 2H), 6.39 (dd, 1H, J=1.8, 3.1), 6.19 (dd, 1H, J=0.8, 3.1), 4.46 (s, 2H), 4.13 (s, 2H), 2.40 (s, 3H). HRMS: calcd for $C_{26}H_{22}N_3O_4$, 440.1610; found, 440.1603.

8-Benzyl-2-((4,5-dimethylfuran-2-yl)methyl)-6-(4-hydroxyphenyl)imidazo[1,2-a]pyrazin-3-yl acetate (P-98): This compound was obtained from O-13 as a beige solid (0.05 g, 22%) using ethyl acetate as a solvent and a chromatography over silica gel (cyclohexane—ethyl acetate 3/1). $^1$H NMR ($CDCl_3$): 7.75 (m, 2H), 7.74 (s, 1H), 7.58 (m, 2H), 7.26 (m, 4H), 6.91 (m, 2H), 5.89 (s, 1H), 4.61 (s, 2H), 4.13 (s, 2H), 2.36 (s, 3H), 2.17 (s, 3H), 1.90 (s, 3H). HRMS: calcd for $C_{28}H_{26}N_3O_4$: 468.1923; found, 468.1922.

8-Benzyl-2-((5-ethylfuran-2-yl)methyl)-6-(4-hydroxyphenyl)imidazo[1,2-a]pyrazin-3-yl acetate (P99): This compound was obtained from O-14 as a beige solid (0.05 g, 45%) using ethyl acetate as a solvent and a chromatography over silica gel (cyclohexane—ethyl acetate 3/1). $^1$H NMR ($CDCl_3$): 7.76 (m, 2H), 7.74 (s, 1H), 7.59 (m, 2H), 7.26 (m, 4H), 6.91 (m, 2H), 6.01 (m, 1H), 5.90 (m, 1H), 4.61 (s, 2H), 4.19 (s, 2H), 2.61 (q, 2H, J=7.6), 2.35 (s, 3H), 1.22 (t, 3H, J=7.6). HRMS: calcd for $C_{28}H_{26}N_3O_4$: 468.1923; found, 468.1929.

8-Benzyl-2-(4-hydroxybenzyl)-6-(4-hydroxyphenyl)imidazo[1,2-a]pyrazin-3-yl acetate (P-100): This compound was obtained from O-9 as a beige solid (0.10 g, 68%) using ethyl acetate as a solvent and a chromatography over silica gel (cyclohexane—ethyl acetate 2/1). $^1$H NMR (DMSO-$d_6$) 9.65 (s, 1H), 9.20 (s, 1H), 8.53 (s, 1H), 7.89 (m, 2H), 7.48 (m, 2H), 7.24 (m, 3H), 7.07 (m, 2H), 6.87 (m, 2H), 6.69 (m, 2H), 4.46 (s, 2H), 3.96 (s, 2H), 2.37 (s, 3H). HRMS: calcd for $C_{28}H_{24}N_3O_4$: 466.1767; found, 466.1758.

2,8-Dibenzyl-6-(3-fluoro-4-hydroxyphenyl)imidazo[1,2-a]pyrazin-3-yl acetate (P101): This compound was obtained from O-15 as a white solid (0.11 g, 24%) using ethyl acetate as a solvent and a chromatography over silica gel (cyclohexane—ethyl acetate 3/1) followed by a recrystallization in toluene/cyclohexane. $^1$H NMR (DMSO-$d_6$): 7.71 (s, 1H), 7.69 (m, 1H), 7.60 (m, 2H), 7.52 (m, 1H), 7.34-7.20 (m, 8H), 7.04 (m, 1H), 6.67 (s (br), 1H), 4.62 (s, 2H), 4.21 (s, 2H), 2.18 (s, 3H). HRMS: calcd for $C_{28}H_{23}FN_3O_3$: 468.1723; found, 468.1725.

General protocol for the generation of solutions of imidazo[1,2-a]pyrazin-3(7H)-one Q by acidic hydrolysis of imidazo[1,2-a]pyrazin-3-yl acetate derivatives P. The considered acetate P (1 mg) was dissolved in DMSO (0.2 mL) and then diluted by adding a solution of acidic ethanol (0.3 ml) made from the addition of 37% hydrochloric acid (100 μl) on 100% ethanol (12 mL). This 0.5 mL solution was incubated at 50° C. for 2 hours to give a stock solution which was then stored at −80° C. As depicted in FIG. 1, in the case of compound P-21, the LC/MS monitoring of the hydrolysis into the corresponding 8-benzyl-2-((5-ethylfuran-2-yl)methyl)-6-phenylimidazo[1,2-a]pyrazin-3(7H)-one (Q-12; see table below) pointed out a complete reaction in less than two hours. Nota: these conditions are only adapted to the hydrolysis of the protecting group (as defined above) of the oxygen on position 2 of the imidazo[1,2-a]pyrazine ring system and not to the hydrolysis of any additional acetyl groups eventually present elsewhere on the substrate of this reaction.

Bioluminescence Properties of a Selection of Imidazo[1,2-a]Pyrazin-3(7H)-One Q Generated in Solution from the Corresponding O-Acetylated Precursors P.

Some of the synthesized substrates described above were evaluated for up to the five following kinds of applications using *Oplophorus*-derived luciferases or complementation of parts of these enzymes. If bioluminescent assays are depending on cell transfection to express luciferase chimeras, then assay methods that are based on light microscope imaging may be preferred for difficult-to-transfect cells to assess the light emission from the individual cells. In the other cases, single-tube or plate-reader luminometer, digital camera (including smartphones), light detector or photographic film integrating the light in the full volume are suitable.

1—In vitro assays of bioluminescence of luciferases or fragments from cell lysate, biologic fluids, or various grade of purified proteins in buffer solution. Measurements are typically monitored by a multi-well plate luminometer or a luminometer reading train of drops sampled in a tubing separated by air bubbles from a liquid handler. This was in particular the main method employed for screening these substrates and assessing their bioluminescence properties.

2—In cellulo assays of bioluminescence of cell or exosome suspension. Cells can be alive in culture media, quiescent in conditions of ATP production inhibition, in soft chemical fixation conditions or in cell permeation conditions. Luciferase reporters or fragments can be fused to proteins targeting the cell surface, the cytoplasm, organelles, the nucleus or the exosomes. Measurements are typically monitored by a multi-well plate luminometer, a luminometer reading train of drops sampled in a tubing separated by air bubbles from a liquid handler, or from a cytometer with bioluminescence setting.

3—In cellulo assays and imaging of bioluminescence of adherent or non-adherent cells, organelles, exosomes, virus, or particles using a light microscope. Protein: luciferase fusion can be expressed by cells and imaged alive in the culture media, quiescent in conditions of ATP production inhibition, in soft chemical fixation conditions of in cell permeation conditions. Protein: luciferase fusion can be added to the media and target the cell surface, cytoplasm, organelles, nucleus, exosomes or eventually carried to target cells either by virus, host-infecting cells or agents, biologic complexes or particles.

4—In vivo assays of bioluminescence of luciferase or fragment used as reporter of proteins expressed in living animals or perfused tissues using a light microscope, light scanners, cameras or bioluminescent imaging systems.

5—Bioluminescence assay of immobilized molecules, particles, complexes, virus or cells on solid 2D (membrane, slide, bead, fibre) or 3D-support (matrix, permeable beads, fibre networks, permeable tissues) with typical application as western and northern blots for protein and DNA target detection in solution, cell lysate or biofluids but also for toxics and compound detection in soils, liquids for testing bio or chemical hazard in the environment. Detection is possible in bioluminometer, digital camera (including smartphones), scanner, imaging system or photo-sensitive film.

1—In vitro assay of bioluminescence.

Figure 2:
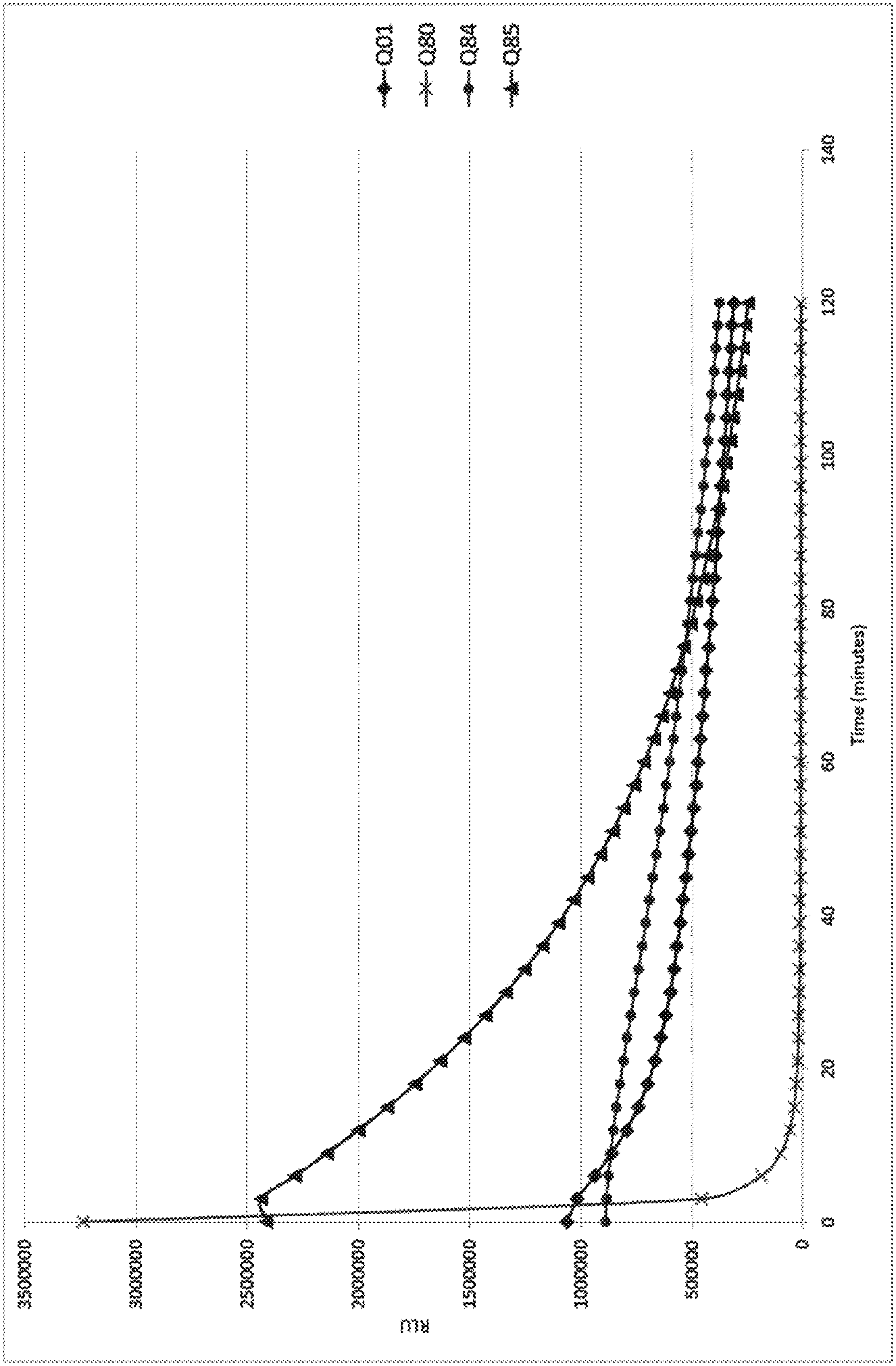
FIG. 2 illustrates the bioluminescence emission over two hours of furimazine (Q-1) and hydroxyfurimazine (Q-80), as well as the imidazo[1,2-a]pyrazin-3(7H)-ones Q-84 and Q-85 of the invention.

The representative bioluminescence curves shown in the FIG. 2 provided an assessment for furimazine (Q-1), 8-benzyl-2-(furan-2-ylmethyl)-6-(4-hydroxyphenyl)imidazo[1,2-a]pyrazin-3 (7/1)-one (Q-80), 8-(2-fluorobenzyl)-2-(furan-2-ylmethyl)-6-phenylimidazo[1,2-a]pyrazin-3(7H)-one (Q-84), and 8-(2-fluorobenzyl)-2-((5-methylfuran-2-yl)methyl)-6-phenylimidazo[1,2-a]pyrazin-3(7H)-one (Q-85) was obtained using a luciferase expressed in vitro as described in the following. The nanoKAZ DNA template was cloned into Thermo Scientific pT7CFE1-based vector and nanoKAZ was expressed using ThermoFisher Scientific 1-Step Human Coupled IVT Kit—DNA (ref. 88881) according to the manufacturer instructions. The resulting reaction mix was diluted 400 times in buffer (DPBS (Gibco)+0.1% (v/v) Tween 20) and conserved at −80° C. The screening of the imidazo[1,2-a]pyrazin-3(7H)-ones was performed in 96 well plates using 50 μL/well of a 1/20 dilution in DPBS (Gibco)+0.1% (v/v) Tween 20 of the nanoKAZ solution. After adding 50 µl/well of a 1/50 dilution of the stock (4.5 mM)imidazo[1,2-a]pyrazin-3(7H)-ones solution in DPBS (Gibco)+0.1% (v/v) Tween 20, luminescence intensity displayed by the different luciferin analogues was measured on a Berthold Centro luminometer (*Renilla* luminescence counting program with an integration time of 1 second), and signal decrease over time was monitored for 2 hours in a kinetic experiment with a 3 minutes increments:

To illustrate the bioluminescence properties improvement achieved for many of the imidazo[1,2-a]pyrazin-3(7H)-ones described here, four values are provided in Table 1: maximum intensity (V1), signal half-life (V2), area under the curve for ten minutes (V3), and area under the curve for two hours (V4), normalized using furimazine (Q-1) as a reference.

The bioluminescence properties of the tested compounds are considered to be improved when at least one of the values V1-V4 is above 1, and when none of the V1-V4 values is 0.05 or below.

TABLE 1 bioluminescence properties of a selection of imidazo[1,2-a]pyrazin-3(7H)-ones

| Codes | Structures | Chemical names (Chemdraw Ultra 14) | V1 | V2 | V3 | V4 |
|---|---|---|---|---|---|---|
| Q-1 (outside the invention) | 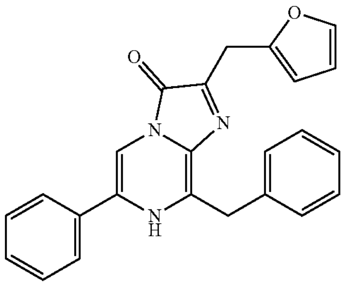 [SMILES: O=c1c(Cc2ccco2)nc2c(Cc3ccccc3)[nH]c(-c3ccccc3)cn1-2] | 8-benzyl-2-(furan-2-ylmethyl)-6-phenylimidazo[1,2-a]pyrazin-3(7H)-one (furimazine) | 1 | 1 | 1 | 1 |
| Q-3 | 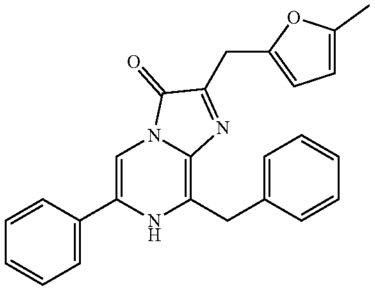 [SMILES: Cc1ccc(Cc2nc3c(Cc4ccccc4)[nH]c(-c4ccccc4)cn-3c2=O)o1] | 8-benzyl-2-((5-methylfuran-2-yl)methyl)-6-phenylimidazo[1,2-a]pyrazin-3(7H)-one | 2.7 | 0.36 | 2.39 | 1.3 |
| Q-12 | 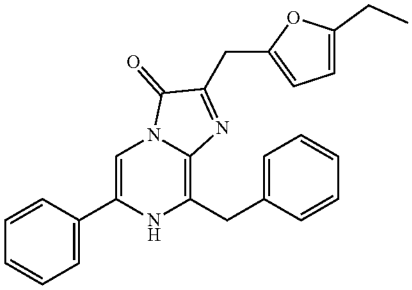 [SMILES: CCc1ccc(Cc2nc3c(Cc4ccccc4)[nH]c(-c4ccccc4)cn-3c2=O)o1] | 8-benzyl-2-((5-ethylfuran-2-yl)methyl)-6-phenylimidazo[1,2-a]pyrazin-3(7H)-one | 2.28 | 0.44 | 2.2 | 1.28 |
| Q-16 | 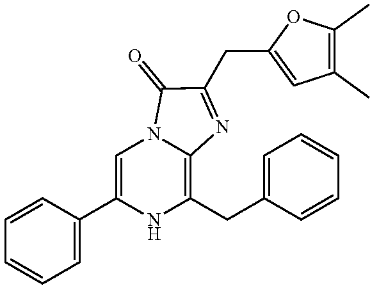 [SMILES: Cc1cc(Cc2nc3c(Cc4ccccc4)[nH]c(-c4ccccc4)cn-3c2=O)oc1C] | 8-benzyl-2-((4,5-dimethylfuran-2-yl)methyl)-6-phenylimidazo[1,2-a]pyrazin-3(7H)-one | 2.07 | 0.3 | 1.88 | 0.93 |

TABLE 1-continued

| bioluminescence properties of a selection of imidazo[1,2-a]pyrazin-3(7H)-ones | | | | | | |
|---|---|---|---|---|---|---|
| Codes | Structures | Chemical names (Chemdraw Ultra 14) | V1 | V2 | V3 | V4 |
| Q-21 | 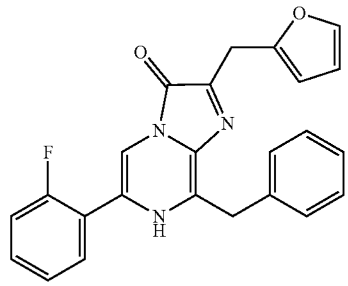 [SMILES: O=c1c(Cc2ccco2)nc2c(Cc3ccccc3)[nH]c(-c3ccccc3F)cn1-2] | 8-benzyl-6-(2-fluorophenyl)-2-(furan-2-ylmethyl)imidazo[1,2-a]pyrazin-3(7H)-one | 1.39 | 0.65 | 1.33 | 1.08 |
| Q-14 | 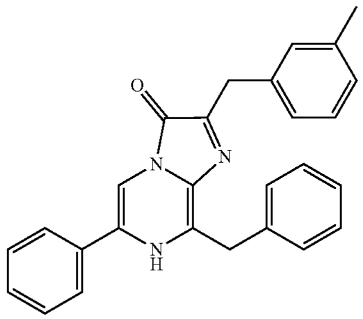 [SMILES: Cc1cccc(Cc2nc3c(Cc4ccccc4)[nH]c(-c4ccccc4)cn-3c2=O)c1] | 8-benzyl-2-(3-methylbenzyl)-6-phenylimidazo[1,2-a]pyrazin-3(7H)-one | 1.8 | 0.38 | 1.66 | 0.96 |
| Q-18 | 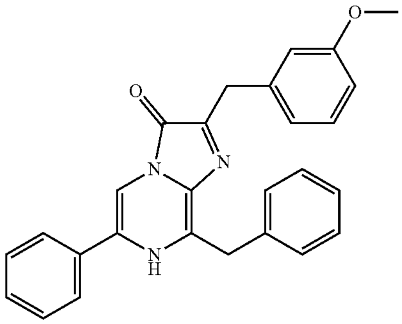 [SMILES: COc1cccc(Cc2nc3c(Cc4ccccc4)[nH]c(-c4ccccc4)cn-3c2=O)c1] | 8-benzyl-2-(3-methoxybenzyl)-6-phenylimidazo[1,2-a]pyrazin-3(7H)-one | 1.53 | 0.44 | 1.41 | 0.97 |
| Q-20 | 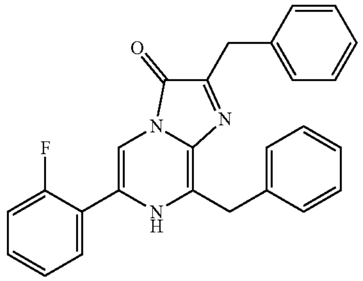 [SMILES: O=c1c(Cc2ccccc2)nc2c(Cc3ccccc3)[nH]c(-c3ccccc3F)cn1-2] | 2,8-dibenzyl-6-(2-fluorophenyl)imidazo[1,2-a]pyrazin-3(7H)-one | 2 | 0.22 | 1.59 | 0.66 |
| Q-27 | 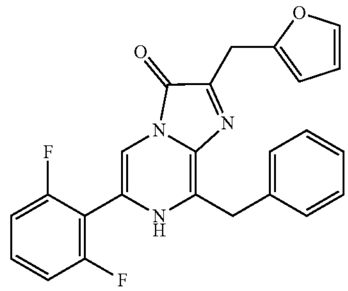 [SMILES: O=c1c(Cc2ccco2)nc2c(Cc3ccccc3)[nH]c(-c3c(F)cccc3F)cn1-2] | 8-benzyl-6-(2,6-difluorophenyl)-2-(furan-2-ylmethyl)imidazo[1,2-a]pyrazin-3(7H)-one | 1.04 | 0.87 | 1.02 | 0.97 |

TABLE 1-continued

| Codes | Structures | Chemical names (Chemdraw Ultra 14) | V1 | V2 | V3 | V4 |
|---|---|---|---|---|---|---|
| bioluminescence properties of a selection of imidazo[1,2-a]pyrazin-3(7H)-ones | | | | | | |
| Q-28 | 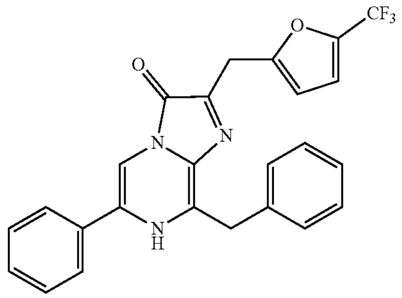 [SMILES: O=c1c(Cc2ccc(C(F)(F)F)o2)nc2c(Cc3ccccc3)[nH]c(-c3ccccc3)cn1-2] | 8-benzyl-6-phenyl-2-((5-(trifluoromethyl)furan-2-yl)methyl)imidazo[1,2-a]pyrazin-3(7H)-one | 1.31 | 0.27 | 1.11 | 0.62 |
| Q-29 | 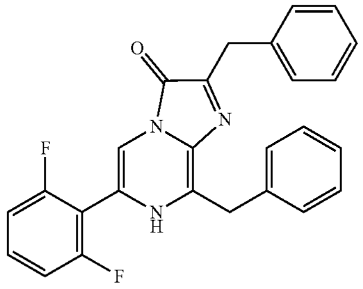 [SMILES: O=c1c(Cc2ccccc2)nc2c(Cc3ccccc3)[nH]c(-c3c(F)cccc3F)cn1-2] | 2,8-dibenzyl-6-(2,6-difluorophenyl)imidazo[1,2-a]pyrazin-3(7H)-one | 1.86 | 0.17 | 1.48 | 0.55 |
| Q-34 | 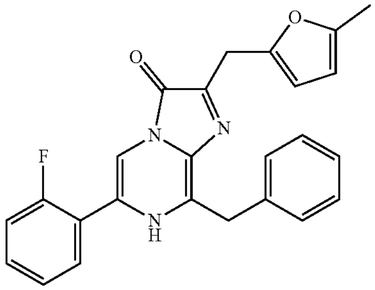 [SMILES: Cc1ccc(Cc2nc3c(Cc4ccccc4)[nH]c(-c4ccccc4F)cn-3c2=O)o1] | 8-benzyl-6-(2-fluorophenyl)-2-((5-methylfuran-2-yl)methyl)imidazo[1,2-a]pyrazin-3(7H)-one | 2.17 | 0.39 | 1.89 | 1.13 |
| Q-36 | 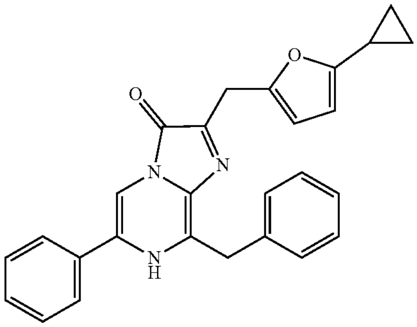 [SMILES: O=c1c(Cc2ccc(C3CC3)o2)nc2c(Cc3ccccc3)[nH]c(-c3ccccc3)cn1-2] | 8-benzyl-2-((5-cyclopropylfuran-2-yl)methyl)-6-phenylimidazo[1,2-a]pyrazin-3(7H)-one | 1.74 | 0.36 | 1.64 | 0.83 |
| Q-41 | 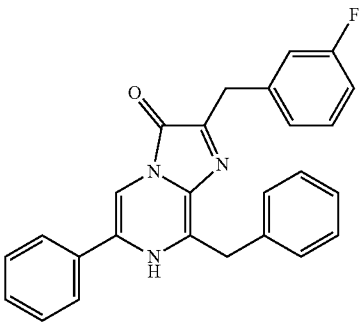 [SMILES: O=c1c(Cc2cccc(F)c2)nc2c(Cc3ccccc3)[nH]c(-c3ccccc3)cn1-2] | 8-benzyl-2-(3-fluorobenzyl)-6-phenylimidazo[1,2-a]pyrazin-3(7H)-one | 1.49 | 0.33 | 1.28 | 0.74 |

TABLE 1-continued bioluminescence properties of a selection of imidazo[1,2-a]pyrazin-3(7H)-ones

| Codes | Structures | Chemical names (Chemdraw Ultra 14) | V1 | V2 | V3 | V4 |
|---|---|---|---|---|---|---|
| Q-51 | 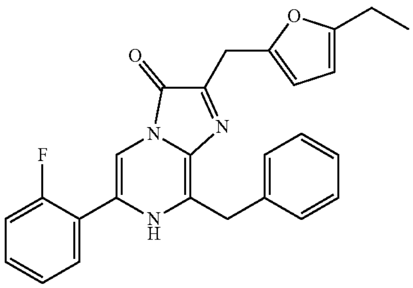 [SMILES: CCc1ccc(Cc2nc3c(Cc4ccccc4)[nH]c(-c4ccccc4F)cn-3c2=O)o1] | 8-benzyl-2-((5-ethylfuran-2-yl)methyl)-6-(2-fluorophenyl)imidazo[1,2-a]pyrazin-3(7H)-one | 2.59 | 0.35 | 2.33 | 1.19 |
| Q-54 | 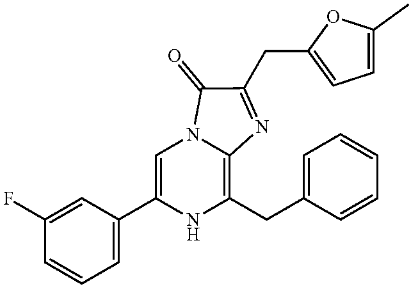 [SMILES: Cc1ccc(Cc2nc3c(Cc4ccccc4)[nH]c(-c4cccc(F)c4)cn-3c2=O)o1] | 8-benzyl-6-(3-fluorophenyl)-2-((5-methylfuran-2-yl)methyl)imidazo[1,2-a]pyrazin-3(7H)-one | 2.73 | 0.3 | 2.32 | 1.22 |
| Q-56 | 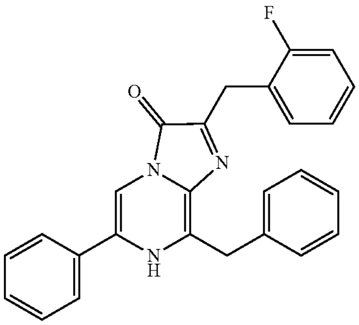 [SMILES: O=c1c(Cc2ccccc2F)nc2c(Cc3ccccc3)[nH]c(-c3ccccc3)cn1-2] | 8-benzyl-2-(2-fluorobenzyl)-6-phenylimidazo[1,2-a]pyrazin-3(7H)-one | 1.84 | 0.24 | 1.51 | 0.7 |
| Q-58 | 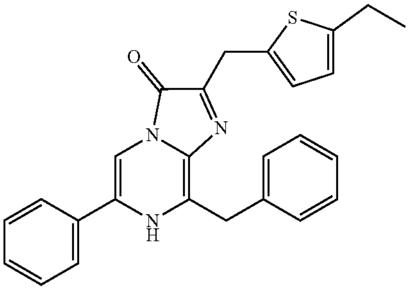 [SMILES: CCc1ccc(Cc2nc3c(Cc4ccccc4)[nH]c(-c4ccccc4)cn-3c2=O)s1] | 8-benzyl-2-((5-ethylthiophen-2-yl)methyl)-6-phenylimidazo[1,2-a]pyrazin-3(7H)-one | 1.71 | 0.32 | 1.61 | 0.69 |
| Q-61 | 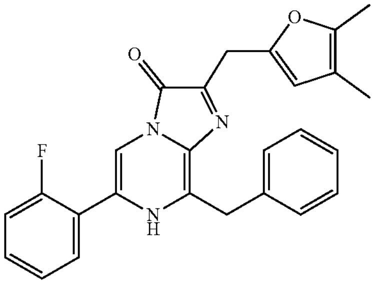 [SMILES: Cc1cc(Cc2nc3c(Cc4ccccc4)[nH]c(-c4ccccc4F)cn-3c2=O)oc1C] | 8-benzyl-2-((4,5-dimethylfuran-2-yl)methyl)-6-(2-fluorophenyl)imidazo[1,2-a]pyrazin-3(7H)-one | 2.13 | 0.28 | 1.97 | 0.78 |

TABLE 1-continued

| bioluminescence properties of a selection of imidazo[1,2-a]pyrazin-3(7H)-ones | | | | | | |
|---|---|---|---|---|---|---|
| Codes | Structures | Chemical names (Chemdraw Ultra 14) | V1 | V2 | V3 | V4 |
| Q-72 | 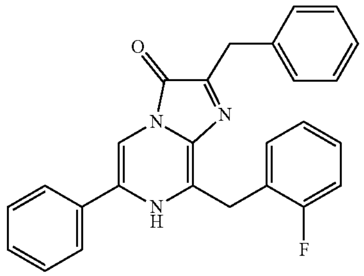 [SMILES: O=c1c(Cc2ccccc2)nc2c(Cc3ccccc3F)[nH]c(-c3ccccc3)cn1-2] | 2-benzyl-8-(2-fluorobenzyl)-6-phenylimidazo[1,2-a]pyrazin-3(7H)-one | 1.49 | 0.5 | 1.49 | 0.85 |
| Q-73 | 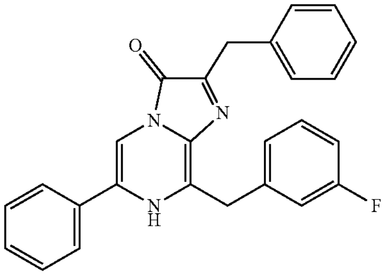 [SMILES: O=c1c(Cc2ccccc2)nc2c(Cc3cccc(F)c3)[nH]c(-c3ccccc3)cn1-2] | 2-benzyl-8-(3-fluorobenzyl)-6-phenylimidazo[1,2-a]pyrazin-3(7H)-one | 1.12 | 0.92 | 1.19 | 0.92 |
| Q-75 (outside the invention) | | 2,8-dibenzyl-6-(4-hydroxyphenyl)imidazo[1,2-a]pyrazin-3(7H)-one | 2.03 | <0.05 | 0.45 | 0.11 |
| Q-80 (outside the invention) | 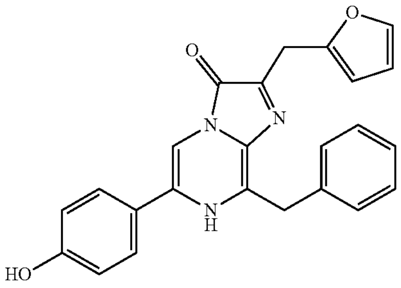 [SMILES: O=c1c(Cc2ccco2)nc2c(Cc3ccccc3)[nH]c(-c3ccc(O)cc3)cn1-2] | 8-benzyl-2-(furan-2-ylmethyl)-6-(4-hydroxyphenyl)imidazo[1,2-a]pyrazin-3(7H)-one | 3.06 | 0.05 | 0.79 | 0.14 |
| Q-81 | 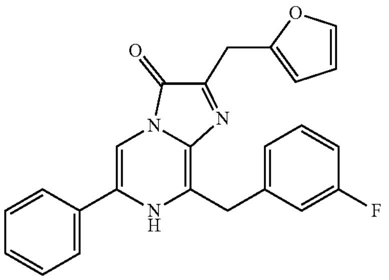 [SMILES: O=c1c(Cc2ccco2)nc2c(Cc3cccc(F)c3)[nH]c(-c3ccccc3)cn1-2] | 8-(3-fluorobenzyl)-2-(furan-2-ylmethyl)-6-phenylimidazo[1,2-a]pyrazin-3(7H)-one | 0.82 | 3.25 | 0.92 | 1.31 |
| Q-82 | 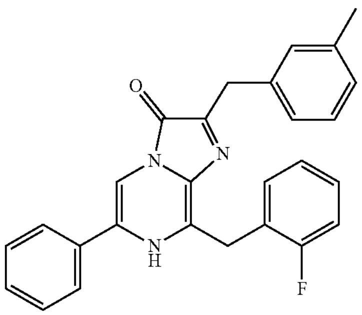 [SMILES: Cc1cccc(Cc2nc3c(Cc4ccccc4F)[nH]c(-c4ccccc4)cn-3c2=O)c1] | 8-(2-fluorobenzyl)-2-(3-methylbenzyl)-6-phenylimidazo[1,2-a]pyrazin-3(7H)-one | 1.36 | 0.57 | 1.38 | 0.84 |

TABLE 1-continued

| bioluminescence properties of a selection of imidazo[1,2-a]pyrazin-3(7H)-ones | | | | | | |
|---|---|---|---|---|---|---|
| Codes | Structures | Chemical names (Chemdraw Ultra 14) | V1 | V2 | V3 | V4 |
| Q-83 | 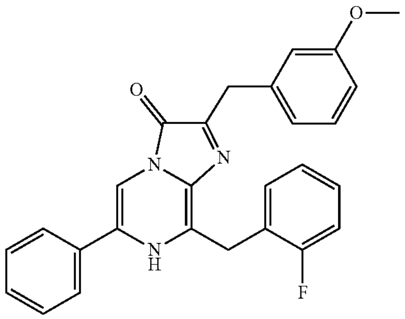 [SMILES: COc1cccc(Cc2nc3c(Cc4ccccc4F)[nH]c(-c4ccccc4)cn-3c2=O)c1] | 8-(2-fluorobenzyl)-2-(3-methoxybenzyl)-6-phenylimidazo[1,2-a]pyrazin-3(7H)-one | 1.46 | 0.71 | 1.49 | 1.12 |
| Q-84 | 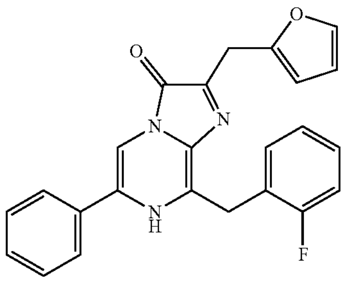 [SMILES: O=c1c(Cc2ccco2)nc2c(Cc3ccccc3F)[nH]c(-c3ccccc3)cn1-2] | 8-(2-fluorobenzyl)-2-(furan-2-ylmethyl)-6-phenylimidazo[1,2-a]pyrazin-3(7H)-one | 0.84 | 2.29 | 0.91 | 1.18 |
| Q-85 | 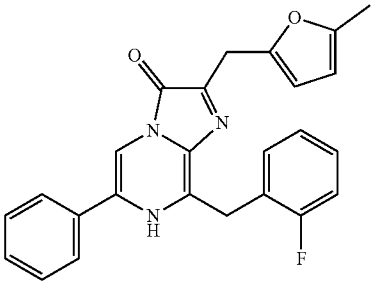 [SMILES: Cc1ccc(Cc2nc3c(Cc4ccccc4F)[nH]c(-c4ccccc4)cn-3c2=O)o1] | 8-(2-fluorobenzyl)-2-((5-methylfuran-2-yl)methyl)-6-phenylimidazo[1,2-a]pyrazin-3(7H)-one | 2.3 | 0.79 | 2.4 | 1.81 |
| Q-86 (outside the invention) | 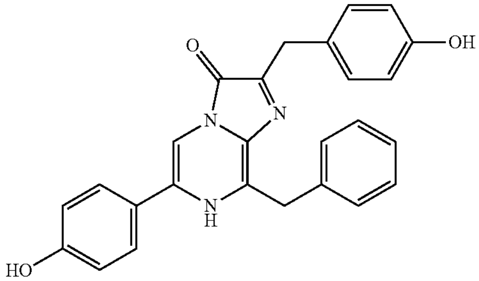 [SMILES: O=c1c(Cc2ccc(O)cc2)nc2c(Cc3ccccc3)[nH]c(-c3ccc(O)cc3)cn1-2] | 8-benzyl-2-(4-hydroxybenzyl)-6-(4-hydroxyphenyl)imidazo[1,2-a]pyrazin-3(7H)-one (coelenterazine) | 0.09 | 0.64 | 0.08 | 0.07 |
| Q-96 | 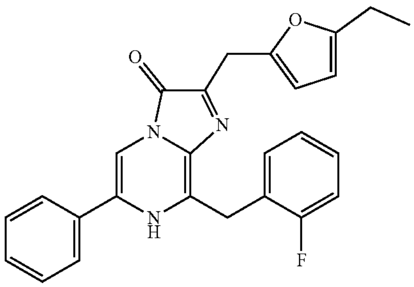 [SMILES: CCc1ccc(Cc2nc3c(Cc4ccccc4F)[nH]c(-c4ccccc4)cn-3c2=O)o1] | 2-((5-ethylfuran-2-yl)methyl)-8-(2-fluorobenzyl)-6-phenylimidazo[1,2-a]pyrazin-3(7H)-one | 2.51 | 0.91 | 2.68 | 1.98 |

TABLE 1-continued bioluminescence properties of a selection of imidazo[1,2-a]pyrazin-3(7H)-ones

| Codes | Structures | Chemical names (Chemdraw Ultra 14) | V1 | V2 | V3 | V4 |
|---|---|---|---|---|---|---|
| Q-97 | 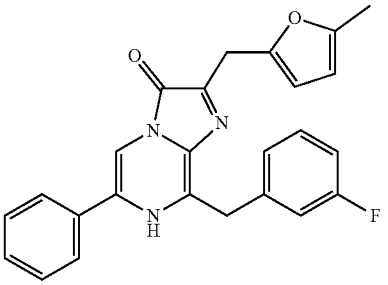 [SMILES: Cc1ccc(Cc2nc3c(Cc4cccc(F)c4)[nH]c(-c4ccccc4)cn-3c2=O)o1] | 8-(3-fluorobenzyl)-2-((5-methylfuran-2-yl)methyl)-6-phenylimidazo[1,2-a]pyrazin-3(7H)-one | 2.04 | 1.27 | 2.20 | 2.04 |
| Q-98 | 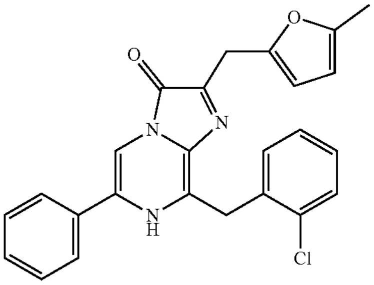 [SMILES: Cc1ccc(Cc2nc3c(Cc4ccccc4Cl)[nH]c(-c4ccccc4)cn-3c2=O)o1] | 8-(2-chlorobenzyl)-2-((5-methylfuran-2-yl)methyl)-6-phenylimidazo[1,2-a]pyrazin-3(7H)-one | 1.18 | 1.27 | 1.28 | 1.20 |
| Q-99 | 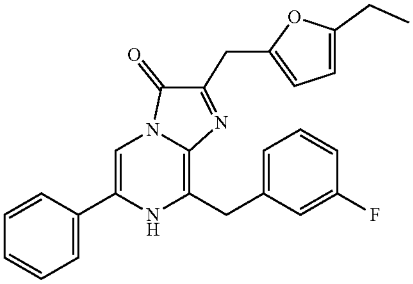 [SMILES: CCc1ccc(Cc2nc3c(Cc4cccc(F)c4)[nH]c(-c4ccccc4)cn-3c2=O)o1] | 2-((5-ethylfuran-2-yl)methyl)-8-(3-fluorobenzyl)-6-phenylimidazo[1,2-a]pyrazin-3(7H)-one | 1.99 | 1.36 | 2.13 | 2.08 |
| Q-100 | 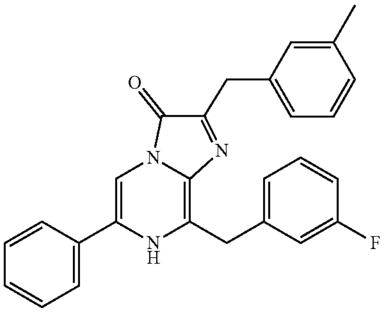 [SMILES: Cc1cccc(Cc2nc3c(Cc4cccc(F)c4)[nH]c(-c4ccccc4)cn-3c2=O)c1] | 8-(3-fluorobenzyl)-2-(3-methylbenzyl)-6-phenylimidazo[1,2-a]pyrazin-3(7H)-one | 1.25 | 0.73 | 1.33 | 1.04 |

By following the hydrolysis protocol described above, the following imidazo[1,2-a]pyrazin-3(7H)-ones luciferins Q were made in situ from the corresponding O-protected imidazo[1,2-a]pyrazines P and evaluated for their bioluminescence properties (maximum intensity (V1), signal half-life (V2), area under the curve for 2 hours (V3), and area under the curve for ten minutes (V4), normalized using furimazine (Q-1) as a reference):

| Codes | Structures | Chemical names (Chemdraw Ultra 14) | V1 | V2 | V3 | V4 |
|---|---|---|---|---|---|---|
| Q-1 (outside the invention) | 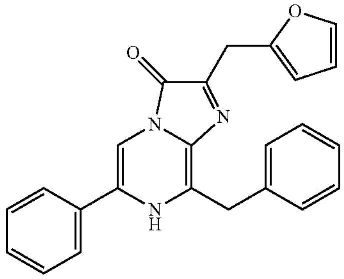 [SMILES: O=c1c(Cc2ccco2)nc2c(Cc3ccccc3)[nH]c(-c3ccccc3)cn1-2] | 8-benzyl-2-(furan-2-ylmethyl)-6-phenylimidazo[1,2-a]pyrazin-3(7H)-one (furimazine) | 1 | 1 | 1 | 1 |
| Q-105 | 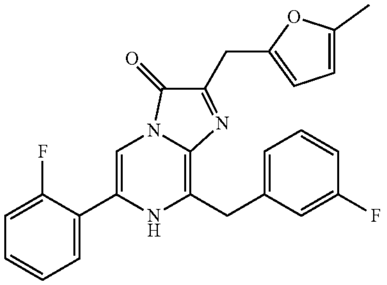 [SMILES: Cc1ccc(Cc2nc3c(Cc4cccc(F)c4)[nH]c(-c4ccccc4F)cn-3c2=O)o1] | 8-(3-fluorobenzyl)-6-(2-fluorophenyl)-2-((5-methylfuran-2-yl)methyl)imidazo[1,2-a]pyrazin-3(7H)-one | 2.04 | 1.27 | 2.01 | 1.72 |
| Q-107 | 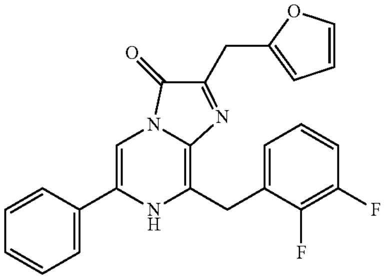 [SMILES: O=c1c(Cc2ccco2)nc2c(Cc3cccc(F)c3F)[nH]c(-c3ccccc3)cn1-2] | 8-(2,3-difluorobenzyl)-2-(furan-2-ylmethyl)-6-phenylimidazo[1,2-a]pyrazin-3(7H)-one | 1.03 | 1.63 | 1.04 | 1.27 |
| Q-108 | 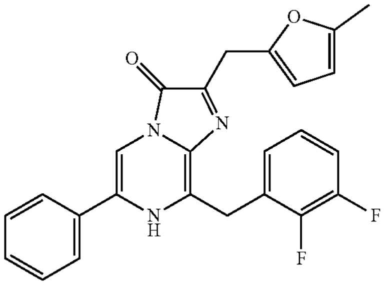 [SMILES: Cc1ccc(Cc2nc3c(Cc4cccc(F)c4F)[nH]c(-c4ccccc4)cn-3c2=O)o1] | 8-(2,3-difluorobenzyl)-2-((5-methylfuran-2-yl)methyl)-6-phenylimidazo[1,2-a]pyrazin-3(7H)-one | 3.15 | 0.53 | 3.09 | 2.1 |
| Q-117 | 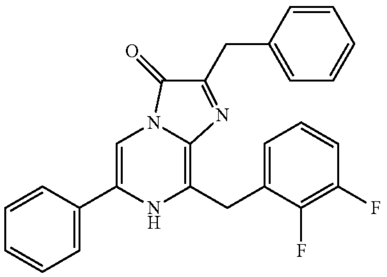 [SMILES: O=c1c(Cc2ccccc2)nc2c(Cc3cccc(F)c3F)[nH]c(-c3ccccc3)cn1-2] | 2-benzyl-8-(2,3-difluorobenzyl)-6-phenylimidazo[1,2-a]pyrazin-3(7H)-one | 2.31 | 0.18 | 1.94 | 0.7 |

-continued

| Codes | Structures | Chemical names (Chemdraw Ultra 14) | V1 | V2 | V3 | V4 |
|---|---|---|---|---|---|---|
| Q-121 | 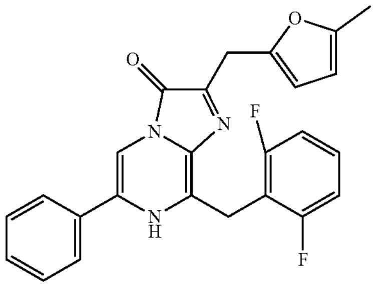 [SMILES: Cc1ccc(Cc2nc3c(Cc4c(F)cccc4F)[nH]c(-c4ccccc4)cn-3c2=O)o1] | 8-(2,6-difluorobenzyl)-2-((5-methylfuran-2-yl)methyl)-6-phenylimidazo[1,2-a]pyrazin-3(7H)-one | 1.41 | 0.94 | 1.43 | 1.37 |
| Q-124 | 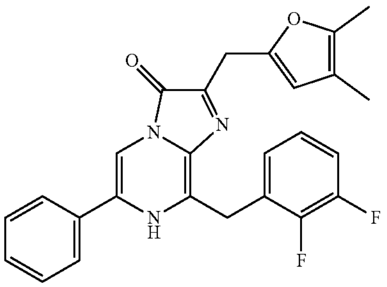 [SMILES: Cc1cc(Cc2nc3c(Cc4cccc(F)c4F)[nH]c(-c4ccccc4)cn-3c2=O)oc1C] | 8-(2,3-difluorobenzyl)-2-((4,5-dimethylfuran-2-yl)methyl)-6-phenylimidazo[1,2-a]pyrazin-3(7H)-one | 2.43 | 0.33 | 2.29 | 1.03 |
| Q-127 | 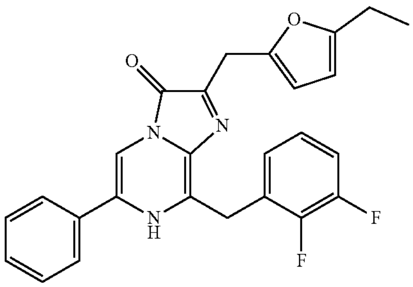 [SMILES: CCc1ccc(Cc2nc3c(Cc4cccc(F)c4F)[nH]c(-c4ccccc4)cn-3c2=O)o1] | 8-(2,3-difluorobenzyl)-2-((5-ethylfuran-2-yl)methyl)-6-phenylimidazo[1,2-a]pyrazin-3(7H)-one | 2.81 | 0.5 | 2.69 | 1.55 |
| Q-129 | 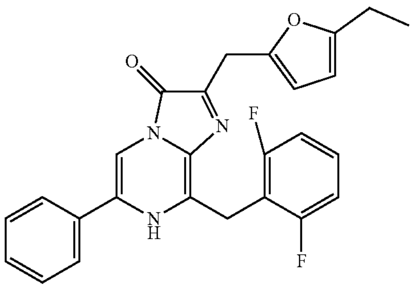 [SMILES: CCc1ccc(Cc2nc3c(Cc4c(F)cccc4F)[nH]c(-c4ccccc4)cn-3c2=O)o1] | 8-(2,6-difluorobenzyl)-2-((5-ethylfuran-2-yl)methyl)-6-phenylimidazo[1,2-a]pyrazin-3(7H)-one | 1.41 | 1 | 1.37 | 1.32 |
| Q-131 | 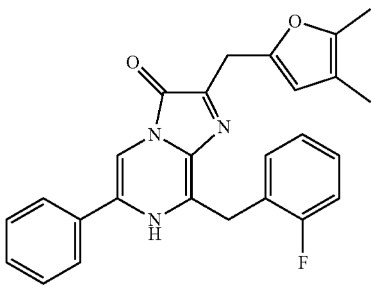 [SMILES: Cc1cc(Cc2nc3c(Cc4ccccc4F)[nH]c(-c4ccccc4)cn-3c2=O)oc1C] | 2-((4,5-dimethylfuran-2-yl)methyl)-8-(2-fluorobenzyl)-6-phenylimidazo[1,2-a]pyrazin-3(7H)-one | 2.01 | 0.39 | 1.9 | 1.02 |

-continued

| Codes | Structures | Chemical names (Chemdraw Ultra 14) | V1 | V2 | V3 | V4 |
|---|---|---|---|---|---|---|
| Q-132 | 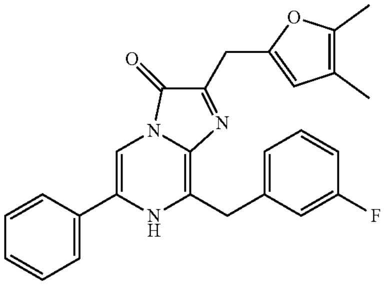 [SMILES: Cc1cc(Cc2nc3c(Cc4cccc(F)c4)[nH]c(-c4ccccc4)cn-3c2=O)oc1C] | 2-((4,5-dimethylfuran-2-yl)methyl)-8-(3-fluorobenzyl)-6-phenylimidazo[1,2-a]pyrazin-3(7H)-one | 1.5 | 0.55 | 1.44 | 1 |
| Q-133 | 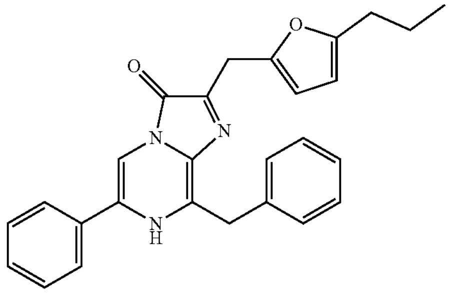 [SMILES: CCCc1ccc(Cc2nc3c(Cc4ccccc4)[nH]c(-c4ccccc4)cn-3c2=O)o1] | 8-benzyl-6-phenyl-2-((5-propylfuran-2-yl)methyl)imidazo[1,2-a]pyrazin-3(7H)-one | 1.26 | 1.12 | 1.23 | 1.33 |
| Q-135 | 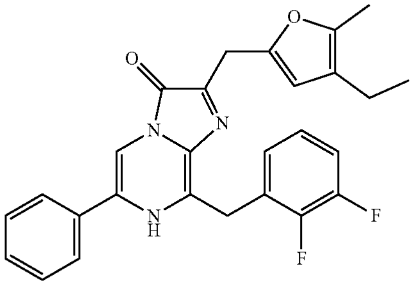 [SMILES: CCc1cc(Cc2nc3c(Cc4cccc(F)c4F)[nH]c(-c4ccccc4)cn-3c2=O)oc1C] | 8-(2,3-difluorobenzyl)-2-((4-ethyl-5-methylfuran-2-yl)methyl)-6-phenylimidazo[1,2-a]pyrazin-3(7H)-one | 1.26 | 0.30 | 0.51 | 1.19 |
| Q-143 | 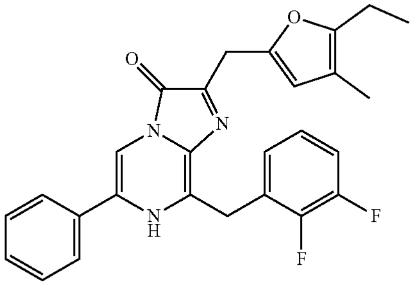 [SMILES: CCc1oc(Cc2nc3c(Cc4cccc(F)c4F)[nH]c(-c4ccccc4)cn-3c2=O)cc1C] | 8-(2,3-difluorobenzyl)-2-((5-ethyl-4-methylfuran-2-yl)methyl)-6-phenylimidazo[1,2-a]pyrazin-3(7H)-one | 1.43 | 0.25 | 0.39 | 1.34 |
| Q-149 | 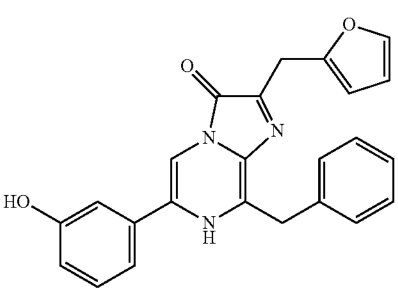 [SMILES: O=c1c(Cc2ccco2)nc2c(Cc3ccccc3)[nH]c(-c3cccc(O)c3)cn1-2] | 8-benzyl-2-(furan-2-ylmethyl)-6-(3-hydroxyphenyl)imidazo[1,2-a]pyrazin-3(7H)-one | 1.12 | 0.64 | 0.85 | 1.05 |

This kind of bioluminescence assay of luciferases in solution is typically used in high throughput screening. These assays aim at measuring the intensity of light emission at single or multiple time points or to assess a process kinetic. Protocols can be adapted to several concentrations of luciferase-tagged proteins and several concentrations of substrates. These measurements do require a high intensity along with a maximum of linearity of the intensity with the substrate concentration for a large dynamic range, stable intensity, ideally for one hour as well as a low background noise. Protein:nanoKAZ chimeras can be expressed from transfected cells. Transfection can be performed using chemical agent, electroporation, or molecular moieties providing cell-absorption properties to linear or circular plasmid or lentiviral vectors. Assays can be performed on transiently transfected cells or after gene integration on constitutively nanoKAZ chimera expressing gene.

Figure 3:
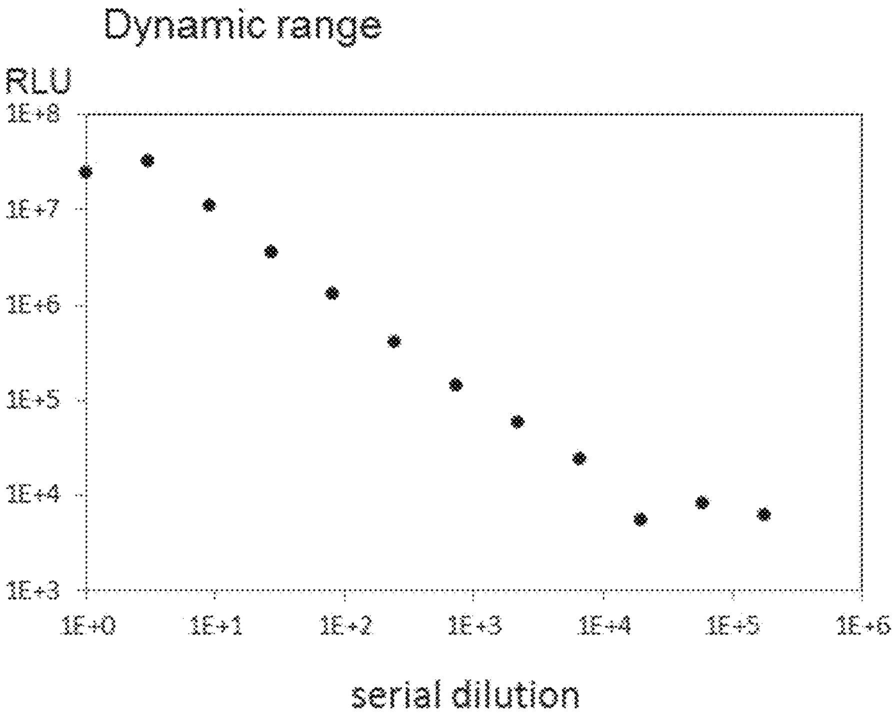
FIG. 3 illustrates dynamic range (relative units (RLU) versus serial dilutions) of nanok AZ, which was plotted using the imidazo[1,2-a]pyrazin-3(7H)-one Q-3.

As depicted in FIG. 3, the dynamic range of nanoKAZ was assessed using luciferin Q-3. The enzyme was diluted three by three times and the bioluminescence has been measured on a constant volume (100 (L) and at constant concentration of the substrate. The bioluminescence is linear with the enzyme concentration over 5 orders of magnitude, overwhelming the detection system. This range can be increase by two orders of magnitude by decreasing 2 times the volume for high enzyme concentration and by increasing two times the volume for low enzyme concentration.

Figure 4:
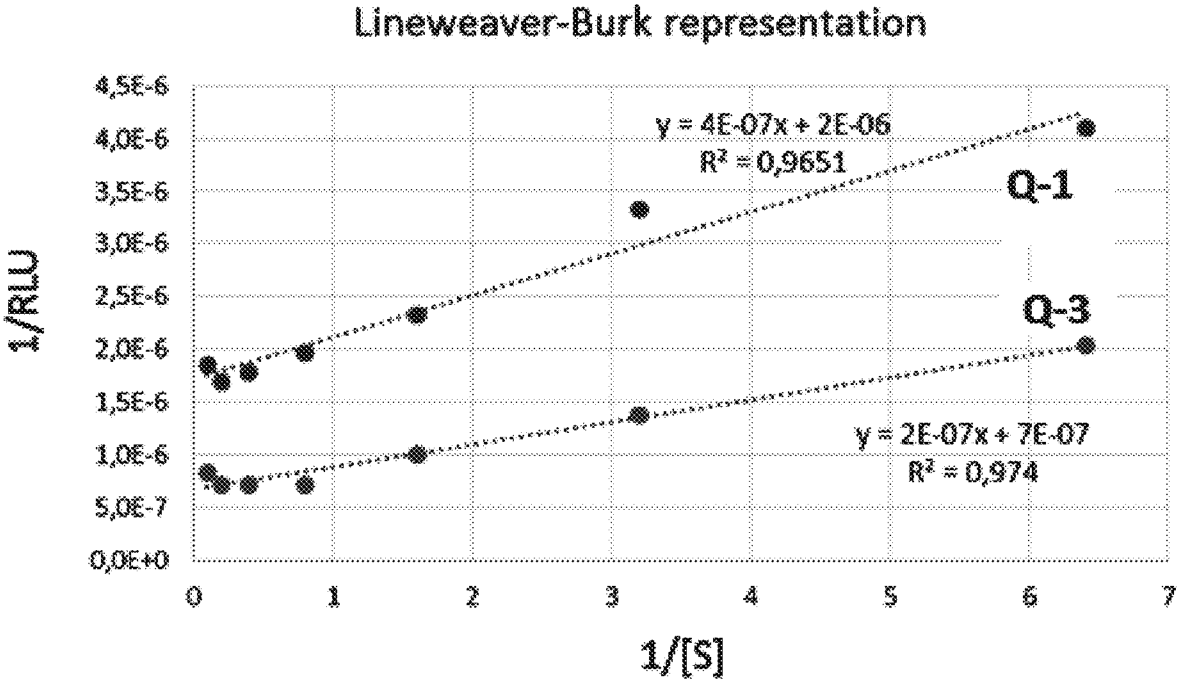
FIG. 4 shows a comparative Lineweaver-Burk representation of the bioluminescent activity of the nanoKAZ using furimazine (Q-1) and imidazo[1,2-a]pyrazin-3(7H)-one Q-3 as substrates: the inverse of the reaction rate (relative units [RLU]/second) is plotted versus the inverse of the substrate concentration ($10^5M^{-1}$), keeping constant the concentration of the enzyme in the both cases. The two dotted lines (linear regression) are converging to the same intercept with the x-axis ($-1/K_m$) and different intercepts with the y-axis ($1/V_{max}$). The equations of the two linear regressions are indicated and the corresponding correlation factors ($R^2$) with the experimental data are reported.

Considering the hypothesis of a Michaelis-Menten mechanism for the nanoKAZ, the $K_m$ and $V_{max}$ were extrapolated from the Lineweaver-Burk representation of the enzyme activity catalyzing either Q-1 or Q-3. The FIG. 4 shows the inverse of the reaction rate versus the inverse of the substrate concentration keeping constant the concentration of the enzyme. The data have been fitted with linear regression with satisfying high correlation factors (R). The $K_m$ are the same for both substrates ($K_m$=2 μM) whereas the $V_{max}$ is 3-times lower for Q-1 ($0.6 \cdot 10^6$ RLU/sec) than for Q-3 ($2.0 \cdot 10^6$ RLU/sec).

This assessment of the protein-luciferase activity can be applied to assay from transiently transfected cells:

- substrate comparison: intensity, stability, catalytic activity, Michaelis constant, catalytic mechanism, inhibition by substrate excess, inhibition by products, inactivation by sub-products.
- optimization of reaction buffer;
- mutation effects on luciferase catalytic activity;
- effect of protein-luciferase linker size, stiffness, composition on luciferase catalytic activity;
- plasmid expression efficiency;
- transfection efficiency;
- regulation of transcription using a regulator domain upstream the luciferase gene in the plasmid;
- assays of protein interactions from the complementation of two fragments of the nanoKAZ used as reporter fused to each protein partner and recovering the luciferase activity upon the association of protein partners.

This assessment of the protein-luciferase activity can be applied to assay from constitutively transfected cells:

- effect of media composition, temperature, gas;
- drug screening of specific gene expression (regulation of factor binding upstream the nanoKAZ gene);
- effect of gene knock-in, knock-down, or knock-out by RNA interference or gene editing on protein expression, cell growth.

2—In Cellulo Assays of Bioluminescence of Cell or Exosome Suspension.

This kind of assays stems from the necessity of performing bioluminescent assessment on cells, Cells can be alive in growth condition using culture media, or in quiescent in conditions using inhibitor of ATP synthesis as sodium oxide or deoxyglucose as the nanoKAZ reaction does not require triphosphate nucleoside. Cells can be killed after a light chemical fixation conditions by addition of paraformaldehyde (0.5%, 20 min at room temperature) then several washing step with PBS. Cell permeation conditions can be also used to keep the cell overall structure with saponin, digitonin or low concentration of Triton X100 in order to get soluble proteins out of cells (eventually the unbound protein-nanoKAZ chimera) or to get proteins in (as eventually the protein-nanoKAZ chimera) for targeting bound cells. Luciferase reporters or fragments can be fused to proteins targeting the cell surface, the cytoplasm, organelles, the nucleus or the exosomes.

As described for in vitro, these in cellulo assays aim at measuring the intensity of light emission at single or multiple time points or along kinetics. Protocols can be adapted to several concentrations of luciferase-tagged proteins and several concentrations of substrates. These measurements require high intensity along with a maximum of linearity of the intensity with the substrate concentration for a large dynamic range, stable intensity along measurements in a one-hour scale, and low noise. Protein-nanoKAZ chimeras can be added in the media to cells, expressed from some specific cells added to a different kind of cells or from overall transfected cells. Transfection can be performed using chemical agent, electroporation, or molecular moieties providing cell-absorption properties to linear or circular plasmid or lentiviral vectors. Assays can be performed on transiently transfected cells or after gene integration on constitutively nanoKAZ chimera expressing gene.

Measurements are typically monitored by a multi-well plate luminometer, a luminometer reading train of drops sampled in a tubing separated by air bubbles from a liquid handler. As opposite to in vitro assay, in cellulo assay can be performed using a cytometer with bioluminescence setting. Four Kinds of Experiments are Performed as Cell-Based Bioluminescent Assay:

2.1 Protein-nanoKAZ binding assay at the untouched cell surface or inside permeabilized cells: the protein-nanoKAZ chimeras can be free or associated to a complex, a bead, a virus, another cell. These cell-based assays are typically developed for hormone and cytokine binding diagnostics, cell targeting diagnostics, cell infectibility diagnostic, drug screening for host cell protection against infections;

2.2 Measurement of the luciferase bioluminescence intensity from individual cell expression of the protein-nanoKAZ chimera from transiently or constitutively transfected cells or chimera import into the cell with auto-import domain fusion, electroporation, or injection. Typically assay development for regulation of gene expression. Screening of drugs. RNAi, pathogens and environmental factors on specific gene regulation;

2.3 Measurement of the luciferase bioluminescence intensity to assay the number of protein-naKAZ (N-end 1-85 fragment) and protein-noKAZ (C-end 86-166 fragment) associated providing luciferase activity recovery by complementation for transfected cells as described for in vitro assays. Typically assay development for protein-protein interaction inside or at the surface of cells and assay of alteration by drugs, RNAi, pathogens and environmental factors;

2.4 Measurement of the luciferase bioluminescence intensity to assay the number of complementation obtained from the addition of protein-nanoKAZ fragment chimeras free or associated to a complex, a bead, a virus, another cell and added to intact cells providing a complementary protein-nanoKAZ fragment chimeras at their surface or inside the permeabilized cells. Identical applications to 2.1 but in which the light is provided by the complementation of nanoKAZ fragments instead of the presence of the full fusion. The stringency of the system reduces the risk of non-specific interactions.

3—In Cellulo Assays and Imaging of Bioluminescence of Adherent or Non-Adherent Cells, Organelles, Exosomes, Virus, or Particles Using a Light Microscope.

The acquisition of bioluminescence using a light microscope provides a quantitative measurement of light emission cell by cell, the main advantage. This is meaningful especially when the transfection efficiency is low in the case of nanoKAZ expression provided by plasmids. While nanoKAZ is active and does not require ATP, cells can be alive in culture media, quiescent in conditions of ATP production inhibition (sodium azide, deoxyglucose), in light chemical fixation conditions (0.5% PFA 20 min at RT then 2 PBS wash), in cell permeation conditions (digitonine, saponine, triton). The higher is the bioluminescence efficiency, the lower is the exposure time and the lower is the sensitivity required for the detector or camera. NanoKAZ with developed substrates such as Q-3 or Q-12 opens the bioluminescence imaging to standard light microscope. The lower the exposure time, the higher the resolution, which is impeded by the motion of living cells. Any gain in light emission enhances the quality of images. Luciferase reporters or fragments can be fused to proteins targeting the cell surface, cytoplasm, organelles, nucleus or exosomes and can be carried by virus, host-infecting cells or agents, biologic complexes, beads or any particles. The second advantage of microscopy is to provide the location of the light emission with a subcellular resolution.

For exposure time from seconds to minutes, the bioluminescence in cells was imaged using a cooled EMCCD camera (Andor) on a wide-field inverted microscope (Axiovent 200, Zeiss) using an air-objective 20×0.75 NA and an apochromat water-objective 63×1.2 NA in a light-tight black box. All light sources came from out of the box through controlled shutters. The microscope has a motorized platine for slides of plate, allowing automated well-plate screening. For shorter exposure time (less than one second), a highly sensitive avalanche photo-diode (PhotekIF) was used as detector in the same microscope system aside the camera. This highly sensitive detector allows screening large number of cells with sub-second exposure times but does give neither subcellular details, organization nor location of bioluminescent moieties but only light on the full cell. The advantages compared to in vitro measurements acquired using luminometers is to restrict the measurement of the photon emission intensity to a single cell in growth conditions and allows fast kinetics. With the enzyme/substrate pair, nanoKAZ/analogue Q-3, the time acquisition for a 96-well plate is in one-hour range when using the standard system with an EMCCD camera, and in one-minute range when using the avalanche photo diode detector. The experience times were extended 3 folds with nanoKAZ/furimazine to get the same quality as with nanok AZ/analogue Q-3. Any increase of the catalytic efficiency and photon emission improves the resolution of images and decreases the duration of the experience.

Figure 5:
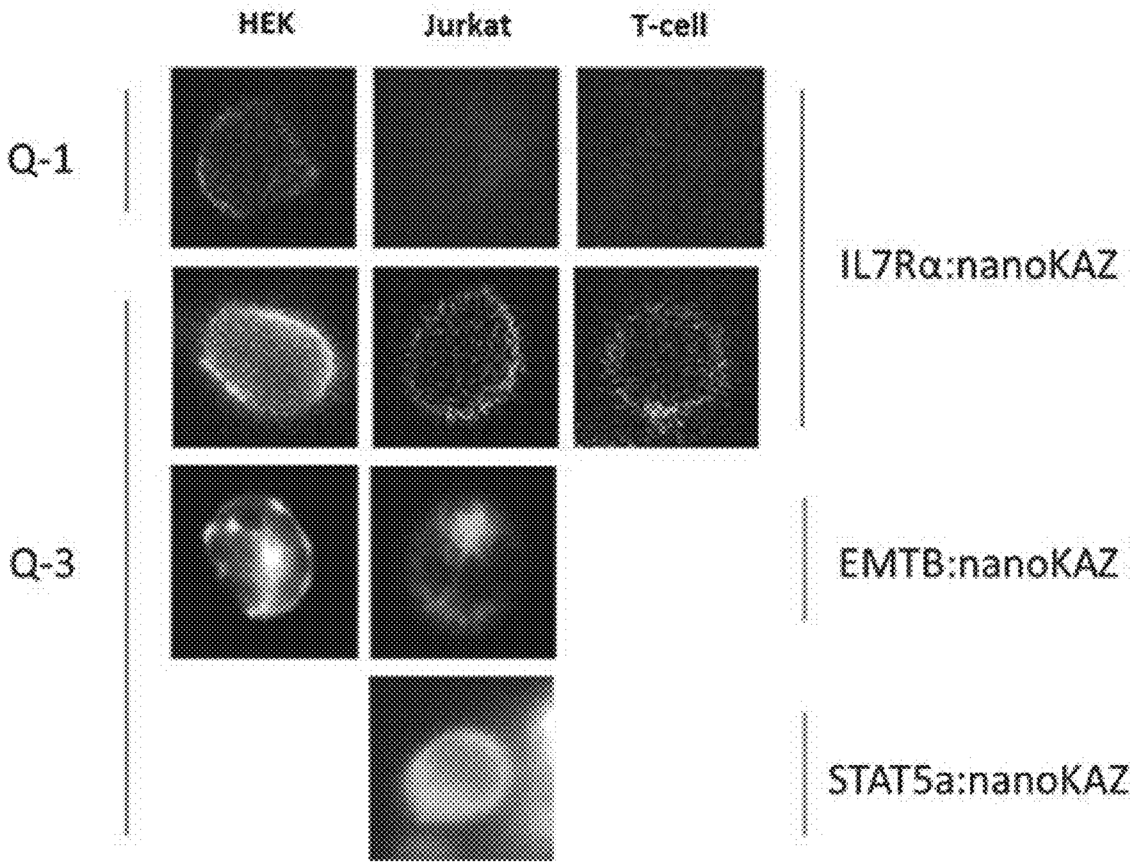
FIG. 5 compares expression and location of protein chimeras fused to the nanoKAZ in transiently transfected HEK and Jurkat cell lines, and primary human T-cells: the cytokine receptor IL7Rα:nanoKAZ at the membrane (top), the enconsin tubulin binding protein EMTB:nanoKAZ associated with microtubules (middle), the transcription factor STAT5a:nanoKAZ dense throughout the cytoplasm and faint in the nucleus (bottom). Images were acquired for one second from live cells using Q-1 (top line) and Q-3 (lines 2-4) substrates showing the subcellular resolution in cell culture conditions and the gain of light emission with Q-3.

NanoKAZ fragment complementation/analogue Q-3 was used as bioluminescent reporter for protein interaction as described above (2.3 and 2.4). HEK and Jurkat cells were cotransfected with two plasmids encoding separately protein partners tagged with either naKAZ or noKAZ as described above. The plasmid pair ratio and the total amounts of plasmids were optimized to get the highest transfection and protein pair expression; various examples are shown in FIG. 5.

4—In Vivo Assays of Bioluminescence of Luciferase or Fragment Used as Reporter of Proteins Expressed in Living Animals or Perfused Tissues Using Light Microscope, Light Scanners, Cameras, of Bioluminescent Imaging Systems.

Furimazine (Q-1) and derivatives have emission spectra centred on 460 nm but present large peaks bleeding beyond 580 nm. The bioluminescence obtained with the analogue Q-3 provides photons with 10% of them having a wavelength beyond 560 nm up to 600 nm. This wide spectra emission toward red is thus allowing the use of the nanok AZ/furimazine for in vivo imaging. The light emission beyond 580 is thousands times higher than red emitting firefly or beetle luciferases. IL7:nanoKAZ and analogue Q-3 were injected in mice. Quantitative images of high quality were acquired with bioluminescence imaging system (Ivis).

5—Bioluminescence Assay of Immobilized Molecules, Particles, Complexes, Virus or Cells on Solid Surface or 3D-Support The typical applications are western and northern blots for protein and DNA target detection from solution, cell lysate or biofluids. These compounds are immobilized on 2D surfaces (membrane, slide, bead, fibre) or 3D support (matrix, gel, permeable bead, fiber networks, permeable tissues). Protein-nanoKAZ can be used to reveal the presence of an interacting target as antibodies nanoKAZ before binding or after binding depending of the alteration of the nanoKAZ activity during the immobilization. These applications could be extended to toxics and compound detection in soils, liquids for testing bio or chemical hazard in the environment when those molecules can be immobilized on the support. Applications could be developed in paper-based microfluidic point of care diagnostic devices using bioluminescence detection (Lab. Chips 2013, 13, 2210-2251). Detection is possible using a bioluminometer, digital camera (including smartphones), scanner, imaging system or photo-sensitive film.

Long Term Stability Property of the O-Acetylated Luciferins Precursors P/(I)

Figure 6A:
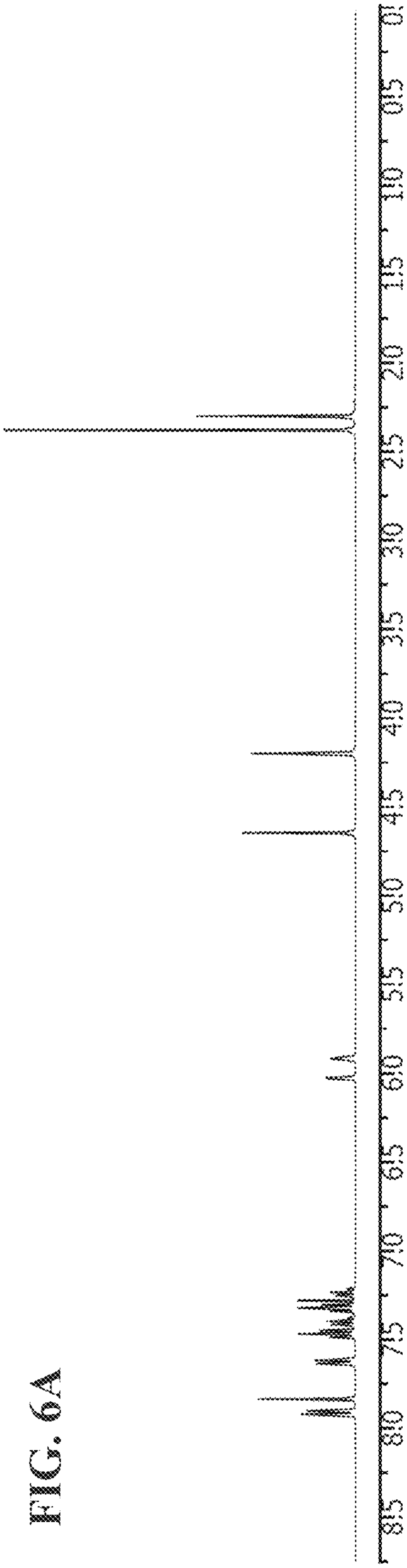
FIGS. 6A-6B depicts a superposition of two $^1$H NMR spectra of the same batch of 1.5 compound 8-benzyl-2-((5-methylfuran-2-yl)methyl)-6-phenylimidazo[1,2-a]pyrazin-3-yl acetate (stored at 4° C.) made on the day of its production (6A) and 30 months after (6B).
Figure 6B:
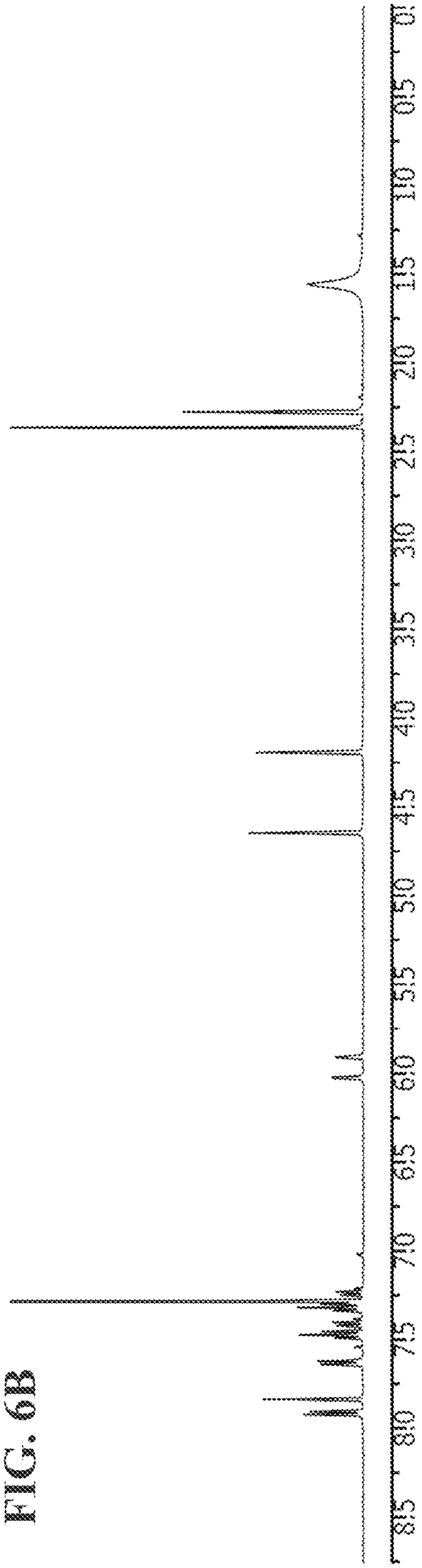

Two $^{1}$H NMR spectra of the same batch of compound 8-benzyl-2-((5-methylfuran-2-yl'methyl)-6-phenylimidazo [1,2-a]pyrazin-3-yl acetate (stored at 4° C.) were made on the day of its production (FIG. 6A) and 30 months after (FIG. 6B) respectively.

The comparison of the two $^{1}$H NMR spectra underlines the advantageous stability of the O-acetylated luciferins precursors with the general formula I.

Similar results were obtained with O-acetylated luciferins precursors stored at room temperature.

The above results are in sharp contrast with the precautions required to maintain the quality of commercially available luciferins such as furimazine or coelenterazine, underlying their very weak storage stability. Indeed, it is recommended to store these luciferins, desiccated or in solution, at −20° C., or for longer storage at −70° C., protected from light, as free of oxygen as possible, being specified that said luciferins may be stored at 4° C. for up to two weeks only

The invention claimed is:

1. A composition comprising:

(a) a compound of formula:

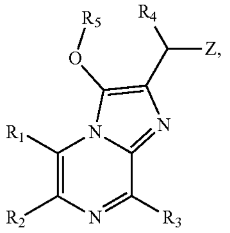

wherein:

$R_1$ represents H;

$R_2$ represents a phenyl, optionally, comprising two substituents, each independently selected from —$CH_3$, —F, —Cl, —OH, and —$NH_2$;

$R_3$ represents a benzyl comprising one or two substituents, each independently selected from —F and —$CF_3$;

$R_4$ represents H;

Z represents a furanyl, optionally, comprising one substituent selected from —$CH_3$ and —F;

$R_5$ represents —C(═O)$R_a$ or —C(═O)O$R_a$;

$R_a$ represents H, $C_1$-$C_6$ alkyl, $C_3$-$C_7$ cycloalkyl, $C_6$-$C_{10}$ aryl, or aralkyl; or (b) a corresponding imidazopyrazinone compound of the above that does not comprise an $R_5$ moiety.

2. The composition of claim 1, wherein:

the $R_2$ comprises two substituents, each independently selected from —F and —$NH_2$;

the $R_3$ comprises one substituent of —F; and the Z represents the furanyl.

3. The composition of claim 1, wherein the compound is selected from:

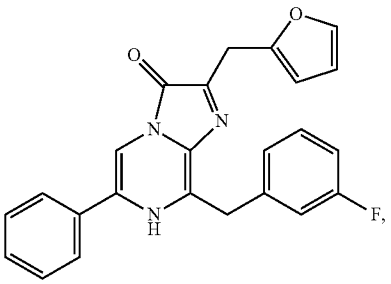

,

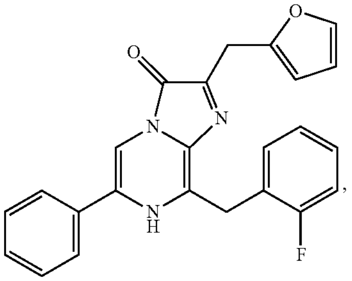

,

-continued

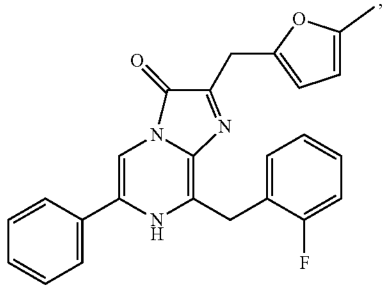

,

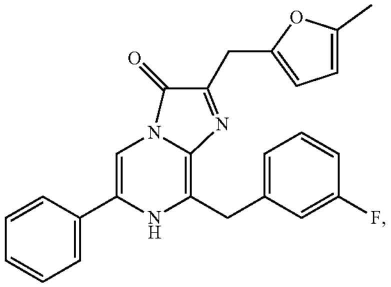

,

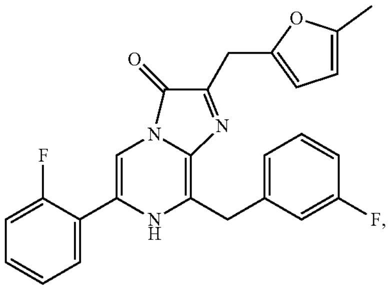

,

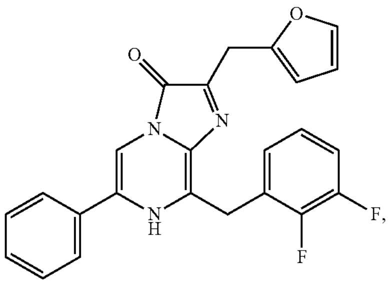

,

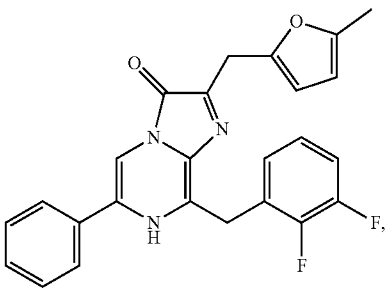

, and

-continued

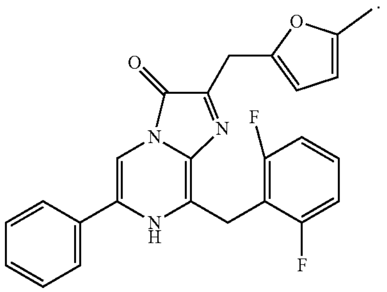

4. A method of detecting and/or measuring an enzymatic activity of luciferase in a sample, the method comprising contacting the compound of the composition of claim 1 with the sample, wherein the contacting comprises contacting the compound comprising $R_5$ with the sample after removal of the $R_5$ or contacting the compound that does not comprise $R_5$ with the sample, and detecting the luminescence signal, wherein the luminescence signal correlates to the presence of enzymatic activity of the luciferase in the sample.

5. The method of claim 4, wherein the luciferase is derived from an *Oplophorus* luciferase.

6. The method of claim 5, wherein the *Oplophorus* luciferase is a nanoKAZ luciferase.

* * * * *